(12) United States Patent
Nakamura et al.

(10) Patent No.: US 9,370,606 B2
(45) Date of Patent: Jun. 21, 2016

(54) SCAFFOLD-FREE SELF-ORGANIZED 3D SYNTHETIC TISSUE

(75) Inventors: Norimasa Nakamura, Nishinomiya (JP); Hideki Yoshikawa, Toyonaka (JP); Wataru Ando, Ibaraki (JP)

(73) Assignee: Two Cells, Co., Ltd., Hiroshima (JP)

(*) Notice: Subject to any disclaimer, the term of this patent is extended or adjusted under 35 U.S.C. 154(b) by 1498 days.

(21) Appl. No.: 11/676,172

(22) Filed: Feb. 16, 2007

(65) Prior Publication Data

US 2008/0004713 A1    Jan. 3, 2008

Related U.S. Application Data

(63) Continuation of application No. 10/566,845, filed as application No. PCT/JP2004/011401 on Aug. 2, 2004, now abandoned.

(30) Foreign Application Priority Data

Aug. 1, 2003    (JP) ................. 2003-285475
Mar. 2, 2004    (JP) ................. 2004-058285

(51) Int. Cl.
| | | |
|---|---|---|
| *C12N 5/00* | (2006.01) | |
| *A61L 27/36* | (2006.01) | |
| *A61L 27/38* | (2006.01) | |
| *C07K 14/78* | (2006.01) | |
| *C12N 5/077* | (2010.01) | |
| *A61K 35/12* | (2015.01) | |

(52) U.S. Cl.
CPC ......... *A61L 27/3633* (2013.01); *A61L 27/3843* (2013.01); *C07K 14/78* (2013.01); *C12N 5/0655* (2013.01); *A61K 35/12* (2013.01)

(58) Field of Classification Search
CPC ...................................................... C12N 5/06
USPC .................. 424/400, 422, 423, 93.1; 435/325
See application file for complete search history.

(56) References Cited

U.S. PATENT DOCUMENTS

| | | | |
|---|---|---|---|
| 5,723,331 A | | 3/1998 | Tubo et al. |
| 5,855,610 A | * | 1/1999 | Vacanti et al. ............... 623/2.13 |
| 6,413,538 B1 | * | 7/2002 | Garcia et al. .................. 424/423 |
| 6,541,024 B1 | * | 4/2003 | Kadiyala et al. ............. 424/426 |
| 2002/0122790 A1 | | 9/2002 | Hunziker ..................... 424/93.7 |
| 2002/0182241 A1 | * | 12/2002 | Borenstein et al. ........... 424/422 |
| 2003/0091979 A1 | | 5/2003 | Eschenhagen .................... 435/4 |
| 2004/0018621 A1 | * | 1/2004 | Reid et al. ..................... 435/370 |

FOREIGN PATENT DOCUMENTS

| | | |
|---|---|---|
| JP | 10-511847 A | 11/1998 |
| WO | 95/30742 | 11/1995 |
| WO | 95/33821 | 12/1995 |
| WO | 96/21003 A1 | 7/1996 |
| WO | 00/51527 A1 | 9/2000 |
| WO | 03/024463 A1 | 3/2003 |

OTHER PUBLICATIONS

Riederer-Henderson et al., In Vitro vol. 19, No. 2, p. 127-133, Feb. 1983.*
Kale et al., "Three-dimensional cellular development is essential for ex vivo formation of human bone," Nature Biotechnology 18:954-958, Sep. 2000.
Kushida et al., "Decrease in culture temperature releases monolayer endothelial cell sheets together with deposited fibronectin matrix from temperature-responsive culture surfaces," J. Biomed. Mater. Res. 45:355-362, 1999.
Brent et al., "A Somitic Compartment of Tendon Progenitors," *Cell* 113:235-248, Apr. 18, 2003.
Bukhari et al., "Time to First Occurrence of Erosions in Inflammatory Polyarthritis," *Arthritis & Rheumatism* 44(6):1248-1253, Jun. 2001.
De Bari et al., "Multipotent Mesenchymal Stem Cells From Adult Human Synovial Membrane," *Arthritis & Rheumatism* 44(8):1928-1942, Aug. 2001.
Dreyer et al., "*Lmx1b* expression during joint and tendon formation: localization and evaluation of potential downstream targets," *Gene Expression Patterns* 4:397-405, 2004.
Hata et al., "L-Ascorbic Acid 2-Phosphate Stimulates Collagen Accumulation, Cell Proliferation, and Formation of a Three-Dimensional Tissuelike Substance by Skin Fibroblasts," *Journal of Cellular Physiology* 138:8-16, 1989.
Havenith et al., "Muscle fiber typing in routinely processed skeletal muscle with monoclonal antibodies," *Histochemistry* 93:497-499, 1990.
Heart Transplant—Lung Transplant, Technical and ethical framework and practice, 3rd Edition, Aug. 31, 1997, 130 pages.
Histopathological Diagnosis of the Rejection of Human Grafted Organs, The Japan Society for Transplantation, The Japanese Society of Pathology, The 2nd Edition, Mar. 2, 2009, 63 pages.

(Continued)

*Primary Examiner* — Ruth Davis
(74) *Attorney, Agent, or Firm* — Seed IP Law Group PLLC

(57) ABSTRACT

The present invention can be used for actual implantation surgery without a scaffold. The present invention provides a synthetic tissue or complex which can be produced by culture and has a high level of differentiation ability. The present invention also provides a therapy and medicament for repairing and/or regenerating tissue using replacement and covering. By culturing cells under specific culture conditions such that medium contains an extracellular matrix synthesis promoting agent, the cells are organized and are easily detached from a culture dish. The present invention was achieved by finding such a phenomenon. In addition, the self contraction of the tissue can be regulated by culturing the tissue in a suspended manner. Therefore, it is possible to regulate the three-dimensional shape of the tissue. The present invention also provides a method for producing an implantable synthetic tissue which does not require a plurality of monolayer cell sheets assembled to form a three-dimensionally structured synthetic tissue. The present invention is characterized by richness in adhesion molecules, nonnecessity of additional fixation at an implantation site, and good biological integration.

4 Claims, 46 Drawing Sheets

(56) References Cited

OTHER PUBLICATIONS

Jankowski et al., "Muscle-derived stem cells," *Gene Therapy* 9:642-647, 2002.

Kulyk et al., "*Sox9* Expression during Chondrogenesis in Micromass Cultures of Embryonic Limb Mesenchyme," *Experimental Cell Research* 255:327-332, 2000.

Lee et al., "Isolation of multipotent mesenchymal stem cells from umbilical cord blood," *Blood* 103(5):1669-1675, Mar. 1, 2004.

Life Science, Report No. 19, Decision Making in Modern Medicine, Chapter 12, Organ Transplant, Jun. 30, 1989, 227 pages.

Pittinger et al., "Multilineage Potential of Adult Human Mesenchymal Stem Cells," *Science* 284:143-147, Apr. 2, 1999.

Salingcarnboriboon et al., "Establishment of tendon-derived cell lines exhibiting pluripotent mesenchymal stem cell-like property," *Experimental Cell Research* 287:289-300, 2003.

Shimizu et al., "Fabrication of Pulsatile Cardiac Tissue Grafts Using a Novel 3-Dimensional Cell Sheet Manipulation Technique and Temperature-Responsive Cell Culture Surfaces," *Circulation Research* 90, 2002, 16 pages.

Takenawa et al., "WASP and WAVE family proteins: key molecules for rapid rearrangement of cortical actin filaments and cell movement," *Journal of Cell Science* 114(10):1801-1809, 2001.

Webster et al., "Isolation of Human Myoblasts with the Fluorescence-Activated Cell Sorter," *Experimental Cell Research* 174:252-265, 1988.

Wickham et al., "Multipotent Stromal Cells Derived From the Infrapatellar Fat Pad of the Knee," *Clinical Orthopaedics and Related Research* 412:196-212, 2003.

Wolfman et al., "Ectopic Induction of Tendon and Ligament in Rats by Growth and Differentiation Factors 5, 6, and 7, Members of the TGF-β Gene Family," *J. Clin. Invest.* 100(2):321-330, Jul. 1997.

Young et al., "The Relationship between SMN, the Spinal Muscular Atrophy Protein, and Nuclear Coiled Bodies in Differentiated Tissues and Cultured Cells," *Experimental Cell Research* 256:365-374, 2000.

Grogan et al., "A static, closed and scaffold-free bioreactor system that permits chondrogenesis in vitro," *OsteoArthritis and Cartilage* 11:403-411, 2003.

Mainil-Varlet et al., "Articular cartilage repair using a tissue-engineered cartilage-like Implant: an animal study," *OsteoArthritis and Cartilage* 9(Supplement A):S6-S15, 2001.

Masuda et al., "A novel two-step method for the formation of tissue-engineered cartilage by mature bovine chondrocytes: the alginate-recovered-chondrocyte (ARC) method," *Journal of Orthopaedic Research* 21:139-148, 2003.

Yamato, "Reconstruction of three-dimensional tissue structures by cell sheet engineering," *Journal of Clinical and Experimental Medicine* 195(3), 6 pages (with partial English translation).

\* cited by examiner

FIG.3
Day 3    Day 7
Day 14    Day 21
(1×10⁶cell/ cm²Asc-2P 1mM)
Day 1  It is difficult to detach cell sheet FIG.4
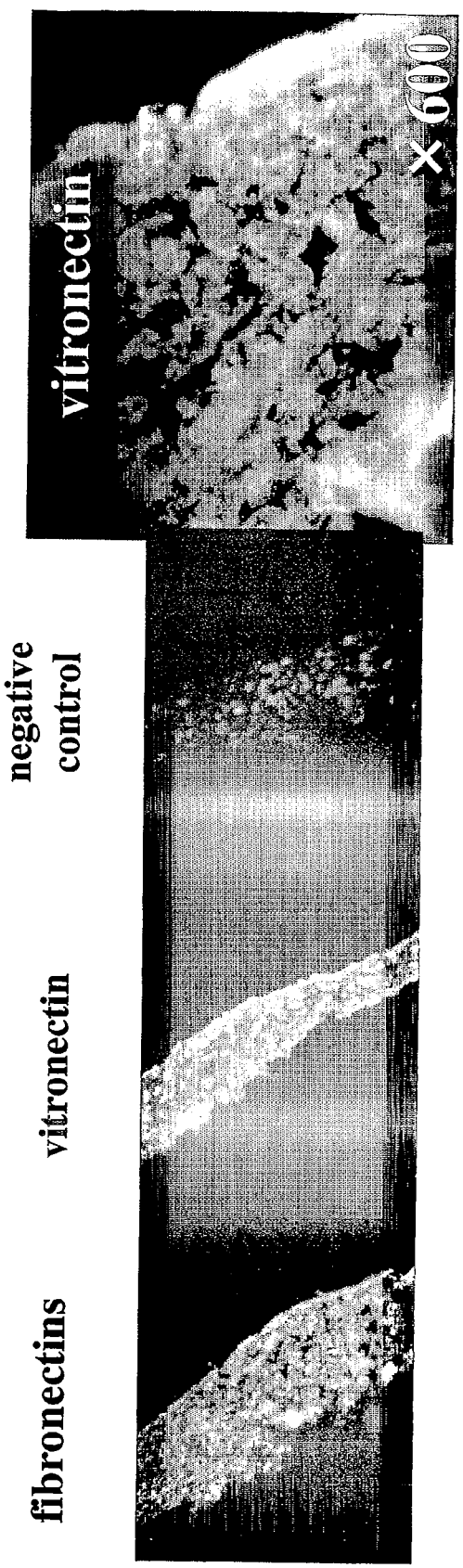

FIG.5
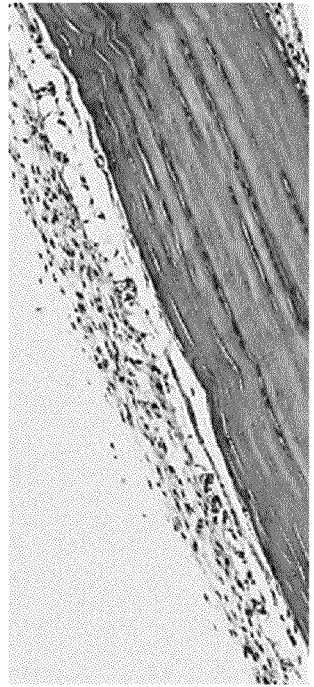
Normal tendon tissue
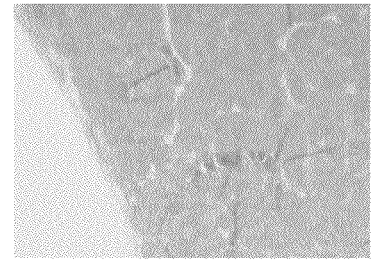
Normal meniscus tissue
Normal cartilage tissue
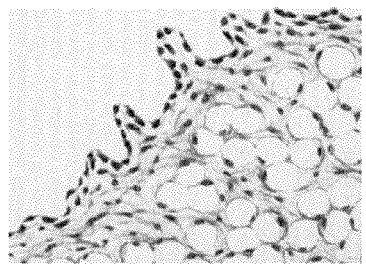
Normal synovial membrane tissue
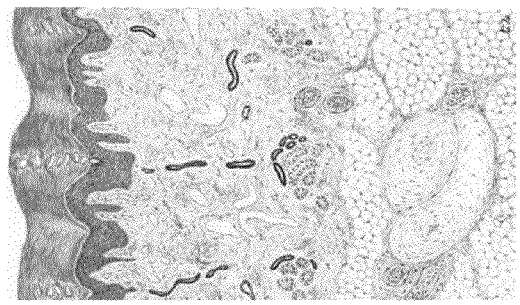
Normal skin FIG.23
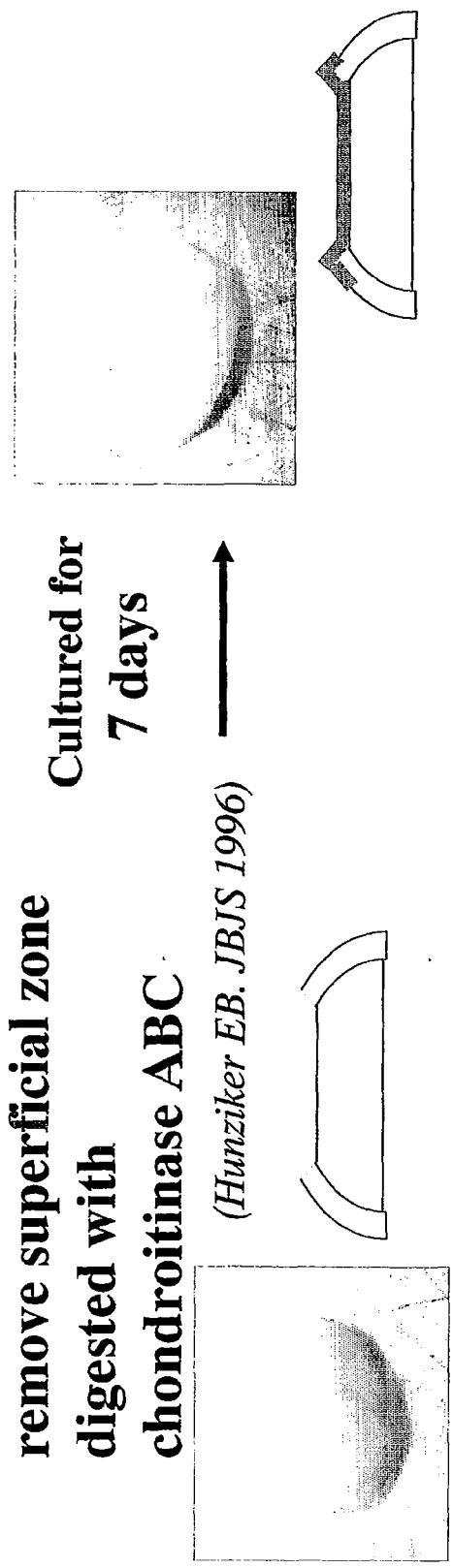
remove superficial zone digested with chondroitinase ABC
(Hunziker EB. JBJS 1996)
Cultured for 7 days
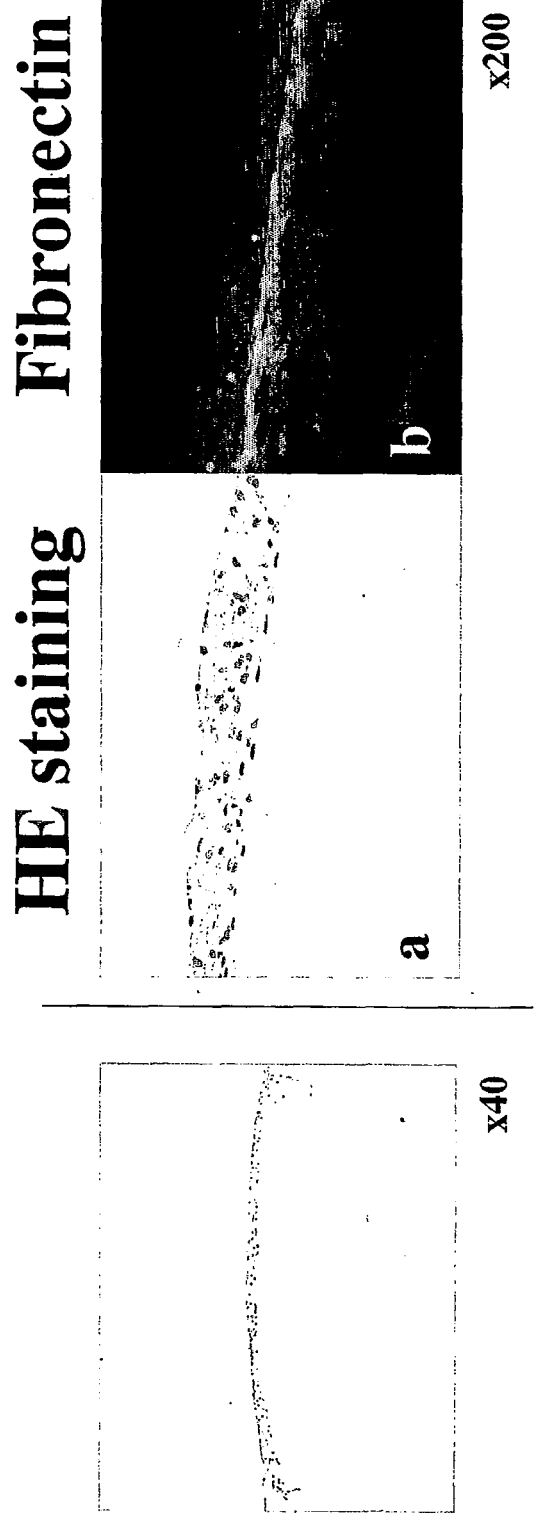
HE staining
Fibronectin
a
b
x40
x200

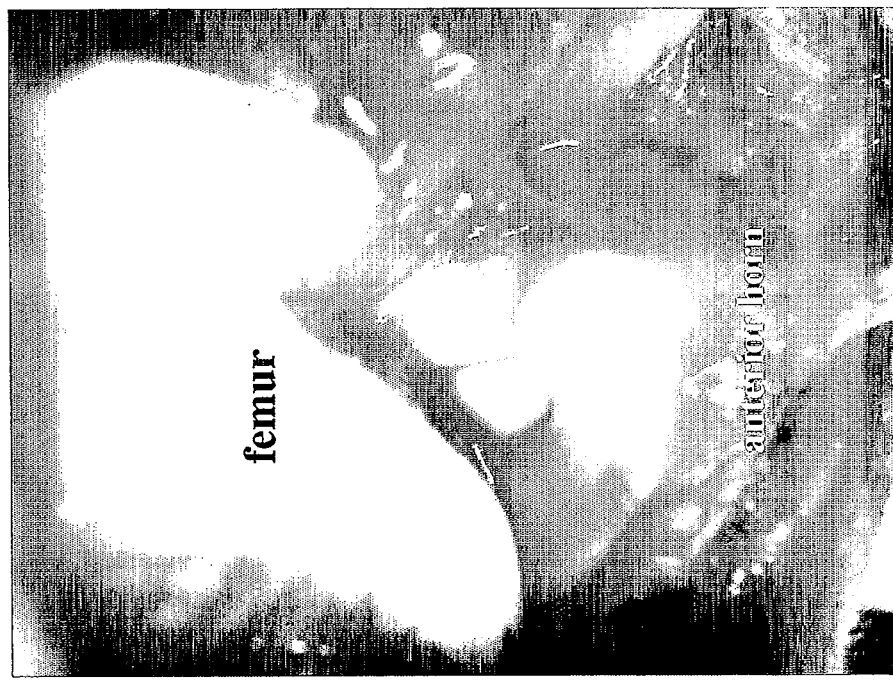
FIG.29

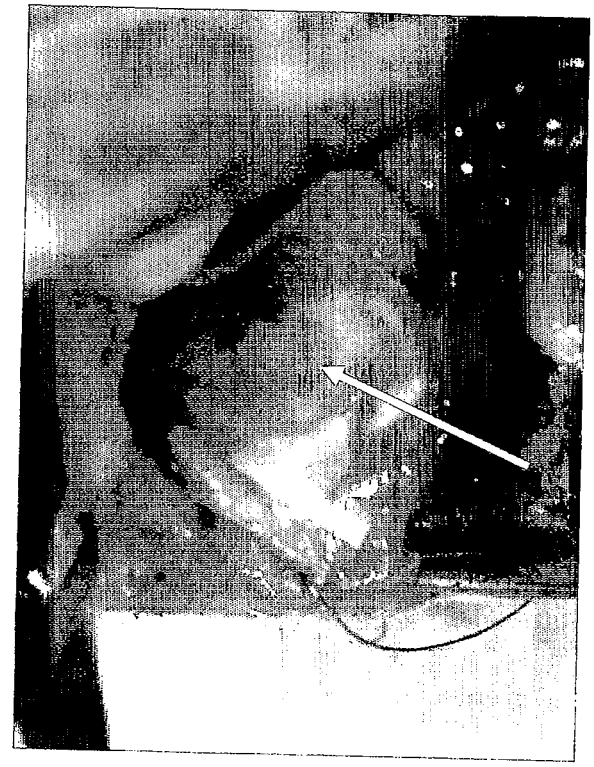
FIG.30
membrana synovialis derived artificial tissue $$H = \frac{F}{A} = \frac{F}{k_1 h_p^2}$$

$$E = \left[\frac{dF}{dh}\right]_{F_{max}} \frac{1-\nu^2}{2 \cdot k_2 \cdot h_{pmax}}$$

$$h_p = h_r + 0.25(h_{max} - h_r)$$

F: load
A: contact projection area
hp: contact depth
k1k2: shape conflict
Fmax: Maximum load
hmax: Maximum displacement
hr: point at which tangential line intersects
dF/dh: Gradient of tangential line of load removal curve
$\nu$ : Poisson's ratio

SEQUENCE LISTING

```
<160> NUMBER OF SEQ ID NOS: 30

<210> SEQ ID NO 1
<211> LENGTH: 6085
<212> TYPE: DNA
<213> ORGANISM: Homo sapiens
<220> FEATURE:
<221> NAME/KEY: CDS
<222> LOCATION: (115)..(5940)

<400> SEQUENCE: 1
tacggctgcg agaagacgac agaagggggt cctgctttaa aaagctccaa gaactgtctc        60
actcccaggc tacatcttct cacttgctaa caaggacctc tgagttcagc agcc atg       117
                                                             Met
                                                              1 agt tca gac tca gaa ttg gct gtt ttt ggg gag gct gct cct ttc ctc       165
```

```
Ser Ser Asp Ser Glu Leu Ala Val Phe Gly Glu Ala Ala Pro Phe Leu
         5                  10                 15 cga aag tct gaa agg gag cgc att gag gcc cag aat agg ccc ttt gat      213
Arg Lys Ser Glu Arg Glu Arg Ile Glu Ala Gln Asn Arg Pro Phe Asp
         20                  25                 30 gcc aaa aca tct gtc ttt gtg gcg gag ccc aaa gaa tcc ttt gtc aaa      261
Ala Lys Thr Ser Val Phe Val Ala Glu Pro Lys Glu Ser Phe Val Lys
         35                  40                 45 ggg acc atc cag agc aga gaa gga gga aaa gtg acg gtg aag act gag      309
Gly Thr Ile Gln Ser Arg Glu Gly Gly Lys Val Thr Val Lys Thr Glu
50                  55                  60                 65 gga gga gcg act ctg aca gtg aag gat gat cag gtc ttc ccc atg aac      357
Gly Gly Ala Thr Leu Thr Val Lys Asp Asp Gln Val Phe Pro Met Asn
                 70                  75                 80 cct ccc aaa tat gac aag atc gag gat atg gcc atg atg act cat ctg      405
Pro Pro Lys Tyr Asp Lys Ile Glu Asp Met Ala Met Met Thr His Leu
                 85                  90                 95 cat gag cct gct gtg ctg tac aac ctc aaa gaa cgt tat gca gcc tgg      453
His Glu Pro Ala Val Leu Tyr Asn Leu Lys Glu Arg Tyr Ala Ala Trp
         100                 105                110 atg atc tac acc tat tca ggt ctc ttc tgt gtc act gtc aac ccc tac      501
Met Ile Tyr Thr Tyr Ser Gly Leu Phe Cys Val Thr Val Asn Pro Tyr
115                 120                 125 aag tgg ctg cct gtg tat aag ccc gag gtg gtg aca gcc tac cga ggc      549
Lys Trp Leu Pro Val Tyr Lys Pro Glu Val Val Thr Ala Tyr Arg Gly
130                 135                 140                145 aaa aag cgc cag ggg gcc ccg ccc cac atc ttc tcc atc tct gac aac      597
Lys Lys Arg Gln Gly Ala Pro Pro His Ile Phe Ser Ile Ser Asp Asn
                 150                 155                160 gcc tat cag ttc atg ctg act gac cga gag aat cag tca atc ctg atc      645
Ala Tyr Gln Phe Met Leu Thr Asp Arg Glu Asn Gln Ser Ile Leu Ile
                 165                 170                175 act gga gaa tct ggt gca ggg aag act gtg aac acc aag cgt gtc atc      693
Thr Gly Glu Ser Gly Ala Gly Lys Thr Val Asn Thr Lys Arg Val Ile
                 180                 185                190 cag tac ttt gca aca att gca gtt act ggt gag aag aag aag gaa gaa      741
Gln Tyr Phe Ala Thr Ile Ala Val Thr Gly Glu Lys Lys Lys Glu Glu
195                 200                 205 att act tct ggc aaa ata cag ggg act ctg gaa gat caa atc atc agt      789
Ile Thr Ser Gly Lys Ile Gln Gly Thr Leu Glu Asp Gln Ile Ile Ser
210                 215                 220                225 gcc aac ccc cta ctg gag gcc ttt ggc aac gcc aag acc gtg agg aat      837
Ala Asn Pro Leu Leu Glu Ala Phe Gly Asn Ala Lys Thr Val Arg Asn
                 230                 235                240 gac aac tcc tct cgc ttt ggt aaa ttc atc aga atc cac ttt ggc act      885
Asp Asn Ser Ser Arg Phe Gly Lys Phe Ile Arg Ile His Phe Gly Thr
                 245                 250                255 act gga aaa ctg gca tct gct gat att gaa aca tat ctg cta gag aag      933
Thr Gly Lys Leu Ala Ser Ala Asp Ile Glu Thr Tyr Leu Leu Glu Lys
         260                 265                 270 tct aga gtt gtt ttc cag ctt aag gct gag aga agt tat cat att ttt      981
Ser Arg Val Val Phe Gln Leu Lys Ala Glu Arg Ser Tyr His Ile Phe
275                 280                 285 tac cag att aca tcg aat aag aaa cca gaa ctt att gaa atg ctt ctg     1029
Tyr Gln Ile Thr Ser Asn Lys Lys Pro Glu Leu Ile Glu Met Leu Leu
290                 295                 300                305 att acc acg aac cca tat gat tac cca ttt gtc agt caa ggg gag atc     1077
Ile Thr Thr Asn Pro Tyr Asp Tyr Pro Phe Val Ser Gln Gly Glu Ile
                 310                 315                320
```

| | |
|---|---|
| agt gtg gcc agc atc gat gat cag gaa gaa ctg atg gcc aca gat agt<br>Ser Val Ala Ser Ile Asp Asp Gln Glu Glu Leu Met Ala Thr Asp Ser<br>325 330 335 | 1125 |
| gct att gat att ttg ggc ttt act aat gaa gaa aag gtc tcc att tac<br>Ala Ile Asp Ile Leu Gly Phe Thr Asn Glu Glu Lys Val Ser Ile Tyr<br>340 345 350 | 1173 |
| aag ctc acg ggg gct gtg atg cat tat ggg aac cta aaa ttt aag caa<br>Lys Leu Thr Gly Ala Val Met His Tyr Gly Asn Leu Lys Phe Lys Gln<br>355 360 365 | 1221 |
| aag cag cgt gag gag caa gca gag cca gat ggc aca gaa gtt gct gac<br>Lys Gln Arg Glu Glu Gln Ala Glu Pro Asp Gly Thr Glu Val Ala Asp<br>370 375 380 385 | 1269 |
| aag gcg gcc tac ctc cag agt ctg aac tct gca gat ctc ctc aaa gct<br>Lys Ala Ala Tyr Leu Gln Ser Leu Asn Ser Ala Asp Leu Leu Lys Ala<br>390 395 400 | 1317 |
| ctc tgc tac ccc agg gtc aag gtc ggc aat gag tat gtc acc aaa ggc<br>Leu Cys Tyr Pro Arg Val Lys Val Gly Asn Glu Tyr Val Thr Lys Gly<br>405 410 415 | 1365 |
| cag act gta gaa cag gtg tcc aac gca gta ggt gct ctg gcc aaa gcc<br>Gln Thr Val Glu Gln Val Ser Asn Ala Val Gly Ala Leu Ala Lys Ala<br>420 425 430 | 1413 |
| gtc tac gag aag atg ttc ctg tgg atg gtt gcc cgc atc aac cag cag<br>Val Tyr Glu Lys Met Phe Leu Trp Met Val Ala Arg Ile Asn Gln Gln<br>435 440 445 | 1461 |
| ctg gac acc aag cag ccc agg cag tac ttc atc ggg gtc ttg gac att<br>Leu Asp Thr Lys Gln Pro Arg Gln Tyr Phe Ile Gly Val Leu Asp Ile<br>450 455 460 465 | 1509 |
| gct ggt ttt gag att ttt gat ttc aac agc ctg gag cag ctg tgc atc<br>Ala Gly Phe Glu Ile Phe Asp Phe Asn Ser Leu Glu Gln Leu Cys Ile<br>470 475 480 | 1557 |
| aac ttc acc aat gag aaa ctg caa cag ttt ttc aac cac cac atg ttc<br>Asn Phe Thr Asn Glu Lys Leu Gln Gln Phe Phe Asn His His Met Phe<br>485 490 495 | 1605 |
| gtg ctg gag cag gag gag tac aag aag gaa ggc atc gag tgg acg ttc<br>Val Leu Glu Gln Glu Glu Tyr Lys Lys Glu Gly Ile Glu Trp Thr Phe<br>500 505 510 | 1653 |
| atc gac ttc ggg atg gac ctg gct gcc tgc atc gag ctc atc gag aag<br>Ile Asp Phe Gly Met Asp Leu Ala Ala Cys Ile Glu Leu Ile Glu Lys<br>515 520 525 | 1701 |
| cct atg ggc atc ttc tcc atc ctg gaa gag gag tgc atg ttc cct aag<br>Pro Met Gly Ile Phe Ser Ile Leu Glu Glu Glu Cys Met Phe Pro Lys<br>530 535 540 545 | 1749 |
| gca aca gac acc tcc ttc aag aac aag ctg tat gac cag cac ctg ggc<br>Ala Thr Asp Thr Ser Phe Lys Asn Lys Leu Tyr Asp Gln His Leu Gly<br>550 555 560 | 1797 |
| aag tct gcc aac ttc cag aag ccc aag gtg gtc aaa ggc aag gcc gag<br>Lys Ser Ala Asn Phe Gln Lys Pro Lys Val Val Lys Gly Lys Ala Glu<br>565 570 575 | 1845 |
| gcc cac ttc gct ctg att cac tat gct ggt gtt gtg gac tac aac att<br>Ala His Phe Ala Leu Ile His Tyr Ala Gly Val Val Asp Tyr Asn Ile<br>580 585 590 | 1893 |
| act ggc tgg ctg gag aag aac aag gac ccc ctg aat gag acc gtg gtt<br>Thr Gly Trp Leu Glu Lys Asn Lys Asp Pro Leu Asn Glu Thr Val Val<br>595 600 605 | 1941 |
| gga ctg tac cag aag tct gca atg aaa act cta gct cag ctc ttc tct<br>Gly Leu Tyr Gln Lys Ser Ala Met Lys Thr Leu Ala Gln Leu Phe Ser<br>610 615 620 625 | 1989 |
| ggg gct caa act gct gaa gga gag gga gct ggc gga ggg gcc aag aaa<br>Gly Ala Gln Thr Ala Glu Gly Glu Gly Ala Gly Gly Gly Ala Lys Lys<br>630 635 640 | 2037 |

| | | | | | | | | | | | | | | | | |
|---|---|---|---|---|---|---|---|---|---|---|---|---|---|---|---|---|
| ggt | ggt | aag | aag | aag | ggc | tct | tct | ttc | cag | aca | gtg | tct | gcc | ctt | ttc | 2085 |
| Gly | Gly | Lys | Lys | Lys | Gly | Ser | Ser | Phe | Gln | Thr | Val | Ser | Ala | Leu | Phe | |
| | | | 645 | | | | 650 | | | | | 655 | | | | |
| aga | gag | aat | ttg | aac | aag | ctg | atg | acc | aac | ctc | agg | agt | acc | cat | cct | 2133 |
| Arg | Glu | Asn | Leu | Asn | Lys | Leu | Met | Thr | Asn | Leu | Arg | Ser | Thr | His | Pro | |
| | | | 660 | | | | 665 | | | | | 670 | | | | |
| cac | ttt | gtg | agg | tgt | atc | atc | ccc | aat | gag | aca | aaa | act | cct | ggt | gcc | 2181 |
| His | Phe | Val | Arg | Cys | Ile | Ile | Pro | Asn | Glu | Thr | Lys | Thr | Pro | Gly | Ala | |
| | | | 675 | | | | 680 | | | | | 685 | | | | |
| atg | gag | cat | gag | ctt | gtc | ctc | cac | cag | ctg | agg | tgt | aac | ggt | gtg | ctg | 2229 |
| Met | Glu | His | Glu | Leu | Val | Leu | His | Gln | Leu | Arg | Cys | Asn | Gly | Val | Leu | |
| 690 | | | | 695 | | | | 700 | | | | | 705 | | | |
| gaa | ggc | atc | cgc | atc | tgt | agg | aaa | gga | ttt | cca | agc | aga | atc | ctt | tat | 2277 |
| Glu | Gly | Ile | Arg | Ile | Cys | Arg | Lys | Gly | Phe | Pro | Ser | Arg | Ile | Leu | Tyr | |
| | | | | 710 | | | | | 715 | | | | | 720 | | |
| gca | gac | ttc | aaa | cag | aga | tac | aag | gta | tta | aat | gca | agt | gca | atc | cct | 2325 |
| Ala | Asp | Phe | Lys | Gln | Arg | Tyr | Lys | Val | Leu | Asn | Ala | Ser | Ala | Ile | Pro | |
| | | | 725 | | | | | 730 | | | | | 735 | | | |
| gaa | ggg | caa | ttc | att | gat | agc | aag | aag | gcc | tct | gag | aag | ctc | ctt | gca | 2373 |
| Glu | Gly | Gln | Phe | Ile | Asp | Ser | Lys | Lys | Ala | Ser | Glu | Lys | Leu | Leu | Ala | |
| | | 740 | | | | | 745 | | | | | 750 | | | | |
| tcc | atc | gac | att | gac | cac | acc | cag | tat | aaa | ttt | ggg | cac | acc | aag | gtc | 2421 |
| Ser | Ile | Asp | Ile | Asp | His | Thr | Gln | Tyr | Lys | Phe | Gly | His | Thr | Lys | Val | |
| | 755 | | | | 760 | | | | | 765 | | | | | | |
| ttt | ttc | aaa | gct | ggt | ctt | ctg | ggg | ctc | cta | gag | gag | atg | cga | gat | gac | 2469 |
| Phe | Phe | Lys | Ala | Gly | Leu | Leu | Gly | Leu | Leu | Glu | Glu | Met | Arg | Asp | Asp | |
| 770 | | | | 775 | | | | 780 | | | | | 785 | | | |
| aag | ctg | gcc | cag | ctg | att | acc | cga | acc | cag | gcc | agg | tgc | aga | ggg | ttc | 2517 |
| Lys | Leu | Ala | Gln | Leu | Ile | Thr | Arg | Thr | Gln | Ala | Arg | Cys | Arg | Gly | Phe | |
| | | | | 790 | | | | | 795 | | | | | 800 | | |
| ttg | gca | aga | gtg | gag | tac | cag | agg | atg | gtg | gag | aga | agg | gag | gcc | atc | 2565 |
| Leu | Ala | Arg | Val | Glu | Tyr | Gln | Arg | Met | Val | Glu | Arg | Arg | Glu | Ala | Ile | |
| | | | 805 | | | | | 810 | | | | | 815 | | | |
| ttc | tgt | atc | cag | tac | aat | atc | aga | tcc | ttc | atg | aat | gtc | aag | cac | tgg | 2613 |
| Phe | Cys | Ile | Gln | Tyr | Asn | Ile | Arg | Ser | Phe | Met | Asn | Val | Lys | His | Trp | |
| | | 820 | | | | | 825 | | | | | 830 | | | | |
| ccc | tgg | atg | aaa | ctc | ttc | ttc | aag | atc | aag | cct | ctg | ttg | aag | agt | gca | 2661 |
| Pro | Trp | Met | Lys | Leu | Phe | Phe | Lys | Ile | Lys | Pro | Leu | Leu | Lys | Ser | Ala | |
| | 835 | | | | 840 | | | | | 845 | | | | | | |
| gaa | act | gag | aag | gag | atg | gcc | acc | atg | aag | gaa | gaa | ttt | cag | aaa | att | 2709 |
| Glu | Thr | Glu | Lys | Glu | Met | Ala | Thr | Met | Lys | Glu | Glu | Phe | Gln | Lys | Ile | |
| 850 | | | | 855 | | | | | 860 | | | | | 865 | | |
| aaa | gac | gaa | ctt | gcc | aag | tca | gag | gca | aaa | agg | aag | gaa | ctg | gaa | gaa | 2757 |
| Lys | Asp | Glu | Leu | Ala | Lys | Ser | Glu | Ala | Lys | Arg | Lys | Glu | Leu | Glu | Glu | |
| | | | 870 | | | | | 875 | | | | | 880 | | | |
| aag | atg | gtg | acg | ctg | ttg | aaa | gaa | aaa | aat | gac | ttg | cag | ctc | caa | gtt | 2805 |
| Lys | Met | Val | Thr | Leu | Leu | Lys | Glu | Lys | Asn | Asp | Leu | Gln | Leu | Gln | Val | |
| | | | 885 | | | | | 890 | | | | | 895 | | | |
| cag | gct | gaa | gcc | gaa | ggc | ttg | gct | gat | gca | gag | gaa | agg | tgt | gac | cag | 2853 |
| Gln | Ala | Glu | Ala | Glu | Gly | Leu | Ala | Asp | Ala | Glu | Glu | Arg | Cys | Asp | Gln | |
| | | 900 | | | | | 905 | | | | | 910 | | | | |
| cta | atc | aaa | acc | aaa | atc | cag | cta | gaa | gcc | aaa | atc | aaa | gag | gtg | act | 2901 |
| Leu | Ile | Lys | Thr | Lys | Ile | Gln | Leu | Glu | Ala | Lys | Ile | Lys | Glu | Val | Thr | |
| | 915 | | | | 920 | | | | | 925 | | | | | | |
| gag | aga | gct | gag | gat | gag | gaa | gag | atc | aat | gct | gag | ctg | aca | gcc | aag | 2949 |
| Glu | Arg | Ala | Glu | Asp | Glu | Glu | Glu | Ile | Asn | Ala | Glu | Leu | Thr | Ala | Lys | |
| 930 | | | | 935 | | | | | 940 | | | | | 945 | | |
| aag | agg | aaa | ctg | gag | gat | gaa | tgt | tca | gaa | ctc | aag | aaa | gac | att | gat | 2997 |
| Lys | Arg | Lys | Leu | Glu | Asp | Glu | Cys | Ser | Glu | Leu | Lys | Lys | Asp | Ile | Asp | |

-continued

```
                     950                 955                 960
gac ctt gag ctg aca ctg gcc aag gtt gag aag gag aaa cat gcc aca      3045
Asp Leu Glu Leu Thr Leu Ala Lys Val Glu Lys Glu Lys His Ala Thr
            965                 970                 975 gaa aac aag gtg aaa aac ctc aca gaa gag atg gca ggt ctg gat gaa      3093
Glu Asn Lys Val Lys Asn Leu Thr Glu Glu Met Ala Gly Leu Asp Glu
        980                 985                 990 acc att gct aag ctg acc aag gag aag aag gct ctc cag gag gcc cac      3141
Thr Ile Ala Lys Leu Thr Lys Glu Lys Lys Ala Leu Gln Glu Ala His
    995                 1000                1005 cag cag acc ctg gat gac ctg cag gca gag gag gac aaa gtc aac          3186
Gln Gln Thr Leu Asp Asp Leu Gln Ala Glu Glu Asp Lys Val Asn
1010                1015                1020 acc ctg acc aaa gct aaa atc aaa ctt gaa caa caa gtg gat gat          3231
Thr Leu Thr Lys Ala Lys Ile Lys Leu Glu Gln Gln Val Asp Asp
1025                1030                1035 ctt gaa ggg tcc ttg gag caa gaa aag aaa ctt cgc atg gac cta          3276
Leu Glu Gly Ser Leu Glu Gln Glu Lys Lys Leu Arg Met Asp Leu
1040                1045                1050 gaa agg gct aag agg aaa ctt gag ggt gac ttg aag ttg gcc caa          3321
Glu Arg Ala Lys Arg Lys Leu Glu Gly Asp Leu Lys Leu Ala Gln
1055                1060                1065 gaa tcc ata atg gac att gaa aat gag aaa cag caa ctt gat gaa          3366
Glu Ser Ile Met Asp Ile Glu Asn Glu Lys Gln Gln Leu Asp Glu
1070                1075                1080 aag ctc aaa aag aaa gag ttt gaa atc agc aat ctg caa agc aag          3411
Lys Leu Lys Lys Lys Glu Phe Glu Ile Ser Asn Leu Gln Ser Lys
1085                1090                1095 att gaa gat gaa cag gca ctt ggc att caa ttg cag aag aaa att          3456
Ile Glu Asp Glu Gln Ala Leu Gly Ile Gln Leu Gln Lys Lys Ile
1100                1105                1110 aaa gaa ttg caa gcc cgc att gag gag ctg gag gag gaa atc gag          3501
Lys Glu Leu Gln Ala Arg Ile Glu Glu Leu Glu Glu Glu Ile Glu
1115                1120                1125 gca gag cgg gcc tcc cgg gcc aaa gca gag aag cag cgc tct gac          3546
Ala Glu Arg Ala Ser Arg Ala Lys Ala Glu Lys Gln Arg Ser Asp
1130                1135                1140 ctc tcc cgg gag ctg gag gag atc agc gag agg ctg gaa gaa gcc          3591
Leu Ser Arg Glu Leu Glu Glu Ile Ser Glu Arg Leu Glu Glu Ala
1145                1150                1155 ggt ggg gcc act tca gcc cag att gag atg aac aag aag cgg gag          3636
Gly Gly Ala Thr Ser Ala Gln Ile Glu Met Asn Lys Lys Arg Glu
1160                1165                1170 gct gag ttc cag aaa atg cgc agg gac ctg gag gag gcc acc cta          3681
Ala Glu Phe Gln Lys Met Arg Arg Asp Leu Glu Glu Ala Thr Leu
1175                1180                1185 cag cat gaa gcc aca gcg gcc acc ctg agg aag aag cat gca gat          3726
Gln His Glu Ala Thr Ala Ala Thr Leu Arg Lys Lys His Ala Asp
1190                1195                1200 agt gtg gcc gag ctt ggg gag cag att gac aac ctg cag cga gtg          3771
Ser Val Ala Glu Leu Gly Glu Gln Ile Asp Asn Leu Gln Arg Val
1205                1210                1215 aag cag aag ctg gag aag gag aag agt gag atg aag atg gag att          3816
Lys Gln Lys Leu Glu Lys Glu Lys Ser Glu Met Lys Met Glu Ile
1220                1225                1230 gat gac ctt gct agt aat gta gaa acg gtc tcc aaa gcc aag gga          3861
Asp Asp Leu Ala Ser Asn Val Glu Thr Val Ser Lys Ala Lys Gly
1235                1240                1245 aac cta gag aaa atg tgc cgg act cta gag gac caa ctg agt gaa          3906
```

```
Asn  Leu  Glu  Lys  Met  Cys  Arg  Thr  Leu  Glu  Asp  Gln  Leu  Ser  Glu
1250                1255                     1260 ctg  aaa  tca  aag  gaa  gag  gag  cag  cag  cgg  ctg  atc  aat  gac  ctg         3951
Leu  Lys  Ser  Lys  Glu  Glu  Glu  Gln  Gln  Arg  Leu  Ile  Asn  Asp  Leu
1265                1270                     1275 act  gcg  cag  agg  ggg  cgc  ctg  cag  act  gaa  tct  ggt  gag  ttt  tca         3996
Thr  Ala  Gln  Arg  Gly  Arg  Leu  Gln  Thr  Glu  Ser  Gly  Glu  Phe  Ser
1280                1285                     1290 cgc  cag  ctt  gat  gaa  aag  gaa  gct  ctg  gtg  tct  cag  tta  tca  aga         4041
Arg  Gln  Leu  Asp  Glu  Lys  Glu  Ala  Leu  Val  Ser  Gln  Leu  Ser  Arg
1295                1300                     1305 ggc  aaa  caa  gcc  ttt  act  caa  cag  att  gaa  gaa  tta  aag  agg  caa         4086
Gly  Lys  Gln  Ala  Phe  Thr  Gln  Gln  Ile  Glu  Glu  Leu  Lys  Arg  Gln
1310                1315                     1320 ctt  gaa  gag  gag  ata  aaa  gcc  aag  aac  gcc  ctg  gcg  cat  gcc  ctg         4131
Leu  Glu  Glu  Glu  Ile  Lys  Ala  Lys  Asn  Ala  Leu  Ala  His  Ala  Leu
1325                1330                     1335 cag  tct  tcc  cgc  cac  gac  tgt  gac  ctg  ctg  cgg  gaa  cag  tat  gag         4176
Gln  Ser  Ser  Arg  His  Asp  Cys  Asp  Leu  Leu  Arg  Glu  Gln  Tyr  Glu
1340                1345                     1350 gag  gag  cag  gaa  tcc  aag  gcc  gag  ctg  cag  aga  gca  ctg  tcc  aag         4221
Glu  Glu  Gln  Glu  Ser  Lys  Ala  Glu  Leu  Gln  Arg  Ala  Leu  Ser  Lys
1355                1360                     1365 gcc  aac  acc  gag  gtt  gcc  caa  tgg  agg  acc  aaa  tac  gag  acg  gac         4266
Ala  Asn  Thr  Glu  Val  Ala  Gln  Trp  Arg  Thr  Lys  Tyr  Glu  Thr  Asp
1370                1375                     1380 gcc  atc  cag  cgc  aca  gag  gag  ctg  gag  gag  gcc  aag  aag  aag  ctg         4311
Ala  Ile  Gln  Arg  Thr  Glu  Glu  Leu  Glu  Glu  Ala  Lys  Lys  Lys  Leu
1385                1390                     1395 gcc  cag  cgg  ctg  cag  gca  gct  gag  gaa  cat  gta  gaa  gct  gtg  aac         4356
Ala  Gln  Arg  Leu  Gln  Ala  Ala  Glu  Glu  His  Val  Glu  Ala  Val  Asn
1400                1405                     1410 gcc  aaa  tgt  gct  tcc  ctc  gaa  aag  acg  aag  cag  cgg  ctg  cag  aat         4401
Ala  Lys  Cys  Ala  Ser  Leu  Glu  Lys  Thr  Lys  Gln  Arg  Leu  Gln  Asn
1415                1420                     1425 gag  gtc  gag  gac  ctc  atg  ctt  gat  gtg  gag  agg  aca  aat  gcc  gcc         4446
Glu  Val  Glu  Asp  Leu  Met  Leu  Asp  Val  Glu  Arg  Thr  Asn  Ala  Ala
1430                1435                     1440 tgt  gcc  gcc  ctt  gac  aaa  aag  caa  agg  aac  ttc  gat  aag  atc  ctg         4491
Cys  Ala  Ala  Leu  Asp  Lys  Lys  Gln  Arg  Asn  Phe  Asp  Lys  Ile  Leu
1445                1450                     1455 gca  gaa  tgg  aaa  cag  aaa  tgt  gag  gaa  acg  cat  gct  gag  ctt  gag         4536
Ala  Glu  Trp  Lys  Gln  Lys  Cys  Glu  Glu  Thr  His  Ala  Glu  Leu  Glu
1460                1465                     1470 gcc  tcc  cag  aag  gag  gcc  cgt  tcc  ctt  ggc  act  gag  ctg  ttc  aag         4581
Ala  Ser  Gln  Lys  Glu  Ala  Arg  Ser  Leu  Gly  Thr  Glu  Leu  Phe  Lys
1475                1480                     1485 ata  aag  aat  gcc  tat  gag  gaa  tct  ttg  gat  cag  cta  gaa  acc  ctg         4626
Ile  Lys  Asn  Ala  Tyr  Glu  Glu  Ser  Leu  Asp  Gln  Leu  Glu  Thr  Leu
1490                1495                     1500 aag  cga  gag  aac  aaa  aac  tta  cag  cag  gag  att  tct  gac  ctc  acg         4671
Lys  Arg  Glu  Asn  Lys  Asn  Leu  Gln  Gln  Glu  Ile  Ser  Asp  Leu  Thr
1505                1510                     1515 gaa  cag  att  gca  gaa  gga  ggg  aaa  cgt  atc  cat  gaa  ctg  gag  aaa         4716
Glu  Gln  Ile  Ala  Glu  Gly  Gly  Lys  Arg  Ile  His  Glu  Leu  Glu  Lys
1520                1525                     1530 ata  aag  aaa  caa  gtg  gaa  caa  gaa  aag  tgt  gaa  ctt  cag  gct  gct         4761
Ile  Lys  Lys  Gln  Val  Glu  Gln  Glu  Lys  Cys  Glu  Leu  Gln  Ala  Ala
1535                1540                     1545
```

| | | | | | | | | | | | |
|---|---|---|---|---|---|---|---|---|---|---|---|
| tta | gaa | gaa | gca | gag | gca | tct | ctt | gaa | cat | gaa | gag | gga | aag | atc | 4806 |
| Leu | Glu | Glu | Ala | Glu | Ala | Ser | Leu | Glu | His | Glu | Glu | Gly | Lys | Ile | |
| 1550 | | | | 1555 | | | | | 1560 | | | | | | |

| ctg | cgc | atc | cag | ctt | gag | ttg | aac | caa | gtc | aag | tct | gag | gtt | gat | 4851 |
| Leu | Arg | Ile | Gln | Leu | Glu | Leu | Asn | Gln | Val | Lys | Ser | Glu | Val | Asp | |
| 1565 | | | | | 1570 | | | | | 1575 | | | | | |

| agg | aaa | att | gct | gaa | aaa | gat | gag | gaa | att | gac | cag | ctg | aag | aga | 4896 |
| Arg | Lys | Ile | Ala | Glu | Lys | Asp | Glu | Glu | Ile | Asp | Gln | Leu | Lys | Arg | |
| 1580 | | | | | 1585 | | | | | 1590 | | | | | |

| aac | cac | att | aga | atc | gtg | gag | tcc | atg | cag | agc | acg | ctg | gat | gct | 4941 |
| Asn | His | Ile | Arg | Ile | Val | Glu | Ser | Met | Gln | Ser | Thr | Leu | Asp | Ala | |
| 1595 | | | | | 1600 | | | | | 1605 | | | | | |

| gag | atc | agg | agt | agg | aat | gat | gcc | att | agg | ctc | aag | aag | aag | atg | 4986 |
| Glu | Ile | Arg | Ser | Arg | Asn | Asp | Ala | Ile | Arg | Leu | Lys | Lys | Lys | Met | |
| 1610 | | | | | 1615 | | | | | 1620 | | | | | |

| gag | gga | gac | ctc | aat | gaa | atg | gaa | atc | cag | ctg | aac | cat | gcc | aac | 5031 |
| Glu | Gly | Asp | Leu | Asn | Glu | Met | Glu | Ile | Gln | Leu | Asn | His | Ala | Asn | |
| 1625 | | | | | 1630 | | | | | 1635 | | | | | |

| cgc | atg | gct | gct | gag | gcc | ctg | agg | aac | tac | agg | aac | acc | caa | ggc | 5076 |
| Arg | Met | Ala | Ala | Glu | Ala | Leu | Arg | Asn | Tyr | Arg | Asn | Thr | Gln | Gly | |
| 1640 | | | | | 1645 | | | | | 1650 | | | | | |

| atc | ctc | aag | gat | acc | cag | atc | cac | ctg | gat | gat | gct | ctc | cgg | agc | 5121 |
| Ile | Leu | Lys | Asp | Thr | Gln | Ile | His | Leu | Asp | Asp | Ala | Leu | Arg | Ser | |
| 1655 | | | | | 1660 | | | | | 1665 | | | | | |

| cag | gag | gac | ctg | aag | gaa | cag | ctg | gcc | atg | gtg | gag | cgc | aga | gcc | 5166 |
| Gln | Glu | Asp | Leu | Lys | Glu | Gln | Leu | Ala | Met | Val | Glu | Arg | Arg | Ala | |
| 1670 | | | | | 1675 | | | | | 1680 | | | | | |

| aac | ctg | ctg | cag | gct | gag | atc | gag | gag | ctg | cgg | gcc | act | ctg | gaa | 5211 |
| Asn | Leu | Leu | Gln | Ala | Glu | Ile | Glu | Glu | Leu | Arg | Ala | Thr | Leu | Glu | |
| 1685 | | | | | 1690 | | | | | 1695 | | | | | |

| cag | aca | gag | agg | agc | aga | aaa | atc | gca | gaa | cag | gag | ctc | ctg | gat | 5256 |
| Gln | Thr | Glu | Arg | Ser | Arg | Lys | Ile | Ala | Glu | Gln | Glu | Leu | Leu | Asp | |
| 1700 | | | | | 1705 | | | | | 1710 | | | | | |

| gcc | agt | gag | cgt | gtt | cag | cta | ctg | cac | acc | cag | aac | acc | agc | ctg | 5301 |
| Ala | Ser | Glu | Arg | Val | Gln | Leu | Leu | His | Thr | Gln | Asn | Thr | Ser | Leu | |
| 1715 | | | | | 1720 | | | | | 1725 | | | | | |

| atc | aac | acc | aag | aag | aag | ctg | gag | aca | gat | att | tcc | caa | atg | caa | 5346 |
| Ile | Asn | Thr | Lys | Lys | Lys | Leu | Glu | Thr | Asp | Ile | Ser | Gln | Met | Gln | |
| 1730 | | | | | 1735 | | | | | 1740 | | | | | |

| gga | gag | atg | gag | gac | att | ctc | cag | gaa | gcc | cgc | aat | gca | gaa | gaa | 5391 |
| Gly | Glu | Met | Glu | Asp | Ile | Leu | Gln | Glu | Ala | Arg | Asn | Ala | Glu | Glu | |
| 1745 | | | | | 1750 | | | | | 1755 | | | | | |

| aag | gcc | aag | aag | gcc | atc | act | gat | gcc | gcc | atg | atg | gct | gag | gag | 5436 |
| Lys | Ala | Lys | Lys | Ala | Ile | Thr | Asp | Ala | Ala | Met | Met | Ala | Glu | Glu | |
| 1760 | | | | | 1765 | | | | | 1770 | | | | | |

| ctg | aag | aag | gag | cag | gac | acc | agc | gcc | cac | ctg | gag | cgg | atg | aag | 5481 |
| Leu | Lys | Lys | Glu | Gln | Asp | Thr | Ser | Ala | His | Leu | Glu | Arg | Met | Lys | |
| 1775 | | | | | 1780 | | | | | 1785 | | | | | |

| aag | aac | atg | gag | cag | acc | gtg | aag | gat | ctg | cag | ctc | cgt | ctg | gat | 5526 |
| Lys | Asn | Met | Glu | Gln | Thr | Val | Lys | Asp | Leu | Gln | Leu | Arg | Leu | Asp | |
| 1790 | | | | | 1795 | | | | | 1800 | | | | | |

| gag | gct | gag | cag | ctg | gcc | ctg | aag | ggt | ggg | aag | aag | cag | atc | cag | 5571 |
| Glu | Ala | Glu | Gln | Leu | Ala | Leu | Lys | Gly | Gly | Lys | Lys | Gln | Ile | Gln | |
| 1805 | | | | | 1810 | | | | | 1815 | | | | | |

| aaa | ctg | gag | gcc | agg | gta | cgg | gag | ctg | gaa | gga | gag | gtt | gag | agt | 5616 |
| Lys | Leu | Glu | Ala | Arg | Val | Arg | Glu | Leu | Glu | Gly | Glu | Val | Glu | Ser | |
| 1820 | | | | | 1825 | | | | | 1830 | | | | | |

| gag | caa | aag | cgt | aat | gct | gag | gct | gtc | aaa | ggt | ctg | cgc | aaa | cat | 5661 |
| Glu | Gln | Lys | Arg | Asn | Ala | Glu | Ala | Val | Lys | Gly | Leu | Arg | Lys | His | |
| 1835 | | | | | 1840 | | | | | 1845 | | | | | |

```
gag  agg  cga  gtg  aag  gaa  ctc  act  tac  cag  acg  gaa  gaa  gat  aga         5706
Glu  Arg  Arg  Val  Lys  Glu  Leu  Thr  Tyr  Gln  Thr  Glu  Glu  Asp  Arg
1850                1855                     1860 aag  aat  att  ctc  agg  ctt  caa  gat  ttg  gta  gat  aaa  ctt  cag  gca         5751
Lys  Asn  Ile  Leu  Arg  Leu  Gln  Asp  Leu  Val  Asp  Lys  Leu  Gln  Ala
1865                1870                     1875 aaa  gtg  aaa  tct  tat  aag  aga  caa  gct  gag  gag  gct  gag  gaa  caa         5796
Lys  Val  Lys  Ser  Tyr  Lys  Arg  Gln  Ala  Glu  Glu  Ala  Glu  Glu  Gln
1880                1885                     1890 tcc  aac  acc  aat  cta  gct  aaa  ttc  cgc  aag  ctc  cag  cat  gag  ctg         5841
Ser  Asn  Thr  Asn  Leu  Ala  Lys  Phe  Arg  Lys  Leu  Gln  His  Glu  Leu
1895                1900                     1905 gag  gag  gcc  gag  gaa  cgg  gct  gac  att  gct  gag  tcc  cag  gtg  aac         5886
Glu  Glu  Ala  Glu  Glu  Arg  Ala  Asp  Ile  Ala  Glu  Ser  Gln  Val  Asn
1910                1915                     1920 aaa  ctg  cgg  gtg  aag  agc  cgg  gag  gtt  cac  aca  aaa  gtc  ata  agt         5931
Lys  Leu  Arg  Val  Lys  Ser  Arg  Glu  Val  His  Thr  Lys  Val  Ile  Ser
1925                1930                     1935 gaa  gag  tga  tcatgtcctg atgccatgga atgactgaag acaggcacaa                        5980
Glu  Glu
1940 aatgtgacat ctttggtcat ttccctctgt aattattgtg tattctaccc tgttgcaaag                 6040 gaaataaagc atagggtagt ttgcaaacaa aaaaaaaaaa aaaaa                                 6085

<210> SEQ ID NO 2
<211> LENGTH: 1941
<212> TYPE: PRT
<213> ORGANISM: Homo sapiens

<400> SEQUENCE: 2

Met Ser Ser Asp Ser Glu Leu Ala Val Phe Gly Glu Ala Ala Pro Phe
1               5                   10                  15

Leu Arg Lys Ser Glu Arg Glu Arg Ile Glu Ala Gln Asn Arg Pro Phe
                20                  25                  30

Asp Ala Lys Thr Ser Val Phe Val Ala Glu Pro Lys Glu Ser Phe Val
            35                  40                  45

Lys Gly Thr Ile Gln Ser Arg Glu Gly Gly Lys Val Thr Val Lys Thr
        50                  55                  60

Glu Gly Gly Ala Thr Leu Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
                100                 105                 110

Trp Met Ile Tyr Thr Tyr Ser Gly Leu Phe Cys Val Thr Val Asn Pro
            115                 120                 125

Tyr Lys Trp Leu Pro Val Tyr Lys Pro Glu Val Val Thr Ala Tyr Arg
        130                 135                 140

Gly Lys Lys Arg Gln Gly Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205
```

-continued

```
Glu Ile Thr Ser Gly Lys Ile Gln Gly Thr Leu Asp Gln Ile Ile
    210                 215                 220
Ser Ala Asn Pro Leu Leu Glu Ala Phe Gly Asn Ala Lys Thr Val Arg
225                 230                 235                 240
Asn Asp Asn Ser Ser Arg Phe Gly Lys Phe Ile Arg Ile His Phe Gly
                245                 250                 255
Thr Thr Gly Lys Leu Ala Ser Ala Asp Ile Glu Thr Tyr Leu Leu Glu
            260                 265                 270
Lys Ser Arg Val Val Phe Gln Leu Lys Ala Glu Arg Ser Tyr His Ile
        275                 280                 285
Phe Tyr Gln Ile Thr Ser Asn Lys Lys Pro Glu Leu Ile Glu Met Leu
    290                 295                 300
Leu Ile Thr Thr Asn Pro Tyr Asp Tyr Pro Phe Val Ser Gln Gly Glu
305                 310                 315                 320
Ile Ser Val Ala Ser Ile Asp Asp Gln Glu Glu Leu Met Ala Thr Asp
                325                 330                 335
Ser Ala Ile Asp Ile Leu Gly Phe Thr Asn Glu Glu Lys Val Ser Ile
            340                 345                 350
Tyr Lys Leu Thr Gly Ala Val Met His Tyr Gly Asn Leu Lys Phe Lys
        355                 360                 365
Gln Lys Gln Arg Glu Glu Gln Ala Glu Pro Asp Gly Thr Glu Val Ala
    370                 375                 380
Asp Lys Ala Ala Tyr Leu Gln Ser Leu Asn Ser Ala Asp Leu Leu Lys
385                 390                 395                 400
Ala Leu Cys Tyr Pro Arg Val Lys Val Gly Asn Glu Tyr Val Thr Lys
                405                 410                 415
Gly Gln Thr Val Glu Gln Val Ser Asn Ala Val Gly Ala Leu Ala Lys
            420                 425                 430
Ala Val Tyr Glu Lys Met Phe Leu Trp Met Val Ala Arg Ile Asn Gln
        435                 440                 445
Gln Leu Asp Thr Lys Gln Pro Arg Gln Tyr Phe Ile Gly Val Leu Asp
    450                 455                 460
Ile Ala Gly Phe Glu Ile Phe Asp Phe Asn Ser Leu Glu Gln Leu Cys
465                 470                 475                 480
Ile Asn Phe Thr Asn Glu Lys Leu Gln Gln Phe Phe Asn His His Met
                485                 490                 495
Phe Val Leu Glu Gln Glu Glu Tyr Lys Lys Glu Gly Ile Glu Trp Thr
            500                 505                 510
Phe Ile Asp Phe Gly Met Asp Leu Ala Ala Cys Ile Glu Leu Ile Glu
        515                 520                 525
Lys Pro Met Gly Ile Phe Ser Ile Leu Glu Glu Cys Met Phe Pro
    530                 535                 540
Lys Ala Thr Asp Thr Ser Phe Lys Asn Lys Leu Tyr Asp Gln His Leu
545                 550                 555                 560
Gly Lys Ser Ala Asn Phe Gln Lys Pro Lys Val Val Lys Gly Lys Ala
                565                 570                 575
Glu Ala His Phe Ala Leu Ile His Tyr Ala Gly Val Val Asp Tyr Asn
            580                 585                 590
Ile Thr Gly Trp Leu Glu Lys Asn Lys Asp Pro Leu Asn Glu Thr Val
        595                 600                 605
Val Gly Leu Tyr Gln Lys Ser Ala Met Lys Thr Leu Ala Gln Leu Phe
    610                 615                 620
```

```
Ser Gly Ala Gln Thr Ala Glu Gly Glu Gly Ala Gly Gly Ala Lys
625                 630                 635                 640

Lys Gly Gly Lys Lys Gly Ser Ser Phe Gln Thr Val Ser Ala Leu
            645                 650                 655

Phe Arg Glu Asn Leu Asn Lys Leu Met Thr Asn Leu Arg Ser Thr His
        660                 665                 670

Pro His Phe Val Arg Cys Ile Ile Pro Asn Glu Thr Lys Thr Pro Gly
        675                 680                 685

Ala Met Glu His Glu Leu Val Leu His Gln Leu Arg Cys Asn Gly Val
690                 695                 700

Leu Glu Gly Ile Arg Ile Cys Arg Lys Gly Phe Pro Ser Arg Ile Leu
705                 710                 715                 720

Tyr Ala Asp Phe Lys Gln Arg Tyr Lys Val Leu Asn Ala Ser Ala Ile
                725                 730                 735

Pro Glu Gly Gln Phe Ile Asp Ser Lys Lys Ala Ser Glu Lys Leu Leu
            740                 745                 750

Ala Ser Ile Asp Ile Asp His Thr Gln Tyr Lys Phe Gly His Thr Lys
        755                 760                 765

Val Phe Phe Lys Ala Gly Leu Leu Gly Leu Leu Glu Glu Met Arg Asp
770                 775                 780

Asp Lys Leu Ala Gln Leu Ile Thr Arg Thr Gln Ala Arg Cys Arg Gly
785                 790                 795                 800

Phe Leu Ala Arg Val Glu Tyr Gln Arg Met Val Glu Arg Arg Glu Ala
                805                 810                 815

Ile Phe Cys Ile Gln Tyr Asn Ile Arg Ser Phe Met Asn Val Lys His
            820                 825                 830

Trp Pro Trp Met Lys Leu Phe Phe Lys Ile Lys Pro Leu Leu Lys Ser
        835                 840                 845

Ala Glu Thr Glu Lys Glu Met Ala Thr Met Lys Glu Glu Phe Gln Lys
850                 855                 860

Ile Lys Asp Glu Leu Ala Lys Ser Glu Ala Lys Arg Lys Glu Leu Glu
865                 870                 875                 880

Glu Lys Met Val Thr Leu Leu Lys Glu Lys Asn Asp Leu Gln Leu Gln
                885                 890                 895

Val Gln Ala Glu Ala Glu Gly Leu Ala Asp Ala Glu Glu Arg Cys Asp
            900                 905                 910

Gln Leu Ile Lys Thr Lys Ile Gln Leu Glu Ala Lys Ile Lys Glu Val
        915                 920                 925

Thr Glu Arg Ala Glu Asp Glu Glu Ile Asn Ala Glu Leu Thr Ala
930                 935                 940

Lys Lys Arg Lys Leu Glu Asp Glu Cys Ser Glu Leu Lys Lys Asp Ile
945                 950                 955                 960

Asp Asp Leu Glu Leu Thr Leu Ala Lys Val Glu Lys Glu Lys His Ala
                965                 970                 975

Thr Glu Asn Lys Val Lys Asn Leu Thr Glu Glu Met Ala Gly Leu Asp
            980                 985                 990

Glu Thr Ile Ala Lys Leu Thr Lys Glu Lys Lys Ala Leu Gln Glu Ala
        995                 1000                1005

His Gln Gln Thr Leu Asp Asp Leu Gln Ala Glu Glu Asp Lys Val
        1010                1015                1020

Asn Thr Leu Thr Lys Ala Lys Ile Lys Leu Glu Gln Gln Val Asp
        1025                1030                1035

Asp Leu Glu Gly Ser Leu Glu Gln Glu Lys Lys Leu Arg Met Asp
```

```
              1040                1045                1050
Leu Glu Arg Ala Lys Arg Lys Leu Glu Gly Asp Leu Lys Leu Ala
              1055                1060                1065
Gln Glu Ser Ile Met Asp Ile Glu Asn Glu Lys Gln Gln Leu Asp
              1070                1075                1080
Glu Lys Leu Lys Lys Lys Glu Phe Glu Ile Ser Asn Leu Gln Ser
              1085                1090                1095
Lys Ile Glu Asp Glu Gln Ala Leu Gly Ile Gln Leu Gln Lys Lys
              1100                1105                1110
Ile Lys Glu Leu Gln Ala Arg Ile Glu Glu Leu Glu Glu Glu Ile
              1115                1120                1125
Glu Ala Glu Arg Ala Ser Arg Ala Lys Ala Glu Lys Gln Arg Ser
              1130                1135                1140
Asp Leu Ser Arg Glu Leu Glu Glu Ile Ser Glu Arg Leu Glu Glu
              1145                1150                1155
Ala Gly Gly Ala Thr Ser Ala Gln Ile Glu Met Asn Lys Lys Arg
              1160                1165                1170
Glu Ala Glu Phe Gln Lys Met Arg Arg Asp Leu Glu Glu Ala Thr
              1175                1180                1185
Leu Gln His Glu Ala Thr Ala Ala Thr Leu Arg Lys Lys His Ala
              1190                1195                1200
Asp Ser Val Ala Glu Leu Gly Glu Gln Ile Asp Asn Leu Gln Arg
              1205                1210                1215
Val Lys Gln Lys Leu Glu Lys Glu Lys Ser Glu Met Lys Met Glu
              1220                1225                1230
Ile Asp Asp Leu Ala Ser Asn Val Glu Thr Val Ser Lys Ala Lys
              1235                1240                1245
Gly Asn Leu Glu Lys Met Cys Arg Thr Leu Glu Asp Gln Leu Ser
              1250                1255                1260
Glu Leu Lys Ser Lys Glu Glu Gln Gln Arg Leu Ile Asn Asp
              1265                1270                1275
Leu Thr Ala Gln Arg Gly Arg Leu Gln Thr Glu Ser Gly Glu Phe
              1280                1285                1290
Ser Arg Gln Leu Asp Glu Lys Glu Ala Leu Val Ser Gln Leu Ser
              1295                1300                1305
Arg Gly Lys Gln Ala Phe Thr Gln Gln Ile Glu Glu Leu Lys Arg
              1310                1315                1320
Gln Leu Glu Glu Glu Ile Lys Ala Lys Asn Ala Leu Ala His Ala
              1325                1330                1335
Leu Gln Ser Ser Arg His Asp Cys Asp Leu Leu Arg Glu Gln Tyr
              1340                1345                1350
Glu Glu Glu Gln Glu Ser Lys Ala Glu Leu Gln Arg Ala Leu Ser
              1355                1360                1365
Lys Ala Asn Thr Glu Val Ala Gln Trp Arg Thr Lys Tyr Glu Thr
              1370                1375                1380
Asp Ala Ile Gln Arg Thr Glu Glu Leu Glu Glu Ala Lys Lys Lys
              1385                1390                1395
Leu Ala Gln Arg Leu Gln Ala Ala Glu Glu His Val Glu Ala Val
              1400                1405                1410
Asn Ala Lys Cys Ala Ser Leu Glu Lys Thr Lys Gln Arg Leu Gln
              1415                1420                1425
Asn Glu Val Glu Asp Leu Met Leu Asp Val Glu Arg Thr Asn Ala
              1430                1435                1440
```

```
Ala Cys Ala Ala Leu Asp Lys Lys Gln Arg Asn Phe Asp Lys Ile
    1445              1450                1455

Leu Ala Glu Trp Lys Gln Lys Cys Glu Thr His Ala Glu Leu
    1460              1465                1470

Glu Ala Ser Gln Lys Glu Ala Arg Ser Leu Gly Thr Glu Leu Phe
    1475              1480                1485

Lys Ile Lys Asn Ala Tyr Glu Glu Ser Leu Asp Gln Leu Glu Thr
    1490              1495                1500

Leu Lys Arg Glu Asn Lys Asn Leu Gln Gln Glu Ile Ser Asp Leu
    1505              1510                1515

Thr Glu Gln Ile Ala Glu Gly Gly Lys Arg Ile His Glu Leu Glu
    1520              1525                1530

Lys Ile Lys Lys Gln Val Glu Gln Glu Lys Cys Glu Leu Gln Ala
    1535              1540                1545

Ala Leu Glu Glu Ala Glu Ala Ser Leu Glu His Glu Glu Gly Lys
    1550              1555                1560

Ile Leu Arg Ile Gln Leu Glu Leu Asn Gln Val Lys Ser Glu Val
    1565              1570                1575

Asp Arg Lys Ile Ala Glu Lys Asp Glu Glu Ile Asp Gln Leu Lys
    1580              1585                1590

Arg Asn His Ile Arg Ile Val Glu Ser Met Gln Ser Thr Leu Asp
    1595              1600                1605

Ala Glu Ile Arg Ser Arg Asn Asp Ala Ile Arg Leu Lys Lys Lys
    1610              1615                1620

Met Glu Gly Asp Leu Asn Glu Met Glu Ile Gln Leu Asn His Ala
    1625              1630                1635

Asn Arg Met Ala Ala Glu Ala Leu Arg Asn Tyr Arg Asn Thr Gln
    1640              1645                1650

Gly Ile Leu Lys Asp Thr Gln Ile His Leu Asp Asp Ala Leu Arg
    1655              1660                1665

Ser Gln Glu Asp Leu Lys Glu Gln Leu Ala Met Val Glu Arg Arg
    1670              1675                1680

Ala Asn Leu Leu Gln Ala Glu Ile Glu Glu Leu Arg Ala Thr Leu
    1685              1690                1695

Glu Gln Thr Glu Arg Ser Arg Lys Ile Ala Glu Gln Glu Leu Leu
    1700              1705                1710

Asp Ala Ser Glu Arg Val Gln Leu Leu His Thr Gln Asn Thr Ser
    1715              1720                1725

Leu Ile Asn Thr Lys Lys Lys Leu Glu Thr Asp Ile Ser Gln Met
    1730              1735                1740

Gln Gly Glu Met Glu Asp Ile Leu Gln Glu Ala Arg Asn Ala Glu
    1745              1750                1755

Glu Lys Ala Lys Lys Ala Ile Thr Asp Ala Ala Met Met Ala Glu
    1760              1765                1770

Glu Leu Lys Lys Glu Gln Asp Thr Ser Ala His Leu Glu Arg Met
    1775              1780                1785

Lys Lys Asn Met Glu Gln Thr Val Lys Asp Leu Gln Leu Arg Leu
    1790              1795                1800

Asp Glu Ala Glu Gln Leu Ala Leu Lys Gly Gly Lys Lys Gln Ile
    1805              1810                1815

Gln Lys Leu Glu Ala Arg Val Arg Glu Leu Glu Gly Glu Val Glu
    1820              1825                1830
```

```
Ser Glu Gln Lys Arg Asn Ala Glu Ala Val Lys Gly  Leu Arg Lys
    1835                1840               1845

His Glu Arg Arg Val Lys Glu  Leu Thr Tyr Gln Thr  Glu Glu Asp
    1850                1855                1860

Arg Lys Asn Ile Leu Arg Leu  Gln Asp Leu Val Asp  Lys Leu Gln
    1865                1870                1875

Ala Lys Val Lys Ser Tyr Lys  Arg Gln Ala Glu Glu  Ala Glu Glu
    1880                1885                1890

Gln Ser Asn Thr Asn Leu Ala  Lys Phe Arg Lys Leu  Gln His Glu
    1895                1900                1905

Leu Glu Glu Ala Glu Glu Arg  Ala Asp Ile Ala Glu  Ser Gln Val
    1910                1915                1920

Asn Lys Leu Arg Val Lys Ser  Arg Glu Val His Thr  Lys Val Ile
    1925                1930                1935

Ser Glu Glu
    1940

<210> SEQ ID NO 3
<211> LENGTH: 6016
<212> TYPE: DNA
<213> ORGANISM: Homo sapiens
<220> FEATURE:
<221> NAME/KEY: CDS
<222> LOCATION: (112)..(5931)

<400> SEQUENCE: 3
atccttcctc aaaattcttg aagtagttgt ctgctttgag cctgccacct tcttcatctg     60
ataatacaag aggtatacct agtccagcac tgccatcaat aacctgcagc c atg agt    117
                                                        Met Ser
                                                        1 tct gac tct gag atg gcc att ttt ggg gag gct gct cct ttc ctc cga    165
Ser Asp Ser Glu Met Ala Ile Phe Gly Glu Ala Ala Pro Phe Leu Arg
    5                   10                  15 aag tct gaa aag gag cga att gaa gct cag aac aag cct ttt gat gcc    213
Lys Ser Glu Lys Glu Arg Ile Glu Ala Gln Asn Lys Pro Phe Asp Ala
 20                  25                  30 aag aca tca gtc ttt gtg gtg gac cct aag gag tcc tac gtg aaa gca    261
Lys Thr Ser Val Phe Val Val Asp Pro Lys Glu Ser Tyr Val Lys Ala
 35                  40                  45                  50 ata gtg cag agc agg gaa ggg ggg aag gtg aca gcc aag acc gaa gct    309
Ile Val Gln Ser Arg Glu Gly Gly Lys Val Thr Ala Lys Thr Glu Ala
                 55                  60                  65 gga gct act gta act gtg aaa gaa gac caa gtc ttc tcc atg aac cct    357
Gly Ala Thr Val Thr Val Lys Glu Asp Gln Val Phe Ser Met Asn Pro
             70                  75                  80 ccc aaa tat gac aag atc gag gac atg gcc atg atg act cac ctg cat    405
Pro Lys Tyr Asp Lys Ile Glu Asp Met Ala Met Met Thr His Leu His
         85                  90                  95 gag cct gct gtg ctg tat aac ctc aaa gag cgt tac gca gcc tgg atg    453
Glu Pro Ala Val Leu Tyr Asn Leu Lys Glu Arg Tyr Ala Ala Trp Met
    100                 105                 110 atc tac acc tac tcg ggc ctc ttc tgt gtc acc gtc aac ccc tac aag    501
Ile Tyr Thr Tyr Ser Gly Leu Phe Cys Val Thr Val Asn Pro Tyr Lys
115                 120                 125                 130 tgg ctg ccg gtg tac aac cct gag gtg gtg aca gcc tac cga ggc aaa    549
Trp Leu Pro Val Tyr Asn Pro Glu Val Val Thr Ala Tyr Arg Gly Lys
                135                 140                 145 aag cgc cag gag gcc cca ccc cat atc ttc tcc atc tct gac aat gcc    597
Lys Arg Gln Glu Ala Pro Pro His Ile Phe Ser Ile Ser Asp Asn Ala
```

-continued

```
                150             155             160
tat cag ttc atg cta act gat cgt gaa aac cag tca atc ttg att act      645
Tyr Gln Phe Met Leu Thr Asp Arg Glu Asn Gln Ser Ile Leu Ile Thr
        165             170             175 gga gaa tct ggt gca ggg aag act gtg aac acg aag cgt gtc atc cag      693
Gly Glu Ser Gly Ala Gly Lys Thr Val Asn Thr Lys Arg Val Ile Gln
180             185             190 tac ttt gca aca att gca gtt act gga gag aag aaa aaa gag gaa cct      741
Tyr Phe Ala Thr Ile Ala Val Thr Gly Glu Lys Lys Lys Glu Glu Pro
195             200             205             210 gcc tct ggc aaa atg cag ggg acc ctt gaa gat caa atc atc agt gct      789
Ala Ser Gly Lys Met Gln Gly Thr Leu Glu Asp Gln Ile Ile Ser Ala
            215             220             225 aac ccc cta ctg gaa gcc ttc ggc aat gcc aag acc gtg agg aat gac      837
Asn Pro Leu Leu Glu Ala Phe Gly Asn Ala Lys Thr Val Arg Asn Asp
        230             235             240 aac tcc tct cgc ttt ggt aaa ttc atc agg atc cat ttt ggt gcc aca      885
Asn Ser Ser Arg Phe Gly Lys Phe Ile Arg Ile His Phe Gly Ala Thr
        245             250             255 ggc aaa ctg gct tct gca gat att gaa aca tat ctg cta gag aag tcc      933
Gly Lys Leu Ala Ser Ala Asp Ile Glu Thr Tyr Leu Leu Glu Lys Ser
260             265             270 cga gtt act ttt cag cta aag gct gaa aga agc tac cac ata ttt tat      981
Arg Val Thr Phe Gln Leu Lys Ala Glu Arg Ser Tyr His Ile Phe Tyr
275             280             285             290 caa atc ctg tcc aat aag aaa cca gag ctc att gaa atg ctt ctg atc     1029
Gln Ile Leu Ser Asn Lys Lys Pro Glu Leu Ile Glu Met Leu Leu Ile
            295             300             305 acc acc aac cca tat gac ttc gca ttt gtc agc caa ggg gaa att act     1077
Thr Thr Asn Pro Tyr Asp Phe Ala Phe Val Ser Gln Gly Glu Ile Thr
        310             315             320 gtg ccc agc att gat gac cag gaa gag ctg atg gcc aca gat agt gct     1125
Val Pro Ser Ile Asp Asp Gln Glu Glu Leu Met Ala Thr Asp Ser Ala
        325             330             335 gtg gac atc ctg ggt ttc act gct gat gaa aag gtg gcc att tac aag     1173
Val Asp Ile Leu Gly Phe Thr Ala Asp Glu Lys Val Ala Ile Tyr Lys
340             345             350 ctc act gga gcc gtg atg cat tat ggg aac atg aaa ttc aag caa aag     1221
Leu Thr Gly Ala Val Met His Tyr Gly Asn Met Lys Phe Lys Gln Lys
355             360             365             370 caa agg gaa gag cag gca gag cca gat ggc acg gaa gtt gct gac aaa     1269
Gln Arg Glu Glu Gln Ala Glu Pro Asp Gly Thr Glu Val Ala Asp Lys
            375             380             385 gct gct tat ctg aca agt ctg aac tct gct gac ctg ctc aaa tct ctc     1317
Ala Ala Tyr Leu Thr Ser Leu Asn Ser Ala Asp Leu Leu Lys Ser Leu
        390             395             400 tgc tat ccc aga gtc aag gtc ggc aat gag ttc gta acc aaa ggc cag     1365
Cys Tyr Pro Arg Val Lys Val Gly Asn Glu Phe Val Thr Lys Gly Gln
        405             410             415 act gtg cag cag gtg tac aac gca gtg ggt gct ctg gcc aaa gcc atc     1413
Thr Val Gln Gln Val Tyr Asn Ala Val Gly Ala Leu Ala Lys Ala Ile
420             425             430 tac gag aag atg ttc ctg tgg atg gtc acc cgc atc aac cag cag ctg     1461
Tyr Glu Lys Met Phe Leu Trp Met Val Thr Arg Ile Asn Gln Gln Leu
435             440             445             450 gac acc aag cag ccc agg cag tac ttc atc ggg gtc ttg gac att gct     1509
Asp Thr Lys Gln Pro Arg Gln Tyr Phe Ile Gly Val Leu Asp Ile Ala
            455             460             465 ggc ttt gag atc ttt gat ttc aac agc ctg gag cag ctg tgc atc aac     1557
```

```
                Gly Phe Glu Ile Phe Asp Phe Asn Ser Leu Glu Gln Leu Cys Ile Asn
                                470                 475                 480 ttc acc aac gag aaa ctg caa cag ttt ttc aac cac cac atg ttc gtg                1605
Phe Thr Asn Glu Lys Leu Gln Gln Phe Phe Asn His His Met Phe Val
            485                 490                 495 ctg gag cag gaa gag tac aag aag gaa ggc atc gag tgg gag ttc att                1653
Leu Glu Gln Glu Glu Tyr Lys Lys Glu Gly Ile Glu Trp Glu Phe Ile
500                 505                 510 gac ttc ggg atg gac ctg gct gcc tgc atc gag ctc atc gag aag cct                1701
Asp Phe Gly Met Asp Leu Ala Ala Cys Ile Glu Leu Ile Glu Lys Pro
515                 520                 525                 530 atg ggc atc ttc tcc atc cta gaa gag gag tgc atg ttc ccc aag gca                1749
Met Gly Ile Phe Ser Ile Leu Glu Glu Glu Cys Met Phe Pro Lys Ala
                535                 540                 545 aca gac acc tcc ttc aag aac aag ctg tat gaa caa cat ctt gga aaa                1797
Thr Asp Thr Ser Phe Lys Asn Lys Leu Tyr Glu Gln His Leu Gly Lys
            550                 555                 560 tcc aac aac ttc cag aag ccc aag cct gcc aaa ggc aag cct gag gct                1845
Ser Asn Asn Phe Gln Lys Pro Lys Pro Ala Lys Gly Lys Pro Glu Ala
        565                 570                 575 cac ttc tca ctg gtg cac tat gcc ggc acc gtg gac tac aac atc gcc                1893
His Phe Ser Leu Val His Tyr Ala Gly Thr Val Asp Tyr Asn Ile Ala
580                 585                 590 ggc tgg ctg gac aaa aac aag gac ccc ctg aat gag act gtg gtg ggg                1941
Gly Trp Leu Asp Lys Asn Lys Asp Pro Leu Asn Glu Thr Val Val Gly
595                 600                 605                 610 ctg tac cag aag tct gca atg aag act ctg gct ttc ctc ttc tct ggg                1989
Leu Tyr Gln Lys Ser Ala Met Lys Thr Leu Ala Phe Leu Phe Ser Gly
                615                 620                 625 gca caa act gct gaa gca gag ggt ggt ggt gga aag aaa ggt ggc aaa                2037
Ala Gln Thr Ala Glu Ala Glu Gly Gly Gly Gly Lys Lys Gly Gly Lys
            630                 635                 640 aag aag ggt tct tct ttc cag aca gtg tca gct ctt ttc agg gag aat                2085
Lys Lys Gly Ser Ser Phe Gln Thr Val Ser Ala Leu Phe Arg Glu Asn
        645                 650                 655 ttg aat aag ctg atg acc aac ttg agg agc act cac ccc cac ttt gtg                2133
Leu Asn Lys Leu Met Thr Asn Leu Arg Ser Thr His Pro His Phe Val
660                 665                 670 cgg tgc atc atc ccc aat gaa act aaa act cct ggt gcc atg gag cat                2181
Arg Cys Ile Ile Pro Asn Glu Thr Lys Thr Pro Gly Ala Met Glu His
675                 680                 685                 690 gag ctt gtc ctg cat cag ctg agg tgt aac ggt gtg ctg gaa ggc atc                2229
Glu Leu Val Leu His Gln Leu Arg Cys Asn Gly Val Leu Glu Gly Ile
                695                 700                 705 cgc atc tgc agg aaa ggc ttc cca agc aga atc ctt tat gca gac ttc                2277
Arg Ile Cys Arg Lys Gly Phe Pro Ser Arg Ile Leu Tyr Ala Asp Phe
            710                 715                 720 aaa cag aga tac aag gtt cta aat gcg agt gct atc cca gag ggt cag                2325
Lys Gln Arg Tyr Lys Val Leu Asn Ala Ser Ala Ile Pro Glu Gly Gln
        725                 730                 735 ttc att gac agc aag aag gct tct gag aaa ctt cta ggg tct att gaa                2373
Phe Ile Asp Ser Lys Lys Ala Ser Glu Lys Leu Leu Gly Ser Ile Glu
740                 745                 750 att gac cac acc cag tac aaa ttc ggt cat acc aag gtt ttc ttc aaa                2421
Ile Asp His Thr Gln Tyr Lys Phe Gly His Thr Lys Val Phe Phe Lys
755                 760                 765                 770 gct ggc ctg ctg gga act cta gaa gaa atg cga gat gaa aag cta gct                2469
Ala Gly Leu Leu Gly Thr Leu Glu Glu Met Arg Asp Glu Lys Leu Ala
                775                 780                 785
```

```
caa ctc atc acg cgc act caa gcc ata tgc agg ggg ttc ctg atg aga    2517
Gln Leu Ile Thr Arg Thr Gln Ala Ile Cys Arg Gly Phe Leu Met Arg
            790                 795                 800 gtg gag ttc aga aag atg atg gag agg aga gag tcc atc ttc tgc att    2565
Val Glu Phe Arg Lys Met Met Glu Arg Arg Glu Ser Ile Phe Cys Ile
        805                 810                 815 cag tac aac atc cgt gct ttc atg aat gtg aag cac tgg ccc tgg atg    2613
Gln Tyr Asn Ile Arg Ala Phe Met Asn Val Lys His Trp Pro Trp Met
820                 825                 830 aag ctg tat ttc aag atc aag ccc ctc ctc aag agt gca gag aca gag    2661
Lys Leu Tyr Phe Lys Ile Lys Pro Leu Leu Lys Ser Ala Glu Thr Glu
835                 840                 845                 850 aag gag atg gcc aac atg aag gaa gaa ttt gag aaa acc aaa gaa gag    2709
Lys Glu Met Ala Asn Met Lys Glu Glu Phe Glu Lys Thr Lys Glu Glu
            855                 860                 865 ctg gct aag aca gag gca aaa agg aaa gaa cta gaa gaa aag atg gtg    2757
Leu Ala Lys Thr Glu Ala Lys Arg Lys Glu Leu Glu Glu Lys Met Val
        870                 875                 880 acg cta atg caa gag aaa aat gac tta caa ctc caa gtt caa gct gaa    2805
Thr Leu Met Gln Glu Lys Asn Asp Leu Gln Leu Gln Val Gln Ala Glu
            885                 890                 895 gca gat gcc ttg gct gat gca gag gaa aga tgt gat cag ttg att aaa    2853
Ala Asp Ala Leu Ala Asp Ala Glu Glu Arg Cys Asp Gln Leu Ile Lys
900                 905                 910 acc aaa atc caa ctt gag gcc aaa atc aaa gag gta act gaa aga gct    2901
Thr Lys Ile Gln Leu Glu Ala Lys Ile Lys Glu Val Thr Glu Arg Ala
915                 920                 925                 930 gag gat gag gaa gag atc aat gct gag ctg aca gcc aag aag agg aaa    2949
Glu Asp Glu Glu Glu Ile Asn Ala Glu Leu Thr Ala Lys Lys Arg Lys
            935                 940                 945 ctg gag gat gaa tgt tca gag ctc aag aaa gac att gat gac ctt gag    2997
Leu Glu Asp Glu Cys Ser Glu Leu Lys Lys Asp Ile Asp Asp Leu Glu
        950                 955                 960 ctg aca ctg gcc aag gtt gag aag gag aaa cat gcc aca gag aac aag    3045
Leu Thr Leu Ala Lys Val Glu Lys Glu Lys His Ala Thr Glu Asn Lys
            965                 970                 975 gtg aaa aac ctc aca gaa gag atg gca ggt ctg gat gaa acc att gct    3093
Val Lys Asn Leu Thr Glu Glu Met Ala Gly Leu Asp Glu Thr Ile Ala
980                 985                 990 aag ctg acc aag gag aag  aag gct ctc cag gag  gcc cac cag cag      3138
Lys Leu Thr Lys Glu Lys  Lys Ala Leu Gln Glu  Ala His Gln Gln
995                      1000                 1005 acc ctg gat gac ctg cag  atg gag gag gac aaa  gtc aac acc ctg      3183
Thr Leu Asp Asp Leu Gln  Met Glu Glu Asp Lys  Val Asn Thr Leu
1010                     1015                 1020 acc aaa gct aaa acc aag  cta gaa cag caa gtg  gac gat ctt gaa      3228
Thr Lys Ala Lys Thr Lys  Leu Glu Gln Gln Val  Asp Asp Leu Glu
1025                     1030                 1035 gga tct ctg gaa caa gaa  aag aaa ctt tgc atg  gac tta gaa aga      3273
Gly Ser Leu Glu Gln Glu  Lys Lys Leu Cys Met  Asp Leu Glu Arg
1040                     1045                 1050 gcc aag aga aaa ctg gag  ggt gac cta aaa ttg  gcc caa gaa tcc      3318
Ala Lys Arg Lys Leu Glu  Gly Asp Leu Lys Leu  Ala Gln Glu Ser
1055                     1060                 1065 aca atg gat aca gaa aat  gac aaa cag caa ctt  aat gag aaa ctc      3363
Thr Met Asp Thr Glu Asn  Asp Lys Gln Gln Leu  Asn Glu Lys Leu
1070                     1075                 1080 aaa aag aaa gag ttt gaa  atg agc aat ctg caa  ggc aag att gaa      3408
Lys Lys Lys Glu Phe Glu  Met Ser Asn Leu Gln  Gly Lys Ile Glu
1085                     1090                 1095
```

| | | | | | | | | | |
|---|---|---|---|---|---|---|---|---|---|
| gat | gaa | caa | gcc | ctt | gca | atg | cag | cta | caa | aag | aag | atc | aaa | gaa | 3453 |
| Asp | Glu | Gln | Ala | Leu | Ala | Met | Gln | Leu | Gln | Lys | Lys | Ile | Lys | Glu | |
| 1100 | | | | 1105 | | | | | 1110 | | | | | | | tta cag gcc cgc att gag gag ctg gag gag gaa atc gag gca gag    3498
Leu Gln Ala Arg Ile Glu Glu Leu Glu Glu Glu Ile Glu Ala Glu
1115            1120                1125 cgg gcc tcc cgg gcc aaa gca gaa aag cag cgc tct gac ctc tcc    3543
Arg Ala Ser Arg Ala Lys Ala Glu Lys Gln Arg Ser Asp Leu Ser
  1130            1135                1140 cgg gag ctg gag gag atc agt gag agg ctg gaa gaa gcc ggt ggg    3588
Arg Glu Leu Glu Glu Ile Ser Glu Arg Leu Glu Glu Ala Gly Gly
1145            1150                1155 gcc act tca gcc cag att gag ttg aac aag aag cgg gag gct gag    3633
Ala Thr Ser Ala Gln Ile Glu Leu Asn Lys Lys Arg Glu Ala Glu
1160            1165                1170 ttc cag aaa atg cgc agg gac ctg gaa gag tcc acc ctg cag cac    3678
Phe Gln Lys Met Arg Arg Asp Leu Glu Glu Ser Thr Leu Gln His
1175            1180                1185 gaa gcc acg gca gct gct ctt cgg aag aag cac gca gat agt gtg    3723
Glu Ala Thr Ala Ala Ala Leu Arg Lys Lys His Ala Asp Ser Val
1190            1195                1200 gct gag ctt ggg aag cag atc gac agc ctt cag cgg gtc aag cag    3768
Ala Glu Leu Gly Lys Gln Ile Asp Ser Leu Gln Arg Val Lys Gln
1205            1210                1215 aag ctg gag aag gaa aag agt gag ctg aag atg gag atc aat gac    3813
Lys Leu Glu Lys Glu Lys Ser Glu Leu Lys Met Glu Ile Asn Asp
1220            1225                1230 ctt gct agt aac atg gag act gtc tcc aaa gcc aag gca aac ttt    3858
Leu Ala Ser Asn Met Glu Thr Val Ser Lys Ala Lys Ala Asn Phe
1235            1240                1245 gag aaa atg tgc cgc acc cta gag gac cag ctt agt gaa ata aaa    3903
Glu Lys Met Cys Arg Thr Leu Glu Asp Gln Leu Ser Glu Ile Lys
1250            1255                1260 aca aag gaa gaa gag cag caa cgc tta ata aat gag ttg tca gcc    3948
Thr Lys Glu Glu Glu Gln Gln Arg Leu Ile Asn Glu Leu Ser Ala
1265            1270                1275 cag aag gca cgt tta cac aca gaa tca ggt gag ttt tca cga cag    3993
Gln Lys Ala Arg Leu His Thr Glu Ser Gly Glu Phe Ser Arg Gln
1280            1285                1290 cta gat gaa aaa gat gct atg gtt tct cag cta tcc cga ggc aaa    4038
Leu Asp Glu Lys Asp Ala Met Val Ser Gln Leu Ser Arg Gly Lys
1295            1300                1305 caa gca ttt aca caa cag att gaa gaa tta aag agg cag cta gaa    4083
Gln Ala Phe Thr Gln Gln Ile Glu Glu Leu Lys Arg Gln Leu Glu
1310            1315                1320 gag gag act aag gcc aag agc act ctg gcc cat gcc ctg cag tca    4128
Glu Glu Thr Lys Ala Lys Ser Thr Leu Ala His Ala Leu Gln Ser
1325            1330                1335 gcc cgc cat gac tgt gac ctg ctg cgg gaa cag tat gag gag gag    4173
Ala Arg His Asp Cys Asp Leu Leu Arg Glu Gln Tyr Glu Glu Glu
1340            1345                1350 cag gaa gcc aag gct gag ctg cag agg gga atg tcc aag gcc aac    4218
Gln Glu Ala Lys Ala Glu Leu Gln Arg Gly Met Ser Lys Ala Asn
1355            1360                1365 agt gag gtt gcc cag tgg agg acc aag tac gag acg gac gcc atc    4263
Ser Glu Val Ala Gln Trp Arg Thr Lys Tyr Glu Thr Asp Ala Ile
1370            1375                1380 cag cgc aca gag gag ctg gag gag gcc aag aag aag cta gcc cag    4308
Gln Arg Thr Glu Glu Leu Glu Glu Ala Lys Lys Lys Leu Ala Gln -continued

| | | | |
|---|---|---|---|
| | 1385 | 1390 | 1395 |
| cgt ctg cag gat gca gaa gaa cat gta gaa gct gtg aat tcc aaa<br>Arg Leu Gln Asp Ala Glu Glu His Val Glu Ala Val Asn Ser Lys<br>1400                       1405                  1410 | | | 4353 |
| tgt gct tct ctt gaa aag aca aag cag agg cta cag aat gaa gta<br>Cys Ala Ser Leu Glu Lys Thr Lys Gln Arg Leu Gln Asn Glu Val<br>1415                       1420                  1425 | | | 4398 |
| gag gac ctc atg att gat gtg gaa cga tct aat gct gcc tgc ata<br>Glu Asp Leu Met Ile Asp Val Glu Arg Ser Asn Ala Ala Cys Ile<br>1430                       1435                  1440 | | | 4443 |
| gct ctc gat aag aag caa aga aac ttt gac aag gtt ctg gca gaa<br>Ala Leu Asp Lys Lys Gln Arg Asn Phe Asp Lys Val Leu Ala Glu<br>1445                       1450                  1455 | | | 4488 |
| tgg aaa cag aag tat gag gaa act cag gct gaa ctt gag gcc tcc<br>Trp Lys Gln Lys Tyr Glu Glu Thr Gln Ala Glu Leu Glu Ala Ser<br>1460                       1465                  1470 | | | 4533 |
| cag aag gag tcg cgt tct ctc agc act gag ctg ttc aag gtg aag<br>Gln Lys Glu Ser Arg Ser Leu Ser Thr Glu Leu Phe Lys Val Lys<br>1475                       1480                  1485 | | | 4578 |
| aat gcc tac gag gaa tcc ctg gat cat ctt gaa act cta aag cga<br>Asn Ala Tyr Glu Glu Ser Leu Asp His Leu Glu Thr Leu Lys Arg<br>1490                       1495                  1500 | | | 4623 |
| gag aat aag aac tta caa cag gag att tct gac ctg aca gag caa<br>Glu Asn Lys Asn Leu Gln Gln Glu Ile Ser Asp Leu Thr Glu Gln<br>1505                       1510                  1515 | | | 4668 |
| att gca gag ggt gga aag cat atc cat gaa ctg gag aaa gta aag<br>Ile Ala Glu Gly Gly Lys His Ile His Glu Leu Glu Lys Val Lys<br>1520                       1525                  1530 | | | 4713 |
| aaa caa ctt gat cat gag aag agt gaa cta cag act tcc cta gag<br>Lys Gln Leu Asp His Glu Lys Ser Glu Leu Gln Thr Ser Leu Glu<br>1535                       1540                  1545 | | | 4758 |
| gaa gca gag gca tct ctt gag cat gaa gaa ggc aaa att ctt cgc<br>Glu Ala Glu Ala Ser Leu Glu His Glu Glu Gly Lys Ile Leu Arg<br>1550                       1555                  1560 | | | 4803 |
| att caa ctt gag cta aat cag gtg aaa tct gag att gac cga aaa<br>Ile Gln Leu Glu Leu Asn Gln Val Lys Ser Glu Ile Asp Arg Lys<br>1565                       1570                  1575 | | | 4848 |
| att gct gaa aaa gat gaa gaa ctc gat cag cta aag agg aac cat<br>Ile Ala Glu Lys Asp Glu Glu Leu Asp Gln Leu Lys Arg Asn His<br>1580                       1585                  1590 | | | 4893 |
| ctc aga gtt gtg gag tca atg cag agt aca ctg gat gct gag atc<br>Leu Arg Val Val Glu Ser Met Gln Ser Thr Leu Asp Ala Glu Ile<br>1595                       1600                  1605 | | | 4938 |
| agg agc aga aat gat gct ctg agg atc aag aag aag atg gag gga<br>Arg Ser Arg Asn Asp Ala Leu Arg Ile Lys Lys Lys Met Glu Gly<br>1610                       1615                  1620 | | | 4983 |
| gat ctt aat gaa atg gaa atc cag ctg aac cat gcc aac cgc cag<br>Asp Leu Asn Glu Met Glu Ile Gln Leu Asn His Ala Asn Arg Gln<br>1625                       1630                  1635 | | | 5028 |
| gct gct gag gca cta agg aat ctt aga aac aca caa gga ata ctg<br>Ala Ala Glu Ala Leu Arg Asn Leu Arg Asn Thr Gln Gly Ile Leu<br>1640                       1645                  1650 | | | 5073 |
| aag gac act cag cta cat ttg gat gat gcc atc aga ggc caa gat<br>Lys Asp Thr Gln Leu His Leu Asp Asp Ala Ile Arg Gly Gln Asp<br>1655                       1660                  1665 | | | 5118 |
| gac ctt aag gaa caa ttg gca atg gtt gag cgc aga gct aac ctg<br>Asp Leu Lys Glu Gln Leu Ala Met Val Glu Arg Arg Ala Asn Leu<br>1670                       1675                  1680 | | | 5163 |
| atg cag gct gaa gtt gaa gag ctc agg gca tcc ctg gaa cgg act | | | 5208 |

|   |   |   |   |   |   |   |   |   |   |   |   |   |   |   |
|---|---|---|---|---|---|---|---|---|---|---|---|---|---|---|
|   | Met | Gln | Ala | Glu | Val | Glu | Leu | Arg | Ala | Ser | Leu | Glu | Arg | Thr |
|   | 1685 |   |   |   | 1690 |   |   |   |   | 1695 |   |   |   |   |

| gag | aga | ggc | agg | aaa | atg | gca | gag | caa | gag | ctt | ctg | gat | gcc | agt | 5253 |
|---|---|---|---|---|---|---|---|---|---|---|---|---|---|---|---|
| Glu | Arg | Gly | Arg | Lys | Met | Ala | Glu | Gln | Glu | Leu | Leu | Asp | Ala | Ser |   |
| 1700 |   |   |   |   | 1705 |   |   |   |   | 1710 |   |   |   |   |   |

| gaa | cgt | gtg | caa | ctt | ctg | cac | act | cag | aac | acc | agc | ctg | atc | aac | 5298 |
|---|---|---|---|---|---|---|---|---|---|---|---|---|---|---|---|
| Glu | Arg | Val | Gln | Leu | Leu | His | Thr | Gln | Asn | Thr | Ser | Leu | Ile | Asn |   |
| 1715 |   |   |   |   | 1720 |   |   |   |   | 1725 |   |   |   |   |   |

| acc | aag | aag | aag | ctg | gaa | aca | gac | att | tcc | caa | atc | cag | gga | gag | 5343 |
|---|---|---|---|---|---|---|---|---|---|---|---|---|---|---|---|
| Thr | Lys | Lys | Lys | Leu | Glu | Thr | Asp | Ile | Ser | Gln | Ile | Gln | Gly | Glu |   |
| 1730 |   |   |   |   | 1735 |   |   |   |   | 1740 |   |   |   |   |   |

| atg | gag | gac | atc | gtc | cag | gaa | gcc | cgc | aat | gca | gag | gag | aag | gcc | 5388 |
|---|---|---|---|---|---|---|---|---|---|---|---|---|---|---|---|
| Met | Glu | Asp | Ile | Val | Gln | Glu | Ala | Arg | Asn | Ala | Glu | Glu | Lys | Ala |   |
| 1745 |   |   |   |   | 1750 |   |   |   |   | 1755 |   |   |   |   |   |

| aag | aag | gcc | atc | act | gat | gct | gcc | atg | atg | gct | gag | gag | ctg | aag | 5433 |
|---|---|---|---|---|---|---|---|---|---|---|---|---|---|---|---|
| Lys | Lys | Ala | Ile | Thr | Asp | Ala | Ala | Met | Met | Ala | Glu | Glu | Leu | Lys |   |
| 1760 |   |   |   |   | 1765 |   |   |   |   | 1770 |   |   |   |   |   |

| aag | gaa | cag | gac | acc | agc | gcc | cac | ctg | gag | cgg | atg | aag | aag | aac | 5478 |
|---|---|---|---|---|---|---|---|---|---|---|---|---|---|---|---|
| Lys | Glu | Gln | Asp | Thr | Ser | Ala | His | Leu | Glu | Arg | Met | Lys | Lys | Asn |   |
| 1775 |   |   |   |   | 1780 |   |   |   |   | 1785 |   |   |   |   |   |

| atg | gag | cag | acc | gtg | aag | gat | ctg | cag | ctc | cgt | ctg | ggt | gag | gct | 5523 |
|---|---|---|---|---|---|---|---|---|---|---|---|---|---|---|---|
| Met | Glu | Gln | Thr | Val | Lys | Asp | Leu | Gln | Leu | Arg | Leu | Gly | Glu | Ala |   |
| 1790 |   |   |   |   | 1795 |   |   |   |   | 1800 |   |   |   |   |   |

| gag | cag | ctg | gcg | ctg | aag | ggt | ggg | aag | aag | cag | atc | cag | aaa | ctg | 5568 |
|---|---|---|---|---|---|---|---|---|---|---|---|---|---|---|---|
| Glu | Gln | Leu | Ala | Leu | Lys | Gly | Gly | Lys | Lys | Gln | Ile | Gln | Lys | Leu |   |
| 1805 |   |   |   |   | 1810 |   |   |   |   | 1815 |   |   |   |   |   |

| gag | gcc | agg | gtg | aga | gag | ctt | gaa | agt | gag | gtg | gaa | agt | gaa | cag | 5613 |
|---|---|---|---|---|---|---|---|---|---|---|---|---|---|---|---|
| Glu | Ala | Arg | Val | Arg | Glu | Leu | Glu | Ser | Glu | Val | Glu | Ser | Glu | Gln |   |
| 1820 |   |   |   |   | 1825 |   |   |   |   | 1830 |   |   |   |   |   |

| aag | cac | aat | gtt | gag | gct | gtc | aag | ggt | ctt | cgc | aaa | cat | gag | aga | 5658 |
|---|---|---|---|---|---|---|---|---|---|---|---|---|---|---|---|
| Lys | His | Asn | Val | Glu | Ala | Val | Lys | Gly | Leu | Arg | Lys | His | Glu | Arg |   |
| 1835 |   |   |   |   | 1840 |   |   |   |   | 1845 |   |   |   |   |   |

| aga | gtg | aag | gaa | ctc | act | tac | cag | act | gag | gag | gac | cgc | aag | aat | 5703 |
|---|---|---|---|---|---|---|---|---|---|---|---|---|---|---|---|
| Arg | Val | Lys | Glu | Leu | Thr | Tyr | Gln | Thr | Glu | Glu | Asp | Arg | Lys | Asn |   |
| 1850 |   |   |   |   | 1855 |   |   |   |   | 1860 |   |   |   |   |   |

| att | ctc | agg | ctg | cag | gac | ttg | gtg | gac | aaa | ttg | caa | acc | aaa | gtc | 5748 |
|---|---|---|---|---|---|---|---|---|---|---|---|---|---|---|---|
| Ile | Leu | Arg | Leu | Gln | Asp | Leu | Val | Asp | Lys | Leu | Gln | Thr | Lys | Val |   |
| 1865 |   |   |   |   | 1870 |   |   |   |   | 1875 |   |   |   |   |   |

| aaa | gct | tac | aag | aga | caa | gct | gaa | gag | gct | gag | gaa | caa | tcc | aat | 5793 |
|---|---|---|---|---|---|---|---|---|---|---|---|---|---|---|---|
| Lys | Ala | Tyr | Lys | Arg | Gln | Ala | Glu | Glu | Ala | Glu | Glu | Gln | Ser | Asn |   |
| 1880 |   |   |   |   | 1885 |   |   |   |   | 1890 |   |   |   |   |   |

| gtc | aac | ctt | gcc | aag | ttc | cgc | aag | ctc | cag | cac | gag | ctg | gag | gag | 5838 |
|---|---|---|---|---|---|---|---|---|---|---|---|---|---|---|---|
| Val | Asn | Leu | Ala | Lys | Phe | Arg | Lys | Leu | Gln | His | Glu | Leu | Glu | Glu |   |
| 1895 |   |   |   |   | 1900 |   |   |   |   | 1905 |   |   |   |   |   |

| gcc | gag | gaa | cgg | gct | gac | att | gct | gag | tcc | caa | gtc | aac | aag | ctg | 5883 |
|---|---|---|---|---|---|---|---|---|---|---|---|---|---|---|---|
| Ala | Glu | Glu | Arg | Ala | Asp | Ile | Ala | Glu | Ser | Gln | Val | Asn | Lys | Leu |   |
| 1910 |   |   |   |   | 1915 |   |   |   |   | 1920 |   |   |   |   |   |

| aga | gtg | aag | agt | cgg | gag | gtt | cac | aca | aaa | gtc | ata | agt | gaa | gag | 5928 |
|---|---|---|---|---|---|---|---|---|---|---|---|---|---|---|---|
| Arg | Val | Lys | Ser | Arg | Glu | Val | His | Thr | Lys | Val | Ile | Ser | Glu | Glu |   |
| 1925 |   |   |   |   | 1930 |   |   |   |   | 1935 |   |   |   |   |   |

| taa ttcattctaa tgaaagaaaa tgtgaccaaa gaaatgcacg aaatgtgaag | 5981 |
|---|---|

| ttctttgtca ctgtcctgta tatcaaggaa ataaa | 6016 |
|---|---|

<210> SEQ ID NO 4
<211> LENGTH: 1939
<212> TYPE: PRT
<213> ORGANISM: Homo sapiens

<400> SEQUENCE: 4

```
Met Ser Ser Asp Ser Glu Met Ala Ile Phe Gly Glu Ala Ala Pro Phe
1               5                   10                  15

Leu Arg Lys Ser Glu Lys Glu Arg Ile Glu Ala Gln Asn Lys Pro Phe
            20                  25                  30

Asp Ala Lys Thr Ser Val Phe Val Asp Pro Lys Glu Ser Tyr Val
        35                  40                  45

Lys Ala Ile Val Gln Ser Arg Glu Gly Gly Lys Val Thr Ala Lys Thr
    50                  55                  60

Glu Ala Gly Ala Thr Val Thr Val Lys Glu Asp Gln Val Phe Ser Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
                100                 105                 110

Trp Met Ile Tyr Thr Tyr Ser Gly Leu Phe Cys Val Thr Val Asn Pro
                115                 120                 125

Tyr Lys Trp Leu Pro Val Tyr Asn Pro Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
                180                 185                 190

Ile Gln Tyr Phe Ala Thr Ile Ala Val Thr Gly Glu Lys Lys Lys Glu
                195                 200                 205

Glu Pro Ala Ser Gly Lys Met Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Ala Thr Gly Lys Leu Ala Ser Ala Asp Ile Glu Thr Tyr Leu Leu Glu
                260                 265                 270

Lys Ser Arg Val Thr Phe Gln Leu Lys Ala Glu Arg Ser Tyr His Ile
                275                 280                 285

Phe Tyr Gln Ile Leu Ser Asn Lys Lys Pro Glu Leu Ile Glu Met Leu
    290                 295                 300

Leu Ile Thr Thr Asn Pro Tyr Asp Phe Ala Phe Val Ser Gln Gly Glu
305                 310                 315                 320

Ile Thr Val Pro Ser Ile Asp Asp Gln Glu Glu Leu Met Ala Thr Asp
                325                 330                 335

Ser Ala Val Asp Ile Leu Gly Phe Thr Ala Asp Glu Lys Val Ala Ile
                340                 345                 350

Tyr Lys Leu Thr Gly Ala Val Met His Tyr Gly Asn Met Lys Phe Lys
    355                 360                 365

Gln Lys Gln Arg Glu Glu Gln Ala Glu Pro Asp Gly Thr Glu Val Ala
    370                 375                 380

Asp Lys Ala Ala Tyr Leu Thr Ser Leu Asn Ser Ala Asp Leu Leu Lys
385                 390                 395                 400

Ser Leu Cys Tyr Pro Arg Val Lys Val Gly Asn Glu Phe Val Thr Lys
                405                 410                 415

Gly Gln Thr Val Gln Gln Val Tyr Asn Ala Val Gly Ala Leu Ala Lys
```

```
                420             425             430
Ala Ile Tyr Glu Lys Met Phe Leu Trp Met Val Thr Arg Ile Asn Gln
            435             440             445

Gln Leu Asp Thr Lys Gln Pro Arg Gln Tyr Phe Ile Gly Val Leu Asp
            450             455             460

Ile Ala Gly Phe Glu Ile Phe Asp Phe Asn Ser Leu Glu Gln Leu Cys
465             470             475             480

Ile Asn Phe Thr Asn Glu Lys Leu Gln Gln Phe Phe Asn His His Met
            485             490             495

Phe Val Leu Glu Gln Glu Glu Tyr Lys Lys Glu Gly Ile Glu Trp Glu
            500             505             510

Phe Ile Asp Phe Gly Met Asp Leu Ala Ala Cys Ile Glu Leu Ile Glu
            515             520             525

Lys Pro Met Gly Ile Phe Ser Ile Leu Glu Glu Glu Cys Met Phe Pro
            530             535             540

Lys Ala Thr Asp Thr Ser Phe Lys Asn Lys Leu Tyr Glu Gln His Leu
545             550             555             560

Gly Lys Ser Asn Asn Phe Gln Lys Pro Lys Pro Ala Lys Gly Lys Pro
                565             570             575

Glu Ala His Phe Ser Leu Val His Tyr Ala Gly Thr Val Asp Tyr Asn
            580             585             590

Ile Ala Gly Trp Leu Asp Lys Asn Lys Asp Pro Leu Asn Glu Thr Val
595             600             605

Val Gly Leu Tyr Gln Lys Ser Ala Met Lys Thr Leu Ala Phe Leu Phe
            610             615             620

Ser Gly Ala Gln Thr Ala Glu Ala Glu Gly Gly Gly Lys Lys Gly
625             630             635             640

Gly Lys Lys Lys Gly Ser Ser Phe Gln Thr Val Ser Ala Leu Phe Arg
                645             650             655

Glu Asn Leu Asn Lys Leu Met Thr Asn Leu Arg Ser Thr His Pro His
            660             665             670

Phe Val Arg Cys Ile Ile Pro Asn Glu Thr Lys Thr Pro Gly Ala Met
            675             680             685

Glu His Glu Leu Val Leu His Gln Leu Arg Cys Asn Gly Val Leu Glu
            690             695             700

Gly Ile Arg Ile Cys Arg Lys Gly Phe Pro Ser Arg Ile Leu Tyr Ala
705             710             715             720

Asp Phe Lys Gln Arg Tyr Lys Val Leu Asn Ala Ser Ala Ile Pro Glu
            725             730             735

Gly Gln Phe Ile Asp Ser Lys Lys Ala Ser Glu Lys Leu Leu Gly Ser
            740             745             750

Ile Glu Ile Asp His Thr Gln Tyr Lys Phe Gly His Thr Lys Val Phe
            755             760             765

Phe Lys Ala Gly Leu Leu Gly Thr Leu Glu Glu Met Arg Asp Glu Lys
            770             775             780

Leu Ala Gln Leu Ile Thr Arg Thr Gln Ala Ile Cys Arg Gly Phe Leu
785             790             795             800

Met Arg Val Glu Phe Arg Lys Met Met Glu Arg Arg Glu Ser Ile Phe
            805             810             815

Cys Ile Gln Tyr Asn Ile Arg Ala Phe Met Asn Val Lys His Trp Pro
            820             825             830

Trp Met Lys Leu Tyr Phe Lys Ile Lys Pro Leu Leu Lys Ser Ala Glu
            835             840             845
```

```
Thr Glu Lys Glu Met Ala Asn Met Lys Glu Glu Phe Glu Lys Thr Lys
    850                 855                 860

Glu Glu Leu Ala Lys Thr Glu Ala Lys Arg Lys Glu Leu Glu Glu Lys
865                 870                 875                 880

Met Val Thr Leu Met Gln Glu Lys Asn Asp Leu Gln Leu Gln Val Gln
                885                 890                 895

Ala Glu Ala Asp Ala Leu Ala Asp Ala Glu Glu Arg Cys Asp Gln Leu
            900                 905                 910

Ile Lys Thr Lys Ile Gln Leu Glu Ala Lys Ile Lys Glu Val Thr Glu
        915                 920                 925

Arg Ala Glu Asp Glu Glu Glu Ile Asn Ala Glu Leu Thr Ala Lys Lys
    930                 935                 940

Arg Lys Leu Glu Asp Glu Cys Ser Leu Lys Lys Asp Ile Asp Asp
945                 950                 955                 960

Leu Glu Leu Thr Leu Ala Lys Val Glu Lys Glu Lys His Ala Thr Glu
                965                 970                 975

Asn Lys Val Lys Asn Leu Thr Glu Glu Met Ala Gly Leu Asp Glu Thr
            980                 985                 990

Ile Ala Lys Leu Thr Lys Glu Lys  Lys Ala Leu Gln Glu  Ala His Gln
        995                 1000                1005

Gln Thr  Leu Asp Asp Leu Gln  Met Glu Glu Asp Lys  Val Asn Thr
    1010                1015                1020

Leu Thr  Lys Ala Lys Thr Lys  Leu Glu Gln Gln Val  Asp Asp Leu
    1025                1030                1035

Glu Gly  Ser Leu Glu Gln Glu  Lys Lys Leu Cys Met  Asp Leu Glu
    1040                1045                1050

Arg Ala  Lys Arg Lys Leu Glu  Gly Asp Leu Lys Leu  Ala Gln Glu
    1055                1060                1065

Ser Thr  Met Asp Thr Glu Asn  Asp Lys Gln Gln Leu  Asn Glu Lys
    1070                1075                1080

Leu Lys  Lys Lys Glu Phe Glu  Met Ser Asn Leu Gln  Gly Lys Ile
    1085                1090                1095

Glu Asp  Glu Gln Ala Leu Ala  Met Gln Leu Gln Lys  Lys Ile Lys
    1100                1105                1110

Glu Leu  Gln Ala Arg Ile Glu  Glu Leu Glu Glu Glu  Ile Glu Ala
    1115                1120                1125

Glu Arg  Ala Ser Arg Ala Lys  Ala Glu Lys Gln Arg  Ser Asp Leu
    1130                1135                1140

Ser Arg  Glu Leu Glu Glu Ile  Ser Glu Arg Leu Glu  Glu Ala Gly
    1145                1150                1155

Gly Ala  Thr Ser Ala Gln Ile  Glu Leu Asn Lys Lys  Arg Glu Ala
    1160                1165                1170

Glu Phe  Gln Lys Met Arg Arg  Asp Leu Glu Glu Ser  Thr Leu Gln
    1175                1180                1185

His Glu  Ala Thr Ala Ala Ala  Leu Arg Lys Lys His  Ala Asp Ser
    1190                1195                1200

Val Ala  Glu Leu Gly Lys Gln  Ile Asp Ser Leu Gln  Arg Val Lys
    1205                1210                1215

Gln Lys  Leu Glu Lys Glu Lys  Ser Glu Leu Lys Met  Glu Ile Asn
    1220                1225                1230

Asp Leu  Ala Ser Asn Met Glu  Thr Val Ser Lys Ala  Lys Ala Asn
    1235                1240                1245
```

```
Phe Glu Lys Met Cys Arg Thr Leu Glu Asp Gln Leu Ser Glu Ile
1250                1255                1260

Lys Thr Lys Glu Glu Glu Gln Gln Arg Leu Ile Asn Glu Leu Ser
1265                1270                1275

Ala Gln Lys Ala Arg Leu His Thr Glu Ser Gly Glu Phe Ser Arg
1280                1285                1290

Gln Leu Asp Glu Lys Asp Ala Met Val Ser Gln Leu Ser Arg Gly
1295                1300                1305

Lys Gln Ala Phe Thr Gln Gln Ile Glu Glu Leu Lys Arg Gln Leu
1310                1315                1320

Glu Glu Glu Thr Lys Ala Lys Ser Thr Leu Ala His Ala Leu Gln
1325                1330                1335

Ser Ala Arg His Asp Cys Asp Leu Leu Arg Glu Gln Tyr Glu Glu
1340                1345                1350

Glu Gln Glu Ala Lys Ala Glu Leu Gln Arg Gly Met Ser Lys Ala
1355                1360                1365

Asn Ser Glu Val Ala Gln Trp Arg Thr Lys Tyr Glu Thr Asp Ala
1370                1375                1380

Ile Gln Arg Thr Glu Glu Leu Glu Glu Ala Lys Lys Lys Leu Ala
1385                1390                1395

Gln Arg Leu Gln Asp Ala Glu Glu His Val Glu Ala Val Asn Ser
1400                1405                1410

Lys Cys Ala Ser Leu Glu Lys Thr Lys Gln Arg Leu Gln Asn Glu
1415                1420                1425

Val Glu Asp Leu Met Ile Asp Val Glu Arg Ser Asn Ala Ala Cys
1430                1435                1440

Ile Ala Leu Asp Lys Lys Gln Arg Asn Phe Asp Lys Val Leu Ala
1445                1450                1455

Glu Trp Lys Gln Lys Tyr Glu Glu Thr Gln Ala Glu Leu Glu Ala
1460                1465                1470

Ser Gln Lys Glu Ser Arg Ser Leu Ser Thr Glu Leu Phe Lys Val
1475                1480                1485

Lys Asn Ala Tyr Glu Glu Ser Leu Asp His Leu Glu Thr Leu Lys
1490                1495                1500

Arg Glu Asn Lys Asn Leu Gln Gln Glu Ile Ser Asp Leu Thr Glu
1505                1510                1515

Gln Ile Ala Glu Gly Gly Lys His Ile His Glu Leu Glu Lys Val
1520                1525                1530

Lys Lys Gln Leu Asp His Glu Lys Ser Glu Leu Gln Thr Ser Leu
1535                1540                1545

Glu Glu Ala Glu Ala Ser Leu Glu His Glu Glu Gly Lys Ile Leu
1550                1555                1560

Arg Ile Gln Leu Glu Leu Asn Gln Val Lys Ser Glu Ile Asp Arg
1565                1570                1575

Lys Ile Ala Glu Lys Asp Glu Glu Leu Asp Gln Leu Lys Arg Asn
1580                1585                1590

His Leu Arg Val Val Glu Ser Met Gln Ser Thr Leu Asp Ala Glu
1595                1600                1605

Ile Arg Ser Arg Asn Asp Ala Leu Arg Ile Lys Lys Lys Met Glu
1610                1615                1620

Gly Asp Leu Asn Glu Met Glu Ile Gln Leu Asn His Ala Asn Arg
1625                1630                1635

Gln Ala Ala Glu Ala Leu Arg Asn Leu Arg Asn Thr Gln Gly Ile
```

|  |  | 1640 |  |  |  | 1645 |  |  |  | 1650 |  |
| --- | --- | --- | --- | --- | --- | --- | --- | --- | --- | --- | --- |

Leu Lys Asp Thr Gln Leu His Leu Asp Asp Ala Ile Arg Gly Gln
     1655               1660               1665

Asp Asp Leu Lys Glu Gln Leu Ala Met Val Glu Arg Arg Ala Asn
     1670               1675               1680

Leu Met Gln Ala Glu Val Glu Glu Leu Arg Ala Ser Leu Glu Arg
     1685               1690               1695

Thr Glu Arg Gly Arg Lys Met Ala Glu Gln Leu Leu Asp Ala
     1700               1705               1710

Ser Glu Arg Val Gln Leu Leu His Thr Gln Asn Thr Ser Leu Ile
     1715               1720               1725

Asn Thr Lys Lys Lys Leu Glu Thr Asp Ile Ser Gln Ile Gln Gly
     1730               1735               1740

Glu Met Glu Asp Ile Val Gln Glu Ala Arg Asn Ala Glu Glu Lys
     1745               1750               1755

Ala Lys Lys Ala Ile Thr Asp Ala Ala Met Met Ala Glu Glu Leu
     1760               1765               1770

Lys Lys Glu Gln Asp Thr Ser Ala His Leu Glu Arg Met Lys Lys
     1775               1780               1785

Asn Met Glu Gln Thr Val Lys Asp Leu Gln Leu Arg Leu Gly Glu
     1790               1795               1800

Ala Glu Gln Leu Ala Leu Lys Gly Gly Lys Lys Gln Ile Gln Lys
     1805               1810               1815

Leu Glu Ala Arg Val Arg Glu Leu Glu Ser Glu Val Glu Ser Glu
     1820               1825               1830

Gln Lys His Asn Val Glu Ala Val Lys Gly Leu Arg Lys His Glu
     1835               1840               1845

Arg Arg Val Lys Glu Leu Thr Tyr Gln Thr Glu Glu Asp Arg Lys
     1850               1855               1860

Asn Ile Leu Arg Leu Gln Asp Leu Val Asp Lys Leu Gln Thr Lys
     1865               1870               1875

Val Lys Ala Tyr Lys Arg Gln Ala Glu Glu Ala Glu Glu Gln Ser
     1880               1885               1890

Asn Val Asn Leu Ala Lys Phe Arg Lys Leu Gln His Glu Leu Glu
     1895               1900               1905

Glu Ala Glu Glu Arg Ala Asp Ile Ala Glu Ser Gln Val Asn Lys
     1910               1915               1920

Leu Arg Val Lys Ser Arg Glu Val His Thr Lys Val Ile Ser Glu
     1925               1930               1935

Glu

```
<210> SEQ ID NO 5
<211> LENGTH: 5925
<212> TYPE: DNA
<213> ORGANISM: Homo sapiens
<220> FEATURE:
<221> NAME/KEY: CDS
<222> LOCATION: (1)..(5820)

<400> SEQUENCE: 5
```

| atg agt tct gac tct gag atg gcc att ttt ggg gag gct gct cct ttc | 48 |
| --- | --- |
| Met Ser Ser Asp Ser Glu Met Ala Ile Phe Gly Glu Ala Ala Pro Phe | |
| 1               5                    10                   15 | |
| | |
| ctc cga aag tct gaa agg gag cga att gaa gcc cag aac aag cct ttt | 96 |
| Leu Arg Lys Ser Glu Arg Glu Arg Ile Glu Ala Gln Asn Lys Pro Phe | |
|                20                    25                   30 | |

```
gat gcc aag aca tca gtc ttt gtg gtg gac cct aag gag tcc ttt gtg     144
Asp Ala Lys Thr Ser Val Phe Val Val Asp Pro Lys Glu Ser Phe Val
        35                  40                  45 aaa gca aca gtg cag agc agg gaa ggg ggg aag gtg aca gct aag acc     192
Lys Ala Thr Val Gln Ser Arg Glu Gly Gly Lys Val Thr Ala Lys Thr
 50                  55                  60 gaa gct gga gct act gta aca gtg aaa gat gac caa gtc ttc ccc atg     240
Glu Ala Gly Ala Thr Val Thr Val Lys Asp Asp Gln Val Phe Pro Met
 65                  70                  75                  80 aac cct ccc aaa tat gac aag atc gag gac atg gcc atg atg act cat     288
Asn Pro Pro Lys Tyr Asp Lys Ile Glu Asp Met Ala Met Met Thr His
                 85                  90                  95 cta cac gag cct gct gtg ctg tac aac ctc aaa gag cgc tac gca gcc     336
Leu His Glu Pro Ala Val Leu Tyr Asn Leu Lys Glu Arg Tyr Ala Ala
            100                 105                 110 tgg atg atc tac acc tac tca ggc ttg ttc tgt gtc act gtc aac ccc     384
Trp Met Ile Tyr Thr Tyr Ser Gly Leu Phe Cys Val Thr Val Asn Pro
        115                 120                 125 tac aag tgg ttg cca gtg tat aat gca gaa gtg gtg aca gcc tac cga     432
Tyr Lys Trp Leu Pro Val Tyr Asn Ala Glu Val Val Thr Ala Tyr Arg
130                 135                 140 ggc aaa aag cgc cag gaa gcc cca ccc cac atc ttc tcc atc tct gac     480
Gly Lys Lys Arg Gln Glu Ala Pro Pro His Ile Phe Ser Ile Ser Asp
145                 150                 155                 160 aat gcc tat cag ttc atg ctg act gat cgg gag aat cag tct atc ttg     528
Asn Ala Tyr Gln Phe Met Leu Thr Asp Arg Glu Asn Gln Ser Ile Leu
                165                 170                 175 atc acc gga gaa tct ggc gca ggg aag act gtg aac acc aag cgt gtc     576
Ile Thr Gly Glu Ser Gly Ala Gly Lys Thr Val Asn Thr Lys Arg Val
            180                 185                 190 atc cag tac ttt gca aca att gca gtt act ggg gag aag aag aag gaa     624
Ile Gln Tyr Phe Ala Thr Ile Ala Val Thr Gly Glu Lys Lys Lys Glu
        195                 200                 205 gaa gtt act tct ggc aaa atg cag ggg act ctg gaa gat caa atc atc     672
Glu Val Thr Ser Gly Lys Met Gln Gly Thr Leu Glu Asp Gln Ile Ile
210                 215                 220 agt gcc aac ccc cta ctg gag gcc ttt ggc aac gcc aag acc gtg agg     720
Ser Ala Asn Pro Leu Leu Glu Ala Phe Gly Asn Ala Lys Thr Val Arg
225                 230                 235                 240 aat gac aac tcc tct cgc ttt ggt aaa ttc atc agg atc cac ttc ggt     768
Asn Asp Asn Ser Ser Arg Phe Gly Lys Phe Ile Arg Ile His Phe Gly
                245                 250                 255 acc aca ggg aaa ctg gct tct gct gat att gaa aca tat ctt ctg gag     816
Thr Thr Gly Lys Leu Ala Ser Ala Asp Ile Glu Thr Tyr Leu Leu Glu
            260                 265                 270 aag tct aga gtt act ttc cag cta aag gct gaa aga agc tat cat att     864
Lys Ser Arg Val Thr Phe Gln Leu Lys Ala Glu Arg Ser Tyr His Ile
        275                 280                 285 ttt tat cag atc atg tct aac aag aag cca gat cta att gaa atg ctc     912
Phe Tyr Gln Ile Met Ser Asn Lys Lys Pro Asp Leu Ile Glu Met Leu
290                 295                 300 ctg atc acc acc aac cca tac gat tat gcc ttc gtc agt caa ggg gag     960
Leu Ile Thr Thr Asn Pro Tyr Asp Tyr Ala Phe Val Ser Gln Gly Glu
305                 310                 315                 320 atc aca gtg ccc agc att gat gac caa gaa gag ttg atg gct aca gat    1008
Ile Thr Val Pro Ser Ile Asp Asp Gln Glu Glu Leu Met Ala Thr Asp
                325                 330                 335 agt gcc att gaa att ctg ggc ttt act tca gat gaa aga gtg tcc atc    1056
Ser Ala Ile Glu Ile Leu Gly Phe Thr Ser Asp Glu Arg Val Ser Ile
```

```
                340                    345                    350
tat aag ctc aca ggg gct gtg atg cat tat ggg aac atg aaa ttc aag      1104
Tyr Lys Leu Thr Gly Ala Val Met His Tyr Gly Asn Met Lys Phe Lys
            355                    360                    365 caa aag cag cgt gag gag caa gct gag cca gat ggc act gaa gtt gct      1152
Gln Lys Gln Arg Glu Glu Gln Ala Glu Pro Asp Gly Thr Glu Val Ala
        370                    375                    380 gac aag gca gcc tat ctc caa aat ctg aac tct gca gat ctg ctc aaa      1200
Asp Lys Ala Ala Tyr Leu Gln Asn Leu Asn Ser Ala Asp Leu Leu Lys
385                    390                    395                    400 gcc ctc tgc tac cct agg gtc aag gtc ggc aat gag tat gtc acc aaa      1248
Ala Leu Cys Tyr Pro Arg Val Lys Val Gly Asn Glu Tyr Val Thr Lys
                405                    410                    415 ggt caa act gtg cag cag gtg tac aat gca gtg ggt gct ctg gcc aaa      1296
Gly Gln Thr Val Gln Gln Val Tyr Asn Ala Val Gly Ala Leu Ala Lys
            420                    425                    430 gct gtc tac gat aag atg ttc ttg tgg atg gtc acc cgc atc aac cag      1344
Ala Val Tyr Asp Lys Met Phe Leu Trp Met Val Thr Arg Ile Asn Gln
        435                    440                    445 cag ctg gac acc aag cag ccc agg cag tac ttc att ggg gtc ttg gac      1392
Gln Leu Asp Thr Lys Gln Pro Arg Gln Tyr Phe Ile Gly Val Leu Asp
450                    455                    460 att gct ggc ttt gag atc ttt gat ttc aac agc ctg gag cag ctg tgc      1440
Ile Ala Gly Phe Glu Ile Phe Asp Phe Asn Ser Leu Glu Gln Leu Cys
465                    470                    475                    480 atc aac ttc acc aat gag aaa ctg caa cag ttt ttc aac cac cac atg      1488
Ile Asn Phe Thr Asn Glu Lys Leu Gln Gln Phe Phe Asn His His Met
                485                    490                    495 ttc gtg ctg gag cag gag gag tac aag aag gaa ggc att gag tgg acg      1536
Phe Val Leu Glu Gln Glu Glu Tyr Lys Lys Glu Gly Ile Glu Trp Thr
            500                    505                    510 ttc att gac ttt ggg atg gac ctg gct gcc tgc atc gag ctc atc gag      1584
Phe Ile Asp Phe Gly Met Asp Leu Ala Ala Cys Ile Glu Leu Ile Glu
        515                    520                    525 aag cct atg ggc atc ttc tcc atc ctg gaa gag gag tgc atg ttc ccc      1632
Lys Pro Met Gly Ile Phe Ser Ile Leu Glu Glu Glu Cys Met Phe Pro
530                    535                    540 aag gcg aca gac acc tcc ttc aag aac aag ctg tat gaa caa cat ctt      1680
Lys Ala Thr Asp Thr Ser Phe Lys Asn Lys Leu Tyr Glu Gln His Leu
545                    550                    555                    560 gga aaa tcc aat aac ttc cag aag ccc aag cct gcc aaa ggc aag cct      1728
Gly Lys Ser Asn Asn Phe Gln Lys Pro Lys Pro Ala Lys Gly Lys Pro
                565                    570                    575 gag gcc cac ttc tct ttg att cac tat gct ggc acc gtg gac tac aac      1776
Glu Ala His Phe Ser Leu Ile His Tyr Ala Gly Thr Val Asp Tyr Asn
            580                    585                    590 att gcc ggc tgg ctt gac aag aac aag gac ccc ctg aat gag act gtg      1824
Ile Ala Gly Trp Leu Asp Lys Asn Lys Asp Pro Leu Asn Glu Thr Val
        595                    600                    605 gtg ggg ctg tac cag aag tct gca atg aag act ctg gct ctc ctc ttt      1872
Val Gly Leu Tyr Gln Lys Ser Ala Met Lys Thr Leu Ala Leu Leu Phe
610                    615                    620 gtt ggg gca acg gga gcg gaa gca gag gct ggc ggt gga aag aaa ggt      1920
Val Gly Ala Thr Gly Ala Glu Ala Glu Ala Gly Gly Gly Lys Lys Gly
625                    630                    635                    640 ggt aag aag aag ggt tct tct ttc cag act gtg tcg gct ctc ttc agg      1968
Gly Lys Lys Lys Gly Ser Ser Phe Gln Thr Val Ser Ala Leu Phe Arg
                645                    650                    655 gag aat ttg aat aag ctg atg acc aac ttg agg agc act cac ccc cac      2016
```

```
                Glu Asn Leu Asn Lys Leu Met Thr Asn Leu Arg Ser Thr His Pro His
                                660                 665                 670 ttt gtg cgg tgc atc atc ccc aat gaa act aaa act cct ggt gcc atg        2064
Phe Val Arg Cys Ile Ile Pro Asn Glu Thr Lys Thr Pro Gly Ala Met
            675                 680                 685 gag cat gag ctt gtc ctg cat cag ctg agg tgt aac ggt gtg ctg gaa        2112
Glu His Glu Leu Val Leu His Gln Leu Arg Cys Asn Gly Val Leu Glu
690                 695                 700 ggc atc cgc atc tgc agg aaa ggc ttc cca agc aga atc ctt tat gca        2160
Gly Ile Arg Ile Cys Arg Lys Gly Phe Pro Ser Arg Ile Leu Tyr Ala
705                 710                 715                 720 gac ttc aaa cag aga tac aag gtg tta aat gca agt gct atc cct gaa        2208
Asp Phe Lys Gln Arg Tyr Lys Val Leu Asn Ala Ser Ala Ile Pro Glu
                725                 730                 735 gga caa ttc atc gat agc aag aag gct tca gag aag ctc ctg ggg tcc        2256
Gly Gln Phe Ile Asp Ser Lys Lys Ala Ser Glu Lys Leu Leu Gly Ser
            740                 745                 750 att gac att gac cac acc cag tat aaa ttt ggt cac acc aag gtc ttt        2304
Ile Asp Ile Asp His Thr Gln Tyr Lys Phe Gly His Thr Lys Val Phe
755                 760                 765 ttc aaa gct ggt ctt ctg ggg ctc cta gag gag atg cga gat gag aag        2352
Phe Lys Ala Gly Leu Leu Gly Leu Leu Glu Glu Met Arg Asp Glu Lys
770                 775                 780 ctg gcc cag ctg att acc cga acc cag gcc atg tgc aga ggg ttc ttg        2400
Leu Ala Gln Leu Ile Thr Arg Thr Gln Ala Met Cys Arg Gly Phe Leu
785                 790                 795                 800 gca aga gtg gag tac cag aaa atg gtg gaa aga aga gag tcc atc ttc        2448
Ala Arg Val Glu Tyr Gln Lys Met Val Glu Arg Arg Glu Ser Ile Phe
                805                 810                 815 tgc atc cag tac aat gtc cgt gcc ttc atg aat gtc aag cac tgg ccc        2496
Cys Ile Gln Tyr Asn Val Arg Ala Phe Met Asn Val Lys His Trp Pro
            820                 825                 830 tgg atg aag ctg tat ttc aag atc aaa ccc ctc ctc aaa agt gca gag        2544
Trp Met Lys Leu Tyr Phe Lys Ile Lys Pro Leu Leu Lys Ser Ala Glu
835                 840                 845 aca gag aag gag atg gcc aac atg aag gaa gaa ttt gag aaa acc aaa        2592
Thr Glu Lys Glu Met Ala Asn Met Lys Glu Glu Phe Glu Lys Thr Lys
850                 855                 860 gaa gag ctg gct aag acc gag gca aaa agg aaa gag ctg gaa gaa aaa        2640
Glu Glu Leu Ala Lys Thr Glu Ala Lys Arg Lys Glu Leu Glu Glu Lys
865                 870                 875                 880 atg gtg act ctg atg caa gaa aaa aat gac ttg caa ctc cag gtt caa        2688
Met Val Thr Leu Met Gln Glu Lys Asn Asp Leu Gln Leu Gln Val Gln
                885                 890                 895 gct gaa gct gac agc ttg gct gat gca gag gaa agg tgt gac cag cta        2736
Ala Glu Ala Asp Ser Leu Ala Asp Ala Glu Glu Arg Cys Asp Gln Leu
            900                 905                 910 atc aaa acc aaa atc cag cta gaa gcc aaa atc aaa gag gtg act gag        2784
Ile Lys Thr Lys Ile Gln Leu Glu Ala Lys Ile Lys Glu Val Thr Glu
915                 920                 925 aga gct gag gat gag gaa gag atc aat gct gag ctg aca gcc aag aag        2832
Arg Ala Glu Asp Glu Glu Glu Ile Asn Ala Glu Leu Thr Ala Lys Lys
                930                 935                 940 agg aaa ctg gag gat gaa tgt tca gaa ctc aag aaa gac att gat gac        2880
Arg Lys Leu Glu Asp Glu Cys Ser Glu Leu Lys Lys Asp Ile Asp Asp
945                 950                 955                 960 ctt gag ctg aca ctg gcc aag gtt gag aag gag aaa cat gcc aca gaa        2928
Leu Glu Leu Thr Leu Ala Lys Val Glu Lys Glu Lys His Ala Thr Glu
            965                 970                 975
```

```
aac aag gtg aaa aac ctc aca gaa gag atg gcg ggt ctg gat gaa acc     2976
Asn Lys Val Lys Asn Leu Thr Glu Glu Met Ala Gly Leu Asp Glu Thr
            980                 985                 990 att gct aag ctg acc aag gag aag  aag gct ctc cag gag  gcc cac cag   3024
Ile Ala Lys Leu Thr Lys Glu Lys  Lys Ala Leu Gln Glu  Ala His Gln
            995                 1000                 1005 cag acc ctg gat gac ctg cag gca gag gag gac aaa  gtc aac acc        3069
Gln Thr Leu Asp Asp Leu Gln Ala Glu Glu Asp Lys  Val Asn Thr
           1010                1015                1020 ctg acc aaa gct aaa atc aaa ctt gaa caa caa gtg gat gat ctt         3114
Leu Thr Lys Ala Lys Ile Lys Leu Glu Gln Gln Val Asp Asp Leu
           1025                1030                1035 gaa gga tct ttg gaa caa gaa aag aaa atc cgg atg gat cta gaa         3159
Glu Gly Ser Leu Glu Gln Glu Lys Lys Ile Arg Met Asp Leu Glu
           1040                1045                1050 aga gca aag aga aaa cta gag gga gac cta aaa ttg gct caa gaa         3204
Arg Ala Lys Arg Lys Leu Glu Gly Asp Leu Lys Leu Ala Gln Glu
           1055                1060                1065 tcc gca atg gat ata gaa aat gac aaa caa caa ctt gat gaa aag         3249
Ser Ala Met Asp Ile Glu Asn Asp Lys Gln Gln Leu Asp Glu Lys
           1070                1075                1080 ctt aaa aag aaa gag ttt gaa atg agc ggt ctg caa agc aag att         3294
Leu Lys Lys Lys Glu Phe Glu Met Ser Gly Leu Gln Ser Lys Ile
           1085                1090                1095 gaa gat gaa caa gcc ctt ggt atg cag ctg cag aag aaa atc aag         3339
Glu Asp Glu Gln Ala Leu Gly Met Gln Leu Gln Lys Lys Ile Lys
           1100                1105                1110 gag tta caa gcc cgc att gag gag ctg gag gag gaa atc gag gca         3384
Glu Leu Gln Ala Arg Ile Glu Glu Leu Glu Glu Glu Ile Glu Ala
           1115                1120                1125 gag cgg gcc tcc cgg gcc aaa gca gag aag cag cgc tct gat ctc         3429
Glu Arg Ala Ser Arg Ala Lys Ala Glu Lys Gln Arg Ser Asp Leu
           1130                1135                1140 tcc cgg gag ctg gag gag atc agt gag agg ctg gaa gaa gcc ggt         3474
Ser Arg Glu Leu Glu Glu Ile Ser Glu Arg Leu Glu Glu Ala Gly
           1145                1150                1155 ggg gcc acc tcg gcc cag att gag atg aac aag aag cgg gaa gct         3519
Gly Ala Thr Ser Ala Gln Ile Glu Met Asn Lys Lys Arg Glu Ala
           1160                1165                1170 gag ttc cag aaa atg cgc agg gac ctg gag gag gcc acc cta cag         3564
Glu Phe Gln Lys Met Arg Arg Asp Leu Glu Glu Ala Thr Leu Gln
           1175                1180                1185 cat gag gcc acg gcg gcc acc ctg agg aag aag cat gca gat agt         3609
His Glu Ala Thr Ala Ala Thr Leu Arg Lys Lys His Ala Asp Ser
           1190                1195                1200 gtg gcc gag ctt ggg gag cag att gac aac ctg cag cga gtg aag         3654
Val Ala Glu Leu Gly Glu Gln Ile Asp Asn Leu Gln Arg Val Lys
           1205                1210                1215 cag aag ctg gag aag gag aag agt gag atg aag atg gag atc gat         3699
Gln Lys Leu Glu Lys Glu Lys Ser Glu Met Lys Met Glu Ile Asp
           1220                1225                1230 gac ctt gct agt aac atg gag act gtc tcc aaa gcc aag gga aac         3744
Asp Leu Ala Ser Asn Met Glu Thr Val Ser Lys Ala Lys Gly Asn
           1235                1240                1245 ctt gaa aag atg tgc cgc gct cta gaa gat caa ctg agt gaa att         3789
Leu Glu Lys Met Cys Arg Ala Leu Glu Asp Gln Leu Ser Glu Ile
           1250                1255                1260 aag acc aag gaa gag gag cag cag cgg ctg atc aat gac ctc aca         3834
Lys Thr Lys Glu Glu Glu Gln Gln Arg Leu Ile Asn Asp Leu Thr
           1265                1270                1275
```

```
gca cag aga gcg cgc ctg caa aca gaa tca ggt gaa tat tca cgc      3879
Ala Gln Arg Ala Arg Leu Gln Thr Glu Ser Gly Glu Tyr Ser Arg
    1280                1285                1290 cag cta gat gaa aag gac aca cta gtt tca cag ctc tcg agg ggc      3924
Gln Leu Asp Glu Lys Asp Thr Leu Val Ser Gln Leu Ser Arg Gly
1295                1300                1305 aaa caa gcc ttt act caa cag att gag gaa ctg aaa agg caa ctt      3969
Lys Gln Ala Phe Thr Gln Gln Ile Glu Glu Leu Lys Arg Gln Leu
    1310                1315                1320 gaa gag gag ata aag gcc aag agt gcc ctg gca cat gcc ctg cag      4014
Glu Glu Glu Ile Lys Ala Lys Ser Ala Leu Ala His Ala Leu Gln
    1325                1330                1335 tcc tcc cgc cat gac tgt gac ctg ctg cgg gaa cag tat gag gag      4059
Ser Ser Arg His Asp Cys Asp Leu Leu Arg Glu Gln Tyr Glu Glu
    1340                1345                1350 gag cag gaa gcc aag gcc gag cta cag aga gca atg tcc aag gcc      4104
Glu Gln Glu Ala Lys Ala Glu Leu Gln Arg Ala Met Ser Lys Ala
    1355                1360                1365 aac agt gag gtt gcc cag tgg agg acc aaa tat gag aca gat gcc      4149
Asn Ser Glu Val Ala Gln Trp Arg Thr Lys Tyr Glu Thr Asp Ala
    1370                1375                1380 atc cag cgc aca gag gag ctg gag gag gcc aag aag aag ctg gct      4194
Ile Gln Arg Thr Glu Glu Leu Glu Glu Ala Lys Lys Lys Leu Ala
    1385                1390                1395 cag cgt ctg cag gat gct gag gaa cat gta gaa gct gtg aat gcc      4239
Gln Arg Leu Gln Asp Ala Glu Glu His Val Glu Ala Val Asn Ala
    1400                1405                1410 aaa tgt gct tcc ctt gag aag acg aag cag agg ctc cag aat gaa      4284
Lys Cys Ala Ser Leu Glu Lys Thr Lys Gln Arg Leu Gln Asn Glu
    1415                1420                1425 gtt gag gac ctc atg att gat gtt gag agg aca aat gct gcc tgt      4329
Val Glu Asp Leu Met Ile Asp Val Glu Arg Thr Asn Ala Ala Cys
    1430                1435                1440 gcc gcc ctg gac aaa aag caa agg aac ttt gat aag atc ctg gca      4374
Ala Ala Leu Asp Lys Lys Gln Arg Asn Phe Asp Lys Ile Leu Ala
    1445                1450                1455 gaa tgg aaa cag aag tgt gaa gaa act cat gct gaa ctt gaa gct      4419
Glu Trp Lys Gln Lys Cys Glu Glu Thr His Ala Glu Leu Glu Ala
    1460                1465                1470 tct caa aag gaa tcc cgc tca ctc agc aca gaa cta ttt aag att      4464
Ser Gln Lys Glu Ser Arg Ser Leu Ser Thr Glu Leu Phe Lys Ile
    1475                1480                1485 aag aat gct tat gag gaa tct tta gac caa ctt gaa acc ttg aaa      4509
Lys Asn Ala Tyr Glu Glu Ser Leu Asp Gln Leu Glu Thr Leu Lys
    1490                1495                1500 cgg gaa aat aag aat ctg cag cag gag att tct gat ctc act gaa      4554
Arg Glu Asn Lys Asn Leu Gln Gln Glu Ile Ser Asp Leu Thr Glu
    1505                1510                1515 cag att gca gaa gga gga aag cgc atc cat gaa ctg gaa aaa ata      4599
Gln Ile Ala Glu Gly Gly Lys Arg Ile His Glu Leu Glu Lys Ile
    1520                1525                1530 aag aag caa gtt gag caa gaa aag tct gaa ctt cag gct gcc tta      4644
Lys Lys Gln Val Glu Gln Glu Lys Ser Glu Leu Gln Ala Ala Leu
    1535                1540                1545 gag gag gca gag gca tct ctt gaa cat gaa gag gga aag atc ctg      4689
Glu Glu Ala Glu Ala Ser Leu Glu His Glu Glu Gly Lys Ile Leu
    1550                1555                1560 cgc atc cag ctt gag ttg aac caa gtc aag tct gag gtt gat agg      4734
Arg Ile Gln Leu Glu Leu Asn Gln Val Lys Ser Glu Val Asp Arg
```

-continued

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 1565 |     |     |     | 1570 |     |     |     | 1575 |     |     |     |      |
| aaa | att | gct | gaa | aaa | gat | gag | gaa | att | gac | cag | atg | aag | aga | aac | 4779 |
| Lys | Ile | Ala | Glu | Lys | Asp | Glu | Glu | Ile | Asp | Gln | Met | Lys | Arg | Asn |      |
|     | 1580 |     |     |     | 1585 |     |     |     | 1590 |     |     |     |     |     |      |
| cac | att | aga | atc | gtg | gag | tcc | atg | cag | agc | aca | ctg | gat | gct | gag | 4824 |
| His | Ile | Arg | Ile | Val | Glu | Ser | Met | Gln | Ser | Thr | Leu | Asp | Ala | Glu |      |
|     | 1595 |     |     |     | 1600 |     |     |     | 1605 |     |     |     |     |     |      |
| atc | agg | agc | agg | aat | gat | gcc | att | agg | ctc | aag | aag | aag | atg | gag | 4869 |
| Ile | Arg | Ser | Arg | Asn | Asp | Ala | Ile | Arg | Leu | Lys | Lys | Lys | Met | Glu |      |
|     | 1610 |     |     |     | 1615 |     |     |     | 1620 |     |     |     |     |     |      |
| gga | gac | ctc | aat | gaa | atg | gaa | atc | cag | ctg | aac | cat | gcc | aac | cgc | 4914 |
| Gly | Asp | Leu | Asn | Glu | Met | Glu | Ile | Gln | Leu | Asn | His | Ala | Asn | Arg |      |
|     | 1625 |     |     |     | 1630 |     |     |     | 1635 |     |     |     |     |     |      |
| atg | gct | gct | gag | gcc | ctg | agg | aac | tat | agg | aac | acc | caa | gcc | atc | 4959 |
| Met | Ala | Ala | Glu | Ala | Leu | Arg | Asn | Tyr | Arg | Asn | Thr | Gln | Ala | Ile |      |
|     | 1640 |     |     |     | 1645 |     |     |     | 1650 |     |     |     |     |     |      |
| ctc | aag | gat | acc | cag | ctc | cac | cta | gat | gat | gct | ctc | cgg | agc | caa | 5004 |
| Leu | Lys | Asp | Thr | Gln | Leu | His | Leu | Asp | Asp | Ala | Leu | Arg | Ser | Gln |      |
|     | 1655 |     |     |     | 1660 |     |     |     | 1665 |     |     |     |     |     |      |
| gag | gac | ctg | aag | gaa | cag | ctg | gct | atg | gtg | gag | cgc | aga | gcc | aac | 5049 |
| Glu | Asp | Leu | Lys | Glu | Gln | Leu | Ala | Met | Val | Glu | Arg | Arg | Ala | Asn |      |
|     | 1670 |     |     |     | 1675 |     |     |     | 1680 |     |     |     |     |     |      |
| ctg | ctg | cag | gct | gag | atc | gag | gaa | cta | cga | gcc | act | ctg | gaa | cag | 5094 |
| Leu | Leu | Gln | Ala | Glu | Ile | Glu | Glu | Leu | Arg | Ala | Thr | Leu | Glu | Gln |      |
|     | 1685 |     |     |     | 1690 |     |     |     | 1695 |     |     |     |     |     |      |
| acg | gag | agg | agc | agg | aaa | atc | gca | gaa | cag | gag | ctc | ctg | gat | gcc | 5139 |
| Thr | Glu | Arg | Ser | Arg | Lys | Ile | Ala | Glu | Gln | Glu | Leu | Leu | Asp | Ala |      |
|     | 1700 |     |     |     | 1705 |     |     |     | 1710 |     |     |     |     |     |      |
| agt | gaa | cgt | gtt | cag | ctc | ctg | cac | acc | cag | aac | acc | agc | ctg | atc | 5184 |
| Ser | Glu | Arg | Val | Gln | Leu | Leu | His | Thr | Gln | Asn | Thr | Ser | Leu | Ile |      |
|     | 1715 |     |     |     | 1720 |     |     |     | 1725 |     |     |     |     |     |      |
| aac | acc | aag | aag | aag | ctg | gag | aca | gac | att | tcc | caa | atc | cag | gga | 5229 |
| Asn | Thr | Lys | Lys | Lys | Leu | Glu | Thr | Asp | Ile | Ser | Gln | Ile | Gln | Gly |      |
|     | 1730 |     |     |     | 1735 |     |     |     | 1740 |     |     |     |     |     |      |
| gag | atg | gaa | gac | atc | atc | cag | gaa | gcc | cgc | aat | gca | gaa | gag | aag | 5274 |
| Glu | Met | Glu | Asp | Ile | Ile | Gln | Glu | Ala | Arg | Asn | Ala | Glu | Glu | Lys |      |
|     | 1745 |     |     |     | 1750 |     |     |     | 1755 |     |     |     |     |     |      |
| gcc | aag | aag | gcc | atc | act | gat | gct | gcc | atg | atg | gct | gag | gag | ctg | 5319 |
| Ala | Lys | Lys | Ala | Ile | Thr | Asp | Ala | Ala | Met | Met | Ala | Glu | Glu | Leu |      |
|     | 1760 |     |     |     | 1765 |     |     |     | 1770 |     |     |     |     |     |      |
| aag | aag | gaa | cag | gac | acc | agc | gcc | cat | ctg | gag | cgg | atg | aag | aag | 5364 |
| Lys | Lys | Glu | Gln | Asp | Thr | Ser | Ala | His | Leu | Glu | Arg | Met | Lys | Lys |      |
|     | 1775 |     |     |     | 1780 |     |     |     | 1785 |     |     |     |     |     |      |
| aac | ttg | gaa | cag | acg | gtg | aag | gac | ctg | cag | cat | cgt | ctg | gat | gag | 5409 |
| Asn | Leu | Glu | Gln | Thr | Val | Lys | Asp | Leu | Gln | His | Arg | Leu | Asp | Glu |      |
|     | 1790 |     |     |     | 1795 |     |     |     | 1800 |     |     |     |     |     |      |
| gct | gag | cag | ctg | gcc | ctg | aag | ggt | ggg | aag | aag | cag | atc | cag | aaa | 5454 |
| Ala | Glu | Gln | Leu | Ala | Leu | Lys | Gly | Gly | Lys | Lys | Gln | Ile | Gln | Lys |      |
|     | 1805 |     |     |     | 1810 |     |     |     | 1815 |     |     |     |     |     |      |
| ctg | gag | gcc | agg | gtt | cgt | gaa | ctt | gaa | ggt | gaa | gtt | gaa | agt | gaa | 5499 |
| Leu | Glu | Ala | Arg | Val | Arg | Glu | Leu | Glu | Gly | Glu | Val | Glu | Ser | Glu |      |
|     | 1820 |     |     |     | 1825 |     |     |     | 1830 |     |     |     |     |     |      |
| cag | aag | cgc | aat | gtt | gaa | gct | gtc | aag | ggt | cta | cgc | aaa | cat | gag | 5544 |
| Gln | Lys | Arg | Asn | Val | Glu | Ala | Val | Lys | Gly | Leu | Arg | Lys | His | Glu |      |
|     | 1835 |     |     |     | 1840 |     |     |     | 1845 |     |     |     |     |     |      |
| aga | aaa | gtg | aag | gaa | ctc | act | tac | caa | act | gag | gaa | gac | cgc | aag | 5589 |
| Arg | Lys | Val | Lys | Glu | Leu | Thr | Tyr | Gln | Thr | Glu | Glu | Asp | Arg | Lys |      |
|     | 1850 |     |     |     | 1855 |     |     |     | 1860 |     |     |     |     |     |      |
| aat | att | ctc | agg | ctg | cag | gac | ctg | gtg | gac | aag | ctg | caa | gca | aag | 5634 |

-continued

| | | | | | | | | | | | | |
|---|---|---|---|---|---|---|---|---|---|---|---|---|
| Asn | Ile | Leu | Arg | Leu | Gln | Asp | Leu | Val | Asp | Lys | Leu | Gln | Ala | Lys |
| | 1865 | | | | 1870 | | | | 1875 | | | |

```
gtg aaa tcc tac aag aga caa gct gaa gaa gcg gag gaa caa tcc      5679
Val Lys Ser Tyr Lys Arg Gln Ala Glu Glu Ala Glu Glu Gln Ser
1880                 1885                 1890 aac gtc aac ctc tcc aaa ttc cgg agg atc cag cac gag ctg gag      5724
Asn Val Asn Leu Ser Lys Phe Arg Arg Ile Gln His Glu Leu Glu
    1895                 1900                 1905 gag gcc gag gaa agg gct gac att gct gag tcc cag gtc aac aag      5769
Glu Ala Glu Glu Arg Ala Asp Ile Ala Glu Ser Gln Val Asn Lys
1910                 1915                 1920 ctg agg gtg aag agc agg gag gtt cac aca aaa atc ata agt gaa      5814
Leu Arg Val Lys Ser Arg Glu Val His Thr Lys Ile Ile Ser Glu
    1925                 1930                 1935 gag taa tttatctaac tgctgaaagg tgaccaaaga aatgcacaaa atgtgaaat    5870
Glu ctttgtcact ccattttgta cttatgactt ttggagataa aaaatttatc tgcca     5925

<210> SEQ ID NO 6
<211> LENGTH: 1939
<212> TYPE: PRT
<213> ORGANISM: Homo sapiens

<400> SEQUENCE: 6

Met Ser Ser Asp Ser Glu Met Ala Ile Phe Gly Glu Ala Ala Pro Phe
1               5                   10                  15

Leu Arg Lys Ser Glu Arg Glu Arg Ile Glu Ala Gln Asn Lys Pro Phe
                20                  25                  30

Asp Ala Lys Thr Ser Val Phe Val Val Asp Pro Lys Glu Ser Phe Val
            35                  40                  45

Lys Ala Thr Val Gln Ser Arg Glu Gly Gly Lys Val Thr Ala Lys Thr
        50                  55                  60

Glu Ala Gly Ala Thr Val Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
                100                 105                 110

Trp Met Ile Tyr Thr Tyr Ser Gly Leu Phe Cys Val Thr Val Asn Pro
            115                 120                 125

Tyr Lys Trp Leu Pro Val Tyr Asn Ala Glu Val Val Thr Ala Tyr Arg
        130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Val Thr Ser Gly Lys Met Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255
```

-continued

Thr Thr Gly Lys Leu Ala Ser Ala Asp Ile Glu Thr Tyr Leu Leu Glu
            260                 265                 270

Lys Ser Arg Val Thr Phe Gln Leu Lys Ala Glu Arg Ser Tyr His Ile
            275                 280                 285

Phe Tyr Gln Ile Met Ser Asn Lys Lys Pro Asp Leu Ile Glu Met Leu
            290                 295                 300

Leu Ile Thr Thr Asn Pro Tyr Asp Tyr Ala Phe Val Ser Gln Gly Glu
305                 310                 315                 320

Ile Thr Val Pro Ser Ile Asp Asp Gln Glu Glu Leu Met Ala Thr Asp
                    325                 330                 335

Ser Ala Ile Glu Ile Leu Gly Phe Thr Ser Asp Glu Arg Val Ser Ile
                340                 345                 350

Tyr Lys Leu Thr Gly Ala Val Met His Tyr Gly Asn Met Lys Phe Lys
            355                 360                 365

Gln Lys Gln Arg Glu Glu Gln Ala Glu Pro Asp Gly Thr Glu Val Ala
            370                 375                 380

Asp Lys Ala Ala Tyr Leu Gln Asn Leu Asn Ser Ala Asp Leu Leu Lys
385                 390                 395                 400

Ala Leu Cys Tyr Pro Arg Val Lys Val Gly Asn Glu Tyr Val Thr Lys
                    405                 410                 415

Gly Gln Thr Val Gln Gln Val Tyr Asn Ala Val Gly Ala Leu Ala Lys
                420                 425                 430

Ala Val Tyr Asp Lys Met Phe Leu Trp Met Val Thr Arg Ile Asn Gln
            435                 440                 445

Gln Leu Asp Thr Lys Gln Pro Arg Gln Tyr Phe Ile Gly Val Leu Asp
            450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                    485                 490                 495

Phe Val Leu Glu Gln Glu Glu Tyr Lys Lys Glu Gly Ile Glu Trp Thr
                500                 505                 510

Phe Ile Asp Phe Gly Met Asp Leu Ala Ala Cys Ile Glu Leu Ile Glu
            515                 520                 525

Lys Pro Met Gly Ile Phe Ser Ile Leu Glu Glu Glu Cys Met Phe Pro
            530                 535                 540

Lys Ala Thr Asp Thr Ser Phe Lys Asn Lys Leu Tyr Glu Gln His Leu
545                 550                 555                 560

Gly Lys Ser Asn Asn Phe Gln Lys Pro Lys Pro Ala Lys Gly Lys Pro
                    565                 570                 575

Glu Ala His Phe Ser Leu Ile His Tyr Ala Gly Thr Val Asp Tyr Asn
                580                 585                 590

Ile Ala Gly Trp Leu Asp Lys Asn Lys Asp Pro Leu Asn Glu Thr Val
            595                 600                 605

Val Gly Leu Tyr Gln Lys Ser Ala Met Lys Thr Leu Ala Leu Leu Phe
            610                 615                 620

Val Gly Ala Thr Gly Ala Glu Ala Glu Ala Gly Gly Gly Lys Lys Gly
625                 630                 635                 640

Gly Lys Lys Lys Gly Ser Ser Phe Gln Thr Val Ser Ala Leu Phe Arg
                    645                 650                 655

Glu Asn Leu Asn Lys Leu Met Thr Asn Leu Arg Ser Thr His Pro His
                660                 665                 670

-continued

```
Phe Val Arg Cys Ile Ile Pro Asn Glu Thr Lys Thr Pro Gly Ala Met
            675                 680                 685
Glu His Glu Leu Val Leu His Gln Leu Arg Cys Asn Gly Val Leu Glu
        690                 695                 700
Gly Ile Arg Ile Cys Arg Lys Gly Phe Pro Ser Arg Ile Leu Tyr Ala
705                 710                 715                 720
Asp Phe Lys Gln Arg Tyr Lys Val Leu Asn Ala Ser Ala Ile Pro Glu
                725                 730                 735
Gly Gln Phe Ile Asp Ser Lys Lys Ala Ser Glu Lys Leu Leu Gly Ser
            740                 745                 750
Ile Asp Ile Asp His Thr Gln Tyr Lys Phe Gly His Thr Lys Val Phe
        755                 760                 765
Phe Lys Ala Gly Leu Leu Gly Leu Leu Glu Glu Met Arg Asp Glu Lys
    770                 775                 780
Leu Ala Gln Leu Ile Thr Arg Thr Gln Ala Met Cys Arg Gly Phe Leu
785                 790                 795                 800
Ala Arg Val Glu Tyr Gln Lys Met Val Glu Arg Arg Glu Ser Ile Phe
                805                 810                 815
Cys Ile Gln Tyr Asn Val Arg Ala Phe Met Asn Val Lys His Trp Pro
            820                 825                 830
Trp Met Lys Leu Tyr Phe Lys Ile Lys Pro Leu Leu Lys Ser Ala Glu
        835                 840                 845
Thr Glu Lys Glu Met Ala Asn Met Lys Glu Glu Phe Glu Lys Thr Lys
    850                 855                 860
Glu Glu Leu Ala Lys Thr Glu Ala Lys Arg Lys Glu Leu Glu Glu Lys
865                 870                 875                 880
Met Val Thr Leu Met Gln Glu Lys Asn Asp Leu Gln Leu Gln Val Gln
                885                 890                 895
Ala Glu Ala Asp Ser Leu Ala Asp Ala Glu Glu Arg Cys Asp Gln Leu
            900                 905                 910
Ile Lys Thr Lys Ile Gln Leu Glu Ala Lys Ile Lys Glu Val Thr Glu
        915                 920                 925
Arg Ala Glu Asp Glu Glu Glu Ile Asn Ala Glu Leu Thr Ala Lys Lys
    930                 935                 940
Arg Lys Leu Glu Asp Glu Cys Ser Glu Leu Lys Lys Asp Ile Asp Asp
945                 950                 955                 960
Leu Glu Leu Thr Leu Ala Lys Val Glu Lys Glu Lys His Ala Thr Glu
                965                 970                 975
Asn Lys Val Lys Asn Leu Thr Glu Glu Met Ala Gly Leu Asp Glu Thr
            980                 985                 990
Ile Ala Lys Leu Thr Lys Glu Lys Lys Ala Leu Gln Glu Ala His Gln
        995                 1000                1005
Gln Thr Leu Asp Asp Leu Gln Ala Glu Glu Asp Lys Val Asn Thr
        1010                1015                1020
Leu Thr Lys Ala Lys Ile Lys Leu Glu Gln Gln Val Asp Asp Leu
        1025                1030                1035
Glu Gly Ser Leu Glu Gln Glu Lys Lys Ile Arg Met Asp Leu Glu
        1040                1045                1050
Arg Ala Lys Arg Lys Leu Glu Gly Asp Leu Lys Leu Ala Gln Glu
        1055                1060                1065
Ser Ala Met Asp Ile Glu Asn Asp Lys Gln Gln Leu Asp Glu Lys
        1070                1075                1080
Leu Lys Lys Lys Glu Phe Glu Met Ser Gly Leu Gln Ser Lys Ile
```

-continued

```
            1085                1090                1095

Glu Asp Glu Gln Ala Leu Gly Met Gln Leu Gln Lys Lys Ile Lys
            1100                1105                1110

Glu Leu Gln Ala Arg Ile Glu Glu Leu Glu Glu Ile Glu Ala
            1115                1120                1125

Glu Arg Ala Ser Arg Ala Lys Ala Glu Lys Gln Arg Ser Asp Leu
            1130                1135                1140

Ser Arg Glu Leu Glu Glu Ile Ser Glu Arg Leu Glu Glu Ala Gly
            1145                1150                1155

Gly Ala Thr Ser Ala Gln Ile Glu Met Asn Lys Lys Arg Glu Ala
            1160                1165                1170

Glu Phe Gln Lys Met Arg Arg Asp Leu Glu Glu Ala Thr Leu Gln
            1175                1180                1185

His Glu Ala Thr Ala Ala Thr Leu Arg Lys Lys His Ala Asp Ser
            1190                1195                1200

Val Ala Glu Leu Gly Glu Gln Ile Asp Asn Leu Gln Arg Val Lys
            1205                1210                1215

Gln Lys Leu Glu Lys Glu Lys Ser Glu Met Lys Met Glu Ile Asp
            1220                1225                1230

Asp Leu Ala Ser Asn Met Glu Thr Val Ser Lys Ala Lys Gly Asn
            1235                1240                1245

Leu Glu Lys Met Cys Arg Ala Leu Glu Asp Gln Leu Ser Glu Ile
            1250                1255                1260

Lys Thr Lys Glu Glu Glu Gln Gln Arg Leu Ile Asn Asp Leu Thr
            1265                1270                1275

Ala Gln Arg Ala Arg Leu Gln Thr Glu Ser Gly Glu Tyr Ser Arg
            1280                1285                1290

Gln Leu Asp Glu Lys Asp Thr Leu Val Ser Gln Leu Ser Arg Gly
            1295                1300                1305

Lys Gln Ala Phe Thr Gln Gln Ile Glu Glu Leu Lys Arg Gln Leu
            1310                1315                1320

Glu Glu Glu Ile Lys Ala Lys Ser Ala Leu Ala His Ala Leu Gln
            1325                1330                1335

Ser Ser Arg His Asp Cys Asp Leu Leu Arg Glu Gln Tyr Glu Glu
            1340                1345                1350

Glu Gln Glu Ala Lys Ala Glu Leu Gln Arg Ala Met Ser Lys Ala
            1355                1360                1365

Asn Ser Glu Val Ala Gln Trp Arg Thr Lys Tyr Glu Thr Asp Ala
            1370                1375                1380

Ile Gln Arg Thr Glu Glu Leu Glu Glu Ala Lys Lys Lys Leu Ala
            1385                1390                1395

Gln Arg Leu Gln Asp Ala Glu Glu His Val Glu Ala Val Asn Ala
            1400                1405                1410

Lys Cys Ala Ser Leu Glu Lys Thr Lys Gln Arg Leu Gln Asn Glu
            1415                1420                1425

Val Glu Asp Leu Met Ile Asp Val Glu Arg Thr Asn Ala Ala Cys
            1430                1435                1440

Ala Ala Leu Asp Lys Lys Gln Arg Asn Phe Asp Lys Ile Leu Ala
            1445                1450                1455

Glu Trp Lys Gln Lys Cys Glu Glu Thr His Ala Glu Leu Glu Ala
            1460                1465                1470

Ser Gln Lys Glu Ser Arg Ser Leu Ser Thr Glu Leu Phe Lys Ile
            1475                1480                1485
```

```
Lys Asn Ala Tyr Glu Glu Ser Leu Asp Gln Leu Glu Thr Leu Lys
1490                1495                1500

Arg Glu Asn Lys Asn Leu Gln Gln Glu Ile Ser Asp Leu Thr Glu
1505                1510                1515

Gln Ile Ala Glu Gly Gly Lys Arg Ile His Glu Leu Glu Lys Ile
1520                1525                1530

Lys Lys Gln Val Glu Gln Glu Lys Ser Glu Leu Gln Ala Ala Leu
1535                1540                1545

Glu Glu Ala Glu Ala Ser Leu Glu His Glu Glu Gly Lys Ile Leu
1550                1555                1560

Arg Ile Gln Leu Glu Leu Asn Gln Val Lys Ser Glu Val Asp Arg
1565                1570                1575

Lys Ile Ala Glu Lys Asp Glu Glu Ile Asp Gln Met Lys Arg Asn
1580                1585                1590

His Ile Arg Ile Val Glu Ser Met Gln Ser Thr Leu Asp Ala Glu
1595                1600                1605

Ile Arg Ser Arg Asn Asp Ala Ile Arg Leu Lys Lys Lys Met Glu
1610                1615                1620

Gly Asp Leu Asn Glu Met Glu Ile Gln Leu Asn His Ala Asn Arg
1625                1630                1635

Met Ala Ala Glu Ala Leu Arg Asn Tyr Arg Asn Thr Gln Ala Ile
1640                1645                1650

Leu Lys Asp Thr Gln Leu His Leu Asp Asp Ala Leu Arg Ser Gln
1655                1660                1665

Glu Asp Leu Lys Glu Gln Leu Ala Met Val Glu Arg Arg Ala Asn
1670                1675                1680

Leu Leu Gln Ala Glu Ile Glu Glu Leu Arg Ala Thr Leu Glu Gln
1685                1690                1695

Thr Glu Arg Ser Arg Lys Ile Ala Glu Gln Glu Leu Leu Asp Ala
1700                1705                1710

Ser Glu Arg Val Gln Leu Leu His Thr Gln Asn Thr Ser Leu Ile
1715                1720                1725

Asn Thr Lys Lys Lys Leu Glu Thr Asp Ile Ser Gln Ile Gln Gly
1730                1735                1740

Glu Met Glu Asp Ile Ile Gln Glu Ala Arg Asn Ala Glu Glu Lys
1745                1750                1755

Ala Lys Lys Ala Ile Thr Asp Ala Ala Met Met Ala Glu Glu Leu
1760                1765                1770

Lys Lys Glu Gln Asp Thr Ser Ala His Leu Glu Arg Met Lys Lys
1775                1780                1785

Asn Leu Glu Gln Thr Val Lys Asp Leu Gln His Arg Leu Asp Glu
1790                1795                1800

Ala Glu Gln Leu Ala Leu Lys Gly Gly Lys Lys Gln Ile Gln Lys
1805                1810                1815

Leu Glu Ala Arg Val Arg Glu Leu Glu Gly Glu Val Glu Ser Glu
1820                1825                1830

Gln Lys Arg Asn Val Glu Ala Val Lys Gly Leu Arg Lys His Glu
1835                1840                1845

Arg Lys Val Lys Glu Leu Thr Tyr Gln Thr Glu Glu Asp Arg Lys
1850                1855                1860

Asn Ile Leu Arg Leu Gln Asp Leu Val Asp Lys Leu Gln Ala Lys
1865                1870                1875
```

```
Val Lys Ser Tyr Lys Arg Gln Ala Glu Glu Ala Glu Glu Gln Ser
        1880                1885                1890
Asn Val Asn Leu Ser Lys Phe Arg Arg Ile Gln His Glu Leu Glu
        1895                1900                1905
Glu Ala Glu Glu Arg Ala Asp Ile Ala Glu Ser Gln Val Asn Lys
        1910                1915                1920
Leu Arg Val Lys Ser Arg Glu Val His Thr Lys Ile Ile Ser Glu
        1925                1930                1935
Glu

<210> SEQ ID NO 7
<211> LENGTH: 2633
<212> TYPE: DNA
<213> ORGANISM: Homo sapiens
<220> FEATURE:
<221> NAME/KEY: CDS
<222> LOCATION: (38)..(2584)

<400> SEQUENCE: 7
ccgcggcaag aacatccctc ccagccagca gattaca atg ctg caa act aag gat      55
                                          Met Leu Gln Thr Lys Asp
                                            1               5 ctc atc tgg act ttg ttt ttc ctg gga act gca gtt tct ctg cag gtg     103
Leu Ile Trp Thr Leu Phe Phe Leu Gly Thr Ala Val Ser Leu Gln Val
           10                  15                  20 gat att gtt ccc agc cag ggg gag atc agc gtt gga gag tcc aaa ttc     151
Asp Ile Val Pro Ser Gln Gly Glu Ile Ser Val Gly Glu Ser Lys Phe
                25                  30                  35 ttc tta tgc caa gtg gca gga gat gcc aaa gat aaa gac atc tcc tgg     199
Phe Leu Cys Gln Val Ala Gly Asp Ala Lys Asp Lys Asp Ile Ser Trp
 40                  45                  50 ttc tcc ccc aat gga gaa aag ctc acc cca aac cag cag cgg atc tca     247
Phe Ser Pro Asn Gly Glu Lys Leu Thr Pro Asn Gln Gln Arg Ile Ser
 55                  60                  65                  70 gtg gtg tgg aat gat gat tcc tcc tcc acc ctc acc atc tat aac gcc     295
Val Val Trp Asn Asp Asp Ser Ser Ser Thr Leu Thr Ile Tyr Asn Ala
                 75                  80                  85 aac atc gac gac gcc ggc att tac aag tgt gtg gtt aca ggc gag gat     343
Asn Ile Asp Asp Ala Gly Ile Tyr Lys Cys Val Val Thr Gly Glu Asp
             90                  95                 100 ggc agt gag tca gag gcc acc gtc aac gtg aag atc ttt cag aag ctc     391
Gly Ser Glu Ser Glu Ala Thr Val Asn Val Lys Ile Phe Gln Lys Leu
        105                 110                 115 atg ttc aag aat gcg cca acc cca cag gag ttc cgg gag ggg gaa gat     439
Met Phe Lys Asn Ala Pro Thr Pro Gln Glu Phe Arg Glu Gly Glu Asp
    120                 125                 130 gcc gtg att gtg tgt gat gtg gtc agc tcc ctc cca cca acc atc atc     487
Ala Val Ile Val Cys Asp Val Val Ser Ser Leu Pro Pro Thr Ile Ile
135                 140                 145                 150 tgg aaa cac aaa ggc cga gat gtc atc ctg aaa aaa gat gtc cga ttc     535
Trp Lys His Lys Gly Arg Asp Val Ile Leu Lys Lys Asp Val Arg Phe
                155                 160                 165 ata gtc ctg tcc aac aac tac ctg cag atc cgg ggc atc aag aaa aca     583
Ile Val Leu Ser Asn Asn Tyr Leu Gln Ile Arg Gly Ile Lys Lys Thr
            170                 175                 180 gat gag ggc act tat cgc tgt gag ggc aga atc ctg gca cgg ggg gag     631
Asp Glu Gly Thr Tyr Arg Cys Glu Gly Arg Ile Leu Ala Arg Gly Glu
        185                 190                 195 atc aac ttc aag gac att cag gtc att gtg aat gtg cca cct acc atc     679
Ile Asn Phe Lys Asp Ile Gln Val Ile Val Asn Val Pro Pro Thr Ile
```

| | | |
|---|---|---|
| cgg gcc agg cag aat att gtg aat gcc acc gcc aac ctc ggc cag tcc<br>Arg Ala Arg Gln Asn Ile Val Asn Ala Thr Ala Asn Leu Gly Gln Ser<br>215                    220                    225                    230 | 727 |
| gtc acc ctg gtg tgc gat gcc gaa cgg ttc cca gag ccc acc atg agc<br>Val Thr Leu Val Cys Asp Ala Glu Arg Phe Pro Glu Pro Thr Met Ser<br>                   235                    240                    245 | 775 |
| tgg aca aag gat ggg gaa cag ata gag caa gag gaa gac gat gag aag<br>Trp Thr Lys Asp Gly Glu Gln Ile Glu Gln Glu Glu Asp Asp Glu Lys<br>          250                    255                    260 | 823 |
| tac atc ttc agc gac gat agt tcc cag ctg acc atc aaa aag gtg gat<br>Tyr Ile Phe Ser Asp Asp Ser Ser Gln Leu Thr Ile Lys Lys Val Asp<br>              265                    270                    275 | 871 |
| aag aac gac gag gct gag tac atc tgc att gct gag aac aag gct ggc<br>Lys Asn Asp Glu Ala Glu Tyr Ile Cys Ile Ala Glu Asn Lys Ala Gly<br>280                    285                    290 | 919 |
| gag cag gat gcg acc atc cac ctc aaa gtc ttt gca aaa ccc aaa atc<br>Glu Gln Asp Ala Thr Ile His Leu Lys Val Phe Ala Lys Pro Lys Ile<br>295                    300                    305                    310 | 967 |
| aca tat gta gag aac cag act gcc atg gaa tta gag gag cag gtc act<br>Thr Tyr Val Glu Asn Gln Thr Ala Met Glu Leu Glu Glu Gln Val Thr<br>              315                    320                    325 | 1015 |
| ctt acc tgt gaa gcc tcc gga gac ccc att ccc tcc atc acc tgg agg<br>Leu Thr Cys Glu Ala Ser Gly Asp Pro Ile Pro Ser Ile Thr Trp Arg<br>                   330                    335                    340 | 1063 |
| act tct acc cgg aac atc agc agc gaa gaa aag act ctg gat ggg cac<br>Thr Ser Thr Arg Asn Ile Ser Ser Glu Glu Lys Thr Leu Asp Gly His<br>              345                    350                    355 | 1111 |
| atg gtg gtg cgt agc cat gcc cgt gtg tcg tcg ctg acc ctg aag agc<br>Met Val Val Arg Ser His Ala Arg Val Ser Ser Leu Thr Leu Lys Ser<br>360                    365                    370 | 1159 |
| atc cag tac act gat gcc gga gag tac atc tgc acc gcc agc aac acc<br>Ile Gln Tyr Thr Asp Ala Gly Glu Tyr Ile Cys Thr Ala Ser Asn Thr<br>375                    380                    385                    390 | 1207 |
| atc ggc cag gac tcc cag tcc atg tac ctt gaa gtg caa tat gcc cca<br>Ile Gly Gln Asp Ser Gln Ser Met Tyr Leu Glu Val Gln Tyr Ala Pro<br>                   395                    400                    405 | 1255 |
| aag cta cag ggc cct gtg gct gtg tac act tgg gag ggg aac cag gtg<br>Lys Leu Gln Gly Pro Val Ala Val Tyr Thr Trp Glu Gly Asn Gln Val<br>          410                    415                    420 | 1303 |
| aac atc acc tgc gag gta ttt gcc tat ccc agt gcc acg atc tca tgg<br>Asn Ile Thr Cys Glu Val Phe Ala Tyr Pro Ser Ala Thr Ile Ser Trp<br>              425                    430                    435 | 1351 |
| ttt cgg gat ggc cag ctg ctg cca agc tcc aat tac agc aat atc aag<br>Phe Arg Asp Gly Gln Leu Leu Pro Ser Ser Asn Tyr Ser Asn Ile Lys<br>440                    445                    450 | 1399 |
| atc tac aac acc ccc tct gcc agc tat ctg gag gtg acc cca gac tct<br>Ile Tyr Asn Thr Pro Ser Ala Ser Tyr Leu Glu Val Thr Pro Asp Ser<br>455                    460                    465                    470 | 1447 |
| gag aat gat ttt ggg aac tac aac tgt act gca gtg aac cgc att ggg<br>Glu Asn Asp Phe Gly Asn Tyr Asn Cys Thr Ala Val Asn Arg Ile Gly<br>                   475                    480                    485 | 1495 |
| cag gag tcc ttc gaa ttc atc ctt gtt caa gca gac acc ccc tct tca<br>Gln Glu Ser Phe Glu Phe Ile Leu Val Gln Ala Asp Thr Pro Ser Ser<br>          490                    495                    500 | 1543 |
| cca tcc atc gac cag gtg gag cca tac tcc agc aca gcc cag gtg cag<br>Pro Ser Ile Asp Gln Val Glu Pro Tyr Ser Ser Thr Ala Gln Val Gln<br>              505                    510                    515 | 1591 |
| ttt gat gaa cca gag gcc aca ggt ggg gtg ccc atc ctc aaa tac aaa | 1639 |

```
                                                          -continued

Phe Asp Glu Pro Glu Ala Thr Gly Gly Val Pro Ile Leu Lys Tyr Lys
    520             525             530 gct gag tgg aga gca gtg ggt gaa gaa gta tgg cat tcc aag tgg tat    1687
Ala Glu Trp Arg Ala Val Gly Glu Glu Val Trp His Ser Lys Trp Tyr
535             540             545             550 gat gcc aag gaa gcc agc atg gag ggc atc gtc acc atc gtg ggc ctg    1735
Asp Ala Lys Glu Ala Ser Met Glu Gly Ile Val Thr Ile Val Gly Leu
                555             560             565 aag ccc gaa aca acg tac gcc gta agg ctg gcg gcg ctc aat ggc aaa    1783
Lys Pro Glu Thr Thr Tyr Ala Val Arg Leu Ala Ala Leu Asn Gly Lys
            570             575             580 ggg ctg ggt gag atc agc gcg gcc tcc gag ttc aag acg cag cca gtc    1831
Gly Leu Gly Glu Ile Ser Ala Ala Ser Glu Phe Lys Thr Gln Pro Val
        585             590             595 caa ggg gaa ccc agt gca cct aag ctc gaa ggg cag atg gga gag gat    1879
Gln Gly Glu Pro Ser Ala Pro Lys Leu Glu Gly Gln Met Gly Glu Asp
    600             605             610 gga aac tct att aaa gtg aac ctg atc aag cag gat gac ggc ggc tcc    1927
Gly Asn Ser Ile Lys Val Asn Leu Ile Lys Gln Asp Asp Gly Gly Ser
615             620             625             630 ccc atc aga cac tat ctg gtc agg tac cga gcg ctc tcc tcc gag tgg    1975
Pro Ile Arg His Tyr Leu Val Arg Tyr Arg Ala Leu Ser Ser Glu Trp
                635             640             645 aaa cca gag atc agg ctc ccg tct ggc agt gac cac gtc atg ctg aag    2023
Lys Pro Glu Ile Arg Leu Pro Ser Gly Ser Asp His Val Met Leu Lys
            650             655             660 tcc ctg gac tgg aat gct gag tat gag gtc tac gtg gtg gct gag aac    2071
Ser Leu Asp Trp Asn Ala Glu Tyr Glu Val Tyr Val Val Ala Glu Asn
        665             670             675 cag caa gga aaa tcc aag gcg gct cat ttt gtg ttc agg acc tcg gcc    2119
Gln Gln Gly Lys Ser Lys Ala Ala His Phe Val Phe Arg Thr Ser Ala
    680             685             690 cag ccc aca gcc atc cca gcc aac ggc agc ccc acc tca ggc ctg agc    2167
Gln Pro Thr Ala Ile Pro Ala Asn Gly Ser Pro Thr Ser Gly Leu Ser
695             700             705             710 acc ggg gcc atc gtg ggc atc ctc atc gtc atc ttc gtc ctg ctc ctg    2215
Thr Gly Ala Ile Val Gly Ile Leu Ile Val Ile Phe Val Leu Leu Leu
                715             720             725 gtg gtt gtg gac atc acc tgc tac ttc ctg aac aag tgt ggc ctg ttc    2263
Val Val Val Asp Ile Thr Cys Tyr Phe Leu Asn Lys Cys Gly Leu Phe
            730             735             740 atg tgc att gcg gtc aac ctg tgt gga aaa gcc ggg ccc ggg gcc aag    2311
Met Cys Ile Ala Val Asn Leu Cys Gly Lys Ala Gly Pro Gly Ala Lys
        745             750             755 ggc aag gac atg gag gag ggc aag gcc gcc ttc tcg aaa gat gag tcc    2359
Gly Lys Asp Met Glu Glu Gly Lys Ala Ala Phe Ser Lys Asp Glu Ser
    760             765             770 aag gag ccc atc gtg gag gtt cga acg gag gag gag agg acc cca aac    2407
Lys Glu Pro Ile Val Glu Val Arg Thr Glu Glu Glu Arg Thr Pro Asn
775             780             785             790 cat gat gga ggg aaa cac aca gag ccc aac gag acc acg cca ctg acg    2455
His Asp Gly Gly Lys His Thr Glu Pro Asn Glu Thr Thr Pro Leu Thr
                795             800             805 gag ccc gag aag ggc ccc gta gaa gca aag cca gag tgc cag gag aca    2503
Glu Pro Glu Lys Gly Pro Val Glu Ala Lys Pro Glu Cys Gln Glu Thr
            810             815             820 gaa acg aag cca gcg cca gcc gaa gtc aag acg gtc ccc aat gac gcc    2551
Glu Thr Lys Pro Ala Pro Ala Glu Val Lys Thr Val Pro Asn Asp Ala
        825             830             835
```

```
aca cag aca aag gag aac gag agc aaa gca tga tgggtgaaga gaaccgagca    2604
Thr Gln Thr Lys Glu Asn Glu Ser Lys Ala
        840                 845 aagatcaaaa taaaaagtga cacagcagc                                      2633

<210> SEQ ID NO 8
<211> LENGTH: 848
<212> TYPE: PRT
<213> ORGANISM: Homo sapiens

<400> SEQUENCE: 8

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Arg Ala Arg Gln Asn Ile Val Asn Ala Thr
    210                 215                 220

Ala Asn Leu Gly Gln Ser Val Thr Leu Val Cys Asp Ala Glu Arg Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350
```

```
Lys Thr Leu Asp Gly His Met Val Arg Ser His Ala Arg Val Ser
        355                 360                 365

Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
                420                 425                 430

Ser Ala Thr Ile Ser Trp Phe Arg Asp Gly Gln Leu Leu Pro Ser Ser
            435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Phe Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
    515                 520                 525

Pro Ile Leu Lys Tyr Lys Ala Glu Trp Arg Ala Val Gly Glu Glu Val
    530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
    595                 600                 605

Gly Gln Met Gly Glu Asp Gly Asn Ser Ile Lys Val Asn Leu Ile Lys
    610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
    675                 680                 685

Val Phe Arg Thr Ser Ala Gln Pro Thr Ala Ile Pro Ala Asn Gly Ser
    690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
    755                 760                 765
```

```
Phe Ser Lys Asp Glu Ser Lys Glu Pro Ile Val Glu Val Arg Thr Glu
        770                 775                 780
Glu Glu Arg Thr Pro Asn His Asp Gly Gly Lys His Thr Glu Pro Asn
785                 790                 795                 800
Glu Thr Thr Pro Leu Thr Glu Pro Glu Lys Gly Pro Val Glu Ala Lys
                805                 810                 815
Pro Glu Cys Gln Glu Thr Glu Thr Lys Pro Ala Pro Ala Glu Val Lys
            820                 825                 830
Thr Val Pro Asn Asp Ala Thr Gln Thr Lys Glu Asn Glu Ser Lys Ala
            835                 840                 845

<210> SEQ ID NO 9
<211> LENGTH: 1692
<212> TYPE: DNA
<213> ORGANISM: Homo sapiens
<220> FEATURE:
<221> NAME/KEY: CDS
<222> LOCATION: (121)..(1080)

<400> SEQUENCE: 9
```

| | |
|---|---|
| attcagactg ccagcacttt gctatctaca gccggggctc ccgagcggca gaaagttccg | 60 |
| gccactctct gccgcttggg ttgggcgaaa gccaggaccg tgccgcgcca ccgccaggat | 120 |

```
atg gag cta ctg tcg cca ccg ctc cgc gac gta gac ctg acg gcc ccc      168
Met Glu Leu Leu Ser Pro Pro Leu Arg Asp Val Asp Leu Thr Ala Pro
1               5                  10                  15 gac ggc tct ctc tgc tcc ttt gcc aca acg gac gac ttc tat gac gac      216
Asp Gly Ser Leu Cys Ser Phe Ala Thr Thr Asp Asp Phe Tyr Asp Asp
                20                  25                  30 ccg tgt ttc gac tcc ccg gac ctg cgc ttc ttc gaa gac ctg gac ccg      264
Pro Cys Phe Asp Ser Pro Asp Leu Arg Phe Phe Glu Asp Leu Asp Pro
            35                  40                  45 cgc ctg atg cac gtg ggc gcg ctc ctg aaa ccc gaa gag cac tcg cac      312
Arg Leu Met His Val Gly Ala Leu Leu Lys Pro Glu Glu His Ser His
        50                  55                  60 ttc ccc gcg gcg gtg cac ccg gcc ccg ggc gca cgt gag gac gag cat      360
Phe Pro Ala Ala Val His Pro Ala Pro Gly Ala Arg Glu Asp Glu His
65                  70                  75                  80 gtg cgc gcg ccc agc ggg cac cac cag gcg ggc cgc tgc cta ctg tgg      408
Val Arg Ala Pro Ser Gly His His Gln Ala Gly Arg Cys Leu Leu Trp
                85                  90                  95 gcc tgc aag gcg tgc aag cgc aag acc acc aac gcc gac cgc cgc aag      456
Ala Cys Lys Ala Cys Lys Arg Lys Thr Thr Asn Ala Asp Arg Arg Lys
                100                 105                 110 gcc gcc acc atg cgc gag cgg cgc cgc ctg agc aaa gta aat gag gcc      504
Ala Ala Thr Met Arg Glu Arg Arg Arg Leu Ser Lys Val Asn Glu Ala
            115                 120                 125 ttt gag aca ctc aag cgc tgc acg tcg agc aat cca aac cag cgg ttg      552
Phe Glu Thr Leu Lys Arg Cys Thr Ser Ser Asn Pro Asn Gln Arg Leu
            130                 135                 140 ccc aag gtg gag atc ctg cgc aac gcc atc cgc tat atc gag ggc ctg      600
Pro Lys Val Glu Ile Leu Arg Asn Ala Ile Arg Tyr Ile Glu Gly Leu
145                 150                 155                 160 cag gct ctg ctg cgc gac cag gac gcc gcg ccc cct ggc gca gcc gcc      648
Gln Ala Leu Leu Arg Asp Gln Asp Ala Ala Pro Pro Gly Ala Ala Ala
                165                 170                 175 ttc tat gcg ccg ggc ccg ctg ccc ccg ggc cgc ggc gag cac tac            696
Phe Tyr Ala Pro Gly Pro Leu Pro Pro Gly Arg Gly Gly Glu His Tyr
                180                 185                 190 agc ggc gac tcc gac gcg tcc agc ccg cgc tcc aac tgc tcc gac ggc      744
```

| | 744 |
|---|---|

```
                Ser Gly Asp Ser Asp Ala Ser Ser Pro Arg Ser Asn Cys Ser Asp Gly
                        195                 200                 205 atg atg gac tac agc ggc ccc ccg agc ggc gcc cgg cgg cgg aac tgc           792
Met Met Asp Tyr Ser Gly Pro Pro Ser Gly Ala Arg Arg Arg Asn Cys
    210                 215                 220 tac gaa ggc gcc tac tac aac gag gcg ccc agc gaa ccc agg ccc ggg           840
Tyr Glu Gly Ala Tyr Tyr Asn Glu Ala Pro Ser Glu Pro Arg Pro Gly
225                 230                 235                 240 aag agt gcg gcg gtg tcg agc cta gac tac ctg tcc agc atc gtg gag           888
Lys Ser Ala Ala Val Ser Ser Leu Asp Tyr Leu Ser Ser Ile Val Glu
                245                 250                 255 cgc atc tcc acc gag agc cct gcg gcg ccc gcc ctc ctg ctg gcg gac           936
Arg Ile Ser Thr Glu Ser Pro Ala Ala Pro Ala Leu Leu Leu Ala Asp
                260                 265                 270 gtg cct tct gag tcg cct ccg cgc agg caa gag gct gcc gcc ccc agc           984
Val Pro Ser Glu Ser Pro Pro Arg Arg Gln Glu Ala Ala Ala Pro Ser
                275                 280                 285 gag gga gag agc agc ggc gac ccc acc cag tca ccg gac gcc gcc ccg          1032
Glu Gly Glu Ser Ser Gly Asp Pro Thr Gln Ser Pro Asp Ala Ala Pro
                290                 295                 300 cag tgc cct gcg ggt gcg aac ccc aac ccg ata tac cag gtg ctc tga          1080
Gln Cys Pro Ala Gly Ala Asn Pro Asn Pro Ile Tyr Gln Val Leu
305                 310                 315 gggggatgtg gccgcccaac cccgccaggg atggtgccct agggtccctc gcgcccaaaa        1140
gattgaactt aaatgccccc ctcccaacag cgctttaaaa gcgccatctc ttgaggtagg        1200
agaggcggag aactgaagtt tccgcccccc ccgacagggc aaggacacag cgcggttttt        1260
tccacgcagc acccttctcg agacccatt gcgatggccg ctccgtgttc ctcggtgggc         1320
cagagctgaa ccttgagggg ctaggttcac gtttctcgcg ccctccatgg tgagaccctc        1380
gcagacctaa ccctgccccg ggatgcaccg gttatttggg ggggcgtgag acagtgcact        1440
ccggtcccaa atgtagcagg tgtaaccgta acccaccccc aacccgtttc ccggttcagg        1500 accactttt gtaatacttt ttgtaatcta ttcctgtaaa taagagttcg tttgccagag         1560
aggagcccct ggggctgtat ttatctctga ggcagggtgt gtggtgctac agggaatttg        1620
tacgtttata ccgcaggcgg gcgagccgcg ggcgctcgct caggtgatca aaataaaggc        1680
gctaatttat aa                                                           1692
```

<210> SEQ ID NO 10
<211> LENGTH: 319
<212> TYPE: PRT
<213> ORGANISM: Homo sapiens

<400> SEQUENCE: 10

```
Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
                20                  25                  30

Pro Cys Phe Asp Ser Pro Asp Leu Arg Phe Phe Glu Asp Leu Asp Pro
            35                  40                  45

Arg Leu Met His Val Gly Ala Leu Leu Lys Pro Glu Glu His Ser His
        50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95
```

```
Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
            115                 120                 125

Phe Glu Thr Leu Lys Arg Cys Thr Ser Ser Asn Pro Asn Gln Arg Leu
        130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Gly Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Ala Arg Arg Arg Asn Cys
        210                 215                 220

Tyr Glu Gly Ala Tyr Tyr Asn Glu Ala Pro Ser Glu Pro Arg Pro Gly
225                 230                 235                 240

Lys Ser Ala Ala Val Ser Ser Leu Asp Tyr Leu Ser Ser Ile Val Glu
                245                 250                 255

Arg Ile Ser Thr Glu Ser Pro Ala Ala Pro Ala Leu Leu Leu Ala Asp
            260                 265                 270

Val Pro Ser Glu Ser Pro Pro Arg Arg Gln Gly Ala Ala Ala Pro Ser
            275                 280                 285

Glu Gly Glu Ser Ser Gly Asp Pro Thr Gln Ser Pro Asp Ala Ala Pro
            290                 295                 300

Gln Cys Pro Ala Gly Ala Asn Pro Asn Pro Ile Tyr Gln Val Leu
305                 310                 315

<210> SEQ ID NO 11
<211> LENGTH: 1427
<212> TYPE: DNA
<213> ORGANISM: Homo sapiens
<220> FEATURE:
<221> NAME/KEY: CDS
<222> LOCATION: (43)..(810)

<400> SEQUENCE: 11
cctctcgctg ccgtccaggt gcaccgcctg cctctcagca gg atg gac gtg atg          54
                                            Met Asp Val Met
                                              1 gat ggc tgc cag ttc tca cct tct gag tac ttc tac gac ggc tcc tgc        102
Asp Gly Cys Gln Phe Ser Pro Ser Glu Tyr Phe Tyr Asp Gly Ser Cys
  5                  10                  15                  20 ata ccg tcc ccc gag ggt gaa ttt ggg gac gag ttt gtg ccg cga gtg        150
Ile Pro Ser Pro Glu Gly Glu Phe Gly Asp Glu Phe Val Pro Arg Val
                 25                  30                  35 gct gcc ttc gga gcg cac aaa gca gag ctg cag ggc tca gat gag gac        198
Ala Ala Phe Gly Ala His Lys Ala Glu Leu Gln Gly Ser Asp Glu Asp
             40                  45                  50 gag cac gtg cga gcg cct acc ggc cac cac cag gct ggt cac tgc ctc        246
Glu His Val Arg Ala Pro Thr Gly His His Gln Ala Gly His Cys Leu
         55                  60                  65 atg tgg gcc tgc aaa gcc tgc aag agg aag tcc acc acc atg gat cgg        294
Met Trp Ala Cys Lys Ala Cys Lys Arg Lys Ser Thr Thr Met Asp Arg
     70                  75                  80 cgg aag gca gcc act atg cgc gag cgg agg cgc ctg aag aag gtc aac        342
Arg Lys Ala Ala Thr Met Arg Glu Arg Arg Arg Leu Lys Lys Val Asn
```

```
cag gct ttc gaa acc ctc aag agg tgt acc acg acc aac ccc aac cag        390
Gln Ala Phe Glu Thr Leu Lys Arg Cys Thr Thr Thr Asn Pro Asn Gln
             105                 110                 115 agg ctg ccc aag gtg gag atc ctc agg aat gcc atc cgc tac atc gag        438
Arg Leu Pro Lys Val Glu Ile Leu Arg Asn Ala Ile Arg Tyr Ile Glu
         120                 125                 130 agc ctg cag gag ttg ctg aga gag cag gtg gag aac tac tat agc ctg        486
Ser Leu Gln Glu Leu Leu Arg Glu Gln Val Glu Asn Tyr Tyr Ser Leu
     135                 140                 145 ccg gga cag agc tgc tcg gag ccc acc agc ccc acc tcc aac tgc tct        534
Pro Gly Gln Ser Cys Ser Glu Pro Thr Ser Pro Thr Ser Asn Cys Ser
 150                 155                 160 gat ggc atg ccc gaa tgt aac agt cct gtc tgg tcc aga aag agc agt        582
Asp Gly Met Pro Glu Cys Asn Ser Pro Val Trp Ser Arg Lys Ser Ser
165                 170                 175                 180 act ttt gac agc atc tac tgt cct gat gta tca aat gta tat gcc aca        630
Thr Phe Asp Ser Ile Tyr Cys Pro Asp Val Ser Asn Val Tyr Ala Thr
                 185                 190                 195 gat aaa aac tcc tta tcc agc ttg gat tgc tta tcc aac ata gtg gac        678
Asp Lys Asn Ser Leu Ser Ser Leu Asp Cys Leu Ser Asn Ile Val Asp
             200                 205                 210 cgg atc acc tcc tca gag caa cct ggg ttg cct ctc cag gat ctg gct        726
Arg Ile Thr Ser Ser Glu Gln Pro Gly Leu Pro Leu Gln Asp Leu Ala
         215                 220                 225 tct ctc tct cca gtt gcc agc acc gat tca cag cct cga act cca ggg        774
Ser Leu Ser Pro Val Ala Ser Thr Asp Ser Gln Pro Arg Thr Pro Gly
     230                 235                 240 gct tct agt tcc agg ctt atc tat cat gtg cta tga actaattttc             820
Ala Ser Ser Ser Arg Leu Ile Tyr His Val Leu
245                 250                 255 tggtctatat gacttcttcc aggagggcct aatacacagg acgaagaagg cttcaaaaag      880
tcccaaacca agacaacatg tacataaaga tttcttttca gttgtaaatt tgtaaagatt      940
accttgccac tttataagaa agtgtattta actaaaaagt catcattgca aataatactt     1000
tcttcttctt tattattctt tgcttagata ttaaatacata gttccagtaa tactatttct    1060
gatagggggc cattgattga gggtagcttg ttcgaatgct taacttatat atacatatat     1120
atatattata aatattgctc atcaaaatgt ctctggtgtt tagagcttta ttttttttctt    1180 taaaacatta aaacagctga gaatcagtta aatggaattt taaatatatt taactatttc    1240
ttttctcttt aatcctttag ttatattgta ttaaataaaa atataatact gcctaatgta    1300
tatattttga tcttttcttg taagaaatgt atcttttaaa tgtaagcaca aaatagtact    1360
ttgtggatca tttcaagata taagaaattt tggaaattcc accataaata aaattttta    1420 ctacaag                                                              1427

<210> SEQ ID NO 12
<211> LENGTH: 255
<212> TYPE: PRT
<213> ORGANISM: Homo sapiens

<400> SEQUENCE: 12

Met Asp Val Met Asp Gly Cys Gln Phe Ser Pro Ser Glu Tyr Phe Tyr
1               5                   10                  15

Asp Gly Ser Cys Ile Pro Ser Pro Glu Gly Glu Phe Gly Asp Glu Phe
            20                  25                  30

Val Pro Arg Val Ala Ala Phe Gly Ala His Lys Ala Glu Leu Gln Gly
```

```
                    35                  40                  45
Ser Asp Glu Asp Glu His Val Arg Ala Pro Thr Gly His His Gln Ala
 50                  55                  60
Gly His Cys Leu Met Trp Ala Cys Lys Ala Cys Lys Arg Lys Ser Thr
 65                  70                  75                  80
Thr Met Asp Arg Arg Lys Ala Ala Thr Met Arg Glu Arg Arg Arg Leu
                 85                  90                  95
Lys Lys Val Asn Gln Ala Phe Glu Thr Leu Lys Arg Cys Thr Thr Thr
                100                 105                 110
Asn Pro Asn Gln Arg Leu Pro Lys Val Glu Ile Leu Arg Asn Ala Ile
            115                 120                 125
Arg Tyr Ile Glu Ser Leu Gln Glu Leu Leu Arg Glu Gln Val Glu Asn
130                 135                 140
Tyr Tyr Ser Leu Pro Gly Gln Ser Cys Ser Glu Pro Thr Ser Pro Thr
145                 150                 155                 160
Ser Asn Cys Ser Asp Gly Met Pro Glu Cys Asn Ser Pro Val Trp Ser
                165                 170                 175
Arg Lys Ser Ser Thr Phe Asp Ser Ile Tyr Cys Pro Asp Val Ser Asn
            180                 185                 190
Val Tyr Ala Thr Asp Lys Asn Ser Leu Ser Ser Leu Asp Cys Leu Ser
        195                 200                 205
Asn Ile Val Asp Arg Ile Thr Ser Ser Glu Gln Pro Gly Leu Pro Leu
210                 215                 220
Gln Asp Leu Ala Ser Leu Ser Pro Val Ala Ser Thr Asp Ser Gln Pro
225                 230                 235                 240
Arg Thr Pro Gly Ala Ser Ser Ser Arg Leu Ile Tyr His Val Leu
                245                 250                 255

<210> SEQ ID NO 13
<211> LENGTH: 675
<212> TYPE: DNA
<213> ORGANISM: Homo sapiens
<220> FEATURE:
<221> NAME/KEY: CDS
<222> LOCATION: (1)..(675)

<400> SEQUENCE: 13 atg gag ctg tat gag aca tcc ccc tac ttc tac cag gaa ccc cgc ttc      48
Met Glu Leu Tyr Glu Thr Ser Pro Tyr Phe Tyr Gln Glu Pro Arg Phe
  1               5                  10                  15 tat gat ggg gaa aac tac ctg cct gtc cac ctc cag ggc ttc gaa cca      96
Tyr Asp Gly Glu Asn Tyr Leu Pro Val His Leu Gln Gly Phe Glu Pro
                 20                  25                  30 cca ggc tac gag cgg acg gag ctc acc ctg agc ccc gag gcc cca ggg     144
Pro Gly Tyr Glu Arg Thr Glu Leu Thr Leu Ser Pro Glu Ala Pro Gly
             35                  40                  45 ccc ctt gag gac aag ggg ctg ggg acc ccc gag cac tgt cca ggc cag     192
Pro Leu Glu Asp Lys Gly Leu Gly Thr Pro Glu His Cys Pro Gly Gln
 50                  55                  60 tgc ctg ccg tgg gcg tgt aag gtg tgt aag agg aag tcg gtg tcc gtg     240
Cys Leu Pro Trp Ala Cys Lys Val Cys Lys Arg Lys Ser Val Ser Val
 65                  70                  75                  80 gac cgg cgg cgg gcg gcc aca ctg agg gag aag cgc agg ctc aag aag     288
Asp Arg Arg Arg Ala Ala Thr Leu Arg Glu Lys Arg Arg Leu Lys Lys
                 85                  90                  95 gtg aat gag gcc ttc gag gcc ctg aag aga agc acc ctg ctc aac ccc     336
Val Asn Glu Ala Phe Glu Ala Leu Lys Arg Ser Thr Leu Leu Asn Pro
            100                 105                 110
```

```
aac cag cgg ctg ccc aag gtg gag atc ctg cgc agt gcc atc cag tac       384
Asn Gln Arg Leu Pro Lys Val Glu Ile Leu Arg Ser Ala Ile Gln Tyr
        115                 120                 125 atc gag cgc ctc cag gcc ctg ctc agc tcc ctc aac cag gag gag cgt       432
Ile Glu Arg Leu Gln Ala Leu Leu Ser Ser Leu Asn Gln Glu Glu Arg
130                 135                 140 gac ctc cgc tac cgg ggc ggg ggg ccc cag cca ggg gtg ccc agc           480
Asp Leu Arg Tyr Arg Gly Gly Gly Pro Gln Pro Gly Val Pro Ser
145                 150                 155                 160 gaa tgc agc tct cac agc gcc tcc tgc agt cca gag tgg ggc agt gca       528
Glu Cys Ser Ser His Ser Ala Ser Cys Ser Pro Glu Trp Gly Ser Ala
                165                 170                 175 ctg gag ttc agc gcc aac cca ggg gat cat ctg ctc acg gct gac cct       576
Leu Glu Phe Ser Ala Asn Pro Gly Asp His Leu Leu Thr Ala Asp Pro
        180                 185                 190 aca gat gcc cac aac ctg cac tcc ctc acc tcc atc gtg gac agc atc       624
Thr Asp Ala His Asn Leu His Ser Leu Thr Ser Ile Val Asp Ser Ile
        195                 200                 205 aca gtg gaa gat gtg tct gtg gcc ttc cca gat gaa acc atg ccc aac       672
Thr Val Glu Asp Val Ser Val Ala Phe Pro Asp Glu Thr Met Pro Asn
210                 215                 220 tag                                                                    675

<210> SEQ ID NO 14
<211> LENGTH: 224
<212> TYPE: PRT
<213> ORGANISM: Homo sapiens

<400> SEQUENCE: 14
```

Met Glu Leu Tyr Glu Thr Ser Pro Tyr Phe Tyr Gln Glu Pro Arg Phe
1               5                   10                  15

Tyr Asp Gly Glu Asn Tyr Leu Pro Val His Leu Gln Gly Phe Glu Pro
                20                  25                  30

Pro Gly Tyr Glu Arg Thr Glu Leu Thr Leu Ser Pro Glu Ala Pro Gly
            35                  40                  45

Pro Leu Glu Asp Lys Gly Leu Gly Thr Pro Glu His Cys Pro Gly Gln
    50                  55                  60

Cys Leu Pro Trp Ala Cys Lys Val Cys Lys Arg Lys Ser Val Ser Val
65                  70                  75                  80

Asp Arg Arg Arg Ala Ala Thr Leu Arg Glu Lys Arg Arg Leu Lys Lys
                85                  90                  95

Val Asn Glu Ala Phe Glu Ala Leu Lys Arg Ser Thr Leu Leu Asn Pro
            100                 105                 110

Asn Gln Arg Leu Pro Lys Val Glu Ile Leu Arg Ser Ala Ile Gln Tyr
        115                 120                 125

Ile Glu Arg Leu Gln Ala Leu Leu Ser Ser Leu Asn Gln Glu Glu Arg
    130                 135                 140

Asp Leu Arg Tyr Arg Gly Gly Gly Pro Gln Pro Gly Val Pro Ser
145                 150                 155                 160

Glu Cys Ser Ser His Ser Ala Ser Cys Ser Pro Glu Trp Gly Ser Ala
                165                 170                 175

Leu Glu Phe Ser Ala Asn Pro Gly Asp His Leu Leu Thr Ala Asp Pro
            180                 185                 190

Thr Asp Ala His Asn Leu His Ser Leu Thr Ser Ile Val Asp Ser Ile
        195                 200                 205

Thr Val Glu Asp Val Ser Val Ala Phe Pro Asp Glu Thr Met Pro Asn

<210> SEQ ID NO 15
<211> LENGTH: 3935
<212> TYPE: DNA
<213> ORGANISM: Homo sapiens
<220> FEATURE:
<221> NAME/KEY: CDS
<222> LOCATION: (373)..(1902)

<400> SEQUENCE: 15

```
ggagagccga aagcggagct cgaaactgac tggaaacttc agtggcgcgg agactcgcca      60
gtttcaaccc cggaaacttt tctttgcagg aggagaagag aagggggtgca agcgccccca     120 cttttgctct ttttcctccc ctcctcctcc tctccaattc gcctcccccc acttggagcg     180
ggcagctgtg aactggccac cccgcgcctt cctaagtgct cgccgcggta gccggccgac     240
gcgccagctt ccccgggagc cgcttgctcc gcatccgggc agccgagggg agaggagccc     300
gcgcctcgag tccccgagcc gccgcggctt ctcgcctttc ccggccacca gccccctgcc     360
ccgggcccgc gt atg aat ctc ctg gac ccc ttc atg aag atg acc gac gag     411
           Met Asn Leu Leu Asp Pro Phe Met Lys Met Thr Asp Glu
             1               5                  10
```

| cag gag aag ggc ctg tcc ggc gcc ccc agc ccc acc atg tcc gag gac | 459 |
|---|---|
| Gln Glu Lys Gly Leu Ser Gly Ala Pro Ser Pro Thr Met Ser Glu Asp | |
| 15                20               25 | |

```
tcc gcg ggc tcg ccc tgc ccg tcg ggc tcg ggc tcg gac acc gag aac     507
Ser Ala Gly Ser Pro Cys Pro Ser Gly Ser Gly Ser Asp Thr Glu Asn
 30               35                  40                  45 acg cgg ccc cag gag aac acg ttc ccc aag ggc gag ccc gat ctg aag     555
Thr Arg Pro Gln Glu Asn Thr Phe Pro Lys Gly Glu Pro Asp Leu Lys
                 50                  55                  60 aag gag agc gag gag gac aag ttc ccc gtg tgc atc cgc gag gcg gtc     603
Lys Glu Ser Glu Glu Asp Lys Phe Pro Val Cys Ile Arg Glu Ala Val
             65                  70                  75 agc cag gtg ctc aaa ggc tac gac tgg acg ctg gtg ccc atg ccg gtg     651
Ser Gln Val Leu Lys Gly Tyr Asp Trp Thr Leu Val Pro Met Pro Val
         80                  85                  90 cgc gtc aac ggc tcc agc aag aac aag ccg cac gtc aag cgg ccc atg     699
Arg Val Asn Gly Ser Ser Lys Asn Lys Pro His Val Lys Arg Pro Met
 95                 100                 105 aac gcc ttc atg gtg tgg gcg cag gcg gcg cgc agg aag ctc gcg gac     747
Asn Ala Phe Met Val Trp Ala Gln Ala Ala Arg Arg Lys Leu Ala Asp
110                 115                 120                 125 cag tac ccg cac ttg cac aac gcc gag ctc agc aag acg ctg ggc aag     795
Gln Tyr Pro His Leu His Asn Ala Glu Leu Ser Lys Thr Leu Gly Lys
                130                 135                 140 ctc tgg aga ctt ctg aac gag agc gag aag cgg ccc ttc gtg gag gag     843
Leu Trp Arg Leu Leu Asn Glu Ser Glu Lys Arg Pro Phe Val Glu Glu
            145                 150                 155 gcg gag cgg ctg cgc gtg cag cac aag aag gac cac ccg gat tac aag     891
Ala Glu Arg Leu Arg Val Gln His Lys Lys Asp His Pro Asp Tyr Lys
        160                 165                 170 tac cag ccg cgg cgg agg aag tcg gtg aag aac ggg cag gcg gag gca     939
Tyr Gln Pro Arg Arg Arg Lys Ser Val Lys Asn Gly Gln Ala Glu Ala
    175                 180                 185 gag gag gcc acg gag cag acg cac atc tcc ccc aac gcc atc ttc aag     987
Glu Glu Ala Thr Glu Gln Thr His Ile Ser Pro Asn Ala Ile Phe Lys
190                 195                 200                 205 gcg ctg cag gcc gac tcg cca cac tcc tcc tcc ggc atg agc gag gtg    1035
Ala Leu Gln Ala Asp Ser Pro His Ser Ser Ser Gly Met Ser Glu Val
                210                 215                 220
```

-continued

|  |  |  |  |  |  |  | 210 |  |  |  | 215 |  |  |  | 220 |  |  |  |
|---|---|---|---|---|---|---|---|---|---|---|---|---|---|---|---|---|---|---|
| cac | tcc | ccc | ggc | gag | cac | tcg | ggg | caa | tcc | cag | ggc | cca | ccg | acc | cca |  |  | 1083 |
| His | Ser | Pro | Gly | Glu | His | Ser | Gly | Gln | Ser | Gln | Gly | Pro | Pro | Thr | Pro |  |  |  |
|  |  |  |  | 225 |  |  |  |  | 230 |  |  |  |  | 235 |  |  |  |  |

```
ccc acc acc ccc aaa acc gac gtg cag ccg ggc aag gct gac ctg aag   1131
Pro Thr Thr Pro Lys Thr Asp Val Gln Pro Gly Lys Ala Asp Leu Lys
            240                 245                 250 cga gag ggg cgc ccc ttg cca gag ggg ggc aga cag ccc cct atc gac   1179
Arg Glu Gly Arg Pro Leu Pro Glu Gly Gly Arg Gln Pro Pro Ile Asp
        255                 260                 265 ttc cgc gac gtg gac atc ggc gag ctg agc agc gac gtc atc tcc aac   1227
Phe Arg Asp Val Asp Ile Gly Glu Leu Ser Ser Asp Val Ile Ser Asn
270                 275                 280                 285 atc gag acc ttc gat gtc aac gag ttt gac cag tac ctg ccg ccc aac   1275
Ile Glu Thr Phe Asp Val Asn Glu Phe Asp Gln Tyr Leu Pro Pro Asn
                290                 295                 300 ggc cac ccg ggg gtg ccg gcc acg cac ggc cag gtc acc tac acg ggc   1323
Gly His Pro Gly Val Pro Ala Thr His Gly Gln Val Thr Tyr Thr Gly
            305                 310                 315 agc tac ggc atc agc agc acc gcg gcc acc ccg gcg agc gcg ggc cac   1371
Ser Tyr Gly Ile Ser Ser Thr Ala Ala Thr Pro Ala Ser Ala Gly His
        320                 325                 330 gtg tgg atg tcc aag cag cag gcg ccg cca ccc ccg cag cag ccc       1419
Val Trp Met Ser Lys Gln Gln Ala Pro Pro Pro Pro Gln Gln Pro
335                 340                 345 cca cag gcc ccg ccg gcc ccg cag gcg ccc ccg cag ccg cag gcg gcg   1467
Pro Gln Ala Pro Pro Ala Pro Gln Ala Pro Pro Gln Pro Gln Ala Ala
350                 355                 360                 365 ccc cca cag cag ccg gcg gca ccc ccg cag cag cca cag gcg cac acg   1515
Pro Pro Gln Gln Pro Ala Ala Pro Pro Gln Gln Pro Gln Ala His Thr
                370                 375                 380 ctg acc acg ctg agc agc gag ccg ggc cag tcc cag cga acg cac atc   1563
Leu Thr Thr Leu Ser Ser Glu Pro Gly Gln Ser Gln Arg Thr His Ile
            385                 390                 395 aag acg gag cag ctg agc ccc agc cac tac agc gag cag cag cag cac   1611
Lys Thr Glu Gln Leu Ser Pro Ser His Tyr Ser Glu Gln Gln Gln His
        400                 405                 410 tcg ccc caa cag atc gcc tac agc ccc ttc aac ctc cca cac tac agc   1659
Ser Pro Gln Gln Ile Ala Tyr Ser Pro Phe Asn Leu Pro His Tyr Ser
415                 420                 425 ccc tcc tac ccg ccc atc acc cgc tca cag tac gac tac acc gac cac   1707
Pro Ser Tyr Pro Pro Ile Thr Arg Ser Gln Tyr Asp Tyr Thr Asp His
430                 435                 440                 445 cag aac tcc agc tcc tac tac agc cac gcg gca ggc cag ggc acc ggc   1755
Gln Asn Ser Ser Ser Tyr Tyr Ser His Ala Ala Gly Gln Gly Thr Gly
                450                 455                 460 ctc tac tcc acc ttc acc tac atg aac ccc gct cag cgc ccc atg tac   1803
Leu Tyr Ser Thr Phe Thr Tyr Met Asn Pro Ala Gln Arg Pro Met Tyr
            465                 470                 475 acc ccc atc gcc gac acc tct ggg gtc cct tcc atc ccg cag acc cac   1851
Thr Pro Ile Ala Asp Thr Ser Gly Val Pro Ser Ile Pro Gln Thr His
        480                 485                 490 agc ccc cag cac tgg gaa caa ccc gtc tac aca cag ctc act cga cct   1899
Ser Pro Gln His Trp Glu Gln Pro Val Tyr Thr Gln Leu Thr Arg Pro
495                 500                 505 tga ggaggcctcc cacgaagggc gaagatggcc gagatgatcc taaaaataac       1952
cgaagaaaga gaggaccaac cagaattccc tttggacatt tgtgtttttt tgttttttta   2012
ttttgttttg ttttttcttc ttcttcttct tccttaaaga catttaagct aaaggcaact  2072
```

```
cgtacccaaa tttccaagac acaaacatga cctatccaag cgcattaccc acttgtggcc    2132
aatcagtggc caggccaacc ttggctaaat ggagcagcga atcaacgag  aaactggact    2192
ttttaaaccc tcttcagagc aagcgtggag gatgatggag aatcgtgtga tcagtgtgct    2252
aaatctctct gcctgtttgg actttgtaat tatttttta  gcagtaatta aagaaaaaag    2312
tcctctgtga ggaatattct ctatttaaa  tattttagt  atgtactgtg tatgattcat    2372
taccattttg aggggattta tacatatttt tagataaaat taaatgctct tatttttcca    2432
acagctaaac tactcttagt tgaacagtgt gccctagctt tcttgcaac  cagagtattt    2492
ttgtacagat ttgctttctc ttacaaaaag aaaaaaaaaa tcctgttgta ttaacattta    2552
aaaacagaat tgtgttatgt gatcagtttt ggggttaac  tttgcttaat tcctcaggct    2612
ttgcgattta aggaggagct gccttaaaaa aaataaagg  ccttattttg caattatggg    2672
agtaaacaat agtctagaga agcatttggt aagctttatc atatatatat tttttaaaga    2732
agagaaaaac accttgagcc ttaaaacggt gctgctggga acatttgca  ctcttttagt    2792
gcatttcctc ctgcctttgc ttgttcactg cagtcttaag aaagaggtaa aaggcaagca    2852
aaggagatga aatctgttct gggaatgttt cagcagccaa taagtgcccg agcacactgc    2912
ccccggttgc ctgcctgggc cccatgtgga aggcagatgc ctgctcgctc tgtcacctgt    2972
gcctctcaga acaccagcag ttaaccttca agacattcca cttgctaaaa ttatttattt    3032
tgtaaggaga ggttttaatt aaaacaaaaa aaaattcttt ttttttttt  tttccaattt    3092
taccttcttt aaaataggtt gttggagctt cctcaaagg  gtatggtcat ctgttgttaa    3152
attatgttct taactgtaac cagtttttt  ttatttatct ctttaatctt tttttattat    3212
taaaagcaag tttctttgta ttcctcaccc tagatttgta taaatgcctt tttgtccatc    3272
cctttttct  ttgttgtttt tgttgaaaac aaactggaaa cttgtttctt tttttgtata    3332
aatgagagat tgcaaatgta gtgtatcact gagtcatttg cagtgttttc tgccacagac    3392
ctttgggctg ccttatattg tgtgtgtgtg tgggtgtgtg tgtgttttga cacaaaaaca    3452
atgcaagcat gtgtcatcca tatttctcta catcttctct tggagtgagg gaggctacct    3512
ggaggggatc agcccactga cagaccttaa tcttaattac tgctgtggct agagagtttg    3572
aggattgctt tttaaaaaag acagcaaact ttttttttta tttaaaaaaa gatatattaa    3632
cagttttaga agtcagtaga ataaaatctt aaagcactca taatatggca tccttcaatt    3692
tctgtataaa agcagatctt tttaaaaaga tacttctgta acttaagaaa cctggcattt    3752
aaatcatatt ttgtctttag gtaaaagctt tggtttgtgt tcgtgttttg tttgtttcac    3812
ttgtttccct cccagcccca aacctttgt  tctctccgtg aaacttacct ttcccttttt    3872
ctttctcttt ttttttttg  tatattattg tttacaataa atatacattg cattaaaaag    3932
aaa                                                                   3935
```

<210> SEQ ID NO 16
<211> LENGTH: 509
<212> TYPE: PRT
<213> ORGANISM: Homo sapiens

<400> SEQUENCE: 16

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

```
Ser Pro Cys Pro Ser Gly Ser Gly Ser Asp Thr Glu Asn Thr Arg Pro
            35                  40                  45

Gln Glu Asn Thr Phe Pro Lys Gly Glu Pro Asp Leu Lys Lys Glu Ser
 50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
                100                 105                 110

Met Val Trp Ala Gln Ala Ala Arg Arg Lys Leu Ala Asp Gln Tyr Pro
            115                 120                 125

His Leu His Asn Ala Glu Leu Ser Lys Thr Leu Gly Lys Leu Trp Arg
            130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
            195                 200                 205

Ala Asp Ser Pro His Ser Ser Ser Gly Met Ser Glu Val His Ser Pro
            210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
            275                 280                 285

Phe Asp Val Asn Glu Phe Asp Gln Tyr Leu Pro Pro Asn Gly His Pro
290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
            340                 345                 350

Pro Pro Ala Pro Gln Ala Pro Pro Gln Pro Gln Ala Ala Pro Pro Gln
            355                 360                 365

Gln Pro Ala Ala Pro Pro Gln Pro Gln Ala His Thr Leu Thr Thr
            370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
            405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
            435                 440                 445

Ser Ser Tyr Tyr Ser His Ala Ala Gly Gln Gly Thr Gly Leu Tyr Ser
```

```
                    450                 455                 460
Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
                500                 505

<210> SEQ ID NO 17
<211> LENGTH: 5060
<212> TYPE: DNA
<213> ORGANISM: Homo sapiens
<220> FEATURE:
<221> NAME/KEY: CDS
<222> LOCATION: (158)..(4621)

<400> SEQUENCE: 17
acgcagagcg ctgctgggct gccgggtctc ccgcttcctc ctcctgctcc aagggcctcc      60
tgcatgaggg cgcggtagag acccggaccc gcgccgtgct cctgccgttt cgctgcgctc    120
cgcccgggcc cggctcagcc aggccccgcg gtgagcc atg att cgc ctc ggg gct     175
                                         Met Ile Arg Leu Gly Ala
                                           1               5 ccc cag tcg ctg gtg ctg ctg acg ctc ctc gtc gcc gct gtc ctt cgg      223
Pro Gln Ser Leu Val Leu Leu Thr Leu Leu Val Ala Ala Val Leu Arg
               10                  15                  20 tgt cag ggc cag gat gtc cag gag gct ggc agc tgt gtg cag gat ggg      271
Cys Gln Gly Gln Asp Val Gln Glu Ala Gly Ser Cys Val Gln Asp Gly
           25                  30                  35 cag agg tat aat gat aag gat gtg tgg aag ccg gag ccc tgc cgg atc      319
Gln Arg Tyr Asn Asp Lys Asp Val Trp Lys Pro Glu Pro Cys Arg Ile
 40                  45                  50 tgt gtc tgt gac act ggg act gtc ctc tgc gac gac ata atc tgt gaa      367
Cys Val Cys Asp Thr Gly Thr Val Leu Cys Asp Asp Ile Ile Cys Glu
 55                  60                  65                  70 gac gtg aaa gac tgc ctc agc cct gag atc ccc ttc gga gag tgc tgc      415
Asp Val Lys Asp Cys Leu Ser Pro Glu Ile Pro Phe Gly Glu Cys Cys
                 75                  80                  85 ccc atc tgc cca act gac ctc gcc act gcc agt ggg caa cca gga cca      463
Pro Ile Cys Pro Thr Asp Leu Ala Thr Ala Ser Gly Gln Pro Gly Pro
             90                  95                 100 aag gga cag aaa gga gaa cct gga gac atc aag gat att gta gga ccc      511
Lys Gly Gln Lys Gly Glu Pro Gly Asp Ile Lys Asp Ile Val Gly Pro
        105                 110                 115 aaa gga cct cct ggg cct cag gga cct gca ggg gaa caa gga ccc aga      559
Lys Gly Pro Pro Gly Pro Gln Gly Pro Ala Gly Glu Gln Gly Pro Arg
    120                 125                 130 ggg gat cgt ggt gac aaa ggt gaa aaa ggt gcc cct gga cct cgt ggc      607
Gly Asp Arg Gly Asp Lys Gly Glu Lys Gly Ala Pro Gly Pro Arg Gly
135                 140                 145                 150 aga gat gga gaa cct ggg acc cct gga aat cct ggc ccc cct ggt cct      655
Arg Asp Gly Glu Pro Gly Thr Pro Gly Asn Pro Gly Pro Pro Gly Pro
                155                 160                 165 ccc ggc ccc cct ggt ccc cct ggt ctt ggt gga aac ttt gct gcc cag      703
Pro Gly Pro Pro Gly Pro Pro Gly Leu Gly Gly Asn Phe Ala Ala Gln
            170                 175                 180 atg gct gga gga ttt gat gaa aag gct ggt ggc gcc cag ttg gga gta      751
Met Ala Gly Gly Phe Asp Glu Lys Ala Gly Gly Ala Gln Leu Gly Val
        185                 190                 195 atg caa gga cca atg ggc ccc atg gga cct cga gga cct cca ggc cct      799
```

```
                Met Gln Gly Pro Met Gly Pro Met Gly Pro Arg Gly Pro Gly Pro
                    200             205             210 gca ggt gct cct ggg cct caa gga ttt caa ggc aat cct ggt gaa cct      847
Ala Gly Ala Pro Gly Pro Gln Gly Phe Gln Gly Asn Pro Gly Glu Pro
215                 220                 225                 230 ggt gaa cct ggt gtc tct ggt ccc atg ggt ccc cgt ggt cct cct ggt      895
Gly Glu Pro Gly Val Ser Gly Pro Met Gly Pro Arg Gly Pro Pro Gly
                235                 240                 245 ccc cct gga aag cct ggt gat gat ggt gaa gct gga aaa cct gga aaa      943
Pro Pro Gly Lys Pro Gly Asp Asp Gly Glu Ala Gly Lys Pro Gly Lys
            250                 255                 260 gct ggt gaa agg ggt ccg cct ggt cct cag ggt gct cgt ggt ttc cca      991
Ala Gly Glu Arg Gly Pro Pro Gly Pro Gln Gly Ala Arg Gly Phe Pro
        265                 270                 275 gga acc cca ggc ctt cct ggt gtc aaa ggt cac aga ggt tat cca ggc     1039
Gly Thr Pro Gly Leu Pro Gly Val Lys Gly His Arg Gly Tyr Pro Gly
    280                 285                 290 ctg gac ggt gct aag gga gag gcg ggt gct cct ggt gtg aag ggt gag     1087
Leu Asp Gly Ala Lys Gly Glu Ala Gly Ala Pro Gly Val Lys Gly Glu
295                 300                 305                 310 agt ggt tcc ccg ggt gag aac gga tct ccg ggc cca atg ggt cct cgt     1135
Ser Gly Ser Pro Gly Glu Asn Gly Ser Pro Gly Pro Met Gly Pro Arg
                315                 320                 325 ggc ctg cct ggt gaa aga gga cgg act ggc cct gct ggc gct gcg ggt     1183
Gly Leu Pro Gly Glu Arg Gly Arg Thr Gly Pro Ala Gly Ala Ala Gly
            330                 335                 340 gcc cga ggc aac gat ggt cag cca ggc ccc gca ggt cct ccg ggt cct     1231
Ala Arg Gly Asn Asp Gly Gln Pro Gly Pro Ala Gly Pro Pro Gly Pro
        345                 350                 355 gtc ggt cct gct ggt ggt cct ggc ttc cct ggt gct cct gga gcc aag     1279
Val Gly Pro Ala Gly Gly Pro Gly Phe Pro Gly Ala Pro Gly Ala Lys
    360                 365                 370 ggt gaa gcc ggc ccc act ggt gcc cgt ggt cct gaa ggt gct caa ggt     1327
Gly Glu Ala Gly Pro Thr Gly Ala Arg Gly Pro Glu Gly Ala Gln Gly
375                 380                 385                 390 cct cgc ggt gaa cct ggt act cct ggg tcc cct ggg cct gct ggt gcc     1375
Pro Arg Gly Glu Pro Gly Thr Pro Gly Ser Pro Gly Pro Ala Gly Ala
                395                 400                 405 tcc ggt aac cct gga aca gat gga att cct gga gcc aaa gga tct gct     1423
Ser Gly Asn Pro Gly Thr Asp Gly Ile Pro Gly Ala Lys Gly Ser Ala
            410                 415                 420 ggt gct cct ggc att gct ggt gct cct ggc ttc cct ggg cca cgg ggt     1471
Gly Ala Pro Gly Ile Ala Gly Ala Pro Gly Phe Pro Gly Pro Arg Gly
        425                 430                 435 cct cct ggc cct caa ggt gca act ggt cct ctg ggc ccg aaa ggt cag     1519
Pro Pro Gly Pro Gln Gly Ala Thr Gly Pro Leu Gly Pro Lys Gly Gln
    440                 445                 450 acg ggt gaa cct ggt att gct ggc ttc aaa ggt gaa caa ggc ccc aag     1567
Thr Gly Glu Pro Gly Ile Ala Gly Phe Lys Gly Glu Gln Gly Pro Lys
455                 460                 465                 470 gga gaa cct ggc cct gct ggc ccc cag gga gcc cct gga ccc gct ggt     1615
Gly Glu Pro Gly Pro Ala Gly Pro Gln Gly Ala Pro Gly Pro Ala Gly
                475                 480                 485 gaa gaa ggc aag aga ggt gcc cgt gga gag cct ggt ggc gtt ggg ccc     1663
Glu Glu Gly Lys Arg Gly Ala Arg Gly Glu Pro Gly Gly Val Gly Pro
            490                 495                 500 atc ggt ccc cct gga gaa aga ggt gct ccc gga aac cgc ggt ttc cca     1711
Ile Gly Pro Pro Gly Glu Arg Gly Ala Pro Gly Asn Arg Gly Phe Pro
        505                 510                 515
```

-continued

| | | |
|---|---|---|
| ggt caa gat ggt ctg gca ggt ccc aag gga gcc cct gga gag cga ggg<br>Gly Gln Asp Gly Leu Ala Gly Pro Lys Gly Ala Pro Gly Glu Arg Gly<br>520 525 530 | | 1759 |
| ccc agt ggt ctt gct ggc ccc aag gga gcc aac ggt gac cct ggc cgt<br>Pro Ser Gly Leu Ala Gly Pro Lys Gly Ala Asn Gly Asp Pro Gly Arg<br>535 540 545 550 | | 1807 |
| cct gga gaa cct ggc ctt cct gga gcc cgg ggt ctc act ggc cgc cct<br>Pro Gly Glu Pro Gly Leu Pro Gly Ala Arg Gly Leu Thr Gly Arg Pro<br>555 560 565 | | 1855 |
| ggt gat gct ggt cct caa ggc aaa gtt ggc cct tct gga gcc cct ggt<br>Gly Asp Ala Gly Pro Gln Gly Lys Val Gly Pro Ser Gly Ala Pro Gly<br>570 575 580 | | 1903 |
| gaa gat ggt cgt cct gga cct cca ggt cct cag ggg gct cgt ggg cag<br>Glu Asp Gly Arg Pro Gly Pro Pro Gly Pro Gln Gly Ala Arg Gly Gln<br>585 590 595 | | 1951 |
| cct ggt gtc atg ggt ttc cct ggc ccc aaa ggt gcc aac ggt gag cct<br>Pro Gly Val Met Gly Phe Pro Gly Pro Lys Gly Ala Asn Gly Glu Pro<br>600 605 610 | | 1999 |
| ggc aaa gct ggt gag aag gga ctg cct ggt gct cct ggt ctg agg ggt<br>Gly Lys Ala Gly Glu Lys Gly Leu Pro Gly Ala Pro Gly Leu Arg Gly<br>615 620 625 630 | | 2047 |
| ctt cct ggc aaa gat ggt gag aca ggt gct gca gga ccc cct ggc cct<br>Leu Pro Gly Lys Asp Gly Glu Thr Gly Ala Ala Gly Pro Pro Gly Pro<br>635 640 645 | | 2095 |
| gct gga cct gct ggt gaa cga ggc gag cag ggt gct cct ggg cca tct<br>Ala Gly Pro Ala Gly Glu Arg Gly Glu Gln Gly Ala Pro Gly Pro Ser<br>650 655 660 | | 2143 |
| ggg ttc cag gga ctt cct ggc cct cct ggt ccc cca ggt gaa ggt gga<br>Gly Phe Gln Gly Leu Pro Gly Pro Pro Gly Pro Pro Gly Glu Gly Gly<br>665 670 675 | | 2191 |
| aaa cca ggt gac cag ggt gtt ccc ggt gaa gct gga gcc cct ggc ctc<br>Lys Pro Gly Asp Gln Gly Val Pro Gly Glu Ala Gly Ala Pro Gly Leu<br>680 685 690 | | 2239 |
| gtg ggt ccc agg ggt gaa cga ggt ttc cca ggt gaa cgt ggc tct ccc<br>Val Gly Pro Arg Gly Glu Arg Gly Phe Pro Gly Glu Arg Gly Ser Pro<br>695 700 705 710 | | 2287 |
| ggt gcc cag ggc ctc cag ggt ccc cgt ggc ctc ccc ggc act cct ggc<br>Gly Ala Gln Gly Leu Gln Gly Pro Arg Gly Leu Pro Gly Thr Pro Gly<br>715 720 725 | | 2335 |
| act gat ggt ccc aaa ggt gca tct ggc cca gca ggc ccc cct ggc gca<br>Thr Asp Gly Pro Lys Gly Ala Ser Gly Pro Ala Gly Pro Pro Gly Ala<br>730 735 740 | | 2383 |
| cag ggc cct cca ggt ctt cag gga atg cct ggc gag agg gga gca gct<br>Gln Gly Pro Pro Gly Leu Gln Gly Met Pro Gly Glu Arg Gly Ala Ala<br>745 750 755 | | 2431 |
| ggt atc gct ggg ccc aaa ggc gac agg ggt gac gtt ggt gag aaa ggc<br>Gly Ile Ala Gly Pro Lys Gly Asp Arg Gly Asp Val Gly Glu Lys Gly<br>760 765 770 | | 2479 |
| cct gag gga gcc cct gga aag gat ggt gga cga ggc ctg aca ggt ccc<br>Pro Glu Gly Ala Pro Gly Lys Asp Gly Gly Arg Gly Leu Thr Gly Pro<br>775 780 785 790 | | 2527 |
| att ggc ccc cct ggc cca gct ggt gct aac ggc gag aag gga gaa gtt<br>Ile Gly Pro Pro Gly Pro Ala Gly Ala Asn Gly Glu Lys Gly Glu Val<br>795 800 805 | | 2575 |
| gga cct cct ggt cct gca gga agt gct ggt gct cgt ggc gct ccg ggt<br>Gly Pro Pro Gly Pro Ala Gly Ser Ala Gly Ala Arg Gly Ala Pro Gly<br>810 815 820 | | 2623 |
| gaa cgt gga gag act ggc ccc ccc gga cca gcg gga ttt gct ggg cct<br>Glu Arg Gly Glu Thr Gly Pro Pro Gly Pro Ala Gly Phe Ala Gly Pro<br>825 830 835 | | 2671 |

-continued

```
cct ggt gct gat ggc cag cct ggg gcc aag ggt gag caa gga gag gcc      2719
Pro Gly Ala Asp Gly Gln Pro Gly Ala Lys Gly Glu Gln Gly Glu Ala
        840                 845                 850 ggc cag aaa ggc gat gct ggt gcc cct ggt cct cag ggc ccc tct gga      2767
Gly Gln Lys Gly Asp Ala Gly Ala Pro Gly Pro Gln Gly Pro Ser Gly
855                 860                 865                 870 gca cct ggg cct cag ggt cct act gga gtg act ggt cct aaa gga gcc      2815
Ala Pro Gly Pro Gln Gly Pro Thr Gly Val Thr Gly Pro Lys Gly Ala
                875                 880                 885 cga ggt gcc caa ggc ccc ccg gga gcc act gga ttc cct gga gct gct      2863
Arg Gly Ala Gln Gly Pro Pro Gly Ala Thr Gly Phe Pro Gly Ala Ala
            890                 895                 900 ggc cgc gtt gga ccc cca ggc tcc aat ggc aac cct gga ccc cct ggt      2911
Gly Arg Val Gly Pro Pro Gly Ser Asn Gly Asn Pro Gly Pro Pro Gly
        905                 910                 915 ccc cct ggt cct tct gga aaa gat ggt ccc aaa ggt gct cga gga gac      2959
Pro Pro Gly Pro Ser Gly Lys Asp Gly Pro Lys Gly Ala Arg Gly Asp
920                 925                 930 agc ggc ccc cct ggc cga gct ggt gaa ccc ggc ctc caa ggt cct gct      3007
Ser Gly Pro Pro Gly Arg Ala Gly Glu Pro Gly Leu Gln Gly Pro Ala
935                 940                 945                 950 gga ccc cct ggc gag aag gga gag cct gga gat gac ggt ccc tct ggt      3055
Gly Pro Pro Gly Glu Lys Gly Glu Pro Gly Asp Asp Gly Pro Ser Gly
                955                 960                 965 gcc gaa ggt cca cca ggt ccc cag ggt ctg gct ggt cag aga ggc atc      3103
Ala Glu Gly Pro Pro Gly Pro Gln Gly Leu Ala Gly Gln Arg Gly Ile
            970                 975                 980 gtc ggt ctg cct ggg caa cgt ggt gag aga gga ttc cct ggc ttg cct      3151
Val Gly Leu Pro Gly Gln Arg Gly Glu Arg Gly Phe Pro Gly Leu Pro
        985                 990                 995 ggc cca tcg ggt gag ccc ggc aag cag ggt gct cct  gga gca tct       3196
Gly Pro Ser Gly Glu Pro Gly Lys Gln Gly Ala Pro  Gly Ala Ser
1000                1005                1010 gga gac aga ggt cct cct ggc ccc gtg ggt cct cct  ggc ctg acg       3241
Gly Asp Arg Gly Pro Pro Gly Pro Val Gly Pro Pro  Gly Leu Thr
        1015                1020                1025 ggt cct gca ggt gaa ccc gga cga gag gga agc ccc  ggt gct gat       3286
Gly Pro Ala Gly Glu Pro Gly Arg Glu Gly Ser Pro  Gly Ala Asp
1030                1035                1040 ggc ccc cct ggc aga gat ggc gct gct gga gtc aag  ggt gat cgt       3331
Gly Pro Pro Gly Arg Asp Gly Ala Ala Gly Val Lys  Gly Asp Arg
        1045                1050                1055 ggt gag act ggt gct gtg gga gct cct gga gcc cct  ggg ccc cct       3376
Gly Glu Thr Gly Ala Val Gly Ala Pro Gly Ala Pro  Gly Pro Pro
1060                1065                1070 ggc tcc cct ggc ccc gct ggt cca act ggc aag caa  gga gac aga       3421
Gly Ser Pro Gly Pro Ala Gly Pro Thr Gly Lys Gln  Gly Asp Arg
        1075                1080                1085 gga gaa gct ggt gca caa ggc ccc atg gga ccc tca  gga cca gct       3466
Gly Glu Ala Gly Ala Gln Gly Pro Met Gly Pro Ser  Gly Pro Ala
1090                1095                1100 gga gcc cgg gga atc cag ggt cct caa ggc ccc aga  ggt gac aaa       3511
Gly Ala Arg Gly Ile Gln Gly Pro Gln Gly Pro Arg  Gly Asp Lys
        1105                1110                1115 gga gag gct gga gag cct ggc gag aga ggc ctg aag  gga cac cgt       3556
Gly Glu Ala Gly Glu Pro Gly Glu Arg Gly Leu Lys  Gly His Arg
1120                1125                1130 ggc ttc act ggt ctg cag ggt ctg ccc ggc cct cct  ggt cct tct       3601
Gly Phe Thr Gly Leu Gln Gly Leu Pro Gly Pro Pro  Gly Pro Ser
```

-continued

|  |  |  |  |
|---|---|---|---|
| 1135 | 1140 | 1145 | |
| gga gac caa ggt gct tct ggt cct gct ggt cct tct ggc cct aga<br>Gly Asp Gln Gly Ala Ser Gly Pro Ala Gly Pro Ser Gly Pro Arg<br>1150                   1155                  1160 | | | 3646 |
| ggt cct cct ggc ccc gtc ggt ccc tct ggc aaa gat ggt gct aat<br>Gly Pro Pro Gly Pro Val Gly Pro Ser Gly Lys Asp Gly Ala Asn<br>1165                   1170                  1175 | | | 3691 |
| gga atc cct ggc ccc att ggg cct cct ggt ccc cgt gga cga tca<br>Gly Ile Pro Gly Pro Ile Gly Pro Pro Gly Pro Arg Gly Arg Ser<br>1180                   1185                  1190 | | | 3736 |
| ggc gaa acc ggt cct gct ggt cct cct gga aat cct ggg ccc cct<br>Gly Glu Thr Gly Pro Ala Gly Pro Pro Gly Asn Pro Gly Pro Pro<br>1195                   1200                  1205 | | | 3781 |
| ggt cct cca ggt ccc cct ggc cct ggc atc gac atg tcc gcc ttt<br>Gly Pro Pro Gly Pro Pro Gly Pro Gly Ile Asp Met Ser Ala Phe<br>1210                   1215                  1220 | | | 3826 |
| gct ggc tta ggc ccg aga gag aag ggc ccc gac ccc ctg cag tac<br>Ala Gly Leu Gly Pro Arg Glu Lys Gly Pro Asp Pro Leu Gln Tyr<br>1225                   1230                  1235 | | | 3871 |
| atg cgg gcc gac cag gca gcc ggt ggc ctg aga cag cat gac gcc<br>Met Arg Ala Asp Gln Ala Ala Gly Gly Leu Arg Gln His Asp Ala<br>1240                     1245                  1250 | | | 3916 |
| gag gtg gat gcc aca ctc aag tcc ctc aac aac cag att gag agc<br>Glu Val Asp Ala Thr Leu Lys Ser Leu Asn Asn Gln Ile Glu Ser<br>1255                   1260                  1265 | | | 3961 |
| atc cgc agc ccc gag ggc tcc cgc aag aac cct gct cgc acc tgc<br>Ile Arg Ser Pro Glu Gly Ser Arg Lys Asn Pro Ala Arg Thr Cys<br>1270                   1275                  1280 | | | 4006 |
| aga gac ctg aaa ctc tgc cac cct gag tgg aag agt gga gac tac<br>Arg Asp Leu Lys Leu Cys His Pro Glu Trp Lys Ser Gly Asp Tyr<br>1285                   1290                  1295 | | | 4051 |
| tgg att gac ccc aac caa ggc tgc acc ttg gac gcc atg aag gtt<br>Trp Ile Asp Pro Asn Gln Gly Cys Thr Leu Asp Ala Met Lys Val<br>1300                     1305                  1310 | | | 4096 |
| ttc tgc aac atg gag act ggc gag act tgc gtc tac ccc aat cca<br>Phe Cys Asn Met Glu Thr Gly Glu Thr Cys Val Tyr Pro Asn Pro<br>1315                   1320                  1325 | | | 4141 |
| gca aac gtt ccc aag aag aac tgg tgg agc agc aag agc aag gag<br>Ala Asn Val Pro Lys Lys Asn Trp Trp Ser Ser Lys Ser Lys Glu<br>1330                   1335                  1340 | | | 4186 |
| aag aaa cac atc tgg ttt gga gaa acc atc aat ggt ggc ttc cat<br>Lys Lys His Ile Trp Phe Gly Glu Thr Ile Asn Gly Gly Phe His<br>1345                   1350                  1355 | | | 4231 |
| ttc agc tat gga gat gac aat ctg gct ccc aac act gcc aac gtc<br>Phe Ser Tyr Gly Asp Asp Asn Leu Ala Pro Asn Thr Ala Asn Val<br>1360                   1365                  1370 | | | 4276 |
| cag atg acc ttc cta cgc ctg ctg tcc acg gaa ggc tcc cag aac<br>Gln Met Thr Phe Leu Arg Leu Leu Ser Thr Glu Gly Ser Gln Asn<br>1375                   1380                  1385 | | | 4321 |
| atc acc tac cac tgc aag aac agc att gcc tat ctg gac gaa gca<br>Ile Thr Tyr His Cys Lys Asn Ser Ile Ala Tyr Leu Asp Glu Ala<br>1390                   1395                  1400 | | | 4366 |
| gct ggc aac ctc aag aag gcc ctc ctc atc cag ggc tcc aat gac<br>Ala Gly Asn Leu Lys Lys Ala Leu Leu Ile Gln Gly Ser Asn Asp<br>1405                   1410                  1415 | | | 4411 |
| gtg gag atc cgg gca gag ggc aat agc agg ttc acg tac act gcc<br>Val Glu Ile Arg Ala Glu Gly Asn Ser Arg Phe Thr Tyr Thr Ala<br>1420                   1425                  1430 | | | 4456 |
| ctg aag gat ggc tgc acg aaa cat acc ggt aag tgg ggc aag act | | | 4501 |

```
Leu Lys Asp Gly Cys Thr Lys His Thr Gly Lys Trp Gly Lys Thr
    1435                1440                1445 gtt atc gag tac cgg tca cag aag acc tca cgc ctc ccc atc att       4546
Val Ile Glu Tyr Arg Ser Gln Lys Thr Ser Arg Leu Pro Ile Ile
    1450                1455                1460 gac att gca ccc atg gac ata gga ggg ccc gag cag gaa ttc ggt       4591
Asp Ile Ala Pro Met Asp Ile Gly Gly Pro Glu Gln Glu Phe Gly
    1465                1470                1475 gtg gac ata ggg ccg gtc tgc ttc ttg taa aaacctgaac ccagaaacaa     4641
Val Asp Ile Gly Pro Val Cys Phe Leu
    1480                1485 cacaatccgt tgcaaaccca aaggacccaa gtactttcca atctcagtca ctctaggact 4701 ctgcactgaa tggctgacct gacctgatgt ccattcatcc caccctctca cagttcggac 4761 tttctcccc tctctttcta agagacctga actgggcaga ctgcaaaata aaatctcggt  4821
gttctattta tttattgtct tcctgtaaga ccttcgggtc aaggcagagg caggaaacta 4881 actggtgtga gtcaaatgcc ccctgagtga ctgcccccag cccaggccag aagacctccc 4941 ttcaggtgcc gggcgcagga actgtgtgtg tcctacacaa tggtgctatt ctgtgtcaaa 5001 cacctctgta ttttttaaaa catcaattga tattaaaaat gaaagatta ttggaaagt   5060

<210> SEQ ID NO 18
<211> LENGTH: 1487
<212> TYPE: PRT
<213> ORGANISM: Homo sapiens

<400> SEQUENCE: 18

Met Ile Arg Leu Gly Ala Pro Gln Ser Leu Val Leu Leu Thr Leu Leu
1               5                   10                  15

Val Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
    210                 215                 220
```

```
Gly Asn Pro Gly Glu Pro Gly Glu Pro Gly Val Ser Gly Pro Met Gly
225                 230                 235                 240

Pro Arg Gly Pro Gly Pro Pro Gly Lys Pro Gly Asp Asp Gly Glu
            245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
            275                 280                 285

His Arg Gly Tyr Pro Gly Leu Asp Gly Ala Lys Gly Glu Ala Gly Ala
            290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
            325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Pro Gly Phe Pro
            355                 360                 365

Gly Ala Pro Gly Ala Lys Gly Glu Ala Gly Pro Thr Gly Ala Arg Gly
            370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
            405                 410                 415

Gly Ala Lys Gly Ser Ala Gly Ala Pro Gly Ile Ala Gly Ala Pro Gly
            420                 425                 430

Phe Pro Gly Pro Arg Gly Pro Pro Gly Pro Gln Gly Ala Thr Gly Pro
            435                 440                 445

Leu Gly Pro Lys Gly Gln Thr Gly Glu Pro Gly Ile Ala Gly Phe Lys
450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
            485                 490                 495

Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
            530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
            565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
            595                 600                 605

Gly Ala Asn Gly Glu Pro Gly Lys Ala Gly Glu Lys Gly Leu Pro Gly
            610                 615                 620

Ala Pro Gly Leu Arg Gly Leu Pro Gly Lys Asp Gly Glu Thr Gly Ala
625                 630                 635                 640

Ala Gly Pro Pro Gly Pro Ala Gly Pro Ala Gly Glu Arg Gly Glu Gln
```

-continued

```
                645                 650                 655
Gly Ala Pro Gly Pro Ser Gly Phe Gln Gly Leu Pro Gly Pro Pro Gly
            660                 665                 670
Pro Pro Gly Glu Gly Gly Lys Pro Gly Asp Gln Gly Val Pro Gly Glu
        675                 680                 685
Ala Gly Ala Pro Gly Leu Val Gly Pro Arg Gly Glu Arg Gly Phe Pro
    690                 695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
            725                 730                 735
Ala Gly Pro Pro Gly Ala Gln Gly Pro Pro Gly Leu Gln Gly Met Pro
        740                 745                 750
Gly Glu Arg Gly Ala Ala Gly Ile Ala Gly Pro Lys Gly Asp Arg Gly
    755                 760                 765
Asp Val Gly Glu Lys Gly Pro Glu Gly Ala Pro Gly Lys Asp Gly Gly
770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
            805                 810                 815
Ala Arg Gly Ala Pro Gly Glu Arg Gly Glu Thr Gly Pro Pro Gly Pro
        820                 825                 830
Ala Gly Phe Ala Gly Pro Pro Gly Ala Asp Gly Gln Pro Gly Ala Lys
    835                 840                 845
Gly Glu Gln Gly Glu Ala Gly Gln Lys Gly Asp Ala Gly Ala Pro Gly
    850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
            885                 890                 895
Gly Phe Pro Gly Ala Ala Gly Arg Val Gly Pro Pro Gly Ser Asn Gly
        900                 905                 910
Asn Pro Gly Pro Pro Gly Pro Pro Gly Pro Ser Gly Lys Asp Gly Pro
    915                 920                 925
Lys Gly Ala Arg Gly Asp Ser Gly Pro Pro Gly Arg Ala Gly Glu Pro
    930                 935                 940
Gly Leu Gln Gly Pro Ala Gly Pro Pro Gly Glu Lys Gly Glu Pro Gly
945                 950                 955                 960
Asp Asp Gly Pro Ser Gly Ala Glu Gly Pro Pro Gly Pro Gln Gly Leu
            965                 970                 975
Ala Gly Gln Arg Gly Ile Val Gly Leu Pro Gly Gln Arg Gly Glu Arg
        980                 985                 990
Gly Phe Pro Gly Leu Pro Gly Pro Ser Gly Glu Pro Gly Lys Gln Gly
    995                 1000                1005
Ala Pro  Gly Ala Ser Gly Asp  Arg Gly Pro Pro Gly  Pro Val Gly
    1010                1015                1020
Pro Pro  Gly Leu Thr Gly Pro  Ala Gly Glu Pro Gly  Arg Glu Gly
    1025                1030                1035
Ser Pro  Gly Ala Asp Gly Pro  Pro Gly Arg Asp Gly  Ala Ala Gly
    1040                1045                1050
Val Lys  Gly Asp Arg Gly Glu  Thr Gly Ala Val Gly  Ala Pro Gly
    1055                1060                1065
```

```
Ala Pro Gly Pro Pro Gly Ser Pro Gly Pro Ala Gly Pro Thr Gly
    1070                1075                1080

Lys Gln Gly Asp Arg Gly Glu Ala Gly Ala Gln Gly Pro Met Gly
    1085                1090                1095

Pro Ser Gly Pro Ala Gly Ala Arg Gly Ile Gln Gly Pro Gln Gly
    1100                1105                1110

Pro Arg Gly Asp Lys Gly Glu Ala Gly Glu Pro Gly Glu Arg Gly
    1115                1120                1125

Leu Lys Gly His Arg Gly Phe Thr Gly Leu Gln Gly Leu Pro Gly
    1130                1135                1140

Pro Pro Gly Pro Ser Gly Asp Gln Gly Ala Ser Gly Pro Ala Gly
    1145                1150                1155

Pro Ser Gly Pro Arg Gly Pro Pro Gly Pro Val Gly Pro Ser Gly
    1160                1165                1170

Lys Asp Gly Ala Asn Gly Ile Pro Gly Pro Ile Gly Pro Pro Gly
    1175                1180                1185

Pro Arg Gly Arg Ser Gly Glu Thr Gly Pro Ala Gly Pro Pro Gly
    1190                1195                1200

Asn Pro Gly Pro Pro Gly Pro Pro Gly Pro Pro Gly Pro Gly Ile
    1205                1210                1215

Asp Met Ser Ala Phe Ala Gly Leu Gly Pro Arg Glu Lys Gly Pro
    1220                1225                1230

Asp Pro Leu Gln Tyr Met Arg Ala Asp Gln Ala Ala Gly Gly Leu
    1235                1240                1245

Arg Gln His Asp Ala Glu Val Asp Ala Thr Leu Lys Ser Leu Asn
    1250                1255                1260

Asn Gln Ile Glu Ser Ile Arg Ser Pro Glu Gly Ser Arg Lys Asn
    1265                1270                1275

Pro Ala Arg Thr Cys Arg Asp Leu Lys Leu Cys His Pro Glu Trp
    1280                1285                1290

Lys Ser Gly Asp Tyr Trp Ile Asp Pro Asn Gln Gly Cys Thr Leu
    1295                1300                1305

Asp Ala Met Lys Val Phe Cys Asn Met Glu Thr Gly Glu Thr Cys
    1310                1315                1320

Val Tyr Pro Asn Pro Ala Asn Val Pro Lys Lys Asn Trp Trp Ser
    1325                1330                1335

Ser Lys Ser Lys Glu Lys Lys His Ile Trp Phe Gly Glu Thr Ile
    1340                1345                1350

Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
    1415                1420                1425

Phe Thr Tyr Thr Ala Leu Lys Asp Gly Cys Thr Lys His Thr Gly
    1430                1435                1440

Lys Trp Gly Lys Thr Val Ile Glu Tyr Arg Ser Gln Lys Thr Ser
    1445                1450                1455
```

```
Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485

<210> SEQ ID NO 19
<211> LENGTH: 7137
<212> TYPE: DNA
<213> ORGANISM: Homo sapiens
<220> FEATURE:
<221> NAME/KEY: CDS
<222> LOCATION: (61)..(7011)

<400> SEQUENCE: 19
cggccaggtg tgtgggactg aagttcttgg agaagggagt ccaactcttc aaggtgaact        60 atg acc act tta ctc tgg gtt ttc gtg act ctg agg gtc atc act gca       108
Met Thr Thr Leu Leu Trp Val Phe Val Thr Leu Arg Val Ile Thr Ala
1               5                   10                  15 gct gtc act gta gaa act tca gac cat gac aac tcg ctg agt gtc agc       156
Ala Val Thr Val Glu Thr Ser Asp His Asp Asn Ser Leu Ser Val Ser
                20                  25                  30 atc ccc caa ccg tcc ccg ctg agg gtc ctc ctg ggg acc tcc ctc acc       204
Ile Pro Gln Pro Ser Pro Leu Arg Val Leu Leu Gly Thr Ser Leu Thr
            35                  40                  45 atc ccc tgc tat ttc atc gac ccc atg cac cct gtg acc acc gcc cct       252
Ile Pro Cys Tyr Phe Ile Asp Pro Met His Pro Val Thr Thr Ala Pro
        50                  55                  60 tct acc gcc cca ctg gcc cca aga atc aag tgg agc cgt gtg tcc aag       300
Ser Thr Ala Pro Leu Ala Pro Arg Ile Lys Trp Ser Arg Val Ser Lys
65                  70                  75                  80 gag aag gag gta gtg ctg ctg gtg gcc act gaa ggg cgc gtg cgg gtc       348
Glu Lys Glu Val Val Leu Leu Val Ala Thr Glu Gly Arg Val Arg Val
                85                  90                  95 aac agt gcc tat cag gac aag gtc tca ctg ccc aac tac ccg gcc atc       396
Asn Ser Ala Tyr Gln Asp Lys Val Ser Leu Pro Asn Tyr Pro Ala Ile
                100                 105                 110 ccc agt gac gcc acc ttg gaa gtc cag agc ctg cgc tcc aat gac tct       444
Pro Ser Asp Ala Thr Leu Glu Val Gln Ser Leu Arg Ser Asn Asp Ser
            115                 120                 125 ggg gtc tac cgc tgc gag gtg atg cat ggc atc gag gac agc gag gcc       492
Gly Val Tyr Arg Cys Glu Val Met His Gly Ile Glu Asp Ser Glu Ala
        130                 135                 140 acc ctg gaa gtc gtg gtg aaa ggc atc gtg ttc cat tac aga gcc atc       540
Thr Leu Glu Val Val Val Lys Gly Ile Val Phe His Tyr Arg Ala Ile
145                 150                 155                 160 tct aca cgc tac acc ctc gac ttt gac agg gcg cag cgg gcc tgc ctg       588
Ser Thr Arg Tyr Thr Leu Asp Phe Asp Arg Ala Gln Arg Ala Cys Leu
                165                 170                 175 cag aac agt gcc atc att gcc acg cct gag cag ctg cag gcc gcc tac       636
Gln Asn Ser Ala Ile Ile Ala Thr Pro Glu Gln Leu Gln Ala Ala Tyr
                180                 185                 190 gaa gac ggc ttc cac cag tgt gac gcc ggc tgg ctg gct gac cag act       684
Glu Asp Gly Phe His Gln Cys Asp Ala Gly Trp Leu Ala Asp Gln Thr
            195                 200                 205 gtc aga tac ccc atc cac act ccc cgg gaa ggc tgc tat gga gac aag       732
Val Arg Tyr Pro Ile His Thr Pro Arg Glu Gly Cys Tyr Gly Asp Lys
        210                 215                 220 gat gag ttt cct ggt gtg agg acg tat ggc atc cga gac acc aac gag       780
Asp Glu Phe Pro Gly Val Arg Thr Tyr Gly Ile Arg Asp Thr Asn Glu
225                 230                 235                 240
```

| | | | | | | | | | | | | | | | |
|---|---|---|---|---|---|---|---|---|---|---|---|---|---|---|---|
| acc | tat | gat | gtg | tac | tgc | ttc | gcc | gag | gag | atg | gag | ggt | gag | gtc | ttt |
| Thr | Tyr | Asp | Val | Tyr | Cys | Phe | Ala | Glu | Glu | Met | Glu | Gly | Glu | Val | Phe |
| | | | | 245 | | | | 250 | | | | | 255 | | |

828

| tat | gca | aca | tct | cca | gag | aag | ttc | acc | ttc | cag | gaa | gca | gcc | aat | gag |
|---|---|---|---|---|---|---|---|---|---|---|---|---|---|---|---|
| Tyr | Ala | Thr | Ser | Pro | Glu | Lys | Phe | Thr | Phe | Gln | Glu | Ala | Ala | Asn | Glu |
| | | | 260 | | | | | 265 | | | | | 270 | | |

876

| tgc | cgg | cgg | ctg | ggt | gcc | cgg | ctg | gcc | acc | acg | ggc | cac | gtc | tac | ctg |
|---|---|---|---|---|---|---|---|---|---|---|---|---|---|---|---|
| Cys | Arg | Arg | Leu | Gly | Ala | Arg | Leu | Ala | Thr | Thr | Gly | His | Val | Tyr | Leu |
| | | 275 | | | | | 280 | | | | | 285 | | | |

924

| gcc | tgg | cag | gct | ggc | atg | gac | atg | tgc | agc | gcc | ggc | tgg | ctg | gcc | gac |
|---|---|---|---|---|---|---|---|---|---|---|---|---|---|---|---|
| Ala | Trp | Gln | Ala | Gly | Met | Asp | Met | Cys | Ser | Ala | Gly | Trp | Leu | Ala | Asp |
| | 290 | | | | | 295 | | | | | 300 | | | | |

972

| cgc | agc | gtg | cgc | tac | ccc | atc | tcc | aag | gcc | cgg | ccc | aac | tgc | ggt | ggc |
|---|---|---|---|---|---|---|---|---|---|---|---|---|---|---|---|
| Arg | Ser | Val | Arg | Tyr | Pro | Ile | Ser | Lys | Ala | Arg | Pro | Asn | Cys | Gly | Gly |
| 305 | | | | 310 | | | | 315 | | | | | | | 320 |

1020

| aac | ctc | ctg | ggc | gtg | agg | acc | gtc | tac | gtg | cat | gcc | aac | cag | acg | ggc |
|---|---|---|---|---|---|---|---|---|---|---|---|---|---|---|---|
| Asn | Leu | Leu | Gly | Val | Arg | Thr | Val | Tyr | Val | His | Ala | Asn | Gln | Thr | Gly |
| | | | | 325 | | | | | 330 | | | | | 335 | |

1068

| tac | ccc | gac | ccc | tca | tcc | cgc | tac | gac | gcc | atc | tgc | tac | aca | ggt | gaa |
|---|---|---|---|---|---|---|---|---|---|---|---|---|---|---|---|
| Tyr | Pro | Asp | Pro | Ser | Ser | Arg | Tyr | Asp | Ala | Ile | Cys | Tyr | Thr | Gly | Glu |
| | | | 340 | | | | | 345 | | | | | 350 | | |

1116

| gac | ttt | gtg | gac | atc | cca | gaa | aac | ttc | ttt | gga | gtg | ggg | ggt | gag | gag |
|---|---|---|---|---|---|---|---|---|---|---|---|---|---|---|---|
| Asp | Phe | Val | Asp | Ile | Pro | Glu | Asn | Phe | Phe | Gly | Val | Gly | Gly | Glu | Glu |
| | | | 355 | | | | | 360 | | | | | 365 | | |

1164

| gac | atc | acc | gtc | cag | aca | gtg | acc | tgg | cct | gac | atg | gag | ctg | cca | ctg |
|---|---|---|---|---|---|---|---|---|---|---|---|---|---|---|---|
| Asp | Ile | Thr | Val | Gln | Thr | Val | Thr | Trp | Pro | Asp | Met | Glu | Leu | Pro | Leu |
| | | 370 | | | | | 375 | | | | | 380 | | | |

1212

| cct | cga | aac | atc | act | gag | ggt | gaa | gcc | cga | ggc | agc | gtg | atc | ctt | acc |
|---|---|---|---|---|---|---|---|---|---|---|---|---|---|---|---|
| Pro | Arg | Asn | Ile | Thr | Glu | Gly | Glu | Ala | Arg | Gly | Ser | Val | Ile | Leu | Thr |
| 385 | | | | | 390 | | | | | 395 | | | | | 400 |

1260

| gta | aag | ccc | atc | ttc | gag | gtc | tcc | ccc | agt | ccc | ctg | gaa | ccc | gag | gag |
|---|---|---|---|---|---|---|---|---|---|---|---|---|---|---|---|
| Val | Lys | Pro | Ile | Phe | Glu | Val | Ser | Pro | Ser | Pro | Leu | Glu | Pro | Glu | Glu |
| | | | | 405 | | | | | 410 | | | | | 415 | |

1308

| ccc | ttc | acg | ttt | gcc | cct | gaa | ata | ggg | gcc | act | gcc | ttc | gct | gag | gtt |
|---|---|---|---|---|---|---|---|---|---|---|---|---|---|---|---|
| Pro | Phe | Thr | Phe | Ala | Pro | Glu | Ile | Gly | Ala | Thr | Ala | Phe | Ala | Glu | Val |
| | | | 420 | | | | | 425 | | | | | 430 | | |

1356

| gag | aat | gag | act | gga | gag | gcc | acc | agg | ccc | tgg | ggc | ttt | ccc | aca | cct |
|---|---|---|---|---|---|---|---|---|---|---|---|---|---|---|---|
| Glu | Asn | Glu | Thr | Gly | Glu | Ala | Thr | Arg | Pro | Trp | Gly | Phe | Pro | Thr | Pro |
| | | | 435 | | | | | 440 | | | | | 445 | | |

1404

| ggc | ctg | ggc | cct | gcc | acg | gca | ttc | acc | agt | gag | gac | ctc | gtc | gtg | cag |
|---|---|---|---|---|---|---|---|---|---|---|---|---|---|---|---|
| Gly | Leu | Gly | Pro | Ala | Thr | Ala | Phe | Thr | Ser | Glu | Asp | Leu | Val | Val | Gln |
| | | 450 | | | | | 455 | | | | | 460 | | | |

1452

| gtg | acc | gct | gtc | cct | ggg | cag | ccg | cat | ttg | cca | ggg | ggg | gtc | gtc | ttc |
|---|---|---|---|---|---|---|---|---|---|---|---|---|---|---|---|
| Val | Thr | Ala | Val | Pro | Gly | Gln | Pro | His | Leu | Pro | Gly | Gly | Val | Val | Phe |
| 465 | | | | | 470 | | | | | 475 | | | | | 480 |

1500

| cac | tac | cgc | ccg | gga | ccc | acc | cgc | tac | tcg | ctg | acc | ttt | gag | gag | gca |
|---|---|---|---|---|---|---|---|---|---|---|---|---|---|---|---|
| His | Tyr | Arg | Pro | Gly | Pro | Thr | Arg | Tyr | Ser | Leu | Thr | Phe | Glu | Glu | Ala |
| | | | | 485 | | | | | 490 | | | | | 495 | |

1548

| cag | cag | gcc | tgc | cct | ggc | acg | ggg | gcg | gtc | att | gcc | tcg | ccg | gag | cag |
|---|---|---|---|---|---|---|---|---|---|---|---|---|---|---|---|
| Gln | Gln | Ala | Cys | Pro | Gly | Thr | Gly | Ala | Val | Ile | Ala | Ser | Pro | Glu | Gln |
| | | | 500 | | | | | 505 | | | | | 510 | | |

1596

| ctc | cag | gcc | gcc | tac | gaa | gca | ggc | tat | gag | cag | tgt | gac | gcc | ggc | tgg |
|---|---|---|---|---|---|---|---|---|---|---|---|---|---|---|---|
| Leu | Gln | Ala | Ala | Tyr | Glu | Ala | Gly | Tyr | Glu | Gln | Cys | Asp | Ala | Gly | Trp |
| | | | 515 | | | | | 520 | | | | | 525 | | |

1644

| ctg | cgg | gac | cag | acc | gtc | aga | tac | ccc | att | gtg | agc | cca | cgg | acc | cca |
|---|---|---|---|---|---|---|---|---|---|---|---|---|---|---|---|
| Leu | Arg | Asp | Gln | Thr | Val | Arg | Tyr | Pro | Ile | Val | Ser | Pro | Arg | Thr | Pro |
| | | 530 | | | | | 535 | | | | | 540 | | | |

1692

| tgc | gtg | ggt | gac | aag | gac | agc | agc | cca | ggg | gtc | agg | acc | tat | ggc | gtg |
|---|---|---|---|---|---|---|---|---|---|---|---|---|---|---|---|
| Cys | Val | Gly | Asp | Lys | Asp | Ser | Ser | Pro | Gly | Val | Arg | Thr | Tyr | Gly | Val |
| 545 | | | | | 550 | | | | | 555 | | | | | 560 |

1740

```
cgc cca tca aca gag acc tac gat gtc tac tgc ttt gta gac aga ctt      1788
Arg Pro Ser Thr Glu Thr Tyr Asp Val Tyr Cys Phe Val Asp Arg Leu
                565                 570                 575 gag ggg gag gtg ttc ttc gcc aca cgc ctt gag cag ttc acc ttc cag      1836
Glu Gly Glu Val Phe Phe Ala Thr Arg Leu Glu Gln Phe Thr Phe Gln
580                 585                 590 gaa gca ctg gag ttc tgt gaa tct cac aat gcc act gcc acc acg ggc      1884
Glu Ala Leu Glu Phe Cys Glu Ser His Asn Ala Thr Ala Thr Thr Gly
                595                 600                 605 cag ctc tac gcc gcc tgg agc cgc ggc ctg gac aag tgc tat gcc ggc      1932
Gln Leu Tyr Ala Ala Trp Ser Arg Gly Leu Asp Lys Cys Tyr Ala Gly
610                 615                 620 tgg ctg gcc gac ggc agc ctc cgc tac ccc atc gtc acc cca agg cct      1980
Trp Leu Ala Asp Gly Ser Leu Arg Tyr Pro Ile Val Thr Pro Arg Pro
625                 630                 635                 640 gcc tgc ggt ggg gac aag cca ggc gtg aga acg gtc tac ctc tac cct      2028
Ala Cys Gly Gly Asp Lys Pro Gly Val Arg Thr Val Tyr Leu Tyr Pro
                645                 650                 655 aac cag acg ggc ctc cca gac cca ctg tcc cgg cac cat gcc ttc tgc      2076
Asn Gln Thr Gly Leu Pro Asp Pro Leu Ser Arg His His Ala Phe Cys
            660                 665                 670 ttc cga ggc att tca gcg gtt cct tct cca gga gaa gaa gag ggt ggc      2124
Phe Arg Gly Ile Ser Ala Val Pro Ser Pro Gly Glu Glu Glu Gly Gly
        675                 680                 685 aca ccc aca tca ccc tct ggt gtg gag gag tgg atc gtg acc caa gtg      2172
Thr Pro Thr Ser Pro Ser Gly Val Glu Glu Trp Ile Val Thr Gln Val
    690                 695                 700 gtt cct ggt gtg gct gct gtc ccc gta gaa gag gag aca act gct gta      2220
Val Pro Gly Val Ala Ala Val Pro Val Glu Glu Glu Thr Thr Ala Val
705                 710                 715                 720 ccc tca ggg gag act act gcc atc cta gag ttc acc acc gag cca gaa      2268
Pro Ser Gly Glu Thr Thr Ala Ile Leu Glu Phe Thr Thr Glu Pro Glu
                725                 730                 735 aac cag aca gaa tgg gaa cca gcc tat acc cca gtg ggc aca tcc ccg      2316
Asn Gln Thr Glu Trp Glu Pro Ala Tyr Thr Pro Val Gly Thr Ser Pro
            740                 745                 750 ctg cca ggg atc ctt cct act tgg cct cct act ggc gcc gaa aca gag      2364
Leu Pro Gly Ile Leu Pro Thr Trp Pro Pro Thr Gly Ala Glu Thr Glu
        755                 760                 765 gaa agt aca gaa ggc cct tct gca act gaa gtg ccc tct gcc tca gag      2412
Glu Ser Thr Glu Gly Pro Ser Ala Thr Glu Val Pro Ser Ala Ser Glu
    770                 775                 780 gaa cca tcc ccc tca gag gtg cca ttc ccc tca gag gag cca tcc ccc      2460
Glu Pro Ser Pro Ser Glu Val Pro Phe Pro Ser Glu Glu Pro Ser Pro
785                 790                 795                 800 tca gag gaa cca ttc ccc tca gtg agg cca ttc ccc tca gtg gag ctg      2508
Ser Glu Glu Pro Phe Pro Ser Val Arg Pro Phe Pro Ser Val Glu Leu
                805                 810                 815 ttc ccc tca gag gag cca ttc ccc tcc aag gag cca tcc ccc tca gag      2556
Phe Pro Ser Glu Glu Pro Phe Pro Ser Lys Glu Pro Ser Pro Ser Glu
            820                 825                 830 gaa cca tca gcc tca gaa gag ccg tat aca cct tca ccc ccc gag ccc      2604
Glu Pro Ser Ala Ser Glu Glu Pro Tyr Thr Pro Ser Pro Pro Glu Pro
        835                 840                 845 agc tgg act gag ctg ccc agc tct ggg gag gaa tct ggg gcc cct gat      2652
Ser Trp Thr Glu Leu Pro Ser Ser Gly Glu Glu Ser Gly Ala Pro Asp
    850                 855                 860 gtc agt ggt gac ttc aca ggc agt gga gat gtt tca gga cac ctt gac      2700
Val Ser Gly Asp Phe Thr Gly Ser Gly Asp Val Ser Gly His Leu Asp
```

```
                                                       -continued
865                 870                 875                 880 ttc agt ggg cag ctg tca ggg gac agg gca agt gga ctg ccc tct gga     2748
Phe Ser Gly Gln Leu Ser Gly Asp Arg Ala Ser Gly Leu Pro Ser Gly
            885                 890                 895 gac ctg gac tcc agt ggt ctt act tcc aca gtg ggc tca ggc ctg act     2796
Asp Leu Asp Ser Ser Gly Leu Thr Ser Thr Val Gly Ser Gly Leu Thr
        900                 905                 910 gtg gaa agt gga cta ccc tca ggg gat gaa gag aga att gag tgg ccc     2844
Val Glu Ser Gly Leu Pro Ser Gly Asp Glu Glu Arg Ile Glu Trp Pro
    915                 920                 925 agc act cct acg gtt ggt gaa ctg ccc tct gga gct gag atc cta gag     2892
Ser Thr Pro Thr Val Gly Glu Leu Pro Ser Gly Ala Glu Ile Leu Glu
930                 935                 940 ggc tct gcc tct gga gtt ggg gat ctc agt gga ctt cct tct gga gaa     2940
Gly Ser Ala Ser Gly Val Gly Asp Leu Ser Gly Leu Pro Ser Gly Glu
945                 950                 955                 960 gtt cta gag acc tct gcc tct gga gta gga gac ctc agt ggg ctt cct     2988
Val Leu Glu Thr Ser Ala Ser Gly Val Gly Asp Leu Ser Gly Leu Pro
                965                 970                 975 tct gga gaa gtt cta gag acc act gcc cct gga gta gag gac atc agc     3036
Ser Gly Glu Val Leu Glu Thr Thr Ala Pro Gly Val Glu Asp Ile Ser
            980                 985                 990 ggg ctt cct tct gga gaa gtt cta gag acc act gcc cct gga gta gag     3084
Gly Leu Pro Ser Gly Glu Val Leu Glu Thr Thr Ala Pro Gly Val Glu
        995                 1000                1005 gac atc agc ggg ctt cct tct gga gaa gtt cta gag acc act gcc         3129
Asp Ile Ser Gly Leu Pro Ser Gly Glu Val Leu Glu Thr Thr Ala
    1010                1015                1020 cct gga gta gag gac atc agc ggg ctt cct tct gga gaa gtt cta         3174
Pro Gly Val Glu Asp Ile Ser Gly Leu Pro Ser Gly Glu Val Leu
    1025                1030                1035 gag acc act gcc cct gga gta gag gac atc agc ggg ctt cct tct         3219
Glu Thr Thr Ala Pro Gly Val Glu Asp Ile Ser Gly Leu Pro Ser
    1040                1045                1050 gga gaa gtt cta gag acc act gcc cct gga gta gag gac atc agc         3264
Gly Glu Val Leu Glu Thr Thr Ala Pro Gly Val Glu Asp Ile Ser
    1055                1060                1065 ggg ctt cct tct gga gaa gtt cta gag acc gct gcc cct gga gta         3309
Gly Leu Pro Ser Gly Glu Val Leu Glu Thr Ala Ala Pro Gly Val
    1070                1075                1080 gag gac atc agc ggg ctt cct tct gga gaa gtt cta gag acc gct         3354
Glu Asp Ile Ser Gly Leu Pro Ser Gly Glu Val Leu Glu Thr Ala
    1085                1090                1095 gcc cct gga gta gag gac atc agc ggg ctt cct tct gga gaa gtt         3399
Ala Pro Gly Val Glu Asp Ile Ser Gly Leu Pro Ser Gly Glu Val
    1100                1105                1110 cta gag acc gct gcc cct gga gta gag gac atc agc ggg ctt cct         3444
Leu Glu Thr Ala Ala Pro Gly Val Glu Asp Ile Ser Gly Leu Pro
    1115                1120                1125 tct gga gaa gtt cta gag acc gct gcc cct gga gta gag gac atc         3489
Ser Gly Glu Val Leu Glu Thr Ala Ala Pro Gly Val Glu Asp Ile
    1130                1135                1140 agc ggg ctt cct tct gga gaa gtt cta gag acc gct gcc cct gga         3534
Ser Gly Leu Pro Ser Gly Glu Val Leu Glu Thr Ala Ala Pro Gly
    1145                1150                1155 gta gag gac atc agc ggg ctt cct tct gga gaa gtt cta gag acc         3579
Val Glu Asp Ile Ser Gly Leu Pro Ser Gly Glu Val Leu Glu Thr
    1160                1165                1170 gct gcc cct gga gta gag gac atc agc ggg ctt cct tct gga gaa         3624
```

-continued

| | | | | | | | | | | | | |
|---|---|---|---|---|---|---|---|---|---|---|---|---|
| Ala | Ala | Pro | Gly | Val | Glu | Asp | Ile | Ser | Gly | Leu | Pro | Ser | Gly | Glu |
| 1175 | | | | | 1180 | | | | | 1185 | | | | |

| gtt | cta | gag | acc | gct | gcc | cct | gga | gta | gag | gac | atc | agc | ggg | ctt | 3669 |
|---|---|---|---|---|---|---|---|---|---|---|---|---|---|---|---|
| Val | Leu | Glu | Thr | Ala | Ala | Pro | Gly | Val | Glu | Asp | Ile | Ser | Gly | Leu | |
| 1190 | | | | 1195 | | | | | 1200 | | | | | | |

| cct | tct | gga | gaa | gtt | cta | gag | act | gct | gcc | cct | gga | gta | gag | gac | 3714 |
|---|---|---|---|---|---|---|---|---|---|---|---|---|---|---|---|
| Pro | Ser | Gly | Glu | Val | Leu | Glu | Thr | Ala | Ala | Pro | Gly | Val | Glu | Asp | |
| 1205 | | | | 1210 | | | | | 1215 | | | | | | |

| atc | agc | ggg | ctt | cct | tct | gga | gaa | gtt | cta | gag | act | gct | gcc | cct | 3759 |
|---|---|---|---|---|---|---|---|---|---|---|---|---|---|---|---|
| Ile | Ser | Gly | Leu | Pro | Ser | Gly | Glu | Val | Leu | Glu | Thr | Ala | Ala | Pro | |
| 1220 | | | | 1225 | | | | | 1230 | | | | | | |

| gga | gta | gag | gac | atc | agc | ggg | ctt | cct | tct | gga | gaa | gtt | cta | gag | 3804 |
|---|---|---|---|---|---|---|---|---|---|---|---|---|---|---|---|
| Gly | Val | Glu | Asp | Ile | Ser | Gly | Leu | Pro | Ser | Gly | Glu | Val | Leu | Glu | |
| 1235 | | | | 1240 | | | | | 1245 | | | | | | |

| act | gct | gcc | cct | gga | gta | gag | gac | atc | agc | ggg | ctt | cct | tct | gga | 3849 |
|---|---|---|---|---|---|---|---|---|---|---|---|---|---|---|---|
| Thr | Ala | Ala | Pro | Gly | Val | Glu | Asp | Ile | Ser | Gly | Leu | Pro | Ser | Gly | |
| 1250 | | | | 1255 | | | | | 1260 | | | | | | |

| gaa | gtt | cta | gag | act | gct | gcc | cct | gga | gta | gag | gac | atc | agc | ggg | 3894 |
|---|---|---|---|---|---|---|---|---|---|---|---|---|---|---|---|
| Glu | Val | Leu | Glu | Thr | Ala | Ala | Pro | Gly | Val | Glu | Asp | Ile | Ser | Gly | |
| 1265 | | | | 1270 | | | | | 1275 | | | | | | |

| ctt | cct | tct | gga | gaa | gtt | cta | gag | act | act | gcc | cct | gga | gta | gag | 3939 |
|---|---|---|---|---|---|---|---|---|---|---|---|---|---|---|---|
| Leu | Pro | Ser | Gly | Glu | Val | Leu | Glu | Thr | Thr | Ala | Pro | Gly | Val | Glu | |
| 1280 | | | | 1285 | | | | | 1290 | | | | | | |

| gag | atc | agc | ggg | ctt | cct | tct | gga | gaa | gtt | cta | gag | act | act | gcc | 3984 |
|---|---|---|---|---|---|---|---|---|---|---|---|---|---|---|---|
| Glu | Ile | Ser | Gly | Leu | Pro | Ser | Gly | Glu | Val | Leu | Glu | Thr | Thr | Ala | |
| 1295 | | | | 1300 | | | | | 1305 | | | | | | |

| cct | gga | gta | gat | gag | atc | agt | ggg | ctt | cct | tct | gga | gaa | gtt | cta | 4029 |
|---|---|---|---|---|---|---|---|---|---|---|---|---|---|---|---|
| Pro | Gly | Val | Asp | Glu | Ile | Ser | Gly | Leu | Pro | Ser | Gly | Glu | Val | Leu | |
| 1310 | | | | 1315 | | | | | 1320 | | | | | | |

| gag | act | act | gcc | cct | gga | gta | gag | gag | atc | agc | ggg | ctt | cct | tct | 4074 |
|---|---|---|---|---|---|---|---|---|---|---|---|---|---|---|---|
| Glu | Thr | Thr | Ala | Pro | Gly | Val | Glu | Glu | Ile | Ser | Gly | Leu | Pro | Ser | |
| 1325 | | | | 1330 | | | | | 1335 | | | | | | |

| gga | gaa | gtt | cta | gag | act | tct | acc | tct | gcg | gta | ggg | gac | ctc | agt | 4119 |
|---|---|---|---|---|---|---|---|---|---|---|---|---|---|---|---|
| Gly | Glu | Val | Leu | Glu | Thr | Ser | Thr | Ser | Ala | Val | Gly | Asp | Leu | Ser | |
| 1340 | | | | 1345 | | | | | 1350 | | | | | | |

| gga | ctt | cct | tct | gga | gga | gaa | gtt | cta | gag | att | tct | gtc | tct | gga | 4164 |
|---|---|---|---|---|---|---|---|---|---|---|---|---|---|---|---|
| Gly | Leu | Pro | Ser | Gly | Gly | Glu | Val | Leu | Glu | Ile | Ser | Val | Ser | Gly | |
| 1355 | | | | 1360 | | | | | 1365 | | | | | | |

| gta | gag | gac | atc | agt | ggg | ctt | cct | tct | gga | gag | gtt | gta | gag | act | 4209 |
|---|---|---|---|---|---|---|---|---|---|---|---|---|---|---|---|
| Val | Glu | Asp | Ile | Ser | Gly | Leu | Pro | Ser | Gly | Glu | Val | Val | Glu | Thr | |
| 1370 | | | | 1375 | | | | | 1380 | | | | | | |

| tct | gcc | tct | gga | ata | gag | gat | gtc | agt | gaa | ctt | cct | tca | gga | gaa | 4254 |
|---|---|---|---|---|---|---|---|---|---|---|---|---|---|---|---|
| Ser | Ala | Ser | Gly | Ile | Glu | Asp | Val | Ser | Glu | Leu | Pro | Ser | Gly | Glu | |
| 1385 | | | | 1390 | | | | | 1395 | | | | | | |

| ggt | cta | gag | acc | tct | gct | tct | gga | gta | gag | gac | ctc | agc | agg | ctc | 4299 |
|---|---|---|---|---|---|---|---|---|---|---|---|---|---|---|---|
| Gly | Leu | Glu | Thr | Ser | Ala | Ser | Gly | Val | Glu | Asp | Leu | Ser | Arg | Leu | |
| 1400 | | | | 1405 | | | | | 1410 | | | | | | |

| cct | tct | gga | gaa | gaa | gtt | cta | gag | att | tct | gcc | tct | gga | ttt | ggg | 4344 |
|---|---|---|---|---|---|---|---|---|---|---|---|---|---|---|---|
| Pro | Ser | Gly | Glu | Glu | Val | Leu | Glu | Ile | Ser | Ala | Ser | Gly | Phe | Gly | |
| 1415 | | | | 1420 | | | | | 1425 | | | | | | |

| gac | ctc | agt | gga | gtt | cct | tct | gga | gga | gaa | ggt | cta | gag | acc | tct | 4389 |
|---|---|---|---|---|---|---|---|---|---|---|---|---|---|---|---|
| Asp | Leu | Ser | Gly | Val | Pro | Ser | Gly | Gly | Glu | Gly | Leu | Glu | Thr | Ser | |
| 1430 | | | | 1435 | | | | | 1440 | | | | | | |

| gct | tct | gaa | gta | ggg | act | gac | ctc | agt | ggg | ctt | cct | tct | gga | agg | 4434 |
|---|---|---|---|---|---|---|---|---|---|---|---|---|---|---|---|
| Ala | Ser | Glu | Val | Gly | Thr | Asp | Leu | Ser | Gly | Leu | Pro | Ser | Gly | Arg | |
| 1445 | | | | 1450 | | | | | 1455 | | | | | | |

| gag | ggt | cta | gag | act | tca | gct | tct | gga | gct | gag | gac | ctc | agt | ggg | 4479 |
|---|---|---|---|---|---|---|---|---|---|---|---|---|---|---|---|
| Glu | Gly | Leu | Glu | Thr | Ser | Ala | Ser | Gly | Ala | Glu | Asp | Leu | Ser | Gly | |
| 1460 | | | | 1465 | | | | | 1470 | | | | | | |

```
ttg cct tct gga aaa gaa gac ttg gtg ggg tca gct tct gga gac       4524
Leu Pro Ser Gly Lys Glu Asp Leu Val Gly Ser Ala Ser Gly Asp
    1475            1480                1485 ttg gac ttg ggc aaa ctg cct tct gga act cta gga agt ggg caa       4569
Leu Asp Leu Gly Lys Leu Pro Ser Gly Thr Leu Gly Ser Gly Gln
1490            1495                1500 gct cca gaa aca agt ggt ctt ccc tct gga ttt agt ggt gag tat       4614
Ala Pro Glu Thr Ser Gly Leu Pro Ser Gly Phe Ser Gly Glu Tyr
    1505            1510                1515 tct ggg gtg gac ctt gga agt ggc cca ccc tct ggc ctg cct gac       4659
Ser Gly Val Asp Leu Gly Ser Gly Pro Pro Ser Gly Leu Pro Asp
1520            1525                1530 ttt agt gga ctt cca tct gga ttc cca act gtt tcc cta gtg gat       4704
Phe Ser Gly Leu Pro Ser Gly Phe Pro Thr Val Ser Leu Val Asp
    1535            1540                1545 tct aca ttg gtg gaa gtg gtc aca gcc tcc act gca agt gaa ctg       4749
Ser Thr Leu Val Glu Val Val Thr Ala Ser Thr Ala Ser Glu Leu
1550            1555                1560 gaa ggg agg gga acc att ggc atc agt ggt gca gga gaa ata tct       4794
Glu Gly Arg Gly Thr Ile Gly Ile Ser Gly Ala Gly Glu Ile Ser
    1565            1570                1575 gga ctg ccc tcc agt gag ctg gac att agt ggg aga gct agt gga       4839
Gly Leu Pro Ser Ser Glu Leu Asp Ile Ser Gly Arg Ala Ser Gly
1580            1585                1590 ctc cct tca gga act gaa ctc agt ggc caa gca tct ggg tct cct       4884
Leu Pro Ser Gly Thr Glu Leu Ser Gly Gln Ala Ser Gly Ser Pro
    1595            1600                1605 gat gtc agt ggg gaa ata cct gga ctc ttt ggt gtc agt gga cag       4929
Asp Val Ser Gly Glu Ile Pro Gly Leu Phe Gly Val Ser Gly Gln
1610            1615                1620 cca tca ggg ttt cct gac act agt ggg gaa aca tct gga gtg act       4974
Pro Ser Gly Phe Pro Asp Thr Ser Gly Glu Thr Ser Gly Val Thr
    1625            1630                1635 gag ctt agc ggg ctg tcc tct gga caa cca ggt gtt agt gga gaa       5019
Glu Leu Ser Gly Leu Ser Ser Gly Gln Pro Gly Val Ser Gly Glu
1640            1645                1650 gca tct gga gtt ctt tat ggc act agt caa ccc ttt ggc ata act       5064
Ala Ser Gly Val Leu Tyr Gly Thr Ser Gln Pro Phe Gly Ile Thr
    1655            1660                1665 gat ctg agt gga gaa aca tct ggg gtc cct gat ctc agt ggg cag       5109
Asp Leu Ser Gly Glu Thr Ser Gly Val Pro Asp Leu Ser Gly Gln
1670            1675                1680 cct tca ggg tta cca ggg ttc agt ggg gca aca tca gga gtc cct       5154
Pro Ser Gly Leu Pro Gly Phe Ser Gly Ala Thr Ser Gly Val Pro
    1685            1690                1695 gac ctg gtt tct ggt acc acg agt ggc agc ggt gaa tct tct ggg       5199
Asp Leu Val Ser Gly Thr Thr Ser Gly Ser Gly Glu Ser Ser Gly
1700            1705                1710 att aca ttt gtg gac acc agt ttg gtt gaa gtg gcc cct act aca       5244
Ile Thr Phe Val Asp Thr Ser Leu Val Glu Val Ala Pro Thr Thr
    1715            1720                1725 ttt aaa gaa gaa gaa ggc tta ggg tct gtg gaa ctc agt ggc ctc       5289
Phe Lys Glu Glu Glu Gly Leu Gly Ser Val Glu Leu Ser Gly Leu
1730            1735                1740 cct tcc gga gag gca gat ctg tca ggc aaa tct ggg atg gtg gat       5334
Pro Ser Gly Glu Ala Asp Leu Ser Gly Lys Ser Gly Met Val Asp
    1745            1750                1755 gtc agt gga cag ttt tct gga aca gtc gat tcc agt ggg ttt aca       5379
Val Ser Gly Gln Phe Ser Gly Thr Val Asp Ser Ser Gly Phe Thr
1760            1765                1770
```

| | | | | | | | | | | | |
|---|---|---|---|---|---|---|---|---|---|---|---|
| tcc | cag | act | ccg | gaa | ttc | agt | ggc | cta | cca | agt | ggc | ata | gct | gag | | 5424 |
| Ser | Gln | Thr | Pro | Glu | Phe | Ser | Gly | Leu | Pro | Ser | Gly | Ile | Ala | Glu | | |
| | 1775 | | | | 1780 | | | | | 1785 | | | | | | |

```
tcc cag act ccg gaa ttc agt ggc cta cca agt ggc ata gct gag        5424
Ser Gln Thr Pro Glu Phe Ser Gly Leu Pro Ser Gly Ile Ala Glu
    1775            1780                1785 gtc agt gga gaa tcc tcc aga gct gag att ggg agc agc ctg ccc        5469
Val Ser Gly Glu Ser Ser Arg Ala Glu Ile Gly Ser Ser Leu Pro
    1790            1795                1800 tcg gga gca tat tat ggc agt gga act cca tct agt ttc ccc acg        5514
Ser Gly Ala Tyr Tyr Gly Ser Gly Thr Pro Ser Ser Phe Pro Thr
    1805            1810                1815 gtc tct ctt gta gac aga act ttg gtg gaa tct gta acc cag gct        5559
Val Ser Leu Val Asp Arg Thr Leu Val Glu Ser Val Thr Gln Ala
    1820            1825                1830 cca aca gcc caa gag gca gga gaa ggg cct tct ggc att tta gaa        5604
Pro Thr Ala Gln Glu Ala Gly Glu Gly Pro Ser Gly Ile Leu Glu
    1835            1840                1845 ctc agt ggt gct cat tct gga gca cca gac atg tct ggg gag cat        5649
Leu Ser Gly Ala His Ser Gly Ala Pro Asp Met Ser Gly Glu His
    1850            1855                1860 tct gga ttt ctg gac cta agt ggg ctg cag tcc ggg ctg ata gag        5694
Ser Gly Phe Leu Asp Leu Ser Gly Leu Gln Ser Gly Leu Ile Glu
    1865            1870                1875 ccc agc gga gag cca cca ggt act cca tat ttt agt ggg gat ttt        5739
Pro Ser Gly Glu Pro Pro Gly Thr Pro Tyr Phe Ser Gly Asp Phe
    1880            1885                1890 gcc agc acc acc aat gta agt gga gaa tcc tct gta gcc atg ggc        5784
Ala Ser Thr Thr Asn Val Ser Gly Glu Ser Ser Val Ala Met Gly
    1895            1900                1905 acc agt gga gag gcc tca gga ctt cca gaa gtt act tta atc act        5829
Thr Ser Gly Glu Ala Ser Gly Leu Pro Glu Val Thr Leu Ile Thr
    1910            1915                1920 tct gag ttc gtg gag ggt gtt act gaa cca act att tct cag gaa        5874
Ser Glu Phe Val Glu Gly Val Thr Glu Pro Thr Ile Ser Gln Glu
    1925            1930                1935 cta ggc caa agg ccc cct gtg aca cac aca ccc cag ctt ttt gag        5919
Leu Gly Gln Arg Pro Pro Val Thr His Thr Pro Gln Leu Phe Glu
    1940            1945                1950 tcc agt gga aaa gtc tcc aca gct ggg gac att agt gga gct acc        5964
Ser Ser Gly Lys Val Ser Thr Ala Gly Asp Ile Ser Gly Ala Thr
    1955            1960                1965 cca gtg ctc cct ggg tct gga gta gaa gta tca tca gtc cca gaa        6009
Pro Val Leu Pro Gly Ser Gly Val Glu Val Ser Ser Val Pro Glu
    1970            1975                1980 tct agc agt gag acg tcc gcc tat cct gaa gct ggg ttc ggg gca        6054
Ser Ser Ser Glu Thr Ser Ala Tyr Pro Glu Ala Gly Phe Gly Ala
    1985            1990                1995 tct gcc gcc cct gag gcc agc aga gaa gat tct ggg tcc cct gat        6099
Ser Ala Ala Pro Glu Ala Ser Arg Glu Asp Ser Gly Ser Pro Asp
    2000            2005                2010 ctg agt gaa acc acc tct gca ttc cac gaa gct aac ctt gag aga        6144
Leu Ser Glu Thr Thr Ser Ala Phe His Glu Ala Asn Leu Glu Arg
    2015            2020                2025 tcc tct ggc cta gga gtg agc ggc agc act ttg aca ttt caa gaa        6189
Ser Ser Gly Leu Gly Val Ser Gly Ser Thr Leu Thr Phe Gln Glu
    2030            2035                2040 ggc gag gcg tcc gct gcc cca gaa gtg agt gga gaa tcc acc acc        6234
Gly Glu Ala Ser Ala Ala Pro Glu Val Ser Gly Glu Ser Thr Thr
    2045            2050                2055 acc agt gat gtg ggg aca gag gca cca ggc ttg cct tca gcc act        6279
Thr Ser Asp Val Gly Thr Glu Ala Pro Gly Leu Pro Ser Ala Thr
```

|  |  |  |  |  |  |  |  |  |  |  |  |  |
|---|---|---|---|---|---|---|---|---|---|---|---|---|
|  |  | 2060 |  |  |  | 2065 |  |  |  | 2070 |  |  |

```
ccc acg gct tct gga gac agg act gaa atc agc gga gac ctg tct      6324
Pro Thr Ala Ser Gly Asp Arg Thr Glu Ile Ser Gly Asp Leu Ser
    2075                2080                2085 ggt cac acc tcg cag ctg ggc gtt gtc atc agc acc agc atc cca      6369
Gly His Thr Ser Gln Leu Gly Val Val Ile Ser Thr Ser Ile Pro
2090                2095                2100 gag tct gag tgg acc cag cag acc cag cgc cct gca gag acg cat      6414
Glu Ser Glu Trp Thr Gln Gln Thr Gln Arg Pro Ala Glu Thr His
    2105                2110                2115 cta gaa att gag tcc tca agc ctc ctg tac tca gga gaa gag act      6459
Leu Glu Ile Glu Ser Ser Ser Leu Leu Tyr Ser Gly Glu Glu Thr
2120                2125                2130 cac aca gtc gaa aca gcc acc tcc cca aca gat gct tcc atc cca      6504
His Thr Val Glu Thr Ala Thr Ser Pro Thr Asp Ala Ser Ile Pro
    2135                2140                2145 gct tct ccg gaa tgg aaa cgt gaa tca gaa tca act gct gca gac      6549
Ala Ser Pro Glu Trp Lys Arg Glu Ser Glu Ser Thr Ala Ala Asp
2150                2155                2160 cag gag gta tgt gag gag ggc tgg aac aag tac cag ggc cac tgt      6594
Gln Glu Val Cys Glu Glu Gly Trp Asn Lys Tyr Gln Gly His Cys
    2165                2170                2175 tac cgc cac ttc ccg gac cgc gag acc tgg gtg gat gct gag cgc      6639
Tyr Arg His Phe Pro Asp Arg Glu Thr Trp Val Asp Ala Glu Arg
2180                2185                2190 cgg tgt cgg gag cag cag tca cac ctg agc agc atc gtc acc ccc      6684
Arg Cys Arg Glu Gln Gln Ser His Leu Ser Ser Ile Val Thr Pro
    2195                2200                2205 gag gag cag gag ttt gtc aac aac aat gcc caa gac tac cag tgg      6729
Glu Glu Gln Glu Phe Val Asn Asn Asn Ala Gln Asp Tyr Gln Trp
2210                2215                2220 atc ggc ctg aac gac agg acc atc gaa ggg gac ttc cgc tgg tca      6774
Ile Gly Leu Asn Asp Arg Thr Ile Glu Gly Asp Phe Arg Trp Ser
    2225                2230                2235 gat gga cac ccc atg caa ttt gag aac tgg cgc ccc aac cag cct      6819
Asp Gly His Pro Met Gln Phe Glu Asn Trp Arg Pro Asn Gln Pro
2240                2245                2250 gac aac ttt ttt gcc gct gga gag gac tgt gtg gtg atg atc tgg      6864
Asp Asn Phe Phe Ala Ala Gly Glu Asp Cys Val Val Met Ile Trp
    2255                2260                2265 cac gag aag ggc gag tgg aat gat gtt ccc tgc aat tac cac ctc      6909
His Glu Lys Gly Glu Trp Asn Asp Val Pro Cys Asn Tyr His Leu
2270                2275                2280 ccc ttc acg tgt aaa aag ggc aca gcc acc acc tac aaa cgc aga      6954
Pro Phe Thr Cys Lys Lys Gly Thr Ala Thr Thr Tyr Lys Arg Arg
    2285                2290                2295 cta cag aag cgg agc tca cgg cac cct cgg agg agc cgc ccc agc      6999
Leu Gln Lys Arg Ser Ser Arg His Pro Arg Arg Ser Arg Pro Ser
2300                2305                2310 aca gcc cac tga gaagagcttc caggacgcac ccaggacgct gagcccagga      7051
Thr Ala His
    2315 gcctgccagg ctgacgtgca tcccacccag acggtgtcct cttcttgtcg ctttttgtca  7111 tataaggaat cccattaaaa aaaaaa                                       7137

<210> SEQ ID NO 20
<211> LENGTH: 2316
<212> TYPE: PRT
<213> ORGANISM: Homo sapiens
```

<400> SEQUENCE: 20

| | | | | | | | | | | | | | | |
|---|---|---|---|---|---|---|---|---|---|---|---|---|---|---|
|Met|Thr|Thr|Leu|Leu|Trp|Val|Phe|Val|Thr|Leu|Arg|Val|Ile|Thr|Ala|
|1| | | |5| | | | |10| | | | |15| |

Ala Val Thr Val Glu Thr Ser Asp His Asp Asn Ser Leu Ser Val Ser
             20              25             30

Ile Pro Gln Pro Ser Pro Leu Arg Val Leu Leu Gly Thr Ser Leu Thr
             35              40             45

Ile Pro Cys Tyr Phe Ile Asp Pro Met His Pro Val Thr Thr Ala Pro
             50              55             60

Ser Thr Ala Pro Leu Ala Pro Arg Ile Lys Trp Ser Arg Val Ser Lys
65              70              75             80

Glu Lys Glu Val Val Leu Leu Val Ala Thr Glu Gly Arg Val Arg Val
             85              90             95

Asn Ser Ala Tyr Gln Asp Lys Val Ser Leu Pro Asn Tyr Pro Ala Ile
             100           105           110

Pro Ser Asp Ala Thr Leu Glu Val Gln Ser Leu Arg Ser Asn Asp Ser
             115           120           125

Gly Val Tyr Arg Cys Glu Val Met His Gly Ile Glu Asp Ser Glu Ala
             130           135           140

Thr Leu Glu Val Val Lys Gly Ile Val Phe His Tyr Arg Ala Ile
145              150             155            160

Ser Thr Arg Tyr Thr Leu Asp Phe Asp Arg Ala Gln Arg Ala Cys Leu
             165           170           175

Gln Asn Ser Ala Ile Ile Ala Thr Pro Glu Gln Leu Gln Ala Ala Tyr
             180           185           190

Glu Asp Gly Phe His Gln Cys Asp Ala Gly Trp Leu Ala Asp Gln Thr
             195           200           205

Val Arg Tyr Pro Ile His Thr Pro Arg Glu Gly Cys Tyr Gly Asp Lys
             210           215           220

Asp Glu Phe Pro Gly Val Arg Thr Tyr Gly Ile Arg Asp Thr Asn Glu
225              230             235            240

Thr Tyr Asp Val Tyr Cys Phe Ala Glu Glu Met Glu Gly Glu Val Phe
             245           250           255

Tyr Ala Thr Ser Pro Glu Lys Phe Thr Phe Gln Glu Ala Ala Asn Glu
             260           265           270

Cys Arg Arg Leu Gly Ala Arg Leu Ala Thr Thr Gly His Val Tyr Leu
             275           280           285

Ala Trp Gln Ala Gly Met Asp Met Cys Ser Ala Gly Trp Leu Ala Asp
             290           295           300

Arg Ser Val Arg Tyr Pro Ile Ser Lys Ala Arg Pro Asn Cys Gly Gly
305              310             315            320

Asn Leu Leu Gly Val Arg Thr Val Tyr Val His Ala Asn Gln Thr Gly
             325           330           335

Tyr Pro Asp Pro Ser Ser Arg Tyr Asp Ala Ile Cys Tyr Thr Gly Glu
             340           345           350

Asp Phe Val Asp Ile Pro Glu Asn Phe Phe Gly Val Gly Gly Glu Glu
             355           360           365

Asp Ile Thr Val Gln Thr Val Thr Trp Pro Asp Met Glu Leu Pro Leu
             370           375           380

Pro Arg Asn Ile Thr Glu Gly Glu Ala Arg Gly Ser Val Ile Leu Thr
385              390             395            400

Val Lys Pro Ile Phe Glu Val Ser Pro Ser Pro Leu Glu Pro Glu Glu

```
                        405                 410                 415
Pro Phe Thr Phe Ala Pro Glu Ile Gly Ala Thr Ala Phe Ala Glu Val
                420                 425                 430
Glu Asn Glu Thr Gly Glu Ala Thr Arg Pro Trp Gly Phe Pro Thr Pro
            435                 440                 445
Gly Leu Gly Pro Ala Thr Ala Phe Thr Ser Glu Asp Leu Val Val Gln
450                 455                 460
Val Thr Ala Val Pro Gly Gln Pro His Leu Pro Gly Val Val Phe
465                 470                 475                 480
His Tyr Arg Pro Gly Pro Thr Arg Tyr Ser Leu Thr Phe Glu Glu Ala
                485                 490                 495
Gln Gln Ala Cys Pro Gly Thr Gly Ala Val Ile Ala Ser Pro Glu Gln
                500                 505                 510
Leu Gln Ala Ala Tyr Glu Ala Gly Tyr Glu Gln Cys Asp Ala Gly Trp
            515                 520                 525
Leu Arg Asp Gln Thr Val Arg Tyr Pro Ile Val Ser Pro Arg Thr Pro
530                 535                 540
Cys Val Gly Asp Lys Asp Ser Ser Pro Gly Val Arg Thr Tyr Gly Val
545                 550                 555                 560
Arg Pro Ser Thr Glu Thr Tyr Asp Val Tyr Cys Phe Val Asp Arg Leu
                565                 570                 575
Glu Gly Glu Val Phe Phe Ala Thr Arg Leu Glu Gln Phe Thr Phe Gln
                580                 585                 590
Glu Ala Leu Glu Phe Cys Glu Ser His Asn Ala Thr Ala Thr Thr Gly
            595                 600                 605
Gln Leu Tyr Ala Ala Trp Ser Arg Gly Leu Asp Lys Cys Tyr Ala Gly
        610                 615                 620
Trp Leu Ala Asp Gly Ser Leu Arg Tyr Pro Ile Val Thr Pro Arg Pro
625                 630                 635                 640
Ala Cys Gly Gly Asp Lys Pro Gly Val Arg Thr Val Tyr Leu Tyr Pro
                645                 650                 655
Asn Gln Thr Gly Leu Pro Asp Pro Leu Ser Arg His His Ala Phe Cys
                660                 665                 670
Phe Arg Gly Ile Ser Ala Val Pro Ser Pro Gly Glu Glu Gly Gly
            675                 680                 685
Thr Pro Thr Ser Pro Ser Gly Val Glu Glu Trp Ile Val Thr Gln Val
            690                 695                 700
Val Pro Gly Val Ala Ala Val Pro Val Glu Glu Thr Thr Ala Val
705                 710                 715                 720
Pro Ser Gly Glu Thr Thr Ala Ile Leu Glu Phe Thr Thr Glu Pro Glu
                725                 730                 735
Asn Gln Thr Glu Trp Glu Pro Ala Tyr Thr Pro Val Gly Thr Ser Pro
            740                 745                 750
Leu Pro Gly Ile Leu Pro Thr Trp Pro Pro Thr Gly Ala Glu Thr Glu
            755                 760                 765
Glu Ser Thr Glu Gly Pro Ser Ala Thr Glu Val Pro Ser Ala Ser Glu
            770                 775                 780
Glu Pro Ser Pro Ser Glu Val Pro Phe Pro Ser Glu Glu Pro Ser Pro
785                 790                 795                 800
Ser Glu Glu Pro Phe Pro Ser Val Arg Pro Phe Pro Ser Val Glu Leu
                805                 810                 815
Phe Pro Ser Glu Glu Pro Phe Pro Ser Lys Glu Pro Ser Pro Ser Glu
                820                 825                 830
```

```
Glu Pro Ser Ala Ser Glu Glu Pro Tyr Thr Pro Ser Pro Pro Glu Pro
        835                 840                 845

Ser Trp Thr Glu Leu Pro Ser Ser Gly Glu Glu Ser Gly Ala Pro Asp
    850                 855                 860

Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
                885                 890                 895

Asp Leu Asp Ser Ser Gly Leu Thr Ser Thr Val Gly Ser Gly Leu Thr
            900                 905                 910

Val Glu Ser Gly Leu Pro Ser Gly Asp Glu Glu Arg Ile Glu Trp Pro
                915                 920                 925

Ser Thr Pro Thr Val Gly Glu Leu Pro Ser Gly Ala Glu Ile Leu Glu
    930                 935                 940

Gly Ser Ala Ser Gly Val Gly Asp Leu Ser Gly Leu Pro Ser Gly Glu
945                 950                 955                 960

Val Leu Glu Thr Ser Ala Ser Gly Val Gly Asp Leu Ser Gly Leu Pro
                965                 970                 975

Ser Gly Glu Val Leu Glu Thr Thr Ala Pro Gly Val Gly Asp Ile Ser
            980                 985                 990

Gly Leu Pro Ser Gly Glu Val Leu Glu Thr Thr Ala Pro Gly Val Glu
            995                 1000                1005

Asp Ile Ser Gly Leu Pro Ser Gly Glu Val Leu Glu Thr Thr Ala
    1010                1015                1020

Pro Gly Val Glu Asp Ile Ser Gly Leu Pro Ser Gly Glu Val Leu
    1025                1030                1035

Glu Thr Thr Ala Pro Gly Val Glu Asp Ile Ser Gly Leu Pro Ser
    1040                1045                1050

Gly Glu Val Leu Glu Thr Thr Ala Pro Gly Val Glu Asp Ile Ser
    1055                1060                1065

Gly Leu Pro Ser Gly Glu Val Leu Glu Thr Ala Ala Pro Gly Val
    1070                1075                1080

Glu Asp Ile Ser Gly Leu Pro Ser Gly Glu Val Leu Glu Thr Ala
    1085                1090                1095

Ala Pro Gly Val Glu Asp Ile Ser Gly Leu Pro Ser Gly Glu Val
    1100                1105                1110

Leu Glu Thr Ala Ala Pro Gly Val Glu Asp Ile Ser Gly Leu Pro
    1115                1120                1125

Ser Gly Glu Val Leu Glu Thr Ala Ala Pro Gly Val Glu Asp Ile
    1130                1135                1140

Ser Gly Leu Pro Ser Gly Glu Val Leu Glu Thr Ala Ala Pro Gly
    1145                1150                1155

Val Glu Asp Ile Ser Gly Leu Pro Ser Gly Glu Val Leu Glu Thr
    1160                1165                1170

Ala Ala Pro Gly Val Glu Asp Ile Ser Gly Leu Pro Ser Gly Glu
    1175                1180                1185

Val Leu Glu Thr Ala Ala Pro Gly Val Glu Asp Ile Ser Gly Leu
    1190                1195                1200

Pro Ser Gly Glu Val Leu Glu Thr Ala Ala Pro Gly Val Glu Asp
    1205                1210                1215

Ile Ser Gly Leu Pro Ser Gly Glu Val Leu Glu Thr Ala Ala Pro
    1220                1225                1230
```

```
Gly Val Glu Asp Ile Ser Gly Leu Pro Ser Gly Glu Val Leu Glu
    1235                1240                1245

Thr Ala Ala Pro Gly Val Glu Asp Ile Ser Gly Leu Pro Ser Gly
    1250                1255                1260

Glu Val Leu Glu Thr Ala Ala Pro Gly Val Glu Asp Ile Ser Gly
    1265                1270                1275

Leu Pro Ser Gly Glu Val Leu Glu Thr Ala Pro Gly Val Glu
    1280                1285                1290

Glu Ile Ser Gly Leu Pro Ser Gly Glu Val Leu Glu Thr Thr Ala
    1295                1300                1305

Pro Gly Val Asp Glu Ile Ser Gly Leu Pro Ser Gly Glu Val Leu
    1310                1315                1320

Glu Thr Thr Ala Pro Gly Val Glu Glu Ile Ser Gly Leu Pro Ser
    1325                1330                1335

Gly Glu Val Leu Glu Thr Ser Thr Ser Ala Val Gly Asp Leu Ser
    1340                1345                1350

Gly Leu Pro Ser Gly Gly Glu Val Leu Glu Ile Ser Val Ser Gly
    1355                1360                1365

Val Glu Asp Ile Ser Gly Leu Pro Ser Gly Glu Val Val Glu Thr
    1370                1375                1380

Ser Ala Ser Gly Ile Glu Asp Val Ser Glu Leu Pro Ser Gly Glu
    1385                1390                1395

Gly Leu Glu Thr Ser Ala Ser Gly Val Glu Asp Leu Ser Arg Leu
    1400                1405                1410

Pro Ser Gly Glu Glu Val Leu Glu Ile Ser Ala Ser Gly Phe Gly
    1415                1420                1425

Asp Leu Ser Gly Val Pro Ser Gly Gly Glu Gly Leu Glu Thr Ser
    1430                1435                1440

Ala Ser Glu Val Gly Thr Asp Leu Ser Gly Leu Pro Ser Gly Arg
    1445                1450                1455

Glu Gly Leu Glu Thr Ser Ala Ser Gly Ala Glu Asp Leu Ser Gly
    1460                1465                1470

Leu Pro Ser Gly Lys Glu Asp Leu Val Gly Ser Ala Ser Gly Asp
    1475                1480                1485

Leu Asp Leu Gly Lys Leu Pro Ser Gly Thr Leu Gly Ser Gly Gln
    1490                1495                1500

Ala Pro Glu Thr Ser Gly Leu Pro Ser Gly Phe Ser Gly Glu Tyr
    1505                1510                1515

Ser Gly Val Asp Leu Gly Ser Gly Pro Pro Ser Gly Leu Pro Asp
    1520                1525                1530

Phe Ser Gly Leu Pro Ser Gly Phe Pro Thr Val Ser Leu Val Asp
    1535                1540                1545

Ser Thr Leu Val Glu Val Val Thr Ala Ser Thr Ala Ser Glu Leu
    1550                1555                1560

Glu Gly Arg Gly Thr Ile Gly Ile Ser Gly Ala Gly Glu Ile Ser
    1565                1570                1575

Gly Leu Pro Ser Ser Glu Leu Asp Ile Ser Gly Arg Ala Ser Gly
    1580                1585                1590

Leu Pro Ser Gly Thr Glu Leu Ser Gly Gln Ala Ser Gly Ser Pro
    1595                1600                1605

Asp Val Ser Gly Glu Ile Pro Gly Leu Phe Gly Val Ser Gly Gln
    1610                1615                1620

Pro Ser Gly Phe Pro Asp Thr Ser Gly Glu Thr Ser Gly Val Thr
```

```
            1625                1630                1635

Glu Leu Ser Gly Leu Ser Ser Gly Gln Pro Gly Val Ser Gly Glu
        1640                1645                1650

Ala Ser Gly Val Leu Tyr Gly Thr Ser Gln Pro Phe Gly Ile Thr
        1655                1660                1665

Asp Leu Ser Gly Glu Thr Ser Gly Val Pro Asp Leu Ser Gly Gln
        1670                1675                1680

Pro Ser Gly Leu Pro Gly Phe Ser Gly Ala Thr Ser Gly Val Pro
        1685                1690                1695

Asp Leu Val Ser Gly Thr Thr Ser Gly Ser Gly Glu Ser Ser Gly
        1700                1705                1710

Ile Thr Phe Val Asp Thr Ser Leu Val Glu Val Ala Pro Thr Thr
        1715                1720                1725

Phe Lys Glu Glu Glu Gly Leu Gly Ser Val Glu Leu Ser Gly Leu
        1730                1735                1740

Pro Ser Gly Glu Ala Asp Leu Ser Gly Lys Ser Gly Met Val Asp
        1745                1750                1755

Val Ser Gly Gln Phe Ser Gly Thr Val Asp Ser Ser Gly Phe Thr
        1760                1765                1770

Ser Gln Thr Pro Glu Phe Ser Gly Leu Pro Ser Gly Ile Ala Glu
        1775                1780                1785

Val Ser Gly Glu Ser Ser Arg Ala Glu Ile Gly Ser Ser Leu Pro
        1790                1795                1800

Ser Gly Ala Tyr Tyr Gly Ser Gly Thr Pro Ser Ser Phe Pro Thr
        1805                1810                1815

Val Ser Leu Val Asp Arg Thr Leu Val Glu Ser Val Thr Gln Ala
        1820                1825                1830

Pro Thr Ala Gln Glu Ala Gly Glu Gly Pro Ser Gly Ile Leu Glu
        1835                1840                1845

Leu Ser Gly Ala His Ser Gly Ala Pro Asp Met Ser Gly Glu His
        1850                1855                1860

Ser Gly Phe Leu Asp Leu Ser Gly Leu Gln Ser Gly Leu Ile Glu
        1865                1870                1875

Pro Ser Gly Glu Pro Pro Gly Thr Pro Tyr Phe Ser Gly Asp Phe
        1880                1885                1890

Ala Ser Thr Thr Asn Val Ser Gly Glu Ser Ser Val Ala Met Gly
        1895                1900                1905

Thr Ser Gly Glu Ala Ser Gly Leu Pro Glu Val Thr Leu Ile Thr
        1910                1915                1920

Ser Glu Phe Val Glu Gly Val Thr Glu Pro Thr Ile Ser Gln Glu
        1925                1930                1935

Leu Gly Gln Arg Pro Pro Val Thr His Thr Pro Gln Leu Phe Glu
        1940                1945                1950

Ser Ser Gly Lys Val Ser Thr Ala Gly Asp Ile Ser Gly Ala Thr
        1955                1960                1965

Pro Val Leu Pro Gly Ser Gly Val Glu Val Ser Ser Val Pro Glu
        1970                1975                1980

Ser Ser Ser Glu Thr Ser Ala Tyr Pro Glu Ala Gly Phe Gly Ala
        1985                1990                1995

Ser Ala Ala Pro Glu Ala Ser Arg Glu Asp Ser Gly Ser Pro Asp
        2000                2005                2010

Leu Ser Glu Thr Thr Ser Ala Phe His Glu Ala Asn Leu Glu Arg
        2015                2020                2025
```

| | | | | | | | | | | |
|---|---|---|---|---|---|---|---|---|---|---|
| Ser | Ser | Gly | Leu | Gly | Val | Ser | Gly | Ser | Thr | Leu | Thr | Phe | Gln | Glu |
| | 2030 | | | | 2035 | | | | 2040 | |

Ser Ser Gly Leu Gly Val Ser Gly Ser Thr Leu Thr Phe Gln Glu
        2030                2035                2040

Gly Glu Ala Ser Ala Ala Pro Glu Val Ser Gly Glu Ser Thr Thr
        2045                2050                2055

Thr Ser Asp Val Gly Thr Glu Ala Pro Gly Leu Pro Ser Ala Thr
        2060                2065                2070

Pro Thr Ala Ser Gly Asp Arg Thr Glu Ile Ser Gly Asp Leu Ser
        2075                2080                2085

Gly His Thr Ser Gln Leu Gly Val Val Ile Ser Thr Ser Ile Pro
        2090                2095                2100

Glu Ser Glu Trp Thr Gln Gln Thr Gln Arg Pro Ala Glu Thr His
        2105                2110                2115

Leu Glu Ile Glu Ser Ser Ser Leu Leu Tyr Ser Gly Glu Glu Thr
        2120                2125                2130

His Thr Val Glu Thr Ala Thr Ser Pro Thr Asp Ala Ser Ile Pro
        2135                2140                2145

Ala Ser Pro Glu Trp Lys Arg Glu Ser Glu Ser Thr Ala Ala Asp
        2150                2155                2160

Gln Glu Val Cys Glu Glu Gly Trp Asn Lys Tyr Gln Gly His Cys
        2165                2170                2175

Tyr Arg His Phe Pro Asp Arg Glu Thr Trp Val Asp Ala Glu Arg
        2180                2185                2190

Arg Cys Arg Glu Gln Gln Ser His Leu Ser Ser Ile Val Thr Pro
        2195                2200                2205

Glu Glu Gln Glu Phe Val Asn Asn Asn Ala Gln Asp Tyr Gln Trp
        2210                2215                2220

Ile Gly Leu Asn Asp Arg Thr Ile Glu Gly Asp Phe Arg Trp Ser
        2225                2230                2235

Asp Gly His Pro Met Gln Phe Glu Asn Trp Arg Pro Asn Gln Pro
        2240                2245                2250

Asp Asn Phe Phe Ala Ala Gly Glu Asp Cys Val Val Met Ile Trp
        2255                2260                2265

His Glu Lys Gly Glu Trp Asn Asp Val Pro Cys Asn Tyr His Leu
        2270                2275                2280

Pro Phe Thr Cys Lys Lys Gly Thr Ala Thr Thr Tyr Lys Arg Arg
        2285                2290                2295

Leu Gln Lys Arg Ser Ser Arg His Pro Arg Arg Ser Arg Pro Ser
        2300                2305                2310

Thr Ala His
        2315

```
<210> SEQ ID NO 21
<211> LENGTH: 1108
<212> TYPE: DNA
<213> ORGANISM: Homo sapiens
<220> FEATURE:
<221> NAME/KEY: CDS
<222> LOCATION: (143)..(1096)

<400> SEQUENCE: 21
gagtgagtga gagggcagag gaaatactca atctgtgcca ctcactgcct tgagcctgct      60
tcctcactcc aggactgcca gaggctcact cccttgagcc tgcttcctca ctccaggact     120
gccagaggaa gcaatcacca aa atg aag act gct tta att ttg ctc agc att     172
                         Met Lys Thr Ala Leu Ile Leu Leu Ser Ile
                           1               5                  10
```

```
ttg gga atg gcc tgt gct ttc tca atg aaa aat ttg cat cga aga gtc    220
Leu Gly Met Ala Cys Ala Phe Ser Met Lys Asn Leu His Arg Arg Val
             15                  20                  25 aaa ata gag gat tct gaa gaa aat ggg gtc ttt aag tac agg cca cga    268
Lys Ile Glu Asp Ser Glu Glu Asn Gly Val Phe Lys Tyr Arg Pro Arg
         30                  35                  40 tat tat ctt tac aag cat gcc tac ttt tat cct cat tta aaa cga ttt    316
Tyr Tyr Leu Tyr Lys His Ala Tyr Phe Tyr Pro His Leu Lys Arg Phe
             45                  50                  55 cca gtt cag ggc agt agt gac tca tcc gaa gaa aat gga gat gac agt    364
Pro Val Gln Gly Ser Ser Asp Ser Ser Glu Glu Asn Gly Asp Asp Ser
         60                  65                  70 tca gaa gag gag gag gaa gaa gag gag act tca aat gaa gga gaa aac    412
Ser Glu Glu Glu Glu Glu Glu Glu Glu Thr Ser Asn Glu Gly Glu Asn
75                  80                  85                  90 aat gaa gaa tcg aat gaa gat gaa gac tct gag gct gag aat acc aca    460
Asn Glu Glu Ser Asn Glu Asp Glu Asp Ser Glu Ala Glu Asn Thr Thr
                 95                 100                 105 ctt tct gct aca aca ctg ggc tat gga gag gac gcc acg cct ggc aca    508
Leu Ser Ala Thr Thr Leu Gly Tyr Gly Glu Asp Ala Thr Pro Gly Thr
             110                 115                 120 ggg tat aca ggg tta gct gca atc cag ctt ccc aag aag gct ggg gat    556
Gly Tyr Thr Gly Leu Ala Ala Ile Gln Leu Pro Lys Lys Ala Gly Asp
         125                 130                 135 ata aca aac aaa gct aca aaa gag aag gaa agt gat gaa gaa gaa gag    604
Ile Thr Asn Lys Ala Thr Lys Glu Lys Glu Ser Asp Glu Glu Glu Glu
     140                 145                 150 gag gaa gag gaa gga aat gaa aac gaa gaa agc gaa gca gaa gtg gat    652
Glu Glu Glu Glu Gly Asn Glu Asn Glu Glu Ser Glu Ala Glu Val Asp
155                 160                 165                 170 gaa aac gaa caa ggc ata aac ggc acc agt acc aac agc aca gag gca    700
Glu Asn Glu Gln Gly Ile Asn Gly Thr Ser Thr Asn Ser Thr Glu Ala
                 175                 180                 185 gaa aac ggc aac ggc agc agc gga gga gac aat gga gaa gaa ggg gaa    748
Glu Asn Gly Asn Gly Ser Ser Gly Gly Asp Asn Gly Glu Glu Gly Glu
             190                 195                 200 gaa gaa agt gtc act gga gcc aat gca gaa ggc acc aca gag acc gga    796
Glu Glu Ser Val Thr Gly Ala Asn Ala Glu Gly Thr Thr Glu Thr Gly
         205                 210                 215 ggg cag ggc aag ggc acc tcg aag aca aca acc tct cca aat ggt ggg    844
Gly Gln Gly Lys Gly Thr Ser Lys Thr Thr Thr Ser Pro Asn Gly Gly
     220                 225                 230 ttt gaa cct aca acc cca cca caa gtc tat aga acc act tcc cca cct    892
Phe Glu Pro Thr Thr Pro Pro Gln Val Tyr Arg Thr Thr Ser Pro Pro
235                 240                 245                 250 ttt ggg aaa acc acc acc gtt gaa tac gag ggg gag tac gaa tac acg    940
Phe Gly Lys Thr Thr Thr Val Glu Tyr Glu Gly Glu Tyr Glu Tyr Thr
                 255                 260                 265 ggc gtc aat gaa tac gac aat gga tat gaa atc tat gaa agt gag aac    988
Gly Val Asn Glu Tyr Asp Asn Gly Tyr Glu Ile Tyr Glu Ser Glu Asn
             270                 275                 280 ggg gaa cct cgt ggg gac aat tac cga gcc tat gaa gat gag tac agc   1036
Gly Glu Pro Arg Gly Asp Asn Tyr Arg Ala Tyr Glu Asp Glu Tyr Ser
         285                 290                 295 tac ttt aaa gga caa ggc tac gat ggc tat gat ggt cag aat tac tac   1084
Tyr Phe Lys Gly Gln Gly Tyr Asp Gly Tyr Asp Gly Gln Asn Tyr Tyr
     300                 305                 310 cac cac cag tga agctccagcc tg                                      1108
His His Gln
```

<210> SEQ ID NO 22
<211> LENGTH: 317
<212> TYPE: PRT
<213> ORGANISM: Homo sapiens

<400> SEQUENCE: 22

```
Met Lys Thr Ala Leu Ile Leu Ser Ile Leu Gly Met Ala Cys Ala
1               5                   10                  15

Phe Ser Met Lys Asn Leu His Arg Arg Val Lys Ile Glu Asp Ser Glu
            20                  25                  30

Glu Asn Gly Val Phe Lys Tyr Arg Pro Arg Tyr Leu Tyr Lys His
        35                  40                  45

Ala Tyr Phe Tyr Pro His Leu Lys Arg Phe Pro Val Gln Gly Ser Ser
    50                  55                  60

Asp Ser Ser Glu Glu Asn Gly Asp Ser Ser Glu Glu Glu Glu
65                  70                  75                  80

Glu Glu Glu Thr Ser Asn Glu Gly Glu Asn Asn Glu Ser Asn Glu
                85                  90                  95

Asp Glu Asp Ser Glu Ala Glu Asn Thr Thr Leu Ser Ala Thr Thr Leu
            100                 105                 110

Gly Tyr Gly Glu Asp Ala Thr Pro Gly Thr Gly Tyr Thr Gly Leu Ala
        115                 120                 125

Ala Ile Gln Leu Pro Lys Lys Ala Gly Asp Ile Thr Asn Lys Ala Thr
    130                 135                 140

Lys Glu Lys Glu Ser Asp Glu Glu Glu Glu Glu Glu Glu Gly Asn
145                 150                 155                 160

Glu Asn Glu Glu Ser Glu Ala Glu Val Asp Glu Asn Glu Gln Gly Ile
                165                 170                 175

Asn Gly Thr Ser Thr Asn Ser Thr Glu Ala Glu Asn Gly Asn Gly Ser
            180                 185                 190

Ser Gly Gly Asp Asn Gly Glu Glu Gly Glu Glu Glu Ser Val Thr Gly
        195                 200                 205

Ala Asn Ala Glu Gly Thr Thr Glu Thr Gly Gly Gln Gly Lys Gly Thr
    210                 215                 220

Ser Lys Thr Thr Thr Ser Pro Asn Gly Gly Phe Glu Pro Thr Thr Pro
225                 230                 235                 240

Pro Gln Val Tyr Arg Thr Thr Ser Pro Pro Phe Gly Lys Thr Thr Thr
                245                 250                 255

Val Glu Tyr Glu Gly Glu Tyr Glu Tyr Thr Gly Val Asn Glu Tyr Asp
            260                 265                 270

Asn Gly Tyr Glu Ile Tyr Glu Ser Glu Asn Gly Glu Pro Arg Gly Asp
        275                 280                 285

Asn Tyr Arg Ala Tyr Glu Asp Glu Tyr Ser Tyr Phe Lys Gly Gln Gly
    290                 295                 300

Tyr Asp Gly Tyr Asp Gly Gln Asn Tyr Tyr His His Gln
305                 310                 315
```

<210> SEQ ID NO 23
<211> LENGTH: 498
<212> TYPE: DNA
<213> ORGANISM: Homo sapiens
<220> FEATURE:
<221> NAME/KEY: CDS
<222> LOCATION: (19)..(321)

```
<400> SEQUENCE: 23
cgcagccacc gagacacc atg aga gcc ctc aca ctc ctc gcc cta ttg gcc        51
                    Met Arg Ala Leu Thr Leu Leu Ala Leu Leu Ala
                     1               5                  10 ctg gcc gca ctt tgc atc gct ggc cag gca ggt gcg aag ccc agc ggt        99
Leu Ala Ala Leu Cys Ile Ala Gly Gln Ala Gly Ala Lys Pro Ser Gly
             15                  20                  25 gca gag tcc agc aaa ggt gca gcc ttt gtg tcc aag cag gag ggc agc       147
Ala Glu Ser Ser Lys Gly Ala Ala Phe Val Ser Lys Gln Glu Gly Ser
         30                  35                  40 gag gta gtg aag aga ccc agg cgc tac ctg tat caa tgg ctg gga gcc       195
Glu Val Val Lys Arg Pro Arg Arg Tyr Leu Tyr Gln Trp Leu Gly Ala
 45                  50                  55 cca gtc ccc tac ccg gat ccc ctg gag ccc agg agg gag gtg tgt gag       243
Pro Val Pro Tyr Pro Asp Pro Leu Glu Pro Arg Arg Glu Val Cys Glu
 60                  65                  70                  75 ctc aat ccg gac tgt gac gag ttg gct gac cac atc ggc ttt cag gag       291
Leu Asn Pro Asp Cys Asp Glu Leu Ala Asp His Ile Gly Phe Gln Glu
                 80                  85                  90 gcc tat cgg cgc ttc tac ggc ccg gtc tag ggtgtcgctc tgctggcctg         341
Ala Tyr Arg Arg Phe Tyr Gly Pro Val
             95                 100 gccggcaacc ccagttctgc tcctctccag gcacccttct ttcctcttcc ccttgccctt     401
gccctgacct cccagcccta tgatgtggg gtccccatca tcccagctgc tcccaaataa      461
actccagaag aggaatctga aaaaaaaaaa aaaaaaa                              498

<210> SEQ ID NO 24
<211> LENGTH: 100
<212> TYPE: PRT
<213> ORGANISM: Homo sapiens

<400> SEQUENCE: 24

Met Arg Ala Leu Thr Leu Leu Ala Leu Leu Ala Ala Leu Cys
 1               5                  10                  15

Ile Ala Gly Gln Ala Gly Ala Lys Pro Ser Gly Ala Glu Ser Ser Lys
             20                  25                  30

Gly Ala Ala Phe Val Ser Lys Gln Glu Gly Ser Glu Val Val Lys Arg
         35                  40                  45

Pro Arg Arg Tyr Leu Tyr Gln Trp Leu Gly Ala Pro Val Pro Tyr Pro
     50                  55                  60

Asp Pro Leu Glu Pro Arg Arg Glu Val Cys Glu Leu Asn Pro Asp Cys
 65                  70                  75                  80

Asp Glu Leu Ala Asp His Ile Gly Phe Gln Glu Ala Tyr Arg Arg Phe
                 85                  90                  95

Tyr Gly Pro Val
            100

<210> SEQ ID NO 25
<211> LENGTH: 2383
<212> TYPE: DNA
<213> ORGANISM: Homo sapiens
<220> FEATURE:
<221> NAME/KEY: CDS
<222> LOCATION: (320)..(1825)

<400> SEQUENCE: 25
ctccttcaag ccctcagtca gttgtgcagg agaaaggggg cggttggctt tctcctttca      60
agaacgagtt attttcagct gctgactgga gacggtgcac gtctggatac gagagcattt    120
```

```
ccactatggg actggataca aacacacacc cggcagactt caagagtctc agactgagga       180
gaaagccttt ccttctgctg ctactgctgc tgccgctgct tttgaaagtc cactcctttc       240 atggttttc ctgccaaacc agaggcacct ttgctgctgc cgctgttctc tttggtgtca       300
ttcagcggct ggccagagg atg aga ctc ccc aaa ctc ctc act ttc ttg ctt       352
                     Met Arg Leu Pro Lys Leu Leu Thr Phe Leu Leu
                      1               5                  10 tgg tac ctg gct tgg ctg gac ctg gaa ttc atc tgc act gtg ttg ggt        400
Trp Tyr Leu Ala Trp Leu Asp Leu Glu Phe Ile Cys Thr Val Leu Gly
            15                  20                  25 gcc cct gac ttg ggc cag aga ccc cag ggg acc agg cca gga ttg gcc        448
Ala Pro Asp Leu Gly Gln Arg Pro Gln Gly Thr Arg Pro Gly Leu Ala
        30                  35                  40 aaa gca gag gcc aag gag agg ccc ccc ctg gcc cgg aac gtc ttc agg        496
Lys Ala Glu Ala Lys Glu Arg Pro Pro Leu Ala Arg Asn Val Phe Arg
    45                  50                  55 cca ggg ggt cac agc tat ggt ggg ggg gcc acc aat gcc aat gcc agg        544
Pro Gly Gly His Ser Tyr Gly Gly Gly Ala Thr Asn Ala Asn Ala Arg
60                  65                  70                  75 gca aag gga ggc acc ggg cag aca gga ggc ctg aca cag ccc aag aag        592
Ala Lys Gly Gly Thr Gly Gln Thr Gly Gly Leu Thr Gln Pro Lys Lys
                80                  85                  90 gat gaa ccc aaa aag ctg ccc ccc aga ccg ggc ggc cct gaa ccc aag        640
Asp Glu Pro Lys Lys Leu Pro Pro Arg Pro Gly Gly Pro Glu Pro Lys
            95                 100                 105 cca gga cac cct ccc caa aca agg cag gct aca gcc cgg act gtg acc        688
Pro Gly His Pro Pro Gln Thr Arg Gln Ala Thr Ala Arg Thr Val Thr
        110                 115                 120 cca aaa gga cag ctt ccc gga ggc aag gca ccc cca aaa gca gga tct        736
Pro Lys Gly Gln Leu Pro Gly Gly Lys Ala Pro Pro Lys Ala Gly Ser
    125                 130                 135 gtc ccc agc tcc ttc ctg ctg aag aag gcc agg gag ccc ggg ccc cca        784
Val Pro Ser Ser Phe Leu Leu Lys Lys Ala Arg Glu Pro Gly Pro Pro
140                 145                 150                 155 cga gag ccc aag gag ccg ttt cgc cca ccc ccc atc aca ccc cac gag        832
Arg Glu Pro Lys Glu Pro Phe Arg Pro Pro Pro Ile Thr Pro His Glu
                160                 165                 170 tac atg ctc tcg ctg tac agg acg ctg tcc gat gct gac aga aag gga        880
Tyr Met Leu Ser Leu Tyr Arg Thr Leu Ser Asp Ala Asp Arg Lys Gly
            175                 180                 185 ggc aac agc agc gtg aag ttg gag gct ggc ctg gcc aac acc atc acc        928
Gly Asn Ser Ser Val Lys Leu Glu Ala Gly Leu Ala Asn Thr Ile Thr
        190                 195                 200 agc ttt att gac aaa ggg caa gat gac cga ggt ccc gtg gtc agg aag        976
Ser Phe Ile Asp Lys Gly Gln Asp Asp Arg Gly Pro Val Val Arg Lys
    205                 210                 215 cag agg tac gtg ttt gac att agt gcc ctg gag aag gat ggg ctg ctg       1024
Gln Arg Tyr Val Phe Asp Ile Ser Ala Leu Glu Lys Asp Gly Leu Leu
220                 225                 230                 235 ggg gcc gag ctg cgg atc ttg cgg aag aag ccc tcg gac acg gcc aag       1072
Gly Ala Glu Leu Arg Ile Leu Arg Lys Lys Pro Ser Asp Thr Ala Lys
                240                 245                 250 cca gcg gcc ccc gga ggc ggg cgg gct gcc cag ctg aag ctg tcc agc       1120
Pro Ala Ala Pro Gly Gly Gly Arg Ala Ala Gln Leu Lys Leu Ser Ser
            255                 260                 265 tgc ccc agc ggc cgg cag ccg gcc tcc ttg ctg gat gtg cgc tcc gtg       1168
Cys Pro Ser Gly Arg Gln Pro Ala Ser Leu Leu Asp Val Arg Ser Val
        270                 275                 280
```

| | | |
|---|---|---|
| cca ggc ctg gac gga tct ggc tgg gag gtg ttc gac atc tgg aag ctc<br>Pro Gly Leu Asp Gly Ser Gly Trp Glu Val Phe Asp Ile Trp Lys Leu<br>285                         290                         295 | | 1216 |
| ttc cga aac ttt aag aac tcg gcc cag ctg tgc ctg gag ctg gag gcc<br>Phe Arg Asn Phe Lys Asn Ser Ala Gln Leu Cys Leu Glu Leu Glu Ala<br>300                         305                        310                       315 | | 1264 |
| tgg gaa cgg ggc agg gcc gtg gac ctc cgt ggc ctg ggc ttc gac cgc<br>Trp Glu Arg Gly Arg Ala Val Asp Leu Arg Gly Leu Gly Phe Asp Arg<br>                   320                        325                       330 | | 1312 |
| gcc gcc cgg cag gtc cac gag aag gcc ctg ttc ctg gtg ttt ggc cgc<br>Ala Ala Arg Gln Val His Glu Lys Ala Leu Phe Leu Val Phe Gly Arg<br>                335                        340                       345 | | 1360 |
| acc aag aaa cgg gac ctg ttc ttt aat gag att aag gcc cgc tct ggc<br>Thr Lys Lys Arg Asp Leu Phe Phe Asn Glu Ile Lys Ala Arg Ser Gly<br>350                         355                        360 | | 1408 |
| cag gac gat aag acc gtg tat gag tac ctg ttc agc cag cgg cga aaa<br>Gln Asp Asp Lys Thr Val Tyr Glu Tyr Leu Phe Ser Gln Arg Arg Lys<br>365                         370                        375 | | 1456 |
| cgg cgg gcc cca ctg gcc act cgc cag ggc aag cga ccc agc aag aac<br>Arg Arg Ala Pro Leu Ala Thr Arg Gln Gly Lys Arg Pro Ser Lys Asn<br>380                       385                         390                       395 | | 1504 |
| ctt aag gct cgc tgc agt cgg aag gca ctg cat gtc aac ttc aag gac<br>Leu Lys Ala Arg Cys Ser Arg Lys Ala Leu His Val Asn Phe Lys Asp<br>                400                        405                       410 | | 1552 |
| atg ggc tgg gac gac tgg atc atc gca ccc ctt gag tac gag gct ttc<br>Met Gly Trp Asp Asp Trp Ile Ile Ala Pro Leu Glu Tyr Glu Ala Phe<br>                   415                        420                       425 | | 1600 |
| cac tgc gag ggg ctg tgc gag ttc cca ttg cgc tcc cac ctg gag ccc<br>His Cys Glu Gly Leu Cys Glu Phe Pro Leu Arg Ser His Leu Glu Pro<br>                  430                        435                       440 | | 1648 |
| acg aat cat gca gtc atc cag acc ctg atg aac tcc atg gac ccc gag<br>Thr Asn His Ala Val Ile Gln Thr Leu Met Asn Ser Met Asp Pro Glu<br>445                         450                        455 | | 1696 |
| tcc aca cca ccc acc tgc tgt gtg ccc acg cgg ctg agt ccc atc agc<br>Ser Thr Pro Pro Thr Cys Cys Val Pro Thr Arg Leu Ser Pro Ile Ser<br>460                         465                        470                       475 | | 1744 |
| atc ctc ttc att gac tct gcc aac aac gtg gtg tat aag cag tat gag<br>Ile Leu Phe Ile Asp Ser Ala Asn Asn Val Val Tyr Lys Gln Tyr Glu<br>                  480                        485                       490 | | 1792 |
| gac atg gtc gtg gag tcg tgt ggc tgc agg tag cagcactggc cctctgtctt<br>Asp Met Val Val Glu Ser Cys Gly Cys Arg<br>                 495                        500 | | 1845 |
| cctgggtggc acatcccaag agcccttcc tgcactcctg gaatcacaga ggggtcagga | | 1905 |
| agctgtggca ggagcatcta cacagcttgg gtgaaagggg attccaataa gcttgctcgc | | 1965 |
| tctctgagtg tgacttgggc taaaggcccc cttttatcca caagttcccc tggctgagga | | 2025 |
| ttgctgcccg tctgctgatg tgaccagtgg caggcacagg tccagggaga cagactctga | | 2085 |
| atgggactga gtcccaggaa acagtgcttt ccgatgagac tcagcccacc atttctcctc | | 2145 |
| acctgggcct tctcagcctc tggactctcc taagcacctc tcaggagagc cacaggtgcc | | 2205 |
| actgcctcct caaatcacat ttgtgcctgg tgacttcctg tccctgggac agttgagaag | | 2265 |
| ctgactgggc aagagtggga gagaagagga gagggcttgg atagagttga ggagtgtgag | | 2325 |
| gctgttagac tgttagattt aaatgtatat tgatgagata aaaagcaaaa ctgtgcct | | 2383 |

<210> SEQ ID NO 26
<211> LENGTH: 501
<212> TYPE: PRT
<213> ORGANISM: Homo sapiens

<400> SEQUENCE: 26

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp

```
                          405                 410                 415
Trp Ile Ile Ala Pro Leu Glu Tyr Glu Ala Phe His Cys Glu Gly Leu
                420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
        450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 27
<211> LENGTH: 1378
<212> TYPE: DNA
<213> ORGANISM: Homo sapiens
<220> FEATURE:
<221> NAME/KEY: CDS
<222> LOCATION: (276)..(1130)

<400> SEQUENCE: 27
ggtagcagca tccaccgggc gggaggtcgg aggcagcaag gccttaaagg ctactgagtg      60
cgccggccgt tccgtgtcca gaacctcccc tactcctccg ccttctcttc cttggccgcc    120
caccgccaag ttccgactcc ggttttcgcc tttgcaaagc ctaaggagga ggttaggaac    180
agccgcgccc cctccctgc ggccgccgcc ccctgcctct cggctctgct ccctgccgcg     240
tgcgcctggg ccgtgcgccc cggcaggcgc cagcc atg tcg atg ctg ccg tcg       293
                                        Met Ser Met Leu Pro Ser
                                          1               5 ttt ggc ttt acg cag gag caa gtg gcg tgc gtg tgc gag gtt ctg cag      341
Phe Gly Phe Thr Gln Glu Gln Val Ala Cys Val Cys Glu Val Leu Gln
              10                  15                  20 caa ggc gga aac ctg gag cgc ctg ggc agg ttc ctg tgg tca ctg ccc      389
Gln Gly Gly Asn Leu Glu Arg Leu Gly Arg Phe Leu Trp Ser Leu Pro
          25                  30                  35 gcc tgc gac cac ctg cac aag aac gag agc gta ctc aag gcc aag gcg      437
Ala Cys Asp His Leu His Lys Asn Glu Ser Val Leu Lys Ala Lys Ala
     40                  45                  50 gtg gtc gcc ttc cac cgc ggc aac ttc cgt gag ctc tac aag atc ctg      485
Val Val Ala Phe His Arg Gly Asn Phe Arg Glu Leu Tyr Lys Ile Leu
 55                  60                  65                  70 gag agc cac cag ttc tcg cct cac aac cac ccc aaa ctg cag caa ctg      533
Glu Ser His Gln Phe Ser Pro His Asn His Pro Lys Leu Gln Gln Leu
                 75                  80                  85 tgg ctg aag gcg cat tac gtg gag gcc gag aag ctg cgc ggc cga ccc      581
Trp Leu Lys Ala His Tyr Val Glu Ala Glu Lys Leu Arg Gly Arg Pro
             90                  95                 100 ctg ggc gcc gtg ggc aaa tat cgg gtg cgc cga aaa ttt cca ctg ccg      629
Leu Gly Ala Val Gly Lys Tyr Arg Val Arg Arg Lys Phe Pro Leu Pro
         105                 110                 115 cgc acc atc tgg gac ggc gag gag acc agc tac tgc ttc aag gag aag      677
Arg Thr Ile Trp Asp Gly Glu Glu Thr Ser Tyr Cys Phe Lys Glu Lys
     120                 125                 130 tcg agg ggt gtc ctg cgg gag tgg tac gcg cac aat ccc tac cca tcg      725
Ser Arg Gly Val Leu Arg Glu Trp Tyr Ala His Asn Pro Tyr Pro Ser
135                 140                 145                 150
```

```
ccg cgt gag aag cgg gag ctg gcc gag gcc acc ggc ctc acc acc acc    773
Pro Arg Glu Lys Arg Glu Leu Ala Glu Ala Thr Gly Leu Thr Thr Thr
            155                 160                 165 cag gtc agc aac tgg ttt aag aac cgg agg caa aga gac cgg gcc gcg    821
Gln Val Ser Asn Trp Phe Lys Asn Arg Arg Gln Arg Asp Arg Ala Ala
        170                 175                 180 gag gcc aag gaa agg gag aac acc gaa aac aat aac tcc tcc tcc aac    869
Glu Ala Lys Glu Arg Glu Asn Thr Glu Asn Asn Asn Ser Ser Ser Asn
        185                 190                 195 aag cag aac caa ctc tct cct ctg gaa ggg ggc aag ccg ctc atg tcc    917
Lys Gln Asn Gln Leu Ser Pro Leu Glu Gly Gly Lys Pro Leu Met Ser
    200                 205                 210 agc tca gaa gag gaa ttc tca cct ccc caa agt cca gac cag aac tcg    965
Ser Ser Glu Glu Glu Phe Ser Pro Pro Gln Ser Pro Asp Gln Asn Ser
215                 220                 225                 230 gtc ctt ctg ctg cag ggc aat atg ggc cac gcc agg agc tca aac tat   1013
Val Leu Leu Leu Gln Gly Asn Met Gly His Ala Arg Ser Ser Asn Tyr
                235                 240                 245 tct ctc ccg ggc tta aca gcc tcg cag ccc agt cac ggc ctg cag acc   1061
Ser Leu Pro Gly Leu Thr Ala Ser Gln Pro Ser His Gly Leu Gln Thr
            250                 255                 260 cac cag cat cag ctc caa gac tct ctg ctc ggc ccc ctc acc tcc agt   1109
His Gln His Gln Leu Gln Asp Ser Leu Leu Gly Pro Leu Thr Ser Ser
        265                 270                 275 ctg gtg gac ttg ggg tcc taa gtggggaggg actggggcct cgaagggatt      1160
Leu Val Asp Leu Gly Ser
        280 cctggagcag caaccactgc agcgactagg gacacttgta aatagaaatc aggaacattt  1220 ttgcagcttg tttctggagt tgtttgcgca taaggaatg gtggactttc acaaatatct  1280 ttttaaaaat caaaaccaac agcgatctca agcttaatct cctcttctct ccaactcttt  1340 ccacttttgc attttccttc ccaatgcaga gatcaggg                          1378

<210> SEQ ID NO 28
<211> LENGTH: 284
<212> TYPE: PRT
<213> ORGANISM: Homo sapiens

<400> SEQUENCE: 28

Met Ser Met Leu Pro Ser Phe Gly Phe Thr Gln Glu Gln Val Ala Cys
1               5                   10                  15

Val Cys Glu Val Leu Gln Gln Gly Gly Asn Leu Glu Arg Leu Gly Arg
            20                  25                  30

Phe Leu Trp Ser Leu Pro Ala Cys Asp His Leu His Lys Asn Glu Ser
        35                  40                  45

Val Leu Lys Ala Lys Ala Val Val Ala Phe His Arg Gly Asn Phe Arg
    50                  55                  60

Glu Leu Tyr Lys Ile Leu Glu Ser His Gln Phe Ser Pro His Asn His
65                  70                  75                  80

Pro Lys Leu Gln Gln Leu Trp Leu Lys Ala His Tyr Val Glu Ala Glu
                85                  90                  95

Lys Leu Arg Gly Arg Pro Leu Gly Ala Val Gly Lys Tyr Arg Val Arg
            100                 105                 110

Arg Lys Phe Pro Leu Pro Arg Thr Ile Trp Asp Gly Glu Glu Thr Ser
        115                 120                 125

Tyr Cys Phe Lys Glu Lys Ser Arg Gly Val Leu Arg Glu Trp Tyr Ala
    130                 135                 140
```

```
His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
            165                 170                 175

Gln Arg Asp Arg Ala Ala Glu Ala Lys Glu Arg Glu Asn Thr Glu Asn
            180                 185                 190

Asn Asn Ser Ser Ser Asn Lys Gln Asn Gln Leu Ser Pro Leu Glu Gly
        195                 200                 205

Gly Lys Pro Leu Met Ser Ser Glu Glu Glu Phe Ser Pro Pro Gln
    210                 215                 220

Ser Pro Asp Gln Asn Ser Val Leu Leu Leu Gln Gly Asn Met Gly His
225                 230                 235                 240

Ala Arg Ser Ser Asn Tyr Ser Leu Pro Gly Leu Thr Ala Ser Gln Pro
                245                 250                 255

Ser His Gly Leu Gln Thr His Gln His Gln Leu Gln Asp Ser Leu Leu
            260                 265                 270

Gly Pro Leu Thr Ser Ser Leu Val Asp Leu Gly Ser
            275                 280

<210> SEQ ID NO 29
<211> LENGTH: 2590
<212> TYPE: DNA
<213> ORGANISM: Homo sapiens
<220> FEATURE:
<221> NAME/KEY: CDS
<222> LOCATION: (546)..(1112)
<220> FEATURE:
<221> NAME/KEY: CDS
<222> LOCATION: (2036)..(2071)

<400> SEQUENCE: 29
caggcgctgg cgcacatggg aggcaaagac agacagggtg cggtcaggca gcagggccag      60
ggcggctggg ttaactcagt tgtgccacgg gagaaaacgg ggtggtgggt tcctcccctc     120
tcccggggac gggggggcact gcagttttgg ggccctgagt aactacagcc cagaagcgac    180
ctcccagttc ctccgcatcc ccagagacgg aacgatgccc ccaaagacca gccccgcccc    240
ccccaccccc gccaaagcgt ggccacagaa ggccgaggga cgcggcgggc gctgctcgag    300
gagcctccgg gctgagaggg gcggggcgtg cgcgggggag gggccgggac gccgctataa    360
aggcgcagct cggggcccg ctccggcccg gacgcacat gtgcgcgcga cgcccggcag    420
ctgccaccgc ggggcgcagc cgagaccccg cgcctcgccc ggccggccc gcgaggcccg     480 cggcggccga aggaggcggc atgagcagcg cgcgacagag ctgacgccgc gccccgcccg    540 gcccc atg tcc ttc gcc acg ctg cgc ccg gcg ccg ccg ggc cgc tac ctg    590
      Met Ser Phe Ala Thr Leu Arg Pro Ala Pro Pro Gly Arg Tyr Leu
      1               5                   10                  15 tac ccc gag gtg agc ccg ctg tcg gag gac gag gac cgc ggc agc gac      638
Tyr Pro Glu Val Ser Pro Leu Ser Glu Asp Glu Asp Arg Gly Ser Asp
                20                  25                  30 agc tcg ggc tcc gac gag aaa ccc tgt cgc gtg cac gcg gcg cgc tgc      686
Ser Ser Gly Ser Asp Glu Lys Pro Cys Arg Val His Ala Ala Arg Cys
            35                  40                  45 ggc ctc cag ggc gcc cgg cgg agg gcg ggg ggc cgg cgg gcc ggg ggc      734
Gly Leu Gln Gly Ala Arg Arg Arg Ala Gly Gly Arg Arg Ala Gly Gly
        50                  55                  60 ggg ggg cca ggg ggc cgg cca ggc cgt gag ccc cgg cag cgg cac acg      782
Gly Gly Pro Gly Gly Arg Pro Gly Arg Glu Pro Arg Gln Arg His Thr
65                  70                  75
```

```
gcg aac gcg cgc gag cga gac cgc acc aac agc gtg aac acg gcc ttc       830
Ala Asn Ala Arg Glu Arg Asp Arg Thr Asn Ser Val Asn Thr Ala Phe
 80              85                  90                  95 acg gcg ctg cgc acg ctg atc ccc acc gag ccc gcc gac cgc aag ctc       878
Thr Ala Leu Arg Thr Leu Ile Pro Thr Glu Pro Ala Asp Arg Lys Leu
            100                 105                 110 tcc aag att gag acg ctg cgc ctg gcc tcc agc tac atc tcg cac ctg       926
Ser Lys Ile Glu Thr Leu Arg Leu Ala Ser Ser Tyr Ile Ser His Leu
                115                 120                 125 ggc aac gtg ctg ctg gcg ggc gag gcc tgc ggc gac gga cag ccc tgc       974
Gly Asn Val Leu Leu Ala Gly Glu Ala Cys Gly Asp Gly Gln Pro Cys
            130                 135                 140 cac tcc ggg ccc gcc ttc ttc cac gcg gcg cgc gcc ggc agc ccc ccg      1022
His Ser Gly Pro Ala Phe Phe His Ala Ala Arg Ala Gly Ser Pro Pro
        145                 150                 155 ccg ccg ccc ccg ccg cct ccc gcc cgc gac ggc gag aac acc cag ccc      1070
Pro Pro Pro Pro Pro Pro Pro Ala Arg Asp Gly Glu Asn Thr Gln Pro
160                 165                 170                 175 aaa cag atc tgc acc ttc tgc ctc agc aac cag aga aag ttg              1112
Lys Gln Ile Cys Thr Phe Cys Leu Ser Asn Gln Arg Lys Leu
                180                 185 gtgagcacgg gccgtggggc gccgaggggg gcctccaacg cgcccctcag cccacacctg    1172
ccaggcagag gaggcgaggc cacacgggca gggctcccca acagggcaca ggcaggcaca    1232
cctgtaacac aggcctgccg ggggctgggg ccttctcctg gggctcctct cgagggcgtc    1292
cctaggacac tcggctccca gtggagtgtg gagtcccctg cagggagctg catgagggt     1352 aagagctagg gatggccaaa ggggcccacc cagggcgggg aggctgggga gctgaccag     1412 gccgctgcaa gcttcccttt tcagtaagtt gaaaggcgga gtgaaaacag ctgagttcag    1472
aaagtaagag gctgcaaggc aagagaggaa ggaccccggg ttcttagccc ctgcggccca    1532
gcactggctt aagccatctt gggcacctgc tgtccgtccc ccacctaggc cgcacaccaa    1592
gacaccaggt cctgtagggc tgcccgagac gtgggccatg ggacacgaag cagaggctg     1652 gcaggagatg tggggctgg gggtgagggc ccctgcagga cgctggcc agctgtgatt       1712 tacagctcct gctgtgcttg gtggcaccgg aaaagcaggg tgagcaggga gaaaatacgg    1772
cacggctttt cccaatcccc atttcctctc cagacagcac gcgcgagctc ctggggcctg    1832
aacatctggg aaatttaatt ttacaatttc ggctgtgcag cagtatgctc ccctccccaa    1892
aacgcttgag ggaagctggg gagagccggg aaggaggtgc cttggcgctg ccacctgag     1952 atggcaccca gcagggaggc cagagaggcg cagactggcg ctgggctctg ccggggcctg    2012
acactcctcc ctcccctctg cag agc aag gac cgc gac aga aag aca gcg att    2065
                          Ser Lys Asp Arg Asp Arg Lys Thr Ala Ile
                              190                 195 cgc agt taggaggtgg ccggcagcag ccaggaggca gacgctgctg ggggaggtgg       2121
Arg Ser
200 acgcccgggg tgactgcaga cagcccccac cttggacctg agctgggcaa ggcccaccgc    2181 aagcatgccc ccaggccagc cctggctgcg agcggggccg agggacagac ggacgtacag    2241 acaggcgccg gcagcgggac tctgcgctgg ccccagcacc tgcccgggcc cactggaact    2301 ttctgcgctg gcttttcttc cggccactgt gtgatggcat cttgtgtttt tgatatgata    2361 atataaagtc tgaaaatttt gtataattaa aaacaaaaca gtatcttcca aatatggagg    2421 ccaactgtcc tcatgaaagg ttcagaatcc accccagcc cccagcctga gcctccattc     2481 ccacccttgg tggtcccatc ctccttgggc caagtacccc ggctccctgg gaagcccca     2541
```

```
ctttccaggc tcagggccac ccctccctgg gctgaggcgg tgaggatgg                  2590
```

<210> SEQ ID NO 30
<211> LENGTH: 201
<212> TYPE: PRT
<213> ORGANISM: Homo sapiens

<400> SEQUENCE: 30

```
Met Ser Phe Ala Thr Leu Arg Pro Ala Pro Pro Gly Arg Tyr Leu Tyr
1               5                   10                  15

Pro Glu Val Ser Pro Leu Ser Glu Asp Glu Arg Gly Ser Asp Ser
            20                  25                  30

Ser Gly Ser Asp Glu Lys Pro Cys Arg Val His Ala Ala Arg Cys Gly
        35                  40                  45

Leu Gln Gly Ala Arg Arg Arg Ala Gly Gly Arg Arg Ala Gly Gly Gly
    50                  55                  60

Gly Pro Gly Gly Arg Pro Gly Arg Glu Pro Arg Gln Arg His Thr Ala
65                  70                  75                  80

Asn Ala Arg Glu Arg Asp Arg Thr Asn Ser Val Asn Thr Ala Phe Thr
                85                  90                  95

Ala Leu Arg Thr Leu Ile Pro Thr Glu Pro Ala Asp Arg Lys Leu Ser
            100                 105                 110

Lys Ile Glu Thr Leu Arg Leu Ala Ser Ser Tyr Ile Ser His Leu Gly
        115                 120                 125

Asn Val Leu Leu Ala Gly Glu Ala Cys Gly Asp Gly Gln Pro Cys His
    130                 135                 140

Ser Gly Pro Ala Phe Phe His Ala Ala Arg Ala Gly Ser Pro Pro Pro
145                 150                 155                 160

Pro Pro Pro Pro Pro Ala Arg Asp Gly Glu Asn Thr Gln Pro Lys
                165                 170                 175

Gln Ile Cys Thr Phe Cys Leu Ser Asn Gln Arg Lys Leu Ser Lys Asp
            180                 185                 190

Arg Asp Arg Lys Thr Ala Ile Arg Ser
        195                 200
```

SCAFFOLD-FREE SELF-ORGANIZED 3D SYNTHETIC TISSUE

CROSS-REFERENCE TO RELATED APPLICATION

This application is a continuation of U.S. patent application Ser. No. 10/566,845, which application is a U.S. National stage application of PCT/JP2004/011401, international filing date of Aug. 2, 2004, which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690128_401C1_SEQUENCE_LISTING.txt. The text file is 313 KB, was created on Feb. 16, 2007, and is being submitted electronically via EFS-Web, concurrent with the filing of the specification.

TECHNICAL FIELD

The present invention relates to the field of regenerative medicine. More particularly, the present invention relates to a synthetic tissue capable of functioning after implantation, a method for producing the same, and use of the same. The synthetic tissue of the present invention has biological integration capability.

BACKGROUND ART

Recently, regenerative therapy has attracted attention as a novel approach to severe organ failure or intractable diseases. Regenerative therapy is a combination of genetic engineering, cell tissue engineering, regenerative medicine, and the like. Many researchers over the world are vigorously working on this important and challenging subject of research in the 21-century advanced medical practice.

The scale of the market associated with regenerative medicine (tissue engineering) is estimated as about 500 billion US dollars in the world and about 50 billion US dollars in Japan according to the material prepared by the New Energy and Industrial Technology Development Organization. Only tissue engineering products account for about 100 billion US dollars in the world. The regenerative medicine is greatly expected to create the next-generation industry.

The present inventors have made efforts to develop regenerative therapy in the field of musculoskeletal and cardiovascular tissues, and have reported a combination therapy of cell implantation and a growth factor administration, or a tissue implantation regeneration therapy based on tissue engineering. However, regenerative therapy based on cell or tissue implantation requires a source of autologous cells. A stable and abundant source of such cells is urgently required and important. A number of cells in musculoskeletal tissue have a high level of self-repairing ability. It has been reported that there is a stem cell among the cells of the musculoskeletal tissue.

It has been demonstrated that a cell derived from skeletal muscle (Jankowiski R. J., Huand J. et al, Gene Ther., 9:642-647, 2002), fat (Wickham M. Q. et al., Clin. Orthop., 2003, 412, 196-212), umbilical cord blood (Lee O. K. et al., Blood, 2004, 103:1669-75), tendon (Salingcarnboriboon R., Exp. Cell. Res., 287:289-300, 2002), bone marrow (Pitterger M. F. et al., Science, 284:143-147, 1999), and synovium (Arthritis Rheum. 2001 44:1928-42) is undifferentiated and has the potential to differentiate into various cells.

Conventionally, when cell therapy is performed for repair or regeneration of tissue, most research employs a biological scaffold to maintain the accumulation of cells, allow cells to grow, maintain pluripotency, protect cells from mechanical stress on a treated site, or the like. However, most scaffolds contain a biological (animal) material, a biomacromolecule material, or the like, of which influence on the safety of organism cannot be fully predicted.

A cell implanting method without a scaffold has been reported by Kushida A., Yamato M., Konno C., Kikuchi A., Sakurai Y., Okano T., J. Biomed. Mater. Res., 45:355-362, 1999, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be assembled, for example.

When a nano-biointerface technology is used to fix a temperature responsive polymer (PIPAAm) onto a plastic mold, such as a Petri dish, for cell culture, the polymer surface is reversibly changed at 31° C. between hydrophilicity and hydrophobicity. Specifically, when the temperature is 31° C. or more, the surface of the Petri dish is hydrophobic so that cells or the like can adhere thereto. In this situation, the cells secrete extracellular matrix (ECM; for example, adhesion molecules which are proteins having a function like a "glue") and adhere to the surface of the Petri dish, so that the cells can grow. See, Okano T., Yamada N., Sakai H., Sakurai Y., J. Biomed. Mater. Res., 1993, 27:1243-1251; Kushida A., Yamato M., Konno C., Kikuchi A., Sakurai Y., Okano T., J. Biomed. Mater. Res. 45:355-362, 1999; and Shimizu T., Yamato M., Akutsu T. et al., Circ. Res., 2002, Feb. 22; 90(3): e40.

When the temperature is 31° C. or less, the surface of the Petri dish is hydrophilic. The cells which have adhered to the Petri dish are readily detached, though the cells still maintain adhesion molecules. This is because the surface of the Petri dish to which the cells have adhered no longer exists at 31° C. or less.

Even when such a Petri dish having a fixed temperature responsive polyer (e.g., tradename: UpCell and RepCell) is used to culture cells and detach the cells, an extracellular matrix is not appropriately provided. Thus, there has been no actually practical synthetic tissue developed. See, Okano T., Yamada N., Sakai H., Sakurai Y., J. Biomed. Mater. Res., 1993, 27:1243-1251; Kushida A., Yamato M., Konno C., Kikuchi A., Sakurai Y., Okano T., J. Biomed. Mater. Res. 45:355-362, 1999; and Shimizu T., Yamato M., Akutsu T. et al., Circ. Res., 2002, Feb. 22; 90(3):e40.

WO00/51527 and WO03/024463 reported that cells are cultured on a semipermeable membrane using alginate gel. However, the resultant tissue is poorly integrated with an extracellular matrix and is not free of a scaffold. In addition, the cells in the tissue are not self organized. The tissue has no self-supporting ability. The cells no longer have a differentiation potential. The tissue loses morphological plasticity in terms of three-dimensional structure. Therefore, the tissue is not suitable for cell implantation.

Use of a scaffold is considered to be problematic in implantation therapy because of adverse side effects. Therefore, there is a demand for the advent of a scaffold-free technique.

Conventional methods for producing tissue sheets have the following drawbacks: it is not possible to produce a very large sized sheet; it is not possible to produce a sheet having biological integration in three dimensions; when a sheet is detached after sheet production, the sheet is broken into pieces; and the like.

Therefore, there is a keen demand for a synthetic tissue, which is developed by culture processes, capable of withstanding an implantation operation, capable of being used in an actual operation.

By conventional techniques, it is difficult to isolate a synthetic tissue from a culture base material after tissue culture, and it is substantially impossible to produce a large sized tissue piece. Therefore, conventional synthetic tissues, such as tissue sheets, cannot be used in medical application in view of size, structure, mechanical strength, and the like. It is difficult to develop a synthetic tissue using conventional techniques. Therefore, unfortunately their supplies are limited.

An object of the present invention is to provide a synthetic tissue produced by cell culture, which is feasible to implantation surgery.

Specifically, an object of the present invention is to provide a synthetic tissue having a three-dimensional structure and self-supporting ability, being free of a scaffold, and maintaining a differentiation potential if the tissue possesses it.

Still another object of the present invention is to provide a method and a pharmaceutical agent for treating an injury of a tissue or the like when a replacement or resurfacing therapy is required.

DISCLOSURE OF THE INVENTION

The above-described objects were achieved in part based on the invention of the following synthetic tissue. When a cell was cultured in medium containing an extracellular matrix (ECM) synthesis promoting agent, cells and ECM produced by the cells are integrated to formed a tissue, which was readily detached from the culture dish.

The above-described objects were achieved by providing a synthetic tissue of the present invention which is free of a scaffold, has self-supporting ability, is easily formed into a three-dimensional structure, has morphological plasticity, has excellent ability to biologically adhere to surroundings, has a differentiation potential, and the like, and finding that the synthetic tissue is effective for a replacement or resurfacing therapy at an injured site.

The present invention also provides a method for producing an implantable synthetic tissue, which has biological integration and does not require assembling layers.

The above-described objects were achieved by finding that the thickness of the synthetic tissue of the present invention can be adjusted to a desired value by regulating a physical or chemical stimulus on the synthetic tissue.

The present inventors realized the formation of a three-dimensional synthetic tissue (cellular therapeutic system) comprising cultured cells (e.g., fat-derived cells, etc.) and material produced by the cells without a scaffold.

The synthetic tissue of the present invention can be constructed into various shapes and has a sufficient strength. Therefore, it is easy to surgically manipulate (e.g., implant, etc.) the synthetic tissue of the present invention. According to the present invention, a large quantity (e.g., $10^6$ to $10^8$) of cells can be securely supplied to a local site by means of tissue implantation.

In the matrix, cell adhesion molecules, such as collagen (e.g., type I, type III), fibronectin, vitronectin, and the like, are present in large amounts. Particularly, the cell adhesion molecules are integrated throughout the matrix.

Therefore, the tissue has excellent ability of biologically adhesion to surroundings of the implanted site. Thus, the synthetic tissue complex biologically adheres to an implanted site tissue very quickly. In addition, by changing culture conditions, the synthetic tissue can be differentiated into a bone or cartilage tissue. The maintenance of a differentiation potential is a feature of the synthetic tissue of the present invention which was first found by the present inventors. The synthetic tissue is effective as a safe and efficient cell therapy system.

An object of the present invention is to provide a clinical application of the synthetic tissue regeneration of a joint tissue. The present invention provides the above-described synthetic tissue or a complex of a cell and a component derived from the cell, thereby making it possible to develop therapies for bone regeneration at a conventionally intractable site, in which both periosteum and bone cortex are inflamed; partial thickness cartilage injury which does not bleach the subchondral bone, and injury of a meniscus, a tendon, a ligament, an intervertebral disk, cardiac muscle in an avascular area or a poor circulation site.

Thus, the present invention provides the following.
1. An implantable synthetic tissue.
2. A synthetic tissue according to item 1, which is biologically organized in the third dimensional direction.
3. A synthetic tissue according to item 1, which has biological integration capability with surroundings.
4. A synthetic tissue according to item 3, wherein the biological integration capability includes capability to adhere to surrounding cells and/or extracellular matrices.
5. A synthetic tissue according to item 1, which comprises cells.
6. A synthetic tissue according to item 1, which is substantially made of cells and a material derived from the cells.
7. A synthetic tissue according to item 1, which is substantially made of cells and an extracellular matrix (ECM) derived from the cells.
8. A synthetic tissue according to item 7, wherein the extracellular matrix contains at least one selected from the group consisting of collagen I, collagen III, vitronectin and fibronectin.
9. A synthetic tissue according to item 7, wherein the extracellular matrix contains collagen I, collagen III, vitronectin and fibronectin.
10. A synthetic tissue according to item 7, wherein the extracellular matrix contains vitronectin.
11. A synthetic tissue according to item 7, wherein the extracellular matrix contains fibronectin.
12. A synthetic tissue according to item 7, wherein the extracellular matrix contains collagen I and collagen III, the collagen constitutes 5% to 25% of the tissue, and the ratio of the collagen I to the collagen III is between 1:10 and 10:1.
13. A synthetic tissue according to item 7, wherein the extracellular matrix and the cells are integrated together into a three-dimensional structure.
14. A synthetic tissue according to item 7, wherein the extracellular matrix is diffusedly distributed in the tissue.
15. A synthetic tissue according to item 1, wherein an extracellular matrix is diffusedly distributed, and the distribution densities of the extracellular matrix in two arbitrary sections of 1 cm$^2$ in the tissue have a ratio within a range of about 1:3 to about 3:1.
16. A synthetic tissue according to item 1, which is heterologous, allogenic, isologous, or autogenous.

17. A synthetic tissue according to item 1, which is free of scaffolds.
18. A synthetic tissue according to item 1, which is used to implant cells.
19. A synthetic tissue according to item 1, which is large sized.
20. A synthetic tissue according to item 1, which has a volume of at least about 20 mm$^3$.
21. A synthetic tissue according to item 1, which is flexible.
22. A synthetic tissue according to item 1, which is expandable and contractile.
23. A synthetic tissue according to item 1, which can withstand heart pulsation.
24. A synthetic tissue according to item 1, which is biologically organized in all three dimensional directions.
25. A synthetic tissue according to item 24, wherein the biological integration is selected from the group consisting of internal binding of extracellular matrix, electrical integration, and intercellular signal transduction.
26. A synthetic tissue according to item 1, which has a tissue strength which allows the synthetic tissue to be clinically applicable.
27. A synthetic tissue according to item 26, wherein the strength is a break strength of about 0.02 N to about 2 N.
28. A synthetic tissue according to item 26, wherein the tissue strength is sufficient to provide self-supporting ability.
29. A synthetic tissue according to item 28, wherein the self-supporting ability is characterized in that the synthetic tissue is not substantially broken when the synthetic tissue is picked up using forceps having a tip area of 0.05 to 3.0 mm$^2$.
30. A synthetic tissue according to item 28, wherein the self-supporting ability is characterized in that the synthetic tissue is not broken when the synthetic tissue is picked up with a hand.
31. A synthetic tissue according to item 26, wherein the site to which the synthetic tissue is intended to be applied, includes a heart.
32. A synthetic tissue according to item 26, wherein the site to which the synthetic tissue is intended to be applied, includes an intervertebral disk, a meniscus, a cartilage, a bone, a ligament, or a tendon.
33. A synthetic tissue according to item 26, wherein:
    the synthetic tissue is a cartilage, an intervertebral disk, a meniscus, a ligament, or a tendon; and
    the synthetic tissue remains attached without an additional fixation procedure, after the synthetic tissue is implanted into an injured portion of the intra-articular tissue.
34. A method for producing a synthetic tissue, comprising the steps of:
    A) providing cells;
    B) placing the cells in a container, the container having cell culture medium containing an ECM synthesis promoting agent and having a sufficient base area which can accommodate a synthetic tissue having a desired size;
    C) culturing the cells in the container along with the cell culture medium containing the ECM synthesis promoting agent for a period of time sufficient for formation of the synthetic tissue having the desired size; and
    D) detaching the cells from the container.
35. A method according to item 34, wherein a stimulus for inducing tissue contraction is applied in the detaching step.
36. A method according to item 35, wherein the stimulus includes a physical or chemical stimulus.
37. A method according to item 36, wherein the physical stimulus includes shaking of the container, pipetting, or deformation of the container.
38. A method according to item 34, wherein the detaching step includes adding an actin regulatory agent.
39. A method according to item 38, wherein the actin regulatory agent includes a chemical substance selected from the group consisting of actin depolymerizing agents and actin polymerizing agents.
40. A method according to item 39, wherein the actin depolymerizing agent is selected from the group consisting, of Slingshot, cofilin, cyclase associated protein (CAP), actin interacting protein 1 (AIP1), actin depolymerizing factor (ADF), destrin, depactin, actophorin, cytochalasin, and NGF (nerve growth factor).
41. A method according to item 39, wherein the actin polymerizing agent is selected from the group consisting of RhoA, mDi, profilin, Rac1, IRSp53, WAVE2, ROCK, LIM kinase, cofilin, cdc42, N-WASP, Arp2/3, Drf3, Mena, lysophosphatidic acid (LPA), insulin, platelet derived growth factor (PDGF) a, PDGFb, chemokine, and transforming growth factor (TGF) β.
42. A method according to item 34, wherein the container is free of scaffolds.
43. A method according to item 34, wherein the cells are first cultured in monolayer culture.
44. A method according to item 34, wherein the ECM synthesis promoting agent includes TGFβ1, TFGβ3, ascorbic acid, ascorbic acid 2-phosphate, or a derivative or salt thereof.
45. A method according to item 44, wherein the ascorbic acid, ascorbic acid 2-phosphate, or the derivative or salt thereof is present at a concentration of at least 0.1 mM.
46. A method according to item 44, wherein the TGFβ1 or TFGβ3 is present at a concentration of at least 1 ng/ml.
47. A method according to item 34, wherein the cells are placed at a concentration of $5 \times 10^4$ to $5 \times 10^6$ cells per 1 cm$^2$, and the ECM synthesis promoting agent is ascorbic acid, ascorbic acid 2-phosphate, or a derivative or salt thereof, and the ascorbic acid, ascorbic acid 2-phosphate, or the derivative or salt thereof is provided at a concentration of at least 0.1 mM.
48. A method according to item 34, further comprising causing the synthetic tissue to detach from the container and self-contract.
49. A method according to item 48, wherein the detaching and self-contraction are achieved by providing a physical stimulus to the container.
50. A method according to item 48, wherein the detachment and self-contraction are achieved by providing a chemical stimulus to the container.
51. A method according to item 34, wherein the sufficient period of time is at least 3 days.
52. A method according to item 34, wherein the sufficient period of time is at least 3 days and a period of time required for the synthetic tissue to be spontaneously detached from the container at a maximum.
53. A method according to item 52, wherein the period of time required for the synthetic tissue to be spontaneously detached from the container is at least 40 days.
54. A method according to item 34, further comprising:
    causing the synthetic tissue to differentiate.
55. A method according to item 54, wherein the differentiation includes osteogenesis, chondrogenesis, adipogenesis, tendon differentiation, and ligament differentiation.
56. A method according to item 55, wherein the osteogenesis is performed in medium containing dexamethasone, β-glycerophosphate, and ascorbic acid 2-phosphate.
57. A method according to item 56, wherein the medium contains at least one selected from the group consisting of BMP (bone morphogenetic protein)-2, BMP-4, and BMP-7.

58. A method according to item 55, wherein the chondrogenesis is performed in medium containing pyrubic acid, dexamethasone, ascorbic acid 2-phosphate, insulin, transferrin, and selenious acid.
59. A method according to item 58, wherein the medium contains at least one selected from the group consisting of BMP-2, BMP-4, BMP-7, TGF (transforming growth factor)-β1 and TGF-β3.
60. A method according to item 54, wherein the differentiation step is performed before or after the detaching step.
61. A method according to item 54, wherein the differentiation step is performed after the detaching step.
62. A method according to item 34, wherein the cell includes cells of 3 or more passages.
63. A method according to item 34, wherein the cells include cells of 3 to 8 passages.
64. A method according to item 34, wherein the cells are provided at a cell density of $5.0 \times 10^4$ to $5.0 \times 10^6$ cells/cm$^2$.
65. A method according to item 34, wherein the cells include myoblasts.
66. A method according to item 34, wherein the cells include fat-derived cells.
67. A method according to item 34, wherein the cells include synovium-derived cells.
68. A method according to item 34, wherein the cells include mesenchymal stem cells.
69. A method according to item 68, wherein the mesenchymal stem cells are derived from an adipose tissue, a synovial membrane, a tendon, a bone, or a bone marrow.
70. A method according to item 34, further comprising:
    producing a plurality of the synthetic tissues and attaching the plurality of the synthetic tissues together to be integrated.
71. A cell culture composition for producing a synthetic tissue from cells, comprising:
    A) an element for maintaining the cells; and
    B) an extracellular matrix synthesis promoting agent.
72. A method according to item 68, wherein the ECM synthesis promoting agent includes TGFβ1, TFGβ3, ascorbic acid, ascorbic acid 2-phosphate, or a derivative or salt thereof.
73. A method according to item 72, wherein TGFβ1 or TFGβ3 is present at a concentration of at least 1 ng/ml, or ascorbic acid, ascorbic acid 2-phosphate, or the derivative or salt thereof is present at a concentration of at least 0.1 mM.
74. A complex for reinforcing a portion of an organism, comprising cells and a component derived from the cells.
75. A complex according to item 74, which has biological integration capability with surroundings.
76. A complex according to item 75, wherein the biological integration capability include capability to adhere to surrounding cells and/or extracellular matrices.
77. A complex according to item 74, which is substantially made of cells and a material derived from the cells.
78. A complex according to item 74, which is substantially made of cells and an extracellular matrix derived from the cells.
79. A synthetic tissue according to item 78, wherein the extracellular matrix is selected from the group consisting of collagen I, collagen III, vitronectin and fibronectin.
80. A complex according to item 78, wherein the extracellular matrix and the cells are integrated together into a three-dimensional structure.
81. A complex according to item 78, wherein the extracellular matrix is provided on a surface of the complex.
82. A complex according to item 78, wherein the extracellular matrix is diffusedly distributed on a surface of the complex.
83. A complex according to item 74, wherein an extracellular matrix is diffusedly distributed on a surface of the complex, and the distribution densities of the extracellular matrix in two arbitrary sections of 1 cm$^2$ in the complex have a ratio within a range of about 1:3 to about 3:1.
84. A complex according to item 78, wherein the extracellular matrix includes fibronectin or vitronectin.
85. A complex according to item 74, which is heterologous, allogenic, isologous, or autogenous.
86. A complex according to item 74, wherein the portion includes a bag-shaped organ.
87. A complex according to item 86, wherein the bag-shaped organ includes a heart.
88. A complex according to item 74, wherein the portion includes a bone or cartilage tissue.
89. A complex according to item 74, wherein the portion includes avascular tissue.
90. A complex according to item 74, wherein the portion includes an intervertebral disk, a meniscus, a ligament, or a tendon.
91. A complex according to item 74, wherein the reinforcement is achieved by replacing the portion with the complex or providing the complex to cover the portion, or both.
92. A complex according to item 74, which resists the expansion and contraction of the portion.
93. A complex according to item 74, which has biological integration.
94. A complex according to item 74, wherein the biological integration selected from the group consisting of internal binding of extracellular matrix, electrical integration, and intercellular signal transduction.
95. A complex according to item 74, which is formed by culturing cells in the presence of an ECM synthesis promoting agent.
96. A complex according to item 74, which has self-supporting ability.
97. A method for reinforcing a portion of an organism, comprising the steps of:
    A) replacing the portion with a complex comprising cells and a component derived from the cells or providing the complex to cover the portion, or both; and
    B) holding the complex for a sufficient period of time for biologically adhering the complex to the portion.
98. A method according to item 97, wherein the adhesion is achieved by adhesion between extracellular matrix and extracellular matrix.
99. A method according to item 97, which has biological integration capability with surroundings.
100. A method according to item 99, wherein the biological integration capability include capability to adhere to surrounding cells and/or extracellular matrices.
101. A method according to item 97, which is substantially made of cells and a material derived from the cells.
102. A method according to item 97, which is substantially made of cells and an extracellular matrix derived from the cells.
103. A method according to item 102, wherein the extracellular matrix contains one selected from the group consisting of collagen I, collagen III, vitronectin and fibronectin.
104. A method according to item 102, wherein the extracellular matrix contains all of collagen I, collagen III, vitronectin and fibronectin.
105. A method according to item 102, wherein the extracellular matrix contains vitronectin.
106. A method according to item 102, wherein the extracellular matrix contains fibronectin.
107. A method according to item 97, wherein an extracellular matrix is provided on a surface of the complex.

108. A method according to item 97, wherein an extracellular matrix is diffusedly distributed on a surface of the complex.

109. A method according to item 97, wherein an extracellular matrix is diffusedly distributed on a surface of the complex, and the distribution densities of the extracellular matrix in two arbitrary sections of 1 cm$^2$ have a ratio within a range of about 1:3 to about 3:1.

110. A complex according to item 97, wherein an extracellular matrix is diffusedly distributed on a surface of the complex, and the distribution densities of the extracellular matrix in two arbitrary sections of 1 cm$^2$ have a ratio within a range of about 1:2 to about 2:1.

111. A method according to item 97, which is heterologous, allogenic, isologous, or autogenous.

112. A method according to item 97, wherein the portion includes a bag-shaped organ.

113. A method according to item 112, wherein the bag-shaped organ includes a heart.

114. A method according to item 97, wherein the complex resists the expansion and contraction of the portion.

115. A method according to item 97, wherein the complex has biological integration.

116. A method according to item 115, wherein the biological integration selected from the group consisting of internal binding of extracellular matrix, electrical integration, and intercellular signal transduction.

117. A method according to item 97, further comprising:
forming the complex by culturing the cells in the presence of an ECM synthesis promoting agent.

118. A method according to item 97, wherein the portion is a heart and the heart has a disease or disorder selected from the group consisting of heart failure, ischemic heart disease, myocardial infarct, cardiomyopathy, myocarditis, hypertrophic cardiomyopathy, dilated phase hypertrophic cardiomyopathy, and dilated cardiomyopathy.

119. A method according to item 97, wherein the portion includes an avascular lesion.

120. A method according to item 97, wherein the portion includes a vascular lesion.

121. A method according to item 97, wherein the portion includes a bone or a cartilage.

122. A method according to item 97, wherein the portion includes an intervertebral disk, a meniscus, a ligament, or a tendon.

123. A method according to item 97, wherein the portion includes a bone or a cartilage, and the bone or the cartilage is damaged or degenerated.

124. A method according to item 97, wherein the portion includes intractable fracture, osteonecrosis, cartilage injury, meniscus injury, ligament injury, tendon injury, cartilage degeneration, meniscus degeneration, intervertebral disk denaturation, ligament degeneration, or tendon degeneration.

125. A method according to item 97, wherein the sufficient period of time is at least 10 days.

126. A method according to item 97, wherein the complex has self-supporting ability.

127. A method according to item 97, which has biological integration capability with surroundings.

128. A method according to item 97, which is substantially made of cells and an extracellular matrix derived from the cells.

129. A method according to item 97, further comprising implanting another synthetic tissue.

130. A method according to item 129, wherein the other synthetic tissue is an artificial bone or a microfibrous collagen medical device.

131. A method according to item 97, which is substantially made of cells and an extracellular matrix derived from the cells, wherein the other synthetic tissue is an artificial bone or a microfibrous collagen medical device.

132. A method according to item 130, the artificial bone includes hydroxyapatite.

133. A method for treating a portion of an organism, comprising the steps of:
A) replacing the portion with a complex comprising cells and a component derived from the cells or providing the complex to cover the portion, or both; and
B) holding the complex for a sufficient period of time for restoring a condition of the portion.

134. A method according to item 133, wherein the treatment is for the treatment, prevention, or reinforcement of a disease, disorder, or condition of a heart, a bone, a cartilage, a ligament, a tendon, a meniscus, or an intervertebral disk.

135. A method according to item 133, wherein the complex has self-supporting ability.

136. A method according to item 133, wherein the complex has biological integration capability with surroundings.

137. A method according to item 133, wherein the complex is substantially made of cells and an extracellular matrix derived from the cells.

138. A method according to item 133, further comprising implanting another synthetic tissue in addition to the replacement or coverage of the portion.

139. A method according to item 138, wherein the other synthetic tissue includes an artificial bone or a microfibrous collagen medical device.

140. A method according to item 133, which is substantially made of cells and an extracellular matrix derived from the cells, wherein the other synthetic tissue includes an artificial bone or a microfibrous collagen medical device.

141. A method according to item 139, the artificial bone includes hydroxyapatite.

142. A method for producing a synthetic tissue, comprising the steps of:
A) providing cells;
B) placing the cells in a container, the container having cell culture medium containing an ECM synthesis promoting agent and having a sufficient base area which can accommodate a synthetic tissue having a desired size;
C) culturing the cells in the container along with the cell culture medium containing the ECM synthesis promoting agent for a period of time sufficient for formation of the synthetic tissue having the desired size; and
D) regulating a thickness of the synthetic tissue by a physical or chemical stimulus to a desired thickness.

143. A method according to item 142, wherein the physical stimulus includes shear stress between the synthetic tissue and the container, deformation of the base of the container, shaking of the container, or pipetting.

144. A method according to item 142, wherein the chemical stimulus is obtained by using a chemical substance selected from the group consisting of actin depolymerizing agents and actin polymerizing agents.

145. A method according to item 144, wherein the actin depolymerizing agent is selected from the group consisting of Slingshot, cofilin, CAP (cyclase associated protein), AIP1 (actin interacting protein 1), ADF (actin depolymerizing factor), destrin, depactin, actophorin, cytochalasin, and NGF (nerve growth factor).

146. A method according to item 144, wherein the actin polymerizing agent is selected from the group consisting of RhoA, mDi, profilin, Rac1, IRSp53, WAVE2, ROCK, LIM kinase, cofilin, cdc42, N-WASP, Arp2/3, Drf3, Mena, LPA (lysophosphatidic acid), insulin, PDGF (platelet derived growth factor), PDGFb, chemokine, and TGF (transforming growth factor) β.

147. A method according to item 144, wherein the desired thickness is regulated by adjusting a ratio of the actin depolymerizing agent to the actin polymerizing agent.

148. A method according to item 142, further comprising:
producing a plurality of the synthetic tissues and attaching the plurality of the synthetic tissues together to be integrated.

149. A tissue complex, comprising an implantable synthetic tissue and another synthetic tissue.

150. A tissue complex according to item 149, wherein the implantable synthetic tissue is substantially made of cells and a material derived from the cells.

151. A tissue complex according to item 149, wherein the implantable synthetic tissue is substantially made of cells and an extracellular matrix derived from the cells.

152. A tissue complex according to item 151, wherein the extracellular matrix is selected from the group consisting of collagen I, collagen III, vitronectin, and fibronectin.

153. A tissue complex according to item 151, wherein the extracellular matrix contains all of collagen I, collagen III, vitronectin, and fibronectin.

154. A tissue complex according to item 149, wherein the other synthetic tissue includes an artificial bone or a microfibrous collagen medical device.

155. A tissue complex according to item 154, the artificial bone includes hydroxyapatite.

156. A tissue complex according to item 149, the implantable synthetic tissue is biologically integrated with the other synthetic tissue.

157. A tissue complex according to item 156, wherein the biological integration is achieved via an extracellular matrix.

158. A composition for use in producing a synthetic tissue having a desired thickness, comprising a chemical substance selected from the group consisting of actin depolymerizing agents and actin polymerizing agents.

159. A composition according to item 158, wherein the actin depolymerizing agent is selected from the group consisting of Slingshot, cofilin, CAP (cyclase associated protein), AIP1 (actin interacting protein 1), ADF (actin depolymerizing factor), destrin, depactin, actophorin, cytochalasin, and NGF (nerve growth factor).

160. A composition according to item 158, wherein the actin polymerizing agent is selected from the group consisting of RhoA, mDi, profilin, Rac1, IRSp53, WAVE2, ROCK, LIM kinase, cofilin, cdc42, N-WASP, Arp2/3, Drf3, Mena, LPA (lysophosphatidic acid), insulin, PDGF (platelet derived growth factor) a, PDGFb, chemokine, and TGF (transforming growth factor) β.

Hereinafter, the present invention will be described by way of preferable examples. It will be understood by those skilled in the art that the examples of the present invention can be appropriately made or carried out based on the description of the present specification and commonly used techniques well known in the art. The function and effect of the present invention can be easily recognized by those skilled in the art.

The present invention provides a scaffold-free synthetic tissue or complex. By providing such a scaffold-free synthetic tissue, a therapeutic method and a therapeutic agent for providing an excellent therapeutic result after implantation can be obtained.

The scaffold-free synthetic tissue of the present invention solves a long outstanding problem with biological formulations, which is attributed to contamination of the scaffold itself. Despite the absence of a scaffold, the therapeutic effect is comparable with, or more satisfactory than conventional techniques.

In addition, when a scaffold is used, the alignment of implanted cells in the scaffold, the cell-to-cell adhesion, the in vivo alteration of the scaffold itself (eliciting inflammation), the integration of the scaffold to recipient tissue, and the like become problematic. These problems can be solved by the present invention.

The synthetic tissue and the complex of the present invention are also self-organized, and have biological integration inside thereof. Also on this point, the present invention is distinguished from conventional cell therapies.

It is easy to form a three-dimensional structure with the synthetic tissue or complex of the present invention, and thus it is easy to design it into a desired form. The versatility of the synthetic tissue and the complex of the present invention should be noted.

The synthetic tissue and the complex of the present invention have biological integration with recipient tissues, such as adjacent tissues, cells, and the like. Therefore, the post-operational stability is satisfactory, and cells are securely supplied to a local site, for example. An effect of the present invention is that the satisfactory biological integration capability allows the formation of a tissue complex with another synthetic tissue or the like, resulting in a complicated therapy.

Another effect of the present invention is that differentiation can be induced after the synthetic tissue or the complex is provided. Alternatively, differentiation is induced before providing a synthetic tissue and/or a complex, and thereafter, the synthetic tissue and/or the complex are developed.

Another effect of the present invention is that the implantation of the synthetic tissue of the present invention provides a satisfactory tissue replacement ability and a comprehensive supply of cells for filling or covering an implanted site, compared to conventional cell-only implantation and sheet implantation.

The present invention provides an implantable synthetic tissue with biological integration capability. The above-described features and effects of the present invention make it possible to treat a site which cannot be considered as an implantation site for conventional synthetic products. The synthetic tissue of the present invention has biological integration and actually works in implantation therapies. The synthetic tissue is for the first time provided by the present invention, but is not provided by conventional techniques. The synthetic tissue or composite of the present invention has the sufficient ability to integrating with adjacent tissues, cells or the like during implantation (preferably, due to extracellular matrix). Therefore, post-operational restoration is excellent. Such a synthetic tissue, which has biological integration capability in all of the three dimensions, cannot be achieved by conventional techniques. Therefore, the present invention provides a therapeutic effect which cannot be achieved by conventional synthetic tissue.

In addition, the present invention provides medical treatment which provides a therapeutic effect by filling, replacing, and/or covering a lesion.

In addition, when the synthetic tissue of the present invention is used in combination with, another synthetic tissue (e.g., an artificial bone made of hydroxyapatite, a microfibrous collagen medical device, etc.), the synthetic tissue of the present invention is biologically integrated with the other synthetic tissue, so that the acceptance of the synthetic tissue makes it possible to organize more complicated tissue complex which is not conventionally expected.

An extracellular matrix or a cell adhesion molecule, such as fibronectin, vitronectin, or the like, is distributed throughout the synthetic tissue of the present invention. In the cell sheet engineering, a cell adhesion molecule is localized on a bottom surface of culture cells which is attached to a Petri dish. In the sheet provided by the cell sheet engineering, cells are major components of the sheet. The sheet is intended to provide a mass of cells with an adhesion molecule attached on the bottom surface. The synthetic tissue of the present invention is a real "tissue" such that an extracellular matrix three-dimensionally integrates with cells. Thus, the present invention is significantly distinguished from conventional techniques including the cell sheet engineering.

A cell implanting method without a scaffold has been reported by a Tokyo Women's Medical University group, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be piled up, for example. Such a problem is solved by the present invention.

A cell/matrix complex developed by the present invention does not require a temperature sensitive culture dish unlike the cell sheet technique. It is easy for the cell/matrix complex to form into a contractile three-dimensional tissue. There is no technique in the world other than the present invention, which can produce a contractile three-dimensional complex having 10 or more layers of cells without using so-called feeder cells, such as rodent stroma cells, in about three weeks. By adjusting conditions for matrix synthesis of the cell, it is possible to produce a complex having a strength which allows surgical manipulation, such as holding or transferring the complex, without a special instrument. Therefore, the present invention is an original, epoch-making technique in the world for reliably and safely perform cell implantation.

BRIEF DESCRIPTION OF THE DRAWINGS

FIG. 3 shows a high magnification view of a synthetic tissue on day 3, 7, 14, and 21 of culture. As can be seen, the synthetic tissue is already developed at day 3 but the matrix is scarce. The matrix is getting dense with time.

FIG. 4 shows an exemplary stained extracellular matrix in a synthetic tissue derived from synovial cells.

FIG. 5 shows exemplary histology of normal tissue (normal skin tissue, synovial membrane tissue, tendon tissue, cartilage tissue, and meniscus tissue).

FIG. 23 shows an in vitro cartilage implantation experiment using a synthetic tissue of the present invention and the results. The upper portion shows a diagram of explant culture. It is shown that a synthetic tissue is adhered to a partial thickness cartilage injury (in vitro). A superficial zone was removed, followed by digestion with chondroitinase ABC (Hinziker E B, JBJS, 1996). The lower left portion is lower magnification histology (×40). The lower right portion is higher magnification histology (×200). As can be seen, the synthetic tissue is tightly attached to the injured surface.

FIG. 29 shows the result of a meniscus repair experiment using a synthetic tissue of the present invention. The left portion of the figure shows that a medial femoral condyle bone and an anterior horn of medial meniscus are exposed. The right figure shows a 6.5-mm defect in a medial knee joint in the anterior horn of medial meniscus.

FIG. 30 shows a meniscus repair procedure. The left portion shows a defect before the implantation of a synovial membrane-derived synthetic tissue (lower left). The right portion shows the defect after the implantation of the synovial membrane-derived synthetic tissue.

DESCRIPTION OF SEQUENCING LIST

Figure 1:
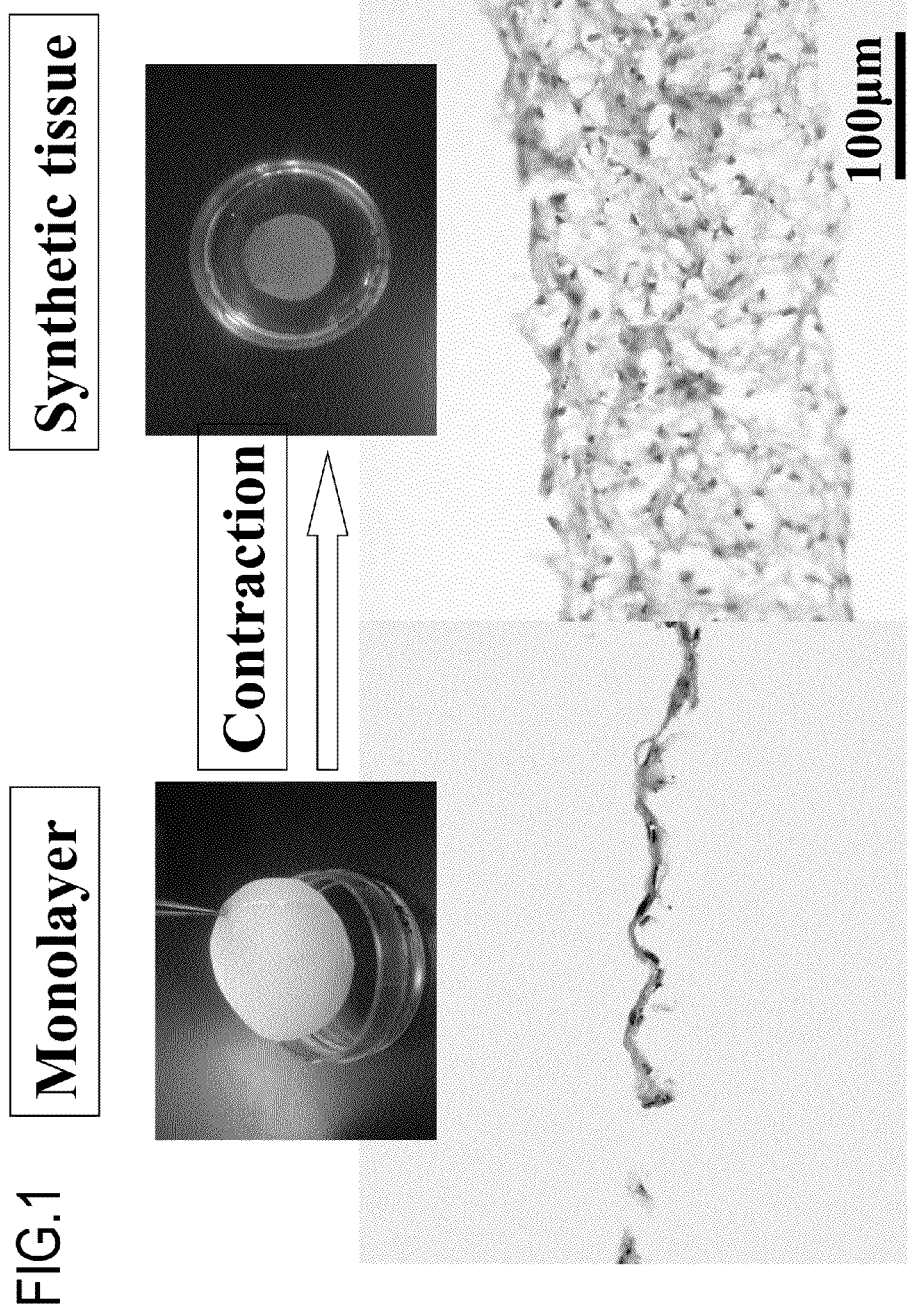
FIG. 1 shows macroscopy and histology of exemplary synthetic tissues using synovial cells.

SEQ ID NO.: 1 indicates the nucleic acid sequence of myosin heavy chain IIa (human: Accession No. NM_017534).

SEQ ID NO.: 2 indicates the amino acid sequence of myosin heavy chain IIa (human: Accession No. NM_017534).

SEQ ID NO.: 3 indicates the nucleic acid sequence of myosin heavy chain IIb (human: Accession No. NM_017533).

SEQ ID NO.: 4 indicates the amino acid sequence of myosin heavy chain IIb (human: Accession No. NM_017533).

SEQ ID NO.: 5 indicates the nucleic acid sequence of myosin heavy chain IId (IIx) (human: Accession No. NM_005963).

SEQ ID NO.: 6 indicates the amino acid sequence of myosin heavy chain IId (IIx) (human: Accession No. NM_005963).

SEQ ID NO.: 7 indicates the nucleic acid sequence of CD56 (human: Accession No. U63041).

SEQ ID NO.: 8 indicates the amino acid sequence of CD56 (human: Accession No. U63041).

SEQ ID NO.: 9 indicates the nucleic acid sequence of human MyoD (GENBANK Accession No. X56677).

SEQ ID NO.: 10 indicates a polypeptide sequence encoded by the nucleic acid sequence of SEQ ID NO.: 2.

SEQ ID NO.: 11 indicates the nucleic acid sequence of human myogenic factor 5 (MYF5) (GENBANK Accession No. NM_005593).

SEQ ID NO.: 12 indicates a polypeptide sequence encoded by the nucleic acid sequence of SEQ ID NO.: 3.

SEQ ID NO.: 13 indicates the nucleic acid sequence of human myogenin (myogenic factor 4) (GENBANK Accession No. BT007233).

SEQ ID NO.: 14 indicates a polypeptide sequence encoded by the nucleic acid sequence of SEQ ID NO.: 13.

SEQ ID NO.: 15 indicates the nucleic acid sequence of Sox9 (human: Accession No. NM_000346=a marker specific to a chondrocyte).

SEQ ID NO.: 16 indicates a polypeptide sequence encoded by the nucleic acid sequence of SEQ ID NO.: 15.

SEQ ID NO.: 17 indicates the nucleic acid sequence of Col 2A1 (human: Accession No. NM_001844=a marker specific to a chondrocyte).

SEQ ID NO.: 18 indicates a polypeptide sequence encoded by the nucleic acid sequence of SEQ ID NO.: 17.

SEQ ID NO.: 19 indicates the nucleic acid sequence of Aggrecan (human: Accession No. NM_001135=a marker specific to a chondrocyte).

SEQ ID NO.: 20 indicates a polypeptide sequence encoded by the nucleic acid sequence of SEQ ID NO.: 19.

SEQ ID NO.: 21 indicates the nuclei acid sequence of Bone sialoprotein (human: Accession No. NM_004967=a marker specific to an osteoblast).

SEQ ID NO.: 22 indicates a polypeptide sequence encoded by the nucleic acid sequence of SEQ ID NO.: 21.

SEQ ID NO.: 23 indicates the nucleic acid sequence of Osteocalcin (human: Accession No. NM_199173=a marker specific to an osteoblast).

SEQ ID NO.: 24 indicates a polypeptide sequence encoded by the nucleic acid sequence of SEQ ID NO.: 23.

SEQ ID NO.: 25 indicates the nucleic acid sequence of GDF5 (human: Accession No. NM_000557=a marker specific to a ligament cell).

SEQ ID NO.: 26 indicates a polypeptide sequence encoded by the nucleic acid sequence of SEQ ID NO.: 25.

SEQ ID NO.: 27 indicates the nucleic acid sequence of Six1 (human: Accession No. NM_005982=a marker specific to a ligament cell).

SEQ ID NO.: 28 indicates a polypeptide sequence encoded by the nucleic acid sequence of SEQ ID NO.: 27.

SEQ ID NO.: 29 indicates the nucleic acid sequence of Scleraxis (human: Accession No. BK000280=a marker specific to a ligament cell).

SEQ ID NO.: 30 indicates a polypeptide sequence encoded by the nucleic acid sequence of SEQ ID NO.: 29.

BEST MODE FOR CARRYING OUT THE INVENTION

The present invention will be described below. It should be understood throughout the present specification that articles for singular forms include the concept of their plurality unless otherwise mentioned. Therefore, articles or adjectives for singular forms (e.g., "a", "an", "the", and the like in English) include the concept of their plurality unless otherwise specified. Also, it should be also understood that terms as used herein have definitions ordinarily used in the art unless otherwise mentioned. Therefore, all technical and scientific terms used herein have the same meanings as commonly understood by those skilled in the relevant art. Otherwise, the present application (including definitions) takes precedence.

DEFINITION OF TERMS

The definitions of specific terms used herein are described below.

(Regenerative Medicine)

As used herein, the term "regeneration" refers to a phenomenon in which when an individual organism loses a portion of tissue, the remaining tissue grows and recovers. The extent or manner of regeneration varies depending among animal species or among tissues in the same individual. Most human tissues have limited regeneration capability, and therefore, complete regeneration is not expected if a large portion of tissue is lost. In the case of severe damage, a tissue may grow which has strong proliferation capability different from that of lost tissue, resulting in incomplete regeneration where the damaged tissue is incompletely regenerated and the function of the tissue cannot be recovered. In this case, a structure made of a bioabsorbable material is used to prevent a tissue having strong proliferation capability from infiltrating the injured portion of the tissue so as to secure space for proliferation of the damaged tissue. Further, by supplementing with a cell growth factor, the regeneration capability of the damaged tissue is enhanced. Such a regeneration technique is applied to cartilages, bones, hearts, and peripheral nerves, for example. It has been so far believed that cartilages, nerve cells, and cardiac muscles have no or poor regeneration capability. Recently, it was reported that there are tissue (somatic stem cells), which have both the capability of differentiating into these tissues and self-proliferation capability. Expectations are running high for regenerative medicine using stem cells. Embryonic stem cells (ES cells) also have the capability of differentiating into all tissues. Efforts have been made to use ES cells for regeneration of complicated organs, such as kidney, liver, and the like, but have not yet been realized.

The term "cell" is herein used in its broadest sense in the art, referring to a structural unit of tissue of a multicellular organism, which is capable of self replicating, has genetic information and a mechanism for expressing it, and is surrounded by a membrane structure which isolates the living body from the outside. In the method of the present invention, any cell can be used as a subject. The number of cells used in the present invention can be counted through an optical microscope. When counting using an optical microscope, the number of nuclei is counted. Tissues are sliced into tissue sections, which are then stained with hematoxylin-eosin (HE) to variegate nuclei derived from extracellular matrices (e.g., elastin or collagen) and cells. These tissue sections are observed under an optical microscope and the number of nuclei in a particular area (e.g., 200 μm×200 μm) can be estimated to be the number of cells. Cells used herein may be either naturally-occurring cells or artificially modified cells (e.g., fusion cells, genetically modified cells, etc.). Examples of cell sources include, but are not limited to, a single-cell culture; the embryo, blood of a normally-grown transgenic animal; a cell mixture of cells derived from normally-grown cell lines; and the like. Primary culture cells may be used. Alternatively, subculture cells may also be used. Preferably, when subculture cells are used, the cells are preferably of 3 to 8 passages. As used herein, cell density may be represented by the number of cells per unit area (e.g., $cm^2$).

As used herein, the term "stem cell" refers to a cell capable of self replication and pluripotency. Typically, stem cells can regenerate an injured tissue. Stem cells used herein may be, but are not limited to, embryonic stem (ES) cells or tissue stem cells (also called tissular stem cell, tissue-specific stem cell, or somatic stem cell). A stem cell may be an artificially produced cell (e.g., fusion cells, reprogrammed cells, or the like used herein) as long as it can have the above-described abilities. Embryonic stem cells are pluripotent stem cells derived from early embryos. An embryonic stem cell was first established in 1981, and has been applied to production of knockout mice since 1989. In 1998, a human embryonic stem cell was established, which is currently becoming available for regenerative medicine. Tissue stem cells have a relatively limited level of differentiation unlike embryonic stem cells. Tissue stem cells are present in tissues and have an undifferentiated intracellular structure. Tissue stem cells have a higher nucleus/cytoplasm ratio and have few intracellular organelles. Most tissue stem cells have pluripotency, along cell cycle, and proliferative ability beyond the life of the individual. As used herein, stem cells may be preferably embryonic stem cells, though tissue stem cells may also be employed depending on the circumstance.

Tissue stem cells are separated into categories of sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, hepatic stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified as long as they can achieve the intended treatment.

The origin of a stem cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells, hematopoietic stem cells, mesenchymal stem cells, and the like. Stem cells of mesoderm origin are mostly present in organs, including hepatic stem cells, pancreatic stem cells, and the like. As used herein, somatic cells may be derived from any mesenchyme. Preferably, somatic cells derived from mesenchyme may be employed.

As cells for use in construction of a synthetic tissue or three-dimensional structure of the present invention, differentiated cells or stem cells derived from the above-described ectoderm, endoderm, or mesoderm may be employed, for example. Examples of such cells include mesenchymal cells. In a certain embodiment, as such cells, myoblasts (e.g., skeletal myoblast, etc.), fibroblasts, synovial cells, and the like may be employed. As such cells, differentiated cells or stem cells can be used as they are. Cells differentiated from stem cells into a desired direction can be used.

As used herein, the term "mesenchymal stem cell" refers to a stem cell found in mesenchyme. The term "mesenchymal stem cell" may be herein abbreviated as "MSC". Mesenchyme refers to a population of free cells which are in the asterodal shape or have irregular projections and bridge gaps between epithelial tissues, and which are recognized in each stage of development of multicellular animals. Mesenchyme also refers to tissue formed with intracellular cement associated with the cells. Mesenchymal stem cells have proliferation ability and the ability to differentiate into osteocytes, chondrocytes, muscle cells, stroma cells, tendon cells, and adipocytes. Mesenchymal stem cells are employed in order to culture or grow bone marrow cells or the like collected from patients, or differentiate them into chondrocytes or osteoblasts. Mesenchymal stem cells are also employed as reconstruction material, such as alveolar bones; bones, cartilages or joints for arthropathy or the like; and the like. There is a large demand for mesenchymal stem cells. A synthetic tissue or three-dimensional structure of the present invention comprising mesenchymal stem cells or differentiated mesenchymal stem cells is particularly useful when a structure is required in these applications.

As used herein, the term "isolated" means that naturally accompanying material is at least reduced, or preferably substantially completely eliminated, in normal circumstances. Therefore, the term "isolated cell" refers to a cell substantially free of other accompanying substances (e.g., other cells, proteins, nucleic acids, etc.) in natural circumstances. The term "isolated tissue" refers to a tissue substantially free of substances other than that tissue (e.g., in the case of synthetic tissues or complexes, substances, scaffolds, sheets, coats, etc. used when the synthetic tissue is produced). As used herein, the term "isolated" refers to a scaffold-free state. Therefore, it will be understood that the synthetic tissue or complex of the present invention in the isolated state may contain components (e.g., medium, etc.) used in the production of it. The term "isolated" in relation to nucleic acids or polypeptides means that, for example, the nucleic acids or the polypeptides are substantially free of cellular substances or culture media when they are produced by recombinant DNA techniques; or precursory chemical substances or other chemical substances when they are chemically synthesized. Isolated nucleic acids are preferably free of sequences naturally flanking the nucleic acid within an organism from which the nucleic acid is derived (i.e., sequences positioned at the 5' terminus and the 3' terminus of the nucleic acid).

As used herein, the term "scaffold-free" indicates that a synthetic tissue does not substantially contain a material (scaffold) which is conventionally used for production of a synthetic tissue. Examples of such a scaffold include, but are not limited to, chemical polymeric compounds, ceramics, or biological formulations such as polysaccharides, collagens, gelatins, hyaluronic acids, and the like. A scaffold is a material which is substantially solid and has a strength which allows it to support cells or tissue.

As used herein, the term "established" in relation to cells refers to a state of a cell in which a particular property (pluripotency) of the cell is maintained and the cell undergoes stable proliferation under culture conditions. Therefore, established stem cells maintain pluripotency.

As used herein, the term "non-embryonic" refers to not being directly derived from early embryos. Therefore, the term "non-embryonic" refers to cells derived from parts of the body other than early embryos. Also, modified embryonic stem cells (e.g., genetically modified or fusion embryonic stem cells, etc.) are encompassed by non-embryonic cells.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, adipocytes, osteocytes, chondrocytes, and the like.

As used herein, the term "tissue" refers to a group of cells having the same function and form in cellular organisms. In multicellular organisms, constituent cells are usually differentiated so that the cells have specialized functions, resulting in division of labor. Therefore, multicellular organisms are not simple cell aggregations, but constitute organic or social cell groups having a certain function and structure. Examples of tissues include, but are not limited to, integument tissue, connective tissue, muscular tissue, nervous tissue, and the like. Tissue targeted by the present invention may be derived from any organ or part of an organism. In a preferable embodiment of the present invention, tissue targeted by the present invention includes, but is not limited to, a bones, a cartilage, a tendon, a ligament, a meniscus, an intervertebral disk, a periosteum, a blood vessel, a blood vessel-like tissue, a heart, a cardiac valve, a pericardium, a dura mater, and the like.

As used herein, the term "cell sheet" refers to a structure comprising a monolayer of cells. Such a cell sheet has at least a two-dimensional biological integration. The sheet having biological integration is characterized in that after the sheet is produced, the connection between cells is not substantially destroyed even when the sheet is handled singly. Such biological integration includes intracellular connection via an extracellular matrix. It will be understood that the cell sheet may partially include a two or three-layer structure.

As used herein, the term "synthetic tissue" refers to tissue having a state different from natural states. Typically, a synthetic tissue is herein prepared by cell culture. Tissue which is removed from an organism and is not subjected to any treatment is not referred to as a synthetic tissue. Therefore, a synthetic tissue may include materials derived from organisms and materials not derived from organisms. The synthetic tissue of the present invention typically comprises a cell and/or a biological material, and may comprise other materials. More preferably, a synthetic tissue of the present invention is composed substantially only of a cell and/or a biological material. Such a biological material is preferably derived from cells constituting the tissue (e.g., extracellular matrix, etc.).

As used herein, the term "implantable synthetic tissue" refers to a synthetic tissue, which can be used for actual clinical implantation and can function as a tissue at the implantation site for a certain period of time after implantation. Implantable synthetic tissue typically has sufficient biocompatibility, sufficient affinity, and the like.

The sufficient strength of an implantable synthetic tissue varies depending on a part targeted by implantation, but can be determined as appropriate by those skilled in the art. The strength is sufficient to provide self-supporting ability, and can be determined depending on the environment of implantation. The strength can be measured by measuring stress or distortion characteristics or conducting s creep characteristics indentation test as described below. The strength may also be evaluated by observing the maximum load.

The sufficient size of an implantable synthetic tissue varies depending on a part targeted by implantation, but can be determined as appropriate by those skilled in the art. The size can be determined depending on the environment of implantation.

However, an implantable synthetic tissue preferably has at least a certain size. Such a size (e.g., area) is at least 1 cm$^2$, preferably at least 2 cm$^2$, more preferably at least 3 cm$^2$, even more preferably at least 4 cm$^2$, at least 5 cm$^2$, at least 6 cm$^2$, at least 7 cm$^2$, at least 8 cm$^2$, at least 9 cm$^2$, at least 10 cm$^2$, at least 15 cm$^2$, or at least 20 cm$^2$. An essence of the present invention is that a synthetic tissue of any size (area, volume) can be produced, i.e., the size is not particularly limited.

When the size is represented by the volume, the size may be, but is not limited to, at least 2 mm$^3$, or at least 40 mm$^3$. The size may be 2 mm$^3$ or less or 40 mm$^3$ or more.

The sufficient thickness of an implantable synthetic tissue varies depending on a part targeted by implantation, but can be determined as appropriate by those skilled in the art. The thickness can be determined depending on the environment of implantation. The thickness may exceed 5 mm. When an implantable synthetic tissue is implanted into the heart, the tissue may only have these minimum thicknesses. When implantable synthetic tissue is used in other applications, the tissue may preferably have a greater thickness. In such a case, for example, an implantable synthetic tissue has preferably a thickness of at least 2 mm, more preferably at least 3 mm, and even more preferably 5 mm. For example, when an implantable synthetic tissue is applied to a bone, a cartilage, a ligament, a tendon, or the like, similar to the case of a heart, the tissue has a thickness of at least about 1 mm (e.g., at least 2 mm, more preferably at least 3 mm, and even more preferably 5 mm), or 5 mm or more or less than 1 mm. An essence of the present invention is that a synthetic tissue or complex of any thickness can be produced, i.e., the size is not particularly limited.

The sufficient biocompatibility of implantable synthetic tissue varies depending on a part targeted by implantation, but can be determined as appropriate by those skilled in the art. However, an implantable synthetic tissue preferably has at least a certain level of biocompatibility. Typically, a desired level of biocompatibility is, for example, such that biological integration to surrounding tissues is achieved without any inflammation, any immune reaction or the like. The present invention is not limited to this. In some cases (e.g., corneas, etc.), an immune reaction is less likely to occur. Therefore, an implantable synthetic tissue has biocompatibility to an extent, which achieves the object of the present invention even when an immune reaction is likely to occur in other organs. Examples of parameters indicating biocompatibility include, but are not limited to, the presence or absence of an extracellular matrix, the presence or absence of an immune reaction, the degree of inflammation, and the like. Such biocompatibility can be determined by examining the compatibility of a synthetic tissue at an implantation site after implantation (e.g., confirming that an implanted synthetic tissue is not destroyed). See "Hito Ishoku Zoki Kyozetsu Hanno no Byori Soshiki Shindan Kijyun Kanbetsu Shindan to Seiken Hyohon no Toriatsukai (Zufu) Jinzo Ishoku, Kanzo Ishoku Oyobi Shinzo Ishoku [Pathological Tissue Diagnosis Criterion for Human Transplanted Organ Rejection Reaction Handling of Differential Diagnosis and Biopsy Specimen (Illustrated Book) Kidney Transplantation, Liver Transplantation and Heart Transplantation]" The Japan Society for Transplantation and The Japanese Society for Pathology editors, Kanehara Shuppan Kabushiki Kaisha (1998). According to this document, biocompatibility is divided into Grade 0, 1A, 1B, 2, 3A, 3B, and 4. At Grade 0 (no acute rejection), no acute rejection reaction, cardiomyocyte failure, or the like is found in biopsy specimens. At Grade 1A (focal, mild acute rejection), there is focal infiltration of large lymphocytes around blood vessels or into interstitial tissue, while there is no damage to cardiomyocytes. This observation is obtained in one or a plurality of biopsy specimens. At Grade 1B (diffuse, mild acute rejection), there is diffuse infiltration of large lymphocytes around blood vessels or into interstitial tissue or both, while there is no damage to cardiomyocytes. At Grade 2 (focal, moderate acute rejection), there is a single observed infiltration focus of inflammatory cells clearly bordered from the surrounding portions. Inflammation cells are large activated lymphocytes and may include eosinophils. Damage to cardiomyocytes associated with modification of cardiac muscle is observed in lesions. At Grade 3A (multifocal, moderate acute rejection), there are multiple infiltration foci of inflammatory cells which are large activated lymphocytes and may include eosinophils. Two or more of the multiple inflammatory infiltration foci of inflammatory cells have damages to cardiomyocytes. In some cases, there is also rough infiltration of inflammatory cells into the endocardium. The infiltration foci are observed in one or a plurality of biopsy specimens. At Grade 3B (multifocal, borderline severe acute rejection), there are more confluent and diffuse infiltration foci of inflammatory cells found in more biopsy specimens than those observed at Grade 3A. There is infiltration of inflammatory cells including large lymphocytes and eosinophils, in some cases neutrophils, as well as damage to cardiomyocytes. There is no hemorrhage. At Grade 4 (severe acute rejection), there is infiltration of various inflammatory cells including activated lymphocytes, eosinophils, and neutrophils. There is always damage to cardiomyocytes and necrosis of cardiomyocytes. Edema, hemorrhage, and/or angitis are also typically observed. Infiltration of inflammatory cells into the endocardium, which is different from the "Quilty" effect, is typically observed. When a therapy is strongly conducted using an immunosuppressant for a considerably long period of time, edema and hemorrhage may be more significant than infiltration.

The sufficient affinity of an implantable synthetic tissue varies depending on a part targeted by implantation, but can be determined as appropriate by those skilled in the art. Examples of parameters for affinity include, but are not limited to, biological integration capability between an implanted synthetic tissue and its implantation site, and the like. Such affinity can be determined based on the presence of biological integration at an implantation site after implantation. Preferable affinity is herein such that an implanted synthetic tissue has the same function as that of a site in which the tissue is implanted, for example.

As used herein, the term "self-supporting ability" in relation to a tissue (e.g., a synthetic tissue, etc.) refers to a property of the synthetic tissue such that when it is restrained on at least one point thereof, it is not substantially destroyed. Self-supporting ability is herein observed if a tissue (e.g., a synthetic tissue) is picked up by using forceps with a tip having a thickness of 0.5 to 3.0 mm (preferably, forceps with a tip having a thickness of 1 to 2 mm or 1 mm; the forceps preferably have a bent tip) and the tissue is not substantially destroyed. Such forceps are commercially available (e.g., from Natsume Seisakusho, etc.). A force exerted for picking up a tissue is comparable with a force typically exerted by a medical practioner handing a tissue. Therefore, the self-supporting ability of a tissue can also be represented by a property such that the tissue is not destroyed when it is picked up by a hand. Such forceps are, for example, but are not limited to, a pair of curved fine forceps (e.g., No. A-11 (tip: 1.0 mm in thickness) and No. A-12-2 (tip: 0.5 mm in thickness) commercially available from Natsume Seisakusho). A bent tip is suitable for picking up a synthetic tissue. The forceps are not limited to a bent tip type.

When a joint is treated, replacement is majorly performed. The strength of a synthetic tissue of the present invention required in such a case is such that a minimum self-supporting ability is obtained. Cells contained in the synthetic tissue are subsequently replaced with cells in an affected portion. The replacing cells produce a matrix which enhances the mechanical strength, so that the joint is healed. It will also be understood that the present invention may be used in conjunction with an artificial joint.

In the present invention, self-supporting ability plays an important role in evaluating the supporting ability of a synthetic tissue which is actually produced. When a synthetic tissue of the present invention is produced, the synthetic tissue is formed in the shape of a cell sheet in a container. Thereafter, the sheet is detached. With conventional techniques, the sheet is usually destroyed due to lack of self-supporting ability. Therefore, in conventional technology, an implantable synthetic tissue cannot be substantially produced. Especially, when a large-sized synthetic tissue is required, conventional techniques are not adequate. According to the technique of the present invention, a synthetic tissue can be produced, which has a sufficient strength which allows the tissue to be detached from a container without being destroying, i.e., the tissue already has self-supporting ability when being detached. This is true even when the synthetic tissue is in the form of a monolayer sheet before being detached. It will be understood that the monolayer may partially include a two or three-layer structure. Thus, it will be understood that the synthetic tissue of the present invention is applicable in substantially any chosen therapy. In addition, typically, after a synthetic tissue is produced and detached, the strength and self-supporting ability of the synthetic tissue are increased as observed in the present invention. Therefore, in the present invention, it will be understood that the self-supporting ability evaluated upon production may be an important aspect. In the present invention, the strength upon implantation is also important. It may also be important to evaluate the self-supporting ability of a synthetic tissue when a predetermined time has passed after the production of the tissue. Therefore, it will be understood that the self supporting ability at the time of implantation after transport, can be determined by calculating the time that has elapsed since production of the tissue, based on the above-described relationship.

As used herein, the term "membranous tissue" refers to a tissue in the form of membrane and is also referred to as "planar tissue". Examples of membranous tissue include tissues of organs (e.g., periosteum, pericardium, duramater, cornea, etc.).

As used herein, the term "organ" refers to a structure which is a specific part of an individual organism where a certain function of the individual organism is locally performed and which is morphologically independent. Generally, in multicellular organisms (e.g., animals and plants), organs are made of several tissues in specific spatial arrangement and tissue is made of a number of cells. Examples of such organs include, but are not limited to, skin, blood vessel, cornea, kidney, heart, liver, umbilical cord, intestine, nerve, lung, placenta, pancreas, brain, joint, bone, cartilage, peripheral limbs, retina, and the like. Examples of such organs include, but are not limited to, organs of the skin system, the parenchyma pancreas system, the pancreatic duct system, the hepatic system, the blood system, the myocardial system, the skeletal muscle system, the osteoblast system, the skeletal myoblast system, the nervous system, the blood vessel endothelial system, the pigment system, the smooth muscle system, the fat system, the bone system, the cartilage system, and the like.

As used herein, the term "bag-shaped organ" refers to an organ which has a three-dimensional expanse and the inside of which may be connected via a tubular tissue to the outside. Examples of bag-shaped organs include, but are not limited to, heart, liver, kidney, stomach, spleen, and the like.

In one embodiment, the present invention targets an intervertebral disk, a cartilage, a joint, a bone, a meniscus, a synovial membrane, a ligament, a tendon, and the like. In a preferable embodiment, the present invention targets blood vessels, blood vessel-like tissue, heart, heart valves, pericardia, dura mater, cornea, and bones. In another preferable embodiment, examples of organs targeted by the present invention include, but are not limited to, skeletal muscle, fat, and the like in addition to what is described above.

As used herein, the term "cover" or "wrap" in relation to a synthetic tissue, a three-dimensional structure, or the like, which is wrapped around a certain part (e.g., an injured site, etc.), means that the synthetic tissue or the like is arranged so as to cover the part (i.e., conceal an injury or the like). The terms "wrap" and "arrange (or locate) so as to cover" are used interchangeably. By observing the spatial relationship between the part and the synthetic tissue or the like, it can be determined whether or not the part is covered by the synthetic tissue or the like. In a preferable embodiment, in a covering step, a synthetic tissue or the like can be wrapped one turn around a certain site.

As used herein, the term "replace" means that a lesion (a site of an organism) is replaced, and cells which have originally been in a lesion are replaced with cells supplied by a synthetic tissue or a complex according to the present invention. Examples of a disease for which replacement is suitable include, but are not limited to, a ruptured site, and the like. The term "fill" may be used in place of the term "replace" in the present specification.

A "sufficient time required for a synthetic tissue to biologically integrate with a part" herein varies depending on a combination of the part and the synthetic tissue, but can be determined as appropriate by those skilled in the art based on the combination. Examples of such a time include, but are not limited to, 1 week, 2 weeks, 1 month, 2 months, 3 months, 6 months, 1 year, and the like, after operation. In the present invention, a synthetic tissue preferably comprises substantially only cells and materials derived from the cells, and therefore, there is no particular material which needs to be extracted after operation. Therefore, the lower limit of the sufficient time is not particularly important. Thus, in this case, a longer time is more preferable. If the time is substantially extremely long, reinforcement is substantially completed.

As used herein, the term "immune reaction" refers to a reaction due to the dysfunction of immunological tolerance between a graft and a host. Examples of immune reactions include, but are not limited to, a hyperacute rejection reaction (within several minutes after implantation) (immune reaction caused by antibodies, such as β-Gal or the like), an acute rejection reaction (reaction caused by cellular immunity about 7 to 21 days after implantation), a chronic rejection reaction (rejection reaction caused by cellular immunity 3 or more months after operation), and the like.

As used herein, the elicitation of an immune reaction can be confirmed by pathological and histological examination of the type, number, or the like of infiltration of (immunological) cells into implanted tissue using staining (e.g., HE staining, etc.), immunological staining, or microscopic inspection of tissue sections.

As used herein, the term "calcification" refers to precipitation of calcareous substances in organisms.

"Calcification" in vivo can be determined herein by staining (e.g., Alizarin Red staining) and measuring calcium concentration. Specifically, implanted tissue is taken out; the tissue section is dissolved by acid treatment or the like; and the atomic absorption of the solution is measured by a trace element quantifying device.

As used herein, the term "within organism(s) (or in organism(s))" or "in vivo" refers to the inner part of organism(s). In a specific context, "within organism(s)" refers to a position at which a subject tissue or organ is placed.

As used herein, "in vitro" indicates that a part of an organism is extracted or released outside the organism for various purposes of research (e.g., in a test tube). The term in vitro is in contrast to the term in vivo.

As used herein, the term "ex vivo" refers to a series of operations where target cells into which a gene will be introduced are extracted from a subject; a therapeutic gene is introduced in vitro into the cells; and the cells are returned into the same subject.

As used herein, the term "material derived from cell(s)" refers to any material originating from the cell(s), including, but not being limited to, materials constituting the cell(s), materials secreted by the cell(s), materials metabolized by the cell(s), and the like. Representative examples of materials derived from cells include, but are not limited to, extracellular matrices, hormones, cytokines, and the like. Materials derived from cells typically have substantially no adverse effect on the cells and their hosts. Therefore, when the material is contained in a synthetic tissue, a three-dimensional structure, or the like, the material typically has substantially no adverse effect on the synthetic tissue, three-dimensional structure, or the like.

As used herein, the term "extracellular matrix" (ECM) refers to a substance existing between somatic cells no matter whether the cells are epithelial cells or non-epithelial cells. Extracellular matrices are typically produced by cells, and therefore, are biological materials. Extracellular matrices are involved in supporting tissue as well as in internal environmental structure essential for survival of all somatic cells. Extracellular matrices are generally produced from connective tissue cells. Some extracellular matrices are secreted from cells possessing basal membrane, such as epithelial cells or endothelial cells. Extracellular matrices are roughly divided into fibrous components and matrices filling there between. Fibrous components include collagen fibers and elastic fibers. A basic component of matrices is a glycosaminoglycan (acidic mucopolysaccharide), most of which is bound to non-collagenous protein to form a polymer of a proteoglycan (acidic mucopolysaccharide-protein complex). In addition, matrices include glycoproteins, such as laminin of basal membrane, microfibrils around elastic fibers, fibers, fibronectins on cell surfaces, and the like. Particularly differentiated tissue has the same basic structure. For example, in hyaline cartilage, chondroblasts characteristically produce a large amount of cartilage matrices including proteoglycans. In bones, osteoblasts produce bone matrices which cause calcification. Herein, examples of typical extracellular matrix include, but not limited to, collagen I, collagen III, collagen V, elastin, vitronectin, fibronectin, proteoglycans (for example, decolin, byglican, fibromodulin, lumican, hyaluronic acid, etc.). Various types of extracellular matrix may be utilized in the present invention as long as cell adhesion is achieved.

In one embodiment of the present invention, the synthetic tissue, three-dimensional structure, or the like of the present invention may be advantageously similar to the composition of an extracellular matrix (e.g., elastin, collagen (e.g., Type I, Type III, Type IV, etc.), laminin, etc.) of a site of an organ for which implantation is intended. In the present invention, extracellular matrices include cell adhesion molecules. As used herein, the terms "cell adhesion molecule" and "adhesion molecule" are used interchangeably, referring to a molecule capable of mediating the joining of two or more cells (cell adhesion) or adhesion between a substrate and a cell. In general, cell adhesion molecules are divided into two groups: molecules involved in cell-cell adhesion (intercellular adhesion) (cell-cell adhesion molecules) and molecules involved in cell-extracellular matrix adhesion (cell-substrate adhesion) (cell-substrate adhesion molecules). A synthetic tissue or three-dimensional structure of the present invention typically comprises such a cell adhesion molecule. Therefore, cell adhesion molecules herein include a protein of a substrate and a protein of a cell (e.g., integrin, etc.) in cell-substrate adhesion. A molecule other than proteins falls within the concept of cell adhesion molecule as long as it can mediate cell adhesion.

It should be noted that the synthetic tissue or complex of the present invention comprises cells and a ■ material (natively) derived from the cell. ■ Therefore, such materials including ECMs form a complicated composition containing collagen I, collagen III, collagen V, elastin, fibronectin, vitronectin, proteoglycans (for example, decolin, byglican, fibromodulin, lumican, hyaluronic acid, etc.) Conventionally a synthetic tissue containing such cell-derived ingredients has not been provided. To obtain a synthetic tissue having such a composition is substantially impossible when an artificial material is used. Thus, a composition containing such ingredients (particularly collagen I, collagen III and the like) is recognized to be a native composition.

More preferably, an extracellular matrix includes all the collagen (for example, Types I, Type III, etc.), vitronectin, and fibronectin. Especially, a synthetic tissue containing vitronectin and/or fibronectin has not been provided before. Therefore, the synthetic tissue and the complex according to the present invention are recognized to be new in this regard.

As used herein, the term "provided" or "distributed" in relation to an extracellular matrix and the synthetic tissue of the present invention indicates that the extracellular matrix is present in the synthetic tissue. It should be understood that such superficial provision can be visualized and observed by immunologically staining an extracellular matrix of interest.

As used herein, the term "in a diffused manner" or "diffusedly" in relation to the distribution of an extracellular matrix indicates that the extracellular matrix is not localized. Such distribution of an extracellular matrix has a ratio of the distribution densities of two arbitrary sections of 1 cm² within a range of typically about 1:10 to about 10:1, and representatively about 1:3 to about 3:1, and preferably about 1:2 to about 2:1, and more preferably about 1:1 (i.e., substantially evenly distributed over the synthetic tissue. When an extracellular matrix is distributed on a surface of the synthetic tissue of the present invention, but not localized, the synthetic tissue of the present invention has biological integration capability evenly with respect to the surrounding. Therefore, the synthetic tissue of the present invention has an excellent effect of recovery after implantation.

For cell-cell adhesion, cadherin, a number of molecules belonging in an immunoglobulin superfamily (NCAML1, ICAM, fasciclin II, III, etc.), selectin, and the like are known, each of which is known to join cell membranes via a specific molecular reaction. Therefore, in one embodiment, the synthetic tissue, three-dimensional structure, or the like of the present invention preferably has substantially the same composition of cadherin, immunoglobulin superfamily molecules, or the like as that of a site for which implantation is intended.

Thus, various molecules are involved in cell adhesion and have different functions. Those skilled in the art can appropriately select a molecule to be contained in a synthetic tissue or three-dimensional structure of the present invention depending on the purpose. Techniques for cell adhesion are well known as described above and as described in, for example, "Saibogaimatorikkusu—Rinsho heno Oyo—[Extracellular matrix—Clinical Applications—], Medical Review.

It can be determined whether or not a certain molecule is a cell adhesion molecule, by an assay, such as biochemical quantification (an SDS-PAG method, a labeled-collagen method, etc.), immunological quantification (an enzyme antibody method, a fluorescent antibody method, an immunohistological study, etc.), a PCR method, a hybridization method, or the like, in which a positive reaction is detected. Examples of such a cell adhesion molecule include, but are not limited to, collagen, integrin, fibronectin, laminin, vitronectin, fibrinogen, an immunoglobulin superfamily member (e.g., CD2, CD4, CD8, ICM1, ICAM2, VCAM1), selectin, cadherin, and the like. Most of these cell adhesion molecules transmit into a cell an auxiliary signal for cell activation due to intercellular interaction as well as cell adhesion. Therefore, an adhesion molecule for use in an implant of the present invention preferably transmits an auxiliary signal for cell activation into a cell. This is because cell activation can promote growth of cells originally present or aggregating in a tissue or organ at an injured site after application of an implant thereto. It can be determined whether or not such an auxiliary signal can be transmitted into a cell, by an assay, such as biochemical quantification (an SDS-PAG method, a labeled-collagen method, etc.), immunological quantification (an enzyme antibody method, a fluorescent antibody method, an immunohistological study, etc.), a PDR method, a hybridization method, or the like, in which a positive reaction is detected.

An example of a cell adhesion molecule is cadherin which is present in many cells capable of being fixed to tissue. Cadherin can be used in a preferable embodiment of the present invention. Examples of a cell adhesion molecule in cells of blood and the immune system which are not fixed to tissue, include, but are not limited to, immunoglobulin superfamily molecules (LFA-3, CD2, CD4, CD8, ICAM-1, ICAM2, VCAM1, etc.); integrin family molecules (LFA-1, Mac-1, gpIIbIIIa, p150, p95, VLA1, VLA2, VLA3, VLA4, VLA5, VLA6, etc.); selectin family molecules (L-selectin, E-selectin, P-selectin, etc.), and the like. Therefore, such a molecule may be useful for treatment of a tissue or organ of blood and the immune system.

Nonfixed cells need to be adhered to a specific tissue in order to act on the tissue. In this case, it is believed that cell-cell adhesion is gradually enhanced via a first adhesion by a selectin molecule or the like which is constantly expressed and a second adhesion by a subsequently activated integrin molecule. Therefore, in the present invention, a cell adhesion molecule for mediating the first adhesion and another cell adhesion molecule for mediating the second adhesion may be used together.

As used herein, the term "actin regulatory agent" refers to a substance which interacts directly or indirectly with actin in cells to change the form or state of the actin. It should be understood that actin regulatory agents are categorized into two classes, actin depolymerizing agents and actin polymerizing agents, depending on the action on actin. Examples of actin depolymerizing agents include, but are not limited to, Slingshot, cofilin, CAP (cyclase associated protein), ADF (actin depolymerizing factor), destrin, depactin, actophorin, cytochalasin, NGF (nerve growth factor), and the like. Examples of actin polymerizing agents include, but are not limited to, RhoA, mDi, profilin, Rac1, IRSp 53, Wave2, profilin, ROCK, Lim kinase, cofilin, cdc42, N-WASP, Arp2/3, Drf3, IRSp53, Mena, LPA (lysophosphatidic acid), insulin, PDGF (platelet-derived growth factor) a, PDGFb, chemokine, TGF (transforming growth factor) b, and the like. The above-described actin regulatory agents include some substances which can be identified by the following assay. Interaction of an actin regulatory agent with respect to actin is assayed as follows. Actin is visualized using an actin staining reagent (Molecular Probes, Texas Red-X phalloidin) or the like. By observing actin aggregation or cell outgrowth under a microscope, the presence of the interaction is determined by confirming the aggregation and reconstruction of actin and/or an increase in the cell outgrowth rate. The determination may be performed quantitatively or qualitatively. The above-described actin regulatory agents are used in the present invention so as to promote the detachment or a multilayer structure of the synthetic tissue. When an actin regulatory agent used in the present invention is derived from an organism, the organism may be a mammalian species, such as human, mouse, bovine, or the like.

The above-described agents involved in actin polymerization control actin polymerization in relation to Rho and the examples of the agents include the following (see, for example, "Saibokokkaku/Undo ga wakaru (Understanding of cytoskeleton/movement)", (Ed./Hiroaki Miki), Yodo-sha).

Actin polymerization (see Takenaka T et al. J. Cell Sci., 114: 1801-1809, 2001)

RhoA→mDi→profilin⇒ actin polymerization

RhoA→ROCK/Rho→LIM kinase→phosphorylation of (suppression)⇒ actin polymerization

Rac1→IRSp53→WAVE2→profilin, Arp2/3⇒ actin polymerization cdc42→N-WASP→profilin, Arp2/3⇒ actin polymerization cdc42→Drf3→IRSp53→Mena⇒ actin polymerization (In the above descriptions, → indicates a singal transduction pathway such as phosphorylation. In the present invention any agent involved in such a pathway can be utilized.

Actin Depolymerization

Slingshot→dephosphorization of cofilin (activation) ⇒ actin depolymerization

Actin depolymerization is controlled by a balance between phosphorylation by LIM kinase activity of cofilin and dephosphorization by Slingshot. As another agent for activating cofilin, CAP (cyclase-associated protein) and AIPI (actin-interacting-protein 1) are identified. It is recognized that any suitable agent can be used.

LPA (lysophosphatidic acid) of any chain length can be used.

Any chemokine can be used. However, examples of preferable chemokine include interleukin 8, MIP-1, SDF-1 and the like.

Any TGFβ can be used. However, examples of preferable TGFβ include TGF-β1 and TGF-β3. TGF-β1 and TGF-β3 has an extracellular matrix generation promoting activity. Thus, in the present invention, TGF-β1 and TGF-β3 are used with an attention.

As used herein, the term "tissue strength" refers to a parameter which indicates a function of a tissue or organ and a physical strength of the tissue or organ. Tissue strength can be generally determined by measuring tensile strength (e.g., break strength, modulus of rigidity, Young's modulus, etc.). Such a general tensile test is well known. By analyzing data obtained by a general tensile test, various data, such as break strength, modulus of rigidity, Young's modulus, and the like, can be obtained. These values can be herein used as indicators of tissue strength. Typically, tissue strength which allows clinical applications is herein required.

Figure 46:
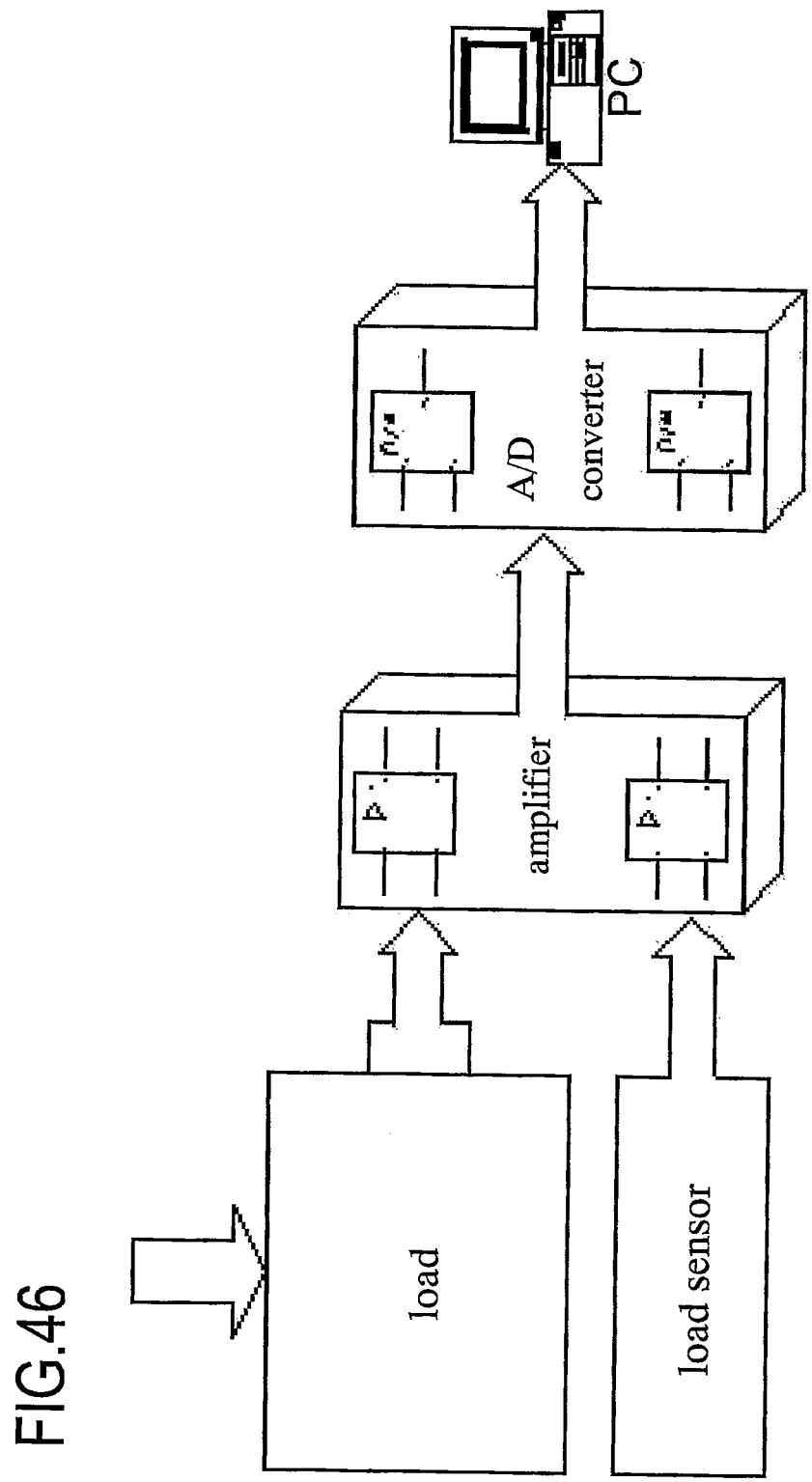
FIG. 46 shows a diagram for explaining a technique for measuring stress and distortion characteristics to determine tensile strength.
Figure 47:
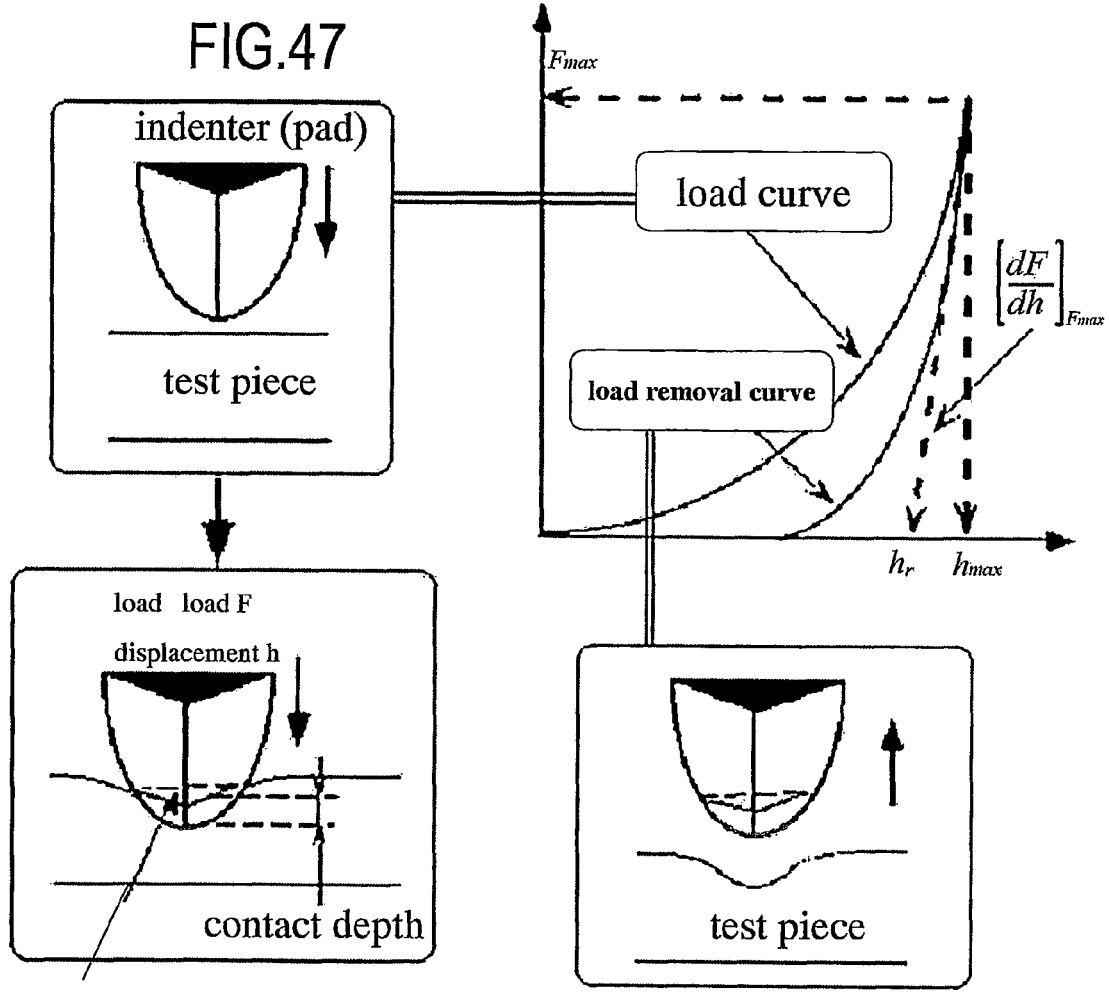
FIG. 47 shows a principle for obtaining a load/removal of a load curve.

The tensile strength of a synthetic tissue, three-dimensional structure, or the like of the present invention can be determined by measuring the stress and distortion characteristics thereof. Briefly, a load is applied to a sample; the resultant distortion and the load are input to respective A/D converters (e.g., ELK-5000) (1 ch: distortion, 2 ch: load); the stress and distortion characteristics are measured to determine the tensile strength of the sample (FIG. 46). Tensile strength can also be determined by testing creep characteristics. A creep characteristics indentation test is conducted to investigate how a sample is extended over time while a constant load is applied to the sample. For small materials, thin materials, and the like, an indentation test is conducted using, for example, a triangular pyramid-shaped indenter with a tip having a radius of about 0.1 μm to about 1 μm. Initially, the indenter is pushed into a test piece so that a load is given to the test piece. When the indenter reaches from several tens of nanometers to several micrometers deep in the test piece, the indenter is drawn off to remove the load. FIG. 47 shows a load/removal of load curve obtained by the above-described test method. Rigidity, Young's modulus, or the like can be obtained based on the behavior of the load and the push depth derived from the curve.

The tensile strength of the synthetic tissue of the present invention may be low. The tensile strength becomes higher when the matrix concentration is increased, and becomes lower when the cell to matrix ratio is increased. The present invention is characterized in that the strength can be adjusted as necessary. The present invention is also characterized in that the strength can be high or low relative to that of a tissue to be implanted. Therefore, it is recognized that the strength can be set to comply with any desired site.

As used herein, the term "physiologically active substance" refers to a substance capable of acting on a cell or tissue. Physiologically active substances include cytokines and growth factors. A cellular physiologically active substance may be naturally-occurring or synthesized. Preferably, a cellular physiologically active substance is one that is produced by a cell or one that has a function similar thereto. As used herein, a cellular physiologically active substance may be in the form of a protein or a nucleic acid or in other forms. In actual practice, cellular physiologically active substances are typically proteins. In the present invention, a physiologically active substance may be used to promote the affinity of an implanted synthetic tissue of the present invention, for example.

The term "cytokine" is used herein in the broadest sense in the art and refers to a physiologically active substance which is produced from a cell and acts on the same or different cell. Cytokines are generally proteins or polypeptides having a function of controlling an immune response, regulating the endocrine system, regulating the nervous system, acting against a tumor, acting against a virus, regulating cell growth, regulating cell differentiation, or the like. Cytokines are herein in the form of a protein or a nucleic acid or in other forms. In actual practice, cytokines are typically proteins.

The terms "growth factor" or "cell growth factor" are used herein interchangeably and each refers to a substance which promotes or controls cell growth. Growth factors are also called "proliferation factors" or "development factors". Growth factors may be added to cell or tissue culture medium, substituting for serum macro molecules. It has been revealed that a number of growth factors have a function of controlling differentiation in addition to a function of promoting cell growth.

Examples of cytokines representatively include, but are not limited to, interleukins, chemokines, hematopoietic factors such as colony stimulating factors, a tumor necrosis factor, interferons, a platelet-derived growth factor (PDGF), an epidermal growth factor (EGF), a fibroblast growth factor (FGF), a hepatocyte growth factor (HGF), a vascular endothelial cell growth factor (VEGF), cardiotrophin, and the like, which have proliferative activity.

Cellular physiologically active substances, such as cytokines, growth factors, and the like, typically have redundancy in function. Accordingly, reference herein to a particular cytokine or growth factor by one name or function also includes any other names or functions by which the factor is known to those of skill in the art, as long as the factor has the activity of a cellular physiologically active substance for use in the present invention. Cytokines or growth factors can be used in a therapeutic or pharmaceutical agent according to a preferable embodiment of the present invention as long as they have preferable activity as described herein.

Therefore, in one embodiment of the present invention, it was revealed that when such a cytokine or growth factor (e.g., BMP-2, etc.) is provided to an implantation site (e.g., an injured site of a cartilage, etc.) concomitantly with a synthetic tissue or three-dimensional structure of the present invention, the affinity of the synthetic tissue or three-dimensional structure and an improvement in the function of the implantation site are observed. Thus, the present invention also provides such a combined therapy.

As used herein, the term "differentiation" refers to a developmental process of the state of the complex parts of organisms, such as cells, tissues, or organs and a process in which a characteristic tissue or organ is formed. The term "differentiation" is mainly used in embryology, developmental biology, and the like. In organisms, various tissues and organs are formed from divisions of a fertilized ovum (a single cell) to an adult. At early developmental stages (i.e., before cell division or after insufficient cell division), each cell or cell group has no morphological or functional feature and is not much distinguishable. Such a state is referred to as "undifferentiated". "Differentiation" may occur at the level of organs. A cell constituting an organ may develop into various cells or cell groups having different features. This phenomenon is also referred to as differentiation within an organ in the formation of the organ. Therefore, a synthetic tissue or three-dimensional structure of the present invention may comprise a tissue including differentiated cells.

When differentiation is required to produce a synthetic tissue of the present invention, the differentiation may be performed either before or after the organization of the cells.

As used herein, the terms "differentiation agent" and "differentiation promoting agent" are used interchangeably and refer to any agent which is known to promote differentiation of cells (e.g., chemical substances, temperature, etc.). Examples of such an agent include, but are not limited to, various environmental factors, such as temperature, humidity, pH, salt concentration, nutrients, metals, gas, organic solvent, pressure, chemical substances (e.g., steroids, antibiotics, etc.), and the like, or arbitrary combinations thereof. Representative examples of differentiation agents include, but are not limited to, cellular physiologically active substances. Representative examples of cellular physiologically active substances include, but are not limited to, DNA demethylating agents (e.g., 5-azacytidine, etc.), histone deacetylating agents (e.g., trichosanthin, etc.), intranuclear receptor ligands (e.g., retinoic acid (ATRA), vitamin $D_3$, T3, etc.), cell growth factors (e.g., activin, IGF-1, FGF, PDGF, TGF-β, BMP2/4, etc.), cytokines (e.g., LIF, IL-2, IL-6, etc.), hexamethylenebisacetoamides, dimethylacetoamides, dibutyl cAMPs, dimethylsulfoxides, iododeoxyuridines, hydroxyl ureas, cytosine arabinosides, mitomycin C, sodium lactate, aphydicolin, fluorodeoxyuridine, polybren hexadimetrine bromide, selenium, and the like.

Specific examples of differentiation agents are described below. These differentiation agents may be used singly or in combination.

A) Cornea: epidermal growth factor (EGF);
B) Skin (keratinocyte): TGF-β, FGF-7 (KGF: keratinocyte growth factor), EGF;
C) Vascular endothelium: VEGF, FGF, angiopoietin;
D) Kidney: LIF, BMP, FGF, GDNF;
E) Heart: HGF, LIF, VEGF;
F) Liver: HGF, TGF-β, IL-6, EGF, VEGF;
G) Umbilical endothelium: VEGF;
H) Intestinal epithelium: EGF, IGF-I, HGF, KGF, TGF-β, IL-1;
I) Nerve: nerve growth factor (NGF), BDNF (brain-derived neurotrophic factor), GDNF (glial-derived neurotrophic factor), neurotrophin, IL-6, TGF-β, TNF;
J) Glia cell: TGF-β, TNF-α, EGF, LIF, IL-6;
K) Peripheral nerve cell: bFGF, LIF, TGF-β, IL-6, VEGF;
L) Lung (alveolar epithelium): TGF-β, IL-13, IL-1β, KGF, HGF;
M) Placenta: growth hormone (GH), IGF, prolactin, LIF, IL-1, activin A, EGF;
N) Pancreatic epithelium: growth hormone, prolactin;
O) Pancreatic Langerhans' cells: TGF-β, IGF, PDGF, EGF, TGF-β, TRH (thyroropin);
P) Synovial cell: FGF, TGF-β (particularly, TGF-β1, TGF-β3);
Q) Osteoblast: BMP (particularly, BMP-2, BMP-4, BMP-7), FGF;
R) Chondroblast: FGF, TGF-β (particularly, TGF-β1, TGF-β3), BMP (particularly, BMP-2, BMP-4, BMP-7), TNF-α, IGF;
S) Retinal cell: FGF, CNTF (cilliary neurotrophic factor);
T) Fat cell: insulin, IGF, LIF; and
U) Muscle cell: LIF, TNF-α, FGF.

As used herein, the term "osteogenesis" indicates that any cell is caused to differentiate into a osteocyte. It is known that osteogenesis is promoted in the presence of dexamethasone, β-glycerophosphate, and ascorbic acid 2-phosphate. An osteogenic agent (BMP, (particularly, BMP-2, BMP-4, BMP-7)) may be added to promote osteogenesis.

As used herein, the term "chondrogenesis" refers to differentiation of any cell into a chondrocyte. It is known that chondrogenesis is promoted in the presence of pyrubic acid, dexamethasone, ascorbic acid 2-phosphate, insulin, transferrine, and selenious acid. An bone morphogenetic protein (BMP, (particularly, BMP-2, BMP-4, BMP-7)), TGF-β (particularly, TGF-β1 and TGF-β3), FGF, TNF-α and the like may be added to promote chondrogenesis.

As used herein, the term "adipogenesis" refers to differentiation of any cell into an adipocyte. It is known that adipogenesis is promoted in the presence of insulin, IGF, LIF, and ascorbic acid 2-phosphate.

As used herein, the terms "implant", "graft", and "tissue graft" are used interchangeably, referring to homologous or heterologous tissue or a cell group, or an artificial material, which is inserted into a particular site of a body and thereafter forms a part of the body. Therefore, a synthetic tissue or three-dimensional structure of the present invention can be used as an implant. Examples of conventional grafts include, but are not limited to, organs or portions of organs, blood vessels, blood vessel-like tissue, heart, cardiac valves, pericardia, dura matter, joint capsule, bone, cartilage, cornea, tooth, and the like. Therefore, grafts encompass any one of these which is inserted into an injured part so as to compensate for the lost portion. Grafts include, but are not limited to, autografts, allografts, and xenografts, which depend on the type of their donor.

As used herein, the term "autograft" (a tissue, a cell, an organ, etc.) refers to a graft (a tissue, a cell, an organ, etc.) which is implanted into the same individual from which the graft is derived. As used herein, the term "autograft" (a tissue, a cell, an organ, etc.) may encompass a graft from a genetically identical individual (e.g. an identical twin) in a broad sense. As used herein, the terms "autologous" and "derived from a subject" are used interchangeably. Therefore, the term "not derived from a subject" in relation to a graft indicates that the graft is not autologous (i.e., heterologous).

As used herein, the term "allograft (a tissue, a cell, an organ, etc.)" refers to a graft (a tissue, a cell, an organ, etc.) which is transplanted from a donor genetically different from, though of the same species, as the recipient. Since an allograft is genetically different from the recipient, the allograft (a tissue, a cell, an organ, etc.) may elicit an immune reaction in the recipient. Examples of such grafts (a tissue, a cell, an organ, etc.) include, but are not limited to, grafts derived from parents (a tissue, a cell, an organ, etc.). The synthetic tissue of the present invention can be an allograft, which has been demonstrated to have satisfactory therapeutic results. Attention should be paid to the synthetic tissue of the present invention.

As used herein, the term "xenograft" (a tissue, a cell, an organ, etc.) refers to a graft (a tissue, a cell, an organ, etc.) which is implanted from a different species. Therefore, for example, when a human is a recipient, a porcine-derived graft (a tissue, a cell, an organ, etc.) is called a xenograft (a tissue, a cell, an organ, etc.).

As used herein, "recipient" (acceptor) refers to an individual which receives a graft (a tissue, a cell, an organ, etc.) or implanted matter (a tissue, a cell, an organ, etc.) and is also called "host". In contrast, an individual providing a graft (a tissue, a cell, an organ, etc.) or implanted matter (a tissue, a cell, an organ, etc.) is called "donor" (provider).

With a synthetic tissue forming technique of the present invention, a synthetic tissue derived from any cell can be used. This is because a synthetic tissue (e.g., membranous tissues, organs, etc.) formed by the method of the present invention can exhibit a desired function while the tissue injury rate is maintained at a level which does not interfere with the therapy (i.e., a low level). Conventionally, tissues or organs are used as grafts without modification. In contrast to this, the present invention provides a tissue comprising three-dimensionally connected cells. Such a synthetic three-dimensional tissue cannot be achieved by conventional techniques, and therefore, constitutes one significant effect of the present invention.

As used herein, the term "subject" refers to an organism to which treatment of the present invention is applied and is also referred to as "patient". A patient or subject may be preferably a human.

Cells optionally used in a synthetic tissue, three-dimensional structure, or tissue graft of the present invention may be derived from a syngeneic origin (self origin), an allogenic origin (non-self origin), or a heterologous origin. In view of rejection reactions, syngeneic cells are preferable. If rejection reactions do not raise problems, allogenic cells may be employed. Cells which elicit rejection reactions can be employed by optionally treating the cells in a manner that overcomes rejection reactions. Procedures for avoiding rejection reactions are known in the art (see, for example, "Shin Gekagaku Taikei, Dai 12 Kan, Zoki Ishoku (Shinzo Ishoku•Hai Ishoku Gijutsuteki, Rinriteki Seibi kara Jisshi ni Mukete [New Whole Surgery, Vol. 12, Organ Transplantation (Heart Transplantation•Lung Transplantation From Technical and Ethical Improvements to Practice)" (Revised 3rd ed.), Nakayama Shoten]. Examples of such methods include, but are not limited to, a method using immunosuppressants or steroidal drugs, and the like. For example, there are currently the following immunosuppressants for preventing rejection reactions: "cyclosporine" (SANDIMMUNE/NEORAL); "tacrolimus" (PROGRAF); "azathioprine" (IMURAN); "steroid hormone" (prednine, methylprednine); and "T-cell antibodies" (OKT3, ATG, etc.). A method which is used worldwide as a preventive immunosuppression therapy in many facilities, is the concurrent use of three drugs: cyclosporine, azathioprine, and steroid hormone. An immunosuppressant is desirably administered concurrently with a pharmaceutical agent of the present invention. The present invention is not limited to this. An immunosuppressant may be administered before or after a regeneration/therapeutic method of the present invention as long as an immunosuppression effect can be achieved.

Cells used in the present invention may be derived from any organism (e.g., vertebrates and invertebrates). Preferably, cells derived from vertebrates are used. More preferably, cells derived from mammals (e.g., primates, rodents, etc.) are used. Even more preferably, cells derived from primates are used. Most preferably, cells derived from a human are used. Typically, cells from the same species as the host are preferably used.

Examples of an affected portion of a subject treated by a synthetic tissue of the present invention include, but are not limited to, the heart suffering from a heart disease (e.g., heart failure, ischemic heart diseases, myocardial infarct, cardiomyopathy, myocarditis, hypertrophic cardiomyopathy, dilated hypertrophic cardiomyopathy, and dilated cardiomyopathy); blood vessels in a pericardium patch, infarcted myocardium lower and upper limbs; a joint injury or denaturation; a cartilage injury or denaturation; osteonecrosis; meniscus injury or denaturation; intervertebral disk denaturation; ligament injury or denaturation; a fracture; implantation to a patient having a joint, cartilage, or bone having bone loss; an injured cornea; and the like.

Tissues targeted by the present invention may be any organ of an organism and may be derived from any organism. Examples of organisms targeted by the present invention include vertebrates and invertebrates. Preferably, organisms targeted by the present invention are mammals (e.g., primates, rodents, etc.). More preferably, organisms targeted by the present invention are primates. Most preferably, organisms targeted by the present invention are humans.

As used herein, the term "flexibility" in relation to a synthetic tissue refers to an ability to resist physical stimuli from external environments (e.g., pressure). A synthetic tissue having flexibility is preferable when the implantation site moves or deforms autonomously or by external effects.

As used herein, the term "extendibility and contractibility" in relation to a synthetic tissue refers to an ability to resist extending or contracting stimuli from external environments (e.g., pulsation). A synthetic tissue having extendibility and contractibility is preferable when the implantation site is subjected to extending or contracting stimuli. Examples of implantation sites, which are subjected to extending or contracting stimuli, include, but are not limited to, heart, muscle, joint, cartilage, tendon, and the like. In one embodiment, extendibility and contractibility capable of withstanding the pulsation motion of the heart may be required.

As used herein, the term "part" or "portion" refers to any part or portion, tissue, cell, or organ in the body. Examples of such parts, tissues, cells, and organs include, but are not limited to, a portion which can be treated with skeletal myoblasts, fibroblasts, synovial cells, stem cells, and the like. A marker specific to a portion may be any parameter, such as a nucleic acid molecule (expression of mRNA), a protein, an extracellular matrix, a specific phenotype, a specific shape of a cell, or the like. Therefore, markers which are not specified herein may be used to identify a synthetic tissue of the present invention as long as these markers can indicate cells derived from a portion. Representative examples of portions, but are not limited to, portions of the heart other than the adult myocardium, portions containing mesenchymal stem cells or cells derived therefrom, other tissues, other organs, myoblasts (e.g., skeletal myoblasts), fibroblasts, synovial cells, and the like.

For observing a cartilage tissue, following markers can be used as index.

Sox9 (human: Accession No. NM_000346) is a marker specific to a chondrocyte. The marker can be confirmed mainly by observing the presence of mRNA (Kulyk W M, Franklin J L, Hoffman L M. Sox9 expression during chondrogenesis in micromass cultures of embryonic limb mesenchyme. Exp Cell Res. 2000 Mar. 15, 255(2):327-32.).

Col 2A1 (human: Accession No. NM_001844) is a marker specific to a chondrocyte. The marker can be confirmed mainly by observing the presence of mRNA (Kulyk W M, Franklin J L, Hoffman L M. Sox9 expression during chondrogenesis in micromass cultures of embryonic limb mesenchyme. Exp Cell Res. 2000 Mar. 15; 255(2):327-32.).

Aggrecan (human: Accession No. NM_001135) is a marker specific to a chondrocyte. The marker can be confirmed mainly by observing the presence of mRNA (Kulyk W M, Franklin J L, Hoffman L M. Sox9 expression during chondrogenesis in micromass cultures of embryonic limb mesenchyme. Exp Cell Res. 2000 Mar. 15; 255(2):327-32.).

Bone sialoprotein (human: Accession No. NM_004967) is a marker specific to an osteoblast. The marker can be confirmed mainly by observing the presence of mRNA (Haase H R, Ivanovski S, Waters M J, Bartold P M. Growth hormone regulates osteogenic marker mRNA expression in human periodontal fibroblasts and alveolar bone-derived cells. Periodontal Res. 2003 August; 38(4):366-74.).

Osteocalcin (human: Accession No. NM_199173) is a marker specific to an osteoblast. The marker can be confirmed mainly by observing the presence of mRNA (Haase H R, Ivanovski S, Waters M J, Bartold P M. Growth hormone regulates osteogenic marker mRNA expression in human periodontal fibroblasts and alveolar bone-derived cells. J Periodontal Res. 2003 August; 38(4):366-74.).

GDF5 (human: Accession No. NM_000557) is a marker specific to a ligament cell. The marker can be confirmed mainly by observing the presence of mRNA (Wolfman N M, Hattersley G, Cox K, Celeste A J, Nelson R, Yamaji N, Dube J L, DiBlasio-Smith E, Nove J, Song J J, Wozney J M, Rosen V. Ectopic induction of tendon and ligament in rats by growth and differentiation factors 5, 6, and 7, members of the TGF-beta gene family. J Clin Invest. 1997 Jul. 15; 100(2):321-30.).

Six1 (human: Accession No. NM_005982) is a marker specific to a ligament cell (Dreyer S D, Naruse T, Morello R, Zabel B, Winterpacht A, Johnson R L, Lee B, Oberg K C. Lmx1b expression during joint and tendon formation: localization and evaluation of potential downstream targets. Gene Expr Patterns. 2004 July; 4(4):397-405.). The marker can be confirmed mainly by observing the presence of mRNA.

Scleraxis (human: Accession No. BK000280) is a marker specific to a ligament cell (Brent A E, Schweitzer R, Tabin C J. A somitic compartment of tendon progenitors. Cell. 2003 Apr. 18; 113(2):235-48.). The marker can be confirmed mainly by observing the presence of mRNA.

A "part other than the myocardium of an adult" and a "part other than the heart of an adult" can be identified using markers characteristic to cells derived from the myocardium of an adult or the heart of an adult including skeletal myoblasts, fibroblasts, synovial cells, stem cells, or the like (hereinafter referred to as a "non-adult myocardial marker" or a "non-adult heart marker", respectively). If the marker is expressed by less than about 100%, preferably less than about 80%, more preferably less than about 50%, even more preferably less than about 25%, in some cases less than about 1%, the above-described parts can be identified. Examples of such markers include, but are not limited to, myosin heavy chain IIa, myosin heavy chain IIb, myosin heavy chain IId (IIx), CD56, MyoD, Myf5, myogenin, and the like. Therefore, non-adult myocardial markers which are not specified herein may be used to identify a synthetic tissue of the present invention as long as these markers can indicate cells derived from parts other than the myocardium of an adult. Also, non-adult heart markers which are not specified herein may be used to identify a synthetic tissue of the present invention as long as these markers can indicate cells derived from parts other than the heart of an adult.

Myosin heavy chain IIa (human: Accession No. NM_017534; SEQ ID NOs. 1 and 2), myosin heavy chain IIb (human: Accession No. NM_017533; SEQ ID NOs. 3 and 4), and myosin heavy chain IId (IIx) (human: Accession No. NM_005963; SEQ ID NOs. 5 and 6) are markers specific to myoblasts (Havenith M. G., Visser R., Schrijvers-van Schendel J. M., Bosman F. T., "Muscle Fiber Typing in Routinely Processed Skeletal Muscle With Monoclonal Antibodies", Histochemistry, 1990; 93(5):497-499). These markers can be confirmed mainly by observing the presence of proteins. An antibody against myosin heavy chain IIa, myosin heavy chain IIb, and myosin heavy chain IId (IIx) is, for example, MY-32 available from Sigma. This antibody is specific to skeletal muscles and does not bind to myocardium (Webster C., Pavlath G. K., Parks D. R., Walsh F. S., Blau H. M., Exp. Cell. Res., 1988 January; 174(1):252-65; and Havenith M. G., Visser R., Schrijvers-van Schendel J. M., Bosman F. T., Muscle Fiber Typing in Routinely Processed Skeletal Muscle with Monoclonal Antibodies, Histochemistry, 1990, 93(5): 497-499).

CD56 (human: Accession No. U63041; SEQ ID NOs. 7 and 8) is a marker specific to myoblasts. This marker can be confirmed mainly by observing the presence of mRNA.

MyoD (human: Accession No. X56677; SEQ ID NOs. 9 and 10) is a marker specific to myoblasts. This marker can be confirmed mainly by observing the presence of mRNA.

Myf5 (human: Accession No. NM_005593; SEQ ID NOs. 11 and 12) is a marker specific to myoblasts. This marker can be confirmed mainly by observing the presence of mRNA.

Myogenin (human: Accession No. BT007233; SEQ ID NOs. 13 and 14) is a marker specific to myoblasts. This marker can be confirmed mainly by observing the presence of mRNA.

In other embodiments, other markers specific to other tissues can be utilized. Examples of such markers include, but are not limited to, Oct-3/4, SSEA-1, Rex-1, Otx2, and the like for embryonic stem cells; VE-cadherin, Flk-1, Tie-1, PECAM1, vWF, c-kit, CD34, Thy1, Sca-1, and the like for endothelial cells; skeletal muscle α actin in addition to the above-described markers for skeletal muscles; Nestin, Glu receptor, NMDA receptor, GFAP, neuregulin-1, and the like for nerve cells; c-kit, CD34, Thy1, Sca-1, GATA-1, GATA-2, FOG, and the like for hematopoietic cells.

As used herein, the term "derived" in relation to cells means that the cells are separated, isolated, or extracted from a cell mass, tissue, or organ in which the cells have been originally present, or that the cells are induced from stem cells.

As used herein, the term "applicable to heart" means that the heart applied has an ability to pulsate. A tissue applicable to heart has strength such that the tissue can withstand dilation and contraction of the pulsating heart. Here, applicability to the heart includes applicability to the myocardium. Applicability to heart may be determined by confirming that a recipient having an implanted graft survives.

As used herein, the term "three-dimensional structure" refers to an object which comprises cells having intracellular intergration or alignment and extends three-dimensionally, particularly matrices are oriented three-dimensionally and cells are arranged three-dimensionally.

As used herein, the term "biological integration" in relation to the relationship between biological entities such as cells means that there is certain interaction between the biological entities. Examples of such interaction includes, but are not limited to, interaction via biological molecules (e.g., extracellular matrix), interaction via signal transduction, electrical interaction (electrical integration, such as synchronization of electrical signals or the like), and the like. Biological integration includes biological integration in a synthetic tissue and biological integration of a synthetic tissue with its surroundings (e.g., surrounding tissues and cells after implantation, etc.). In order to confirm interactions, an assay appropriate to a characteristic of the interaction is employed. In order to confirm physical interactions via biological molecules, the strength of a synthetic tissue, a three-dimensional structure, or the like is measured (e.g., a tensile test). In order to confirm interaction via signal transduction, gene expression or the like is investigated. In order to confirm electrical interactions, the electric potential of a synthetic tissue, a three-dimensional structure, or the like is measured to determine whether or not the electric potential is propagated with constant waves. In the present invention, biological integration is provided in all three dimensions. Preferably, there is biological integration substantially uniformly in all directions in a three-dimensional space. In another embodiment, the synthetic tissue, a three-dimensional structure, and the like, which has substantially uniform two-dimensional biological integration and slightly weaker biological integration in the third dimension, may be employed. Biological integration via an extracellular matrix can be confirmed based on the degree of staining by staining the extracellular matrix. As a method for observing biological integration in vivo, there is an integration experiment using cartilage. In this experiment, a surface of the cartilage is removed and digested with chondroitinase ABC (Hunziker E. B. et al., J. Bone Joint Surg. Am., 1996 May; 78(5): 721-33). Thereafter, a tissue of interest is implanted onto a cut surface, followed by culturing for about 7; days. The subsequent integration is observed (FIG. 23). It will be understood that a capability to adhere to surrounding cells can be determined with the above-described cartilage experiment.

A synthetic tissue, three-dimensional structure, or the like of the present invention may be provided using known preparation methods, as a pharmaceutical product, or alternatively, as an animal drug, a quasi-drug, a marine drug, a cosmetic product, and the like.

Animals targeted by the present invention include any organism as long as it has organs (e.g., animals (e.g., vertebrates, invertebrate)). Preferably, the animal is a vertebrate (e.g., Myxiniformes, Petronyzoniformes, Chondrichthyes, Osteichthyes, amphibian, reptilian, avian, mammalian, etc.), more preferably mammalian (e.g., monotremata, marsupialia, edentate, dermoptera, chiroptera, carnivore, insectivore, proboscidea, perissodactyla, artiodactyla, tubulidentata, pholidota, sirenia, cetacean, primates, rodentia, lagomorpha, etc.). Illustrative examples of a subject include, but are not limited to, animals, such as cattle, pigs, horses, chickens, cats, dogs, and the like. More preferably, primates (e.g., chimpanzee, Japanese monkey, human, etc.) are used. Most preferably, a human is used. This is because there is limitation to implantation therapies.

When the present invention is used as a pharmaceutical agent, it may further comprise a pharmaceutically acceptable carrier or the like. A pharmaceutically acceptable carrier contained in a medicament of the present invention includes any material known in the art.

Examples of such a pharmaceutically acceptable carrier include, but are not limited to, antioxidants, preservatives, colorants, flavoring agents, diluents, emulsifiers, suspending agents, solvents, fillers, bulking agents, buffers, delivery vehicles, agricultural or pharmaceutical adjuvants, and the like.

The amount of a pharmaceutical agent (e.g., a synthetic tissue, a pharmaceutical compound used in conjunction therewith, etc.) used in the treatment method of the present invention can be easily determined by those skilled in the art with reference to the purpose of use, a target disease (type, severity, and the like), the patient's age, weight, sex, and case history, the form or type of the cell, and the like. The frequency of the treatment method of the present invention applied to a subject (or patient) is also determined by those skilled in the art with respect to the purpose of use, target disease (type, severity, and the like), the patient's age, weight, sex, and case history, the progression of the therapy, and the like. Examples of the frequency include once per day to several months (e.g., once per week to once per month). Preferably, administration is performed once per week to month with reference to the progression.

As used herein, the term "administer" in relation to a synthetic tissue, three-dimensional structure, or the like of the present invention or a pharmaceutical agent comprising it, means that they are administered singly or in combination with other therapeutic agents. A synthetic tissue of the present invention may be introduced into therapy sites (e.g., impaired heart, etc.) by the following methods, in the following forms, and in the following amounts. Examples of the introduction methods include, but are not limited to, direct attachment, suture after attachment, insertion, and the like. For example, a synthetic tissue and a three-dimensional structure of the present invention may be applied by the above-described methods to an impaired site of ischemic myocardial tissue caused by myocardial infarct, angina pectoris, or the like. Combinations may be administered either concomitantly (e.g., as an admixture), separately but simultaneously or concurrently; or sequentially. This includes presentations in which the combined agents are administered together as a therapeutic mixture, and also procedures in which the combined agents are administered separately but simultaneously (e.g., a synthetic tissue or the like is directly provided by operation, while other pharmaceutical agents are provided by intravenous injection). "Combination" administration further includes the separate administration of one of the compounds or agents given first, followed by the second.

As used herein, the term "reinforcement" means that the function of a targeted part of an organism is improved.

As used herein, the term "instructions" describe how to handle reagents, usage, a preparation method, a method of producing a synthetic tissue, a method of administering a medicament of the present invention, a method for diagnosis, or the like for persons who administer, or are administered, the medicament or the like or persons who diagnose or are diagnosed (e.g., physicians, patients, and the like). The instructions describe a statement indicating an appropriate method for administering a diagnostic, a medicament, or the like of the present invention. The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the Internet).

As used herein, the term "extracellular matrix synthesis promoting agent" or "ECM synthesis promoting agent" refers to an agent which promotes the production of an extracellular matrix of a cell. In the present invention, when an ECM synthesis promoting agent is added to a cell sheet, an environment which promotes self-contraction of cells after a cell sheet is detached from a culture container. The sheet is biologically organized in three-dimensional directions. Examples of such an agent representatively include agents capable of promoting the secretion of an extracellular matrix (e.g., TGF-β1, TGF-β3, etc.). Examples of an ECM synthesis promoting agent representatively include, but are not limited to, TGF-β1, TGF-β3, ascorbic acid, ascorbic acid 2-phosphate, or a derivative or salt thereof. Preferably, an ECM synthesis promoting agent may be preferably a component of an extracellular matrix of a part targeted by application and/or a component(s) capable of promoting the secretion of an extracellular matrix in an amount similar thereto. When an ECM synthesis promoting agent comprises a plurality of components, the components may be components of an extracellular matrix of a part targeted by application and/or components capable of promoting the secretion of an extracellular matrix in an amount similar thereto.

As used herein, the term "ascorbic acid or a derivative thereof" includes ascorbic acid and an analog thereto (e.g., ascorbic acid 2-phosphate, ascorbic acid 1-phosphate, etc.), and a salt thereof (e.g., sodium salt, magnesium salt, etc.). Ascorbic acid is preferably, but is not limited to, an L-isomer.

DESCRIPTION OF THE PREFERRED EMBODIMENTS

Hereinafter, preferable embodiments of the present invention will be described. The following embodiments are provided for a better understanding of the present invention and the scope of the present invention should not be limited to the following description. It will be clearly appreciated by those skilled in the art that variations and modifications can be made without departing from the scope of the present invention with reference to the specification.

In an aspect of the present invention, the synthetic tissue and complex of the present invention is free of injury caused by a protein degrading enzyme, such as, representatively, dispase, trypsin, or the like, during culture. Therefore, the synthetic tissue and complex, which is detached from the base material, can be recovered as a cell mass holding proteins between cells (e.g., an extracellular matrix) and having a certain level of strength. The synthetic tissue and complex also retain intact functions, such as an intracellular linking manner, alignment, and the like. When typical protein degrading enzymes (e.g., trypsin, etc.) are used to detach the three-dimensional structure or synthetic tissue, substantially no cell-to-cell link or cell-to-extracellular matrix link are retained, so that cells are individually separated. Among these protein degrading enzymes, dispase destroys basement membrane-like proteins between cells and base materials substantially completely. In this case, however, the resultant three-dimensional structure or synthetic tissue has weak strength. In contrast, the three-dimensional structure or synthetic tissue of the present invention can both substantially completely retain each of the desmosome structure and the basement membrane-like protein, resulting in the above-described various effects.

In the method of the present invention, the period of time required for culture may be determined depending on the application of the synthetic tissue or three-dimensional structure. In order to detach and recover the cultured synthetic tissue or three-dimensional structure from the support material, the cultured synthetic tissue or three-dimensional structure is detached directly, or with macromolecular membrane being attached thereto. Note that the synthetic tissue or three-dimensional structure may be detached in culture medium in which cells have been cultured, or alternatively, in other isotonic solutions. Such solutions may be selected depending on the purpose. When a monolayer cell sheet is prepared, examples of the macromolecular membrane, which is optionally attached to the cell sheet or three-dimensional structure, include, but are not limited to, hydrophilized polyvinylidene difluoride (PVDF), polypropylene, polyethylene, cellulose and derivatives thereof, chitin, chitosan, collagen, paper (e.g., Japan paper, etc.), urethane, net-like or stockinette-like macromolecular materials (e.g., spandex, etc.), and the like. When a net-like or stockinette-like macromolecular material is employed, the synthetic tissue or complex has a higher degree of freedom, so that the contraction/relaxation function thereof can be increased. A method for producing the synthetic tissue or three-dimensional structure comprising cells of the present invention is not particularly limited. For example, the synthetic tissue or three-dimensional structure of the present invention can be produced by utilizing the above-described cultured cell sheet attached to a macromolecular membrane.

In order to detach and recover the synthetic tissue or complex with a high yield from the cell culture support, the cell culture support is tapped or shaken, or the medium is stirred with a pipette. These procedures may be performed singly or in combination. In addition, the synthetic tissue or complex may be detached and recovered by deforming the base of the culture container or rinsing the container with isotonic solution or the like. By stretching the synthetic tissue or complex in a specific direction after being detached from the base material, the complex is provided with alignment. Stretching may be performed by using a tensile device (e.g., Tensilon, etc.), or simply forceps, or the like. A stretching method is not particularly limited. By providing alignment, it is possible to confer directionality to the motion of the cell sheet or complex itself. Therefore, for example, it is possible to allow the synthetic tissue or complex to move in accordance with the motion of a specific organ. The synthetic tissue or complex can be efficiently applied to organs.

The thus-obtained synthetic tissue or complex cannot be obtained by conventional techniques.

The synthetic tissue and the complex according to the present invention includes an abundance of adhesion molecules such as extracellular matrix which may include collagen (types I, III, etc.), vironectin, and fibronectin, and can be accepted by the surrounding tissue. Thus, implanted cells can be stably accepted by the implantation site. In conventional cell implantation, it was difficult for cells to be stably accepted by the implantation site not only in cells implantation without a scaffold, but also in cell implantation using an additional stabilizing treatment (e.g., sewing of a patch, scaffold, etc.). However, use of the present invention facilitates stabilization. When only cells are used, reinforcement by another tissue, fixing scaffold, or the like is necessary. According to the present invention, without requiring such means, cells which may have pluripotency included in the synthetic tissue or complex can be stably accepted by the implantation portion without an additional fixing means.

(Preparation of Synthetic Tissue Using an ECM Synthesis Promoting Agent)

In another aspect, the present invention provides a method for producing a synthetic tissue. The method for producing a synthetic tissue comprises the steps of: A) providing a cell; B) placing the cell in a container containing a cell culture medium including an ECM synthesis promoting agent, wherein the container has a base with an area sufficient to accommodate a desired size of the synthetic tissue; and C) culturing the cell in the container for a period of time sufficient to form the synthetic tissue having the desired size.

The above-described cell may be any cell. A method for providing a cell is well known in the art. For example, a tissue is extracted and cells are isolated from the tissue. Alternatively, cells are isolated from body fluid containing blood cells or the like. Alternatively, a cell line is prepared in an artificial culture. The present invention is not limited to this. Cells used herein may be any stem cells or differentiated cells, particularly including myoblasts, mesenchymal stem cells, adipocytes, synovial cells, bone marrow cells, and the like. Examples of mesenchymal stem cells used herein include adipose tissue-derived stem cells, bone marrow-derived stem cells, and the like.

The method for producing a synthetic tissue of the present invention employs a cell culture medium containing an ECM synthesis promoting agent. Examples of such an ECM synthesis promoting agent include, but are not limited to, ascorbic acid or a derivative thereof, ascorbic acid 1-phosphate, ascorbic acid 2-phosphate, L-ascorbic acid, and the like.

The cell culture medium used in the present invention may be any medium which allows a cell of interest to grow. Examples of such a medium include, but are not limited to, DMEM, MEM, F12, DME, RPMI1640, MCDB104, 199, MCDB153, L15, SkBM, Basal medium, and the like which are supplemented with glucose, FCS (fetal calf serum), antibiotics (penicillin, streptomycin, etc.) as appropriate.

The container used in the present invention may be any container typically used in the art which has a base with an area sufficient to accommodate a desired size of the synthetic tissue. Examples of such a container include, but are not limited to, petri dishes, flasks, mold containers, and the like, and preferably containers having a large area of the base (e.g., at least 1 $cm^2$). The material of the container may be any material and include, but are not limited to, glass, plastic (e.g., polystyrene, polycarbonate, etc.), silicone, and the like.

In a preferable embodiment, the method for producing a synthetic tissue according to the present invention further comprises detaching a produced synthetic tissue. As used herein, the term "detach" indicates that after a synthetic tissue of the present invention is formed in a container, the synthetic tissue is removed from the container. The detachment can be achieved by, for example, physical means (e.g., pipetting of medium, etc.), chemical means (addition of a substance), or the like. In the present invention, a synthetic tissue can be detached by providing a stimulus around the synthetic tissue by physical means or chemical means, but not by aggressive means (e.g., treatment with a protein degrading enzyme, etc.) to the synthetic tissue. Thus, the present invention provides ease of handling, which cannot be conventionally achieved, and the resulting synthetic tissue is substantially intact, resulting in a high-performance implant.

In a preferable embodiment, the present invention further comprises detaching cells which construct a synthetic tissue. In a more preferable embodiment, the detaching step includes applying a stimulus for contracting a synthetic tissue, including a physical stimulus (e.g., pipetting, etc.) Such a physical stimulus is not directly applied to the produced synthetic tissue. This is a preferable feature of the present invention. Since a physical stimulus is not directly applied to a synthetic tissue, it is possible to suppress damage to the synthetic tissue. Alternatively, the detaching step includes chemical means, such as adding an actin regulatory agent. Such an actin regulatory agent includes a chemical substance selected from the group consisting of actin depolymerizing agents and actin polymerizing agents. Examples of actin depolymerizing agents include, but are not limited to, ADF (actin depolymerizing factor), destrin, depactin, actophorin, cytochalasin, NGF (nerve growth factor), and the like. Examples of actin polymerizing agents include, but are not limited to, LPA (lysophosphatidic acid), insulin, PDGFm, chemokine, TGF b, and the like.

Though not wishing to be bound by any theory, these actin regulatory agents may cause actomyocin-based cytoskeleton to contract or extend, thereby regulating contraction and extension of a cell itself. As a result, a synthetic tissue itself may be promoted to or inhibited from being detached from the base of a container.

In another embodiment, the synthetic tissue and complex of the present invention are characterized in that they are produced from cells which are cultured in monolayer culture. Despite monolayer culture, synthetic tissues having various thicknesses can be constructed. This is an unexpected effect. Conventionally, for example, a thick tissue cannot be constructed without using a multilayer structure when a temperature responsive sheet or the like is used. The present invention is the first to achieve a method for constructing a three-dimensional structure, which does not require a scaffold and can construct the contractile organization including ten or more layers. A typical cell implantation method which does not employ a scaffold is a cell sheet engineering technique utilizing a temperature sensitive culture dish disclosed by Kushida A., Yamato M., Konno C., Kikuchi A., Sakurai Y., Okano T., J. Biomed. Mater. Res., 45:355-362, 1999. The technique has won international recognition as an original technique. However, this cell sheet technique has a problem in that a single sheet is weak in many cases, and requires modification such as layering sheets for obtaining the strength resistant to an surgical operation such as implantation.

A cell/matrix complex developed by the present invention does not require a temperature sensitive culture dish unlike the cell sheet technique. The cell/matrix complex is easy to form into a contractile three-dimensional tissue. There is no technique in the world other than the present invention, which can produce a contractile three-dimensional complex having 10 or more layers without using so-called feeder cells, such as rodent stroma cells, after approximately three weeks. By adjusting conditions for matrix production of the synovial cell, it is possible to produce a complex having a strength which allows surgical manipulation, such as holding or transferring the complex, without a special instrument. Therefore, the present invention is an original, epoch-making technique in the world for reliably and safely perform cell implantation.

In a preferable embodiment, the ECM synthesis promoting agent used in the method for producing a synthetic tissue of the present invention includes ascorbic acid 2-phosphate (Hata R., Senoo H., J. Cell Physiol., 1989, 138(1):8-16). In the present invention, by adding a certain amount or more of ascorbic acid 2-phosphate, it is possible to promote production of an extracellular matrix, so that the resultant synthetic tissue or complex is made strong to become easy to be detached. Thereafter, self contraction is elicited by applying a stimulus for detachment. Hata et al. do not report that, after adding such an ascorbic acid and culturing, a tissue becomes strong and obtains a property to be easy to be detached. Though not wishing to be bound by any theory, a significant difference is that Hata et al. used a significantly different cell density. Hata et al. does not suggest an effect of making a tissue rigid. Such an effect that the tissue is made rigid, an effect of contraction, and an effect that the tissue becomes easy to be detached are first found in the present invention. The synthetic tissue according to the present invention is recognized to be totally different from the synthetic tissue which has been fabricated conventionally at least on the point that it is produced through the process of making rigid, contraction, and detachment.

Contraction when the culture is detached and promotion in constructing a three-dimensional structure, a contractile three-dimensional tissue, or the like are suprising effects. Such effects have not been reported conventionally.

In a preferable embodiment, ascorbic acid 2-phosphate used in the present invention typically has a concentration of at least 0.01 mM, preferably at least 0.05 mM, more preferably at least 0.1 mM, even more preferably at least 0.2 mM, still more preferably at least 0.5 mM, and still even more preferably 1.0 mM. Herein, any concentration of 0.1 mM or higher may be employed. However, there may be an aspect in which a concentration of 10 mM or lower is desired.

In a certain preferable embodiment, the ECM synthesis promoting agent of the present invention includes ascorbic acid 2-phosphate or a salt thereof, and L-ascorbic acid or a salt thereof.

In a preferable embodiment, after the culturing step, the synthetic tissue production method of the present invention further comprises, detaching the synthetic tissue and allowing the synthetic tissue to perform self contraction. The detachment can be accelerated by applying a physical stimulus (e.g., application of shear stress, pipetting, deformation of the container, etc.). Self-contraction naturally takes place when a stimulus is applied after the detachment. When a chemical stimulus is applied, self-contraction and detachment occurs simultaneously. By self-contraction, biological integration is accelerated particularly in the third dimension (the direction perpendicular to the two-dimensional directions in the case of tissue on a sheet). Therefore, a synthetic tissue of the present invention may have a three-dimensional structure.

In a synthetic tissue production method of the present invention, the sufficient time preferably means at least 3 days, though it varies depending on the application of a synthetic tissue of interest. An exemplary period of time is 3 to 7 days.

In another embodiment, the synthetic tissue production method of the present invention may further comprise causing a synthetic tissue to differentitate. By differentiation, the synthetic tissue can have a form closer to that of a desired tissue. An example of such differentiation is, but is not limited to, chondrogenesis and osteogenesis. In a preferable embodiment, osteogenesis may be performed in medium containing dexamethasone, β-glycerophosphate, and ascorbic acid 2-phosphate. More preferably, bone morphogenetic proteins (BMPs) are added. This is because such BMP-2, BMP-4, and BMP-7 proteins promote osteogenesis.

In another embodiment, a method of producing the synthetic tissue of the present invention is a process of differentiating a synthetic tissue. A form of differentiation includes performing a differentiation of cartilage. In the preferable embodiment, chondrogenesis is performed in a medium including pyruvic acid, dexamethasone, ascorbic acid 2-phosphate, insulin, transferrin, and selenious acid. More preferably, bone morphogenetic proteins (such as BMP-2, BMP-4, BMP-7), transforming growth factors (such as TGF-β1, TGF-β3) are added. This is because such BMPs promote chondrogenesis.

An important point in the present invention is that it is possible to fabricate a tissue having a pluripotency into various differentiated cells such as bone, cartilage, and the like. Conventionally, differentiation into a cartilage tissue is difficult in other synthetic tissues which are scaffold-free. If a certain size is required, conventionally, it was necessary to coculture with a scaffold, construct a three-dimensional structure, and add a chondrogenesis medium. Conventionally, scaffold-free differentiation into cartilage was difficult. The present invention is the first to enable differentiation into cartilage in a synthetic tissue. This is not an effect which has been obtained conventionally, and is a characteristic effect of the present invention. In a treatment which aims to regenerate a tissue, a method for performing a treatment efficiently and safely by using a tissue of sufficient size without a scaffold was difficult. The present invention achieves a significant effect on this point. Particularly, the present invention is significant on the point that it becomes possible to easily manipulate differentiated cells such as cartilage, which has been impossible conventionally. Conventionally, for example, cells can be collected to a pellete shape and the aggregation of cells can be differentiated to obtain a tissue of about 2 mm³. For obtaining a tissue larger than this size, it was necessary to use a scaffold.

The differentiation step in synthetic tissue production of the present invention may be performed before or after providing cells.

In the present invention, primary culture cells can be used. The present invention is not limited to this. Subcultured cells (e.g., three or more passages) can also be used. Preferably, when subculture cells are used, the cells are preferably of four passages or more, more preferably of 5 passages or more, and even more preferably of 6 passages or more. The upper limit of cell density is increased with an increase in the number of passages within a certain range. This is because a denser synthetic tissue can be produced. The present invention is not limited to this. It seems that a certain range of passages (e.g., 3 to 8 passages) are preferable.

In the present invention, the cells are preferably provided at a cell density of $5.0 \times 10^4/cm^2$ or more. The present invention is not limited to this. This is because a higher cell density can provide a synthetic tissue having a greater strength. It will be understood that the lower limit of the cell density may be lower than the above-described density. It will also be understood that those skilled in the art can define the lower limit based on the present specification.

In one embodiment of the present invention, for example, a myoblast, a synovial cell, an adipocyte, and a mesenchymal stem sell (e.g., derived from adipose tissue or bone marrow)

can be used. The present invention is not limited to this. These cells can be applied to, for example, a heart, a bone, a cartilage, a tendon, a ligament, a joint, a meniscus, and the like.

(Synthetic Tissue and Complex)

In another aspect, the present invention provides a functional synthetic tissue or complex. The functional synthetic tissue of the present invention is herein an implantable synthetic tissue. Attempts have been heretofore made to produce synthetic tissues by cell culture. However, there were no synthetic tissues suitable for implantation in terms of size, strength, physical injuries when it is detached from a culture container, or the like. The present invention provides a tissue culture method in which cells are cultured in the presence of an ECM synthesis promoting agent as described above, so that there is no problem in terms of size, strength, and the like and there is no difficulty in detaching tissues. An implantable synthetic tissue is provided only after such a tissue culture method is achieved.

Another aspect of the present invention provides cells, and a complex including factors derived from the cells. Herein, it is recognized that, preferably, the complex substantially comprises cells, and the factors derived from the cells. Herein, the complex of the present invention is provided for reinforcing, repairing, or regenerating a part of an organism.

As used herein, the term "complex" means that cells and other components are integrated into a complex by some kind of interactivity. Therefore, the complex of the present invention often has an appearance like a synthetic tissue, and it is recognized that the meaning of the term "complex" overlaps with what is referred to by a synthetic tissue.

The present invention provides a scaffold-free synthetic tissue or complex. A therapeutic method and a therapeutic agent for providing an excellent condition after implantation can be obtained by providing such a scaffold-free synthetic tissue.

The scaffold-free synthetic tissue of the present invention solves a long outstanding problem with biological formulations, which is attributed to contamination of the scaffold itself. Despite the absence of a scaffold, the therapeutic effect is comparable with, or more satisfactory than, conventional techniques.

In addition, when a scaffold is used, the alignment of implanted cells in the scaffold, the cell-to-cell adhesion, the in vivo alteration of the scaffold itself (eliciting inflammation), the acceptance of the scaffold by the recipient tissue, and the like become problematic. These problems can be solved by the present invention.

The synthetic tissue and the complex of the present invention are also self-organized, and have biological integration inside thereof. Also in this point, the present invention is distinguished from conventional cell therapies.

The synthetic tissue and the complex of the present invention are easily used to form a three-dimensional structure, and is thus easy to be designed into a desired form. The versatility of the synthetic tissue and the complex of the present invention should be noted.

The synthetic tissue and the complex of the present invention have biological integration with recipient tissues, such as surrounding tissues, cells, and the like. Therefore, the post-operational acceptance is satisfactory, and cells are reliably supplied to a local site, for example. An effect of the present invention is that the satisfactory biological integration capability allows the formation of a tissue complex with another synthetic tissue or the like, resulting in a complicated therapy.

Another effect of the present invention is that differentiation can be induced after the synthetic tissue or the complex is provided. Alternatively, differentiation is induced before providing a synthetic tissue and/or a complex, and thereafter, the synthetic tissue and/or the complex are formed.

Another effect of the present invention is that the cell implantation of the present invention provides a satisfactory replacement ability and a comprehensive supply of cells for covering an implanted site, compared to conventional cell-only implantation and sheet implantation.

The present invention provides an implantable synthetic tissue. The above-described features and effects of the present invention become it possible to treat a site which cannot be considered as an implantation site for conventional synthetic products. The present invention makes it possible to provide a synthetic tissue or a three-dimensional structure using not only a heart muscle but also cells derived from other parts. The synthetic tissue of the present invention has biological integration and actually works in implantation therapies. The synthetic tissue is first provided by the present invention, but is not provided by conventional techniques.

In addition, the present invention provides medical treatment which provides a therapeutic effect by filling, replacing, and/or covering an affected portion.

In addition, when the synthetic tissue of the present invention is used in combination with another synthetic tissue (e.g., an artificial bone made of hydroxyapatite, a microfibrous collagen medical device, etc.), the synthetic tissue of the present invention is biologically integrated with the other synthetic tissue, so that the acceptance of the synthetic tissue can be improved to an extent which is not conventionally expected.

An extracellular matrix or a cell adhesion molecule, such as fibronectin, vitronectin, or the like, is distributed throughout the synthetic tissue of the present invention. In the cell sheet engineering, a cell adhesion molecule is localized on a surface of culture cells which is attached to a culture dish. In the sheet of the cell sheet engineering, cells are major components of the sheet. The sheet is nearly a mass of cells, on the bottom surface of which an adhesion molecule (glue) is added. The synthetic tissue of the present invention is a real "tissue" such that an extracellular matrix wraps cells. Thus, the present invention is significantly distinguished from conventional techniques.

A cell implanting method without a scaffold has been reported by Kushida A., Yamato M., Konno C., Kikuchi A., Sakurai Y., Okano T., J. Biomed. Mater. Res., 45:355-362, 1999, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be assembled, for example. Such a problem is solved by the present invention.

A cell/matrix complex developed by the present invention does not require a temperature sensitive culture dish unlike the cell sheet technique. The cell/matrix complex is easily formed into a contractile three-dimensional tissue. There is no technique in the world other than the present invention, which can produce a contractile three-dimensional complex having 10 or more layers without using so-called feeder cells, such as rodent stroma cells, after approximately three weeks. By adjusting conditions for matrix production of the synovial cell, it is possible to produce a complex having a strength which allows surgical manipulation, such as holding or transferring the complex, without a special instrument. Therefore, the present invention is an original, epoch-making technique in the world for reliably and safely performing cell implantation.

In a preferable embodiment, the synthetic tissue of the present invention has a biological integration capability to the surroundings. As used herein the term "surroundings" typically means surroundings to be implanted, and examples thereof include tissues, cells and the like. The biological integration capability with surrounding tissues, cells, and the like can be confirmed by, for example, photomicrograph, physical test, staining of a biological marker, or the like. Conventional synthetic tissues have a low affinity for adjacent tissues in which they are implanted. It was not even assumed that conventional synthetic tissues have the biological integration capability. Conventional synthetic tissues depend on a regeneration capability of an organism, and serves as a temporary solution until autologous cells gather and regenerate. These conventional synthetic tissues are not intended to for a permanent use. Therefore, the synthetic tissue of the present invention should be contemplated as an implantation treatment in the true sense. The biological integration capability referred to by in the present invention preferably includes an adhesion capability to surrounding cells. Such an adhesion capability can be measured by an in vitro culturing assay (see FIG. 23) with a tissue section (e.g., a cartilage section).

As used herein, the term "disease" to be treated by the present invention refers to any disease accompanying degeneration, necrosis, injury or the like, and examples thereof including, osteoarthritis, osteochondral injury, intractable fracture, osteonecrosis, cartilage injury, meniscus injury, ligament injury, tendon injury, cartilage degeneration, meniscus degeneration, intervertebral disk denaturation, ligament degeneration, or tendon degeneration, or any heart diseases having an injured tissue. Examples of such heart diseases include heart failure, intractable heart failure, myocardial infarct, cardiomyopathy, dilated cardiomyopathy, hypertrophic cardiomyopathy, dilated phase hypertrophic cardiomyopathy, and the like. The combined therapy of the present invention may be applied to a regeneration of an injury in an organ other than a heart, as long as regeneration of a tissue injury is the goal. In a specific embodiment, a disease to be treated by the method of the present invention is intractable heart failure.

As used herein, the term "prophylaxis" or "prevention" in relation to a certain disease or disorder refers to a treatment which keeps such a condition from happening before the condition is caused, or causes the condition to occur at a reduced level or to be delayed.

As used herein, the term "therapy" in relation to a certain disease or disorder means that when such a condition occurs, such a disease or disorder is prevented from deteriorating, preferably is retained as it is, more preferably is diminished, and even more preferably extinguished. As used herein, the term "radical therapy" refers to a therapy which eradicates the root or cause of a pathological process. Therefore, when a radical therapy is made for a disease, there in principle is no recurrence of the disease.

As used herein, the term "prognosis" is also referred to as "prognostic treatment". The term "prognosis" in relation to a certain disease or disorder refers to a diagnosis or treatment of such a condition after a therapy.

In a preferable embodiment, the synthetic tissue or complex of the present invention has a three-dimensional, biological integration. As described in other portions of the specification, examples of biological integration include, but are not limited to, physical integration or connection via extracellular matrices, electrical integration, and the like. Particularly, in a preferable embodiment including the cells, it is important that extracellular matrix in a tissue is biologically organized. Such a synthetic tissue which is biologically organized has not been provided. Thus, the synthetic tissue of this embodiment according to the present invention is new also in view of the structure. Further, the preferable embodiment having a biological integration capability with the surroundings provides a synthetic tissue which has not exist conventionally on the point that the synthetic tissue can form a part of an organism after implantation. The present invention can provide an synthetic tissue which does not include any cell, even a cell which has been frozen once and died. The tissue is still unique on the point that it has an affinity with the surrounding even in such a case.

In one embodiment, the synthetic tissue of the present invention is different from conventional synthetic tissues in that the former comprises a cell. Particularly, a high density that the density of $5 \times 10^6/cm^2$ at maximum can be included is important. The present invention is important on the point that it is suitable for implanting cells rather than implanting the tissue.

Preferably, a synthetic tissue of the present invention substantially comprise cells or a material derived from the cells. Since the synthetic tissue is composed substantially of only cells and a cell-derived material (e.g., extracellular matrix, etc.), the synthetic tissue can have an increased level of biocompatibility and affinity. As used herein, the terms "substantially comprise . . . ", "substantially made of . . . ", and "substantially contain . . . " mean that cells and substanced derived from the cells are included, and also any other substance may be included as long as it does not cause any harmful effect (herein, mainly, bad effect on implantation), and should understood as such herein. Such substances which do not cause any harmful effect are known to those skilled in the art or can be confirmed by conducting an easy test. Typically, such substances are, but not limited to, any additives permitted by the Health, Labor and Welfare Ministry, Food and Drug Administration (FDA) or the like, ingredients involved in cell culture, and the like. The cell-derived material representatively includes extracellular matrices. Particularly, the synthetic tissue or complex of the present invention preferably comprises a cell and an extracellular matrix at an appropriate ratio thereof. Such an appropriate ratio of a cell and an extracellular matrix is from about 1:3 to about 20:1. The strength of the tissue is adjusted by the ratio between a cell and an extracellular matrix. The ratio between a cell and an extracellular matrix is adjusted for use in accordance with application of cell implantation and physical environment at the implantation site. Preferable ratio varies depending on the treatment to be aimed. Such a variation is apparent to those skilled in the art and can be estimated by investigating the ratio of a cell in an organ which is a target and an extracellular matrix.

Preferably, a synthetic tissue substantially comprising cells and an extracellular matrix derived from the cells has not been known. Therefore, the present invention provides a totally new synthetic tissue.

Preferably, an extracellular matrix which forms the present invention includes, collagen I, collagen III, vitronectin, fibronectin, and the like. It is preferable that a variety of extracellular matrix includes all the listed ingredients, and that they are integrated and mixed. Alternatively, it is preferable that extracellular matrix is dispersed across the entire body. Such a distribution has a significant effect on the point that compatibility and affinity with the environment can be improved when implanted. The present invention is known to be characterized in that adhesion to intercellular matrix which promotes cell adhesion to a matrix, cell extension, and cell chemotaxis is also promoted by including collagen (Types I, III), vitronectin, fibronectin, and the like. However, a synthetic tissue which includes collagen (Types I, III), vitronectin, fibronectin, and the like has not been provided. It is not intended to be constrained by the theory, but, collagen (Types I, III), vitronectin, fibronectin, and the like are contemplated to have a function in exercising the biological integration capability with the surrounding. Therefore, in the preferable embodiment, it is advantageous that vitronectin are positioned to be dispersed on a surface of the synthetic tissue or complex of the present invention. It is considered that adhesion, affinity, and stability after implantation are significantly different.

It is preferable that the fibronectin is also positioned in the synthetic tissue or complex of the present invention. It is known that fibronectin has a function in cell adhesion, control of a shape of a cell, and adjustment in cell migration. A synthetic tissue in which fibronectin is expressed has not been provided. It is not intended to be constrained by the theory, fibronection is also contemplated to have a function in exercising the biological integration capability with the surrounding. Therefore, in the preferable embodiment, it is advantageous that fibronectin are also positioned to be dispersed on a surface of the synthetic tissue or complex of the present invention. It is considered that adhesion, affinity, and stability after implantation are significantly different.

In the preferred embodiment, it is understood that to position extracellular matrix used in the present invention on the synthetic tissue or complex can be readily achieved by the synthetic tissue production method of the present invention. It is also understood that the production method is not limited to this.

In more preferable embodiment, it is advantageous to position the extracellular matrix used in the present invention to be dispersed. Positioning extracellular matrix into such a dispersed state was impossible in conventional synthetic tissues. It is understood the present invention is the first to provide such a tissue.

In the preferred embodiment, regarding extracellular matrix positioned to be dispersed on the synthetic tissue or complex, when distribution densities in any two section of $cm^2$ are compared, the ratio is preferably within the range of about 1:3 to 3:1. Measurement of distribution densities can be performed by any method known in the field of the art, for example, immune staining or the like.

In the preferred embodiment, regarding extracellular matrix used in the present invention, when distribution densities in any two section of 1 $cm^2$ are compared, the ratio is preferably within the range of about 1:2 to 2:1, and further preferably, about 1.5:1 to 1.5:1. It is advantageous that extracellular matrix is uniformly dispersed. Preferably, extracellular matrix is dispersed substantially uniform, but it is not limited to this.

In one embodiment, extracellular matrix positioned in the present invention may include collagen I, collagen III, vitronectin, fibronectin or the like.

In an alternative embodiment, the synthetic tissue or complex of the present invention may employ heterologous cells, allogenic cells, isogenic cells or autologous cells. In the present invention, it is found that even allogenic cells, particularly, mesenchymal cells are used, no adverse reactions, such as immune rejection reactions, is generated. Thus, the present invention ends to the development of the treatment of ex vivo, and also a therapy which produces a synthetic tissue using cells of others and utilize the tissue without using an immuno rejection suppressor or the like.

In one preferred embodiment, the cells included in the synthetic tissue or complex of the present invention may be stem cells, differentiation cells, or they may include both. In the preferred embodiment, the cells included the three directional structure are mesenchymal cells. It is not intended to be restrained to the theory, the mesenchymal cells are preferably used because the mesenchymal cells are highly compatible with various organs such as heart, and may have capability to differentiate into various organs such as a heart.

Such mesenchymal cells may be mesenchymal stem cells, or may be mesenchymal differentiation cells.

Examples of the mesenchymal cells used in the present invention include, but not limited to, bone marrow cells, adipocyte, synovial cell, myoblast, skeletal muscle cells, and the like. Examples of mesenchymal cells as used herein include stem cells derived from an adipose tissue, stem cells derived from a bone marrow, and the like.

In the preferred embodiment, it is advantageous that the cells used in the present invention are cells derived from the subject to which the synthetic tissue or complex is applied. In such a case, cells as used herein also referred to as autologous cells. By using autologous cells, immune rejection reactions can be prevented or reduced.

Alternatively, in another embodiment, the cells as used herein may not be cells derived from a subject to which the synthetic tissue or complex is applied. In such a case, it is preferable that measures are taken to prevent immune rejection reactions.

The synthetic tissue or complex of the present invention may be provided as a drug. Alternatively, the synthetic tissue or complex may be prepared by a physician for therapy, or, a physician may first prepare the cells, and then the third party may culture the cells and prepare as a third-dimension structure for use in a surgery. In such a case, culturing cells is not necessarily performed by a physician, but can be performed by those skilled in the art of cell culture. Those skilled in the art can determine culturing conditions in accordance with a variety of the cells and an implantation site to be targeted after reading the disclosure herein.

In another embodiment, the synthetic tissue or complex of the present invention is preferably isolated. In this case, the term "isolate" means that the synthetic tissue is detached from a scaffold, a support, and a culture medium used in culture. If a synthetic tissue of the present invention is substantially free of materials, such as a scaffold and the like, it is possible to suppress adverse reactions after implantation, such as immune rejection reactions, inflammation reactions, and the like.

The base area of the synthetic tissue according to the present invention may be, for example, 1 $cm^2$ to 20 $cm^2$. However, the area is not limited to this range and may be smaller than 1 $cm^2$, or greater than 20 $cm^2$. It is understood that the essential feature of the present invention is that a tissue of any size (area, volume) can be produced, and it is not limited in the size.

In a preferable embodiment, the synthetic tissue of the present invention is thick. The term "thick" in relation to a synthetic tissue typically means that the synthetic tissue has a thickness which provides a strength sufficient to cover a site to which the synthetic tissue is implanted. Such a thickness is, for example, at least about 50 μm, more preferably at least about 100 μm, at least about 200 μm, at least about 300 μm, even more preferably at least about 400 μm, still more preferably at least about 500 μm, and still even more preferably about 1 mm. It is recognized that, in some cases, a tissue having a thickness of 3 mm or greater and a tissue having a thickness of 5 mm or greater can be produced. Alternatively, such a thickness may be, 1 mm or less. It is understood that an essential feature of the present invention is that a tissue or a complex having any thickness can produced, and the tissue or complex is not limited in the size.

The present invention provides a scaffold-free synthetic tissue or complex. By providing such a scaffold-free synthetic tissue, a therapeutic method and a therapeutic agent for providing an excellent condition after implantation can be obtained.

The scaffold-free synthetic tissue of the present invention solves a long outstanding problem with biological formulations, which is attributed to contamination of the scaffold itself. Despite the absence of a scaffold, the therapeutic effect is comparable with or more satisfactory than conventional techniques.

In addition, when a scaffold is used, the alignment of implanted cells in the scaffold, the cell-to-cell adhesion, the in vivo alteration of the scaffold itself (eliciting inflammation), the acceptance of the scaffold to recipient tissue, and the like become problematic. These problems can be solved by the present invention.

The synthetic tissue and the complex of the present invention are also self-organized, and have biological integration inside thereof. Also in this point, the present invention is distinguished from conventional cell therapies.

The synthetic tissue and the complex of the present invention are easy to form a three-dimensional structure, and is thus easy to be designed into a desired form. The versatility of the synthetic tissue and the complex of the present invention should be noted.

The synthetic tissue and the complex of the present invention have biological integration with recipient tissues, such as surrounding tissues, cells, and the like. Therefore, the post-operational acceptance is satisfactory, and cells are reliably supplied to a local site, for example. An effect of the present invention is that the satisfactory biological integration capability allows the formation of a tissue complex with another synthetic tissue or the like, resulting in a more complex therapy.

Another effect of the present invention is that differentiation can be induced after the synthetic tissue or the complex is provided. Alternatively, differentiation is induced before providing a synthetic tissue and/or a complex, and thereafter, the synthetic tissue and/or the complex are formed.

Another effect of the present invention is that the cell implantation of the present invention provides a satisfactory replacement and a comprehensive supply of cells for covering an implanted site, compared to conventional cell-only implantation and sheet implantation.

The present invention provides an implantable synthetic tissue having biological integration capability. The above-described features and effects of the present invention become it possible to treat a site which cannot be considered as an implantation site for conventional synthetic products. The present invention makes it possible to provide a synthetic tissue or a three-dimensional structure. The synthetic tissue of the present invention has biological integration and actually works in implantation therapies. The synthetic tissue is first provided by the present invention, but is not provided by conventional techniques.

In addition, the present invention provides medical treatment which provides a therapeutic effect by filling, replacing, and/or covering an affected portion.

In addition, when the synthetic tissue of the present invention is used in combination with another synthetic tissue (e.g., an artificial bone made of hydroxyapatite, a microfibrous collagen medical device, etc.), the synthetic tissue of the present invention is biologically integrated with the other synthetic tissue, so that the acceptance of the synthetic tissue can be improved to an extent which is not conventionally expected.

An extracellular matrix or a cell adhesion molecule, such as fibronectin, vitronectin, or the like, is distributed throughout the synthetic tissue of the present invention. In cell sheet engineering, a cell adhesion molecule is localized on a surface of culture cells which is attached to a culture dish. In the sheet of the cell sheet engineering, the cells are major components of the sheet. The sheet is nearly a mass of cells, on the bottom surface of which an adhesion molecule (glue) is added. On the other hand, the synthetic tissue of the present invention is a real "tissue" such that an extracellular matrix covers cells. Thus, the present invention is significantly distinguished from conventional techniques.

A cell implanting method without a scaffold has been reported by Kushida A., Yamato M., Konno C., Kikuchi A., Sakurai Y., Okano T., J. Biomed. Mater. Res., 45:355-362, 1999, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be assembled, for example. Such a problem is solved by the present invention.

A cell/matrix complex developed by the present invention does not require a temperature sensitive culture dish unlike the cell sheet technique. The cell/matrix complex is easy to form into a contractile three-dimensional tissue. There is no technique in the world other than the present invention, which can produce a contractile three-dimensional complex having 10 or more layers without using so-called feeder cells, such as rodent stroma cells, at about three weeks. By adjusting conditions for matrix production of the cell, it is possible to produce a complex having a strength which allows surgical manipulation, such as holding or transferring the complex, without a special instrument. Therefore, the present invention is an original, epoch-making technique in the world for reliably and safely performing cell implantation.

In another embodiment, the synthetic tissue or complex of the present invention is flexible. Due to the flexibility, the synthetic tissue is particularly suitable for reinforcement of motile organs. Examples of motile organs include, but are not limited to, hearts, blood vessels, muscles, and the like.

In another embodiment, the synthetic tissue or complex of the present invention has dilation/contraction ability. Due to the dilation/contraction ability, the synthetic tissue is suitable for organs which expand and contract, including, for example, hearts, muscles, and the like. The dilation/contraction ability cannot be achieved by cell sheet or the like prepared by conventional methods. Preferably, a synthetic tissue of the present invention has a sufficient strength to withstand the pulsation motion of a heart. The strength sufficient to withstand pulsation motion is, but is not limited to, at least about 50% of the strength of naturally-occurring myocardium, preferably at least about 75%, and more preferably at least about 100%.

In a preferable embodiment, the synthetic tissue or complex of the present invention has biological integration in all three dimensions. There are some synthetic tissues prepared by conventional methods, which have biological integration in two dimensions to some degree. However, no tissue having biological integration in all three dimensions can be prepared by conventional methods. Therefore, since the synthetic tissue of the present invention has biological integration in all three dimensions, the synthetic tissue is substantially implantable in any application.

Examples of biological integration which is an indicator of a synthetic tissue or complex of the present invention, include, but are not limited to, interconnection of extracellular matrices, electrical integration, the presence of intracellular signal transduction, and the like. The interaction of extracellular matrices can be observed with a microscope by staining intracellular adhesion as appropriate. Electrical integration can be observed by measuring electric potential.

In a preferable embodiment, the synthetic tissue of the present invention has a sufficient tissue strength for clinical applications. The sufficient tissue strength for clinical applications varies depending on a site to which the synthetic tissue is applied. Such a strength can be determined by those skilled in the art with reference to the disclosure of the specification and techniques well known in the art. The tensile strength of the synthetic tissue of the present invention may be low. The tensile strength becomes higher when the matrix concentration is increased, and becomes lower when the cell ratio is increased. The present invention is characterized in that the strength can be adjusted as necessary. The present invention is also characterized in that the strength can approximate to be high or low relative to that of a tissue to be implanted. Therefore, it is recognized that the goal can be set to comply with any site.

In another embodiment, it is preferable that a strength of the synthetic tissue or complex is sufficient for having a self-supporting ability. Conventional synthetic tissues do not have a self-supporting ability after production. Therefore, when conventional synthetic tissues are transferred, at least a part of them are injured. However, when the technique of the present invention is used, the synthetic tissue having the self-supporting ability is provided. This means that the present invention provides the synthetic tissue which cannot be provided by conventional techniques. Preferable self-supporting ability is such that, when a tissue is picked up with a tweezers having tips of 0.5 to 3 mm (preferably, tips of 1 to 2 mm, and more preferably, tips of 1 mm), the tissue is not substantially destroyed. Herein, whether the tissue is not substantially destroyed can be confirmed with eyes, but can be confirmed by performing, for example, a water leakage test after the tissue is picked up in the above-described conditions and confirming that water does not leak. Alternatively, the self-supporting ability as described above can also be confirmed by not being destroyed when picked up by fingers, instead of tweezers.

In a particular embodiment of the present invention, the above-described clinical application is intended to a bone, a joint, a cartilage, a meniscus, a tendon, a ligament, a kidney, a liver, a synovial membrane, a heart, and the like. The origin of cells contained in the synthetic tissue of the present invention is not affected by clinical applications.

Also, when a synthetic tissue of the present invention is applied to a cartilage, the attachment ability of the synthetic tissue can be tested by determining whether or not the synthetic tissue remains attached without an additional fixation procedure when the synthetic tissue is implanted into an injured portion of the intra-articular tissue (e.g., 2, 3 minutes after).

In another aspect, the present invention provides a cell culture composition for producing synthetic tissue from a cell. The cell culture composition contains an ingredient (e.g., commercially available medium, etc.) for maintaining or growing the cell, and an ECM synthesis promoting agent. The ECM synthesis promoting agent has been described in detail in the above description of the synthetic tissue production method. Therefore, the ECM synthesis promoting agent includes ascorbic acid or a derivative thereof (e.g., TGF-β1, TGF-β3, ascorbic acid 1-phosphate or a salt thereof, ascorbic acid 2-phosphate or a salt thereof, L-ascorbic acid or a salt thereof, etc.). The culture composition of the present invention contains ascorbic acid 2-phosphate or a salt thereof at a concentration of at least 0.1 mM. Alternatively, in the case of a condensed culture composition, the condensed culture composition contains ascorbic acid 2-phosphate or a salt thereof at a concentration which becomes at least 0.1 mM after preparation. Ascorbic acid 2-phosphate or a salt thereof contained in the culture composition of the present invention is present at a concentration of at least 0.1 mM. When the culture composition of the present invention is condensed, ascorbic acid 2-phosphate or a salt thereof contained therein is present at a concentration of at least 0.1 mM after formulation. It seems that 0.1 mM or more ascorbic acids have substantially a constant effect. Thus, 0.1 mM can be said to be sufficient. For TGF-β1 and TGF-β3, 1 ng/ml or more, representatively 10 ng/ml, may be sufficient.

Alternatively, the present invention may provide a composition for producing a synthetic tissue, comprising such an ECM synthesis promoting agent.

In another embodiment of the present invention, an ECM synthesis promoting agent used in the synthetic tissue production method of the present invention includes ascorbic acid 2-phosphate (Hata R., Senoo H., J. Cell Physiol., 1989, 138 (1):8-16). In the present invention, by adding an at least predetermined amount of ascorbic acid 2-phosphate, the production of an extracellular matrix is promoted. As a result, the resultant synthetic tissue or complex is made rigid, and therefore, becomes easy to be detached. Thereafter, the tissue undergoes self-contraction in response to a stimulus of detachment. Hata et al. does not disclose that the culture in medium supplemented with ascorbic acid causes the tissue to be rigid and thus confers to the tissue a property of being easily detached. Though not wishing to be bound by any theory, a significant difference between the present invention and Hata et al. is present in cell density. Also, Hata et al. does not suggest the effect of facilitating detachment of cells from a container for culture. The present invention is the first to find the effect of tissue contraction on development of three-dimensional synthetic tissue from monolayer cultured cells. The synthetic tissue of the present invention can be absolutely distinguished from conventional synthetic tissues, since the synthetic tissue of the present invention is produced via the procedures of tissue detachment and subsequent tissue contraction.

In a preferable embodiment, ascorbic acid 2-phosphate used in the present invention is typically present at a concentration of at least 0.01 mM, preferably at least 0.05 mM, more preferably at least 0.1 mM, even more preferably at least 0.2 mM, and still more preferably at least 0.5 mM, and still even more preferably 1.0 mM.

In one embodiment of the present invention, the cell density is, but is not particularly limited to, $5 \times 10^4$ to $5 \times 10^6$ cells per 1 $cm^2$. These conditions may be, for example, applied to myoblast. In this case, preferably, the ECM synthesis promoting agent may be ascorbic acids and may be provided at a concentration of at least 0.1 mM. This is because a thick synthetic tissue can be produced. In this case, if the concentration is increased, a synthetic tissue having a dense extracellular matrix is produced. If the concentration is low, the amount of an extracellular matrix is decreased but the self-supporting ability is maintained.

(Synthetic Tissue for Replacement and Coverage)

In another aspect, the present invention provides a synthetic tissue or complex for reinforcement of a portion of an animal organism. The synthetic tissue or complex capable of such reinforcement is a technique achieved only after the synthetic tissue production method of the present invention is provided. Since the synthetic tissue or complex of the present invention has self-supporting ability, it can be used in applications which are not conventionally provided (e.g., filling (replacement) reinforcement, whole reinforcement, no-leakage reinforcement, coverage, etc.). The present invention has a significant effect such that the filling and replacement reinforcement (i.e., cell supply) was significantly improved. The present invention also allows differentiation induction, which enlarges the range of application of the present invention.

In a specific embodiment of the present invention, the above-described reinforcement may be achieved by disposing a synthetic tissue of the present invention to cover the above-described portion. It is not possible to use a synthetic tissue provided by conventional methods to perform treatment by covering the above-described portion (i.e., replacement and/or coverage application). Thus, the synthetic tissue of the present invention can provide applications which cannot be achieved by conventional techniques.

Therefore, in the above-described specific embodiment, the synthetic tissue or complex of the present invention is resistant to dilation/contraction of the above-described portion.

In a preferable embodiment, the synthetic tissue or complex of the present invention advantageously has biological integration.

In another preferable embodiment, the biological integration includes at least one of interconnection of extracellular matrices, electrical integration, and intracellular signal transduction.

In another preferable embodiment, the synthetic tissue or complex for reinforcement of the present invention is formed by culturing a cell in the presence of an ECM synthesis promoting agent.

In another embodiment, the synthetic tissue or complex for reinforcement of the present invention comprises a cell (autologous cell) derived from an animal to be treated (e.g., a human). More preferably, a synthetic tissue for reinforcement of the present invention comprises only a cell(s) (autologous cell) derived from an animal to be treated (e.g., a human) as a cell source.

Applications for the therapy utilizing the present invention include, for example: cartilage full thickness injury, cartilage partial injury; osteochondral injury; osteonecrosis; osteoarthritis; meniscus injury; ligament injury (chronic injury, degenerative tear, biological augmentation for reconstruction surgery, etc.); rotator cuff (particularly, chronic injury, degenerative tear, etc.); delayed union; nonunion; skeletal muscle repair/regeneration; cardiac muscle repair; (augmenting the repair of necrotic tissue by ischemic-heart disease) or the like.

(Therapy Using Replacement and Coverage)

In another aspect, the present invention provides a method for reinforcement of a portion of an animal organism. The method comprises the steps of: A) disposing a synthetic tissue or complex to replace or cover the portion; and B) holding the synthetic tissue or complex for a time sufficient to connect to the portion. Herein, to position a portion for replacement typically means to perform debridement or curettage of an affected portion as necessary, to position the synthetic tissue or complex of the present invention on the lesion, and to allow it to stand so as to promote replacement. An objective of such replacement is to fill cells. Techniques known in the art can be combined and used. The step of disposing the synthetic tissue to cover the portion can be carried out using a technique well known in the art. The sufficient time varies depending on a combination of the portion and the synthetic tissue, and can be easily determined as appropriate by those skilled in the art depending on the combination. Examples of such a time include, but are not limited to, 1 week, 2 weeks, 1 month, 2 months, 3 months, 6 months, 1 year, and the like. In the present invention, a synthetic tissue preferably comprises substantially only cell(s) and material (s) derived from the cell. Therefore, there is no particular material which needs to be extracted after operation. The lower limit of the sufficient time is not particularly important. In this case, it can be said that the longer the time, the more preferable the synthetic tissue. If the time is sufficiently extremely long, it can be said that reinforcement is substantially completed. Therefore, the time is not particularly limited. The synthetic tissue of the present invention is also characterized in that it is easily handled, is not destroyed during an actual treatment, and facilitates a surgery due to its self-supporting ability.

In another embodiment, in a reinforcement method of the present invention, the above-described portion preferably includes bag-shaped organs (e.g., hearts, livers, kidneys, etc.). In order to reinforce such a bag-shaped tissue, it is necessary to replace or cover the organ. A synthetic tissue resistant to applications for replacement or covering is first provided by the present invention. Therefore, the reinforcement method of the present invention is advantageous over conventional techniques.

Alternatively, the above-described portion may include a bone or cartilage. Examples of such portions include, but not limited to, meniscus, ligament, tendon, and the like. By the method of the present invention a disease, injury, or condition of a heart, bone, cartilage, ligament, tendon, or meniscus may be treated, prevented or reinforced.

Particularly, in the reinforcement method of the present invention, a synthetic tissue or complex of the present invention is resistant to dilation/contraction of the above-described portion. Examples of such dilation/contraction include, but are not limited to, the pulsation motion of a heart, the contraction of a muscle, and the like.

In another preferable embodiment, in the reinforcement method of the present invention, a synthetic tissue or complex of the present invention has biological integration (e.g., interconnection of extracellular matrices, electrical integration, intracellular signal transduction, etc.). The biological integration is preferably provided in all three dimensions.

In another preferable embodiment, the reinforcement method of the present invention further comprises culturing a cell in the presence of an ECM synthesis promoting agent to form a synthetic tissue or complex of the present invention. An implantation/regeneration technique using the method which comprises the step of culturing a cell in the presence of an ECM synthesis promoting agent cannot be provided by conventional techniques. The method provides a therapy for diseases (e.g., cartilage injury, intractable bone fracture, etc.), which cannot be achieved by conventional therapies.

In a preferable embodiment, in the reinforcement method of the present invention, the cell used in the synthetic tissue or complex of the present invention is derived from an animal to which the synthetic tissue is to be implanted (i.e., an autologous cell). By using an autologous cell, adverse side effects, such as immune rejection reactions or the like, can be avoided.

In another preferable embodiment, the portion is a heart.

Applications for the therapy utilizing the present invention include, for example: cartilage full thickness injury, cartilage partial injury; osteochondral injury; osteonecrosis; osteoarthritis; meniscus injury; ligament injury (chronic injury, degenerative tear, biological augmentation for reconstruction surgery, etc.); rotator cuff (particularly, chronic injury, degenerative tear, etc.); delayed union; nonunion; skeletal muscle repair/regeneration; cardiac muscle repair; (augmenting the repair of necrotic tissue by ischemic-heart disease) or the like.

For some organs, it is said that it is difficult to radically treat a specific disease, disorder, or condition thereof (e.g., refractory heart diseases). However, the present invention provides the above-described effect, thereby making possible a treatment which cannot be achieved by conventional techniques. It has been clarified that the present invention can be applied to radical therapy. Therefore, the present invention has usefulness which cannot be achieved by conventional medicaments.

Thus, the present invention provides a method for treating a portion of an organism of an animal, comprising: A) positioning the synthetic tissue or complex so as to cover the portion; and B) retaining the synthetic tissue for a time period which is sufficient for the condition of the portion of the organism to be improved. Such an improvement in the condition can be determined can be determined in accordance with the function of the portion to be treated. For example, when a heart should be treated, an improvement in the condition can be determined by checking a cardiac function (heartbeat, bloodstream, or the like). If a bone should be treated, an improvement in the condition can be determined by observing osteogensis by using roentgen, CT scan, or the like. In the case of a bone, an improvement in the condition can be determined by measuring its strength or by evaluating bone marrow and/or a bone substance by using MRI. If a cartilage or meniscus should be treated, a surface of a joint can be observed by an arthroscopy. Further, it is possible to determine an improvement in the condition by performing a biomechanical inspection under arthroscopy. It is also possible to determine an improvement in the condition by confirming a repairing condition by using MRI. Regarding ligament, it is possible to determine by confirming whether there is laxity by a joint stability inspection. Further, an improvement of the condition can be determined by confirming a continuousness of a tissue by an MRI. In the case of any tissue, it is possible to determine whether the condition is improved by performing a biopsy of the tissue and making a histological evaluation.

In a preferred embodiment the treatment treats, prevents, prognosis, or enhances a disease, injury, or condition of a heart, bone, cartilage, ligament, tendon, or meniscus. Preferably, the synthetic tissue or the complex has a self-supporting ability. For such a synthetic tissue, those skilled in the art can use a synthetic tissue of any form described above herein, and a variant thereof.

(Combined Therapy)

In another aspect, the present invention provides a regeneration therapy which uses a cytokine, such as BMP (e.g., BMP-2, BMP-4, BMP-7, etc.), TGF-$\beta$1, TGF-$\beta$3, HGF, FGF, IGF, or the like, in combination with a synthetic tissue.

Some cytokines used in the present invention are already commercially available (e.g., BMP (Yamanouchi Pharmaceutical), bFGF2 (Kaken Pharmaceutical), TGF-$\beta$1 (for research only, HGF-101 from Toyo Boseki, etc.). However, these cytokines can be prepared by various methods and can be used in the present invention if they are purified to an extent which allows them to be used as a medicament. A certain cytokine can be obtained as follows: primary cultured cells or an established cell line capable of producing the cytokine is cultured; and the cytokine is separated from the culture supernatant or the like, followed by purification. Alternatively, a gene encoding the cytokine is incorporated into an appropriate vector by a genetic engineering technique; the vector is inserted into an appropriate host to transform the host; a recombinant cytokine of interest can be obtained from the supernatant of the transformed host culture (e.g., Nature, 342, 440(1989); Japanese Laid-Open Publication No. 5-111383; Biochem-Biophys. Res. Commun., 163, 967 (1989), etc.). The above-described host cell is not particularly limited and can be various host cells conventionally used in genetic engineering techniques, including, for example, *Escherichia coli*, yeast, animal cells, and the like. The thus-obtained cytokine may have one or more amino acid substitutions, deletions and/or additions in the amino acid sequence as long as it has substantially the same action as that of the naturally-occurring cytokine. Examples of a method for introducing the cytokine into patients in the present invention include, but are not limited to, a Sendai virus (HVJ) liposome method with high safety and efficiency (Molecular Medicine, 30, 1440-1448(1993); Jikken Igaku (Experimental Medicine), 12, 1822-1826 (1994)), an electrical gene introduction method, a shotgun gene introduction method, a ultrasonic gene introduction method, and the like. In another preferable embodiment, the above-described cytokines can be administered in the form of proteins.

(Production Method of Synthetic Tissue Having Desired Thickness)

Another aspect of the present invention provides a method for producing a synthetic tissue or complex having a desired thickness. This method comprises: A) providing cells; B) positioning the cells in a container having the base area sufficient for accommodating the synthetic tissue or complex having the desired size, which contains an ECM synthesis promoting agent (e.g., ascorbic acids, TGF-$\beta$1, TGF-$\beta$3, etc.); C) culturing the cells in the container with a cell culture medium including the ECM synthesis promoting agent for a time sufficient for forming the synthetic tissue or complex having the desired size to convert the cells into a synthetic tissue; and D) adjusting the thickness of the synthetic tissue to obtain a desired thickness by a physical stimulation or a chemical stimulation. Herein, the steps of providing the cells, positioning the cells, stimulating and converting into the tissue or complex are described with respect to the production method for the synthetic tissue or complex of the present invention in detail., and it is understood that any embodiment can be employed.

Next, examples of the physical or chemical stimulation to be used may include, but not limited to, use pipetting, use of actin interacting substance. Pipetting may be preferable because operation is easy and no harmful substance is produced. Alternatively, examples of the chemical stimulation to be used may include actin depolymerizing factors and actin polymerizing factor. Examples of such an actin depolymerizing factor may include ADF (actin depolymerizing factor), destrin, depactin, actophorin, cytochalasin, NGF (nerve growth factor) and the like. Examples of the actin polymerizing factor include LPA (lysophosphatidic acid), insulin, PDGFa, PDGFb, chemokine, and TGFb. The polymerization or depolymerization of actin can be observed by checking the activity to actin. It is possible to test any substance whether it has such an activity. It is understood that a substance which is tested as such and identified can be used for achieving the desired thickness in production of the synthetic tissue of the present invention. For example, in the present invention, the adjustment of the desired thickness can be achieved by adjusting the ratio between the actin depolymerizing factor and actin polymerizing factor.

(Composite Tissue)

Another aspect of the present invention also provides a tissue complex including an implantable synthetic tissue and another synthetic tissue. Herein, another tissue may either be a synthetic tissue included within the scope of the present invention, or a synthetic tissue out of the scope (i.e., conventional tissues). Conventional tissues (e.g., an artificial bone, microfibrous collagen medical device, etc.) do not have a biological integrating ability or have a biological integrating ability which cannot stand the practical use. Thus, it was almost impossible to form such a tissue complex. It is understood that, according to the present invention, a cartilage can be combined to a bone for treatment. For the case of a cavity in a bone or the like, particularly, for the case of treatment of bone cartilage complex, by using a tissue complex of an artificial bone (e.g., hydroxyapatite construct such as NEO BONE, a microfibrous collagen medical device, etc.) and the synthetic tissue or complex of the present invention, it is possible to treat the bone by the artificial bone, and the cartilage on the bone by the synthetic tissue at the same time. It is understood that the synthetic tissue or complex of the present invention is combined to an artificial bone and used for treatment. Herein, the implantable synthetic tissue or complex of the present invention substantially comprises, for example, cells and substances derived from the cells, and more preferably, cells and extracellular matrix derived from the cells. The extracellular matrix as used herein is selected from the group consisting of collagen I, collagen III, vitronectin, and fibronectin.

As used herein, the term "tissue complex" refers to a tissue obtained by combining a synthetic tissue or complex of the present invention with another synthetic tissue (including a synthetic tissue or complex of the present invention). Such a tissue complex can be used for a treatment of a plurality of tissues. For example, such a tissue complex can be used for treatment of both cartilage and bone.

In the case there is a large defect of soft tissue (e.g., menisucus, etc.), the synthetic tissue of the present invention can be coupled to another synthetic tissue (microfibrous collagen medical device (e.g., CMI (Amgen, USA), Integran® (Nippon Zoki Pharmaceutical), hyaluronic acid gel, collagen gel, agarose gel, alginate gel, beads etc.) to promote biological integration between another synthetic tissue and an implantation cells.

Preferably, in the complex of the present invention, an implantable synthetic tissue and another synthetic tissue are biologically integrated. Such integration can be produced by culturing two tissues in contact. Such a biological integration is mediated by extracellular matrix.

Hereinafter, the present invention will be described by way of examples. Examples described below are provided only for illustrative purposes. Accordingly, the scope of the present invention is not limited except as by the appended claims.

EXAMPLES

In the examples below, animals were treated in accordance with rules defined by Osaka University (Japan) and were cared for in the spirit of animal protection.

Example 1

Synovial Cell

In this example, various synovial cells were used to produce a synthetic tissue as follows.

<Preparation of Cells>

Synovial cells were collected from a knee joint of a pig (LWD ternary hybrid, 2-3 months old upon removal of cells), followed by treatment with collagenase. The cells were cultured and subcultured in 10% FBS-DMEM medium (FBS was obtained from HyClone, DMEM was obtained from GIBCO). It has been reported that 10th passage synovial cells still have pluripotency. Although cells of 10 or less passages were used in this example, cells of more than 10 passages may be used depending on the application. Autotransplantation was performed for humans, where a sufficient number of cells were used and the cells were cultured for a short period of time so as to reduce the risk of infection or the like.

Considering these points, cells of various passages were used. Actually, primary culture cells, first passage cells, second passage cells, third passage cells, fourth passage cells, fifth passage cells, sixth passage cells, eighth passage cells, and tenth passage cells were used in experiments. These cells were used for synthetic tissues.

<Preparation of Synthetic Tissue>

Synovial cells ($4.0 \times 10^6$) were cultured in 2 ml of 10% FBS-DMEM medium in a 35-mm dish, a 60-mm dish, or 100-mm dish (BD Biosciences, culture dish and multiwell cell culture plate). In this case, ascorbic acid was added. The dishes, the ascorbic acid concentrations, and the cell concentration are described below.

Dishes: BD Biosciences, cell culture dishes and multiwell cell culture plates

Ascorbic acid 2-phosphate: 0 mM, 0.1 mM, 0.5 mM; 1 mM, 2 mM, and 5 mM

The number of cells: $5 \times 10^4$ cells/cm$^2$, $1 \times 10^5$ cells/cm$^2$, $2.5 \times 10^5$ cells/cm$^2$, $4.0 \times 10^5$ cells/cm$^2$, $5 \times 10^5$ cells/cm$^2$, $7.5 \times 10^5$ cells/cm$^2$, $1 \times 10^6$ cells/cm$^2$, $5 \times 10^6$ cells/cm$^2$, and $1 \times 10^7$ cells/cm$^2$ Medium was exchanged two times per week until the end of a predetermined culture period. At the end of the culture period, a cell sheet was detached from the dish by pipetting circumferentially around the dish using a 100-µl pipetteman. After detachment, the cell sheet was made as flat as possible by lightly shaking the dish. Thereafter, 1 ml of medium was added to completely suspend the cell sheet. The cell sheet was allowed to stand for two hours, resulting in the contraction of the cell sheet into a three-dimensional form. Thus, a synthetic tissue was obtained (FIG. 1).

<Hematoxylin-Eosin (HE) Staining>

The acceptance or vanishment of cells in a sheet was observed by HE staining. The procedure is described as follows. A sample is optionally deparaffinized (e.g., with pure ethanol), followed by washing with water. The sample is immersed in Omni's hematoxylin for 10 min. Thereafter, the sample is washed with running water, followed by color development with ammonia in water for 30 sec. Thereafter, the sample is washed with running water for 5 min and is stained with eosin hydrochloride solution for 2 min, followed by dehydration, clearing, and mounting.

Various Extracellular Matrix Staining
1. Make 5 µm thick sections from frozen block.
2. Sections are fixed in acetone at −20° C. for 5-10 mins.
   (Paraffin blocks should be deparaffinized and rehydrated).
3. Endogenous peroxide activity is blocked in 0.3% $H_2O_2$ in methanol for 20 mins at RT.
   (1 ml 30% $H_2O_2$+99 ml methanol)
4. Wash with PBS (3×5 mins).
5. Incubate with primary monoclonal antibody (A mouse or rabbit antibody against each extracellular matrix protein) in a moist chamber at 4° C. for overnight (1 µl antibody+200 µl PBS per slide).

6. Next day wash with PBS (3×5 mins).
7. Apply anti mouse and anti rabbit no. 1 Biotynalated link for 30 mins-1 hrs at RT.
(apply about 3 drops directly on slide).
8. Wash with PBS (3×5 mins).
9. Apply about 3 drops directly Streptavidin HRP no. 2 for LSAB. 10-15 mins.
10. Wash with PBS (3×5 mins).
11. Apply DAB (5 ml DAB+5 µl $H_2O_2$).
12. Observe under microscope for brownish colour.
13. Dip in water for 5 mins.
14. Apply HE for 30 sec-1 min.
15. Wash several times.
16. Ion exchange water wash 1 time.
17. 80% ethanol wash for 1 min.
18. 90% ethanol wash for 1 min.
19. 100% ethanol wash for 1 min (3 times).
20. Xylene wash for 1 min (3 times), Coverslip.
21. Examine color development.

Figure 2:
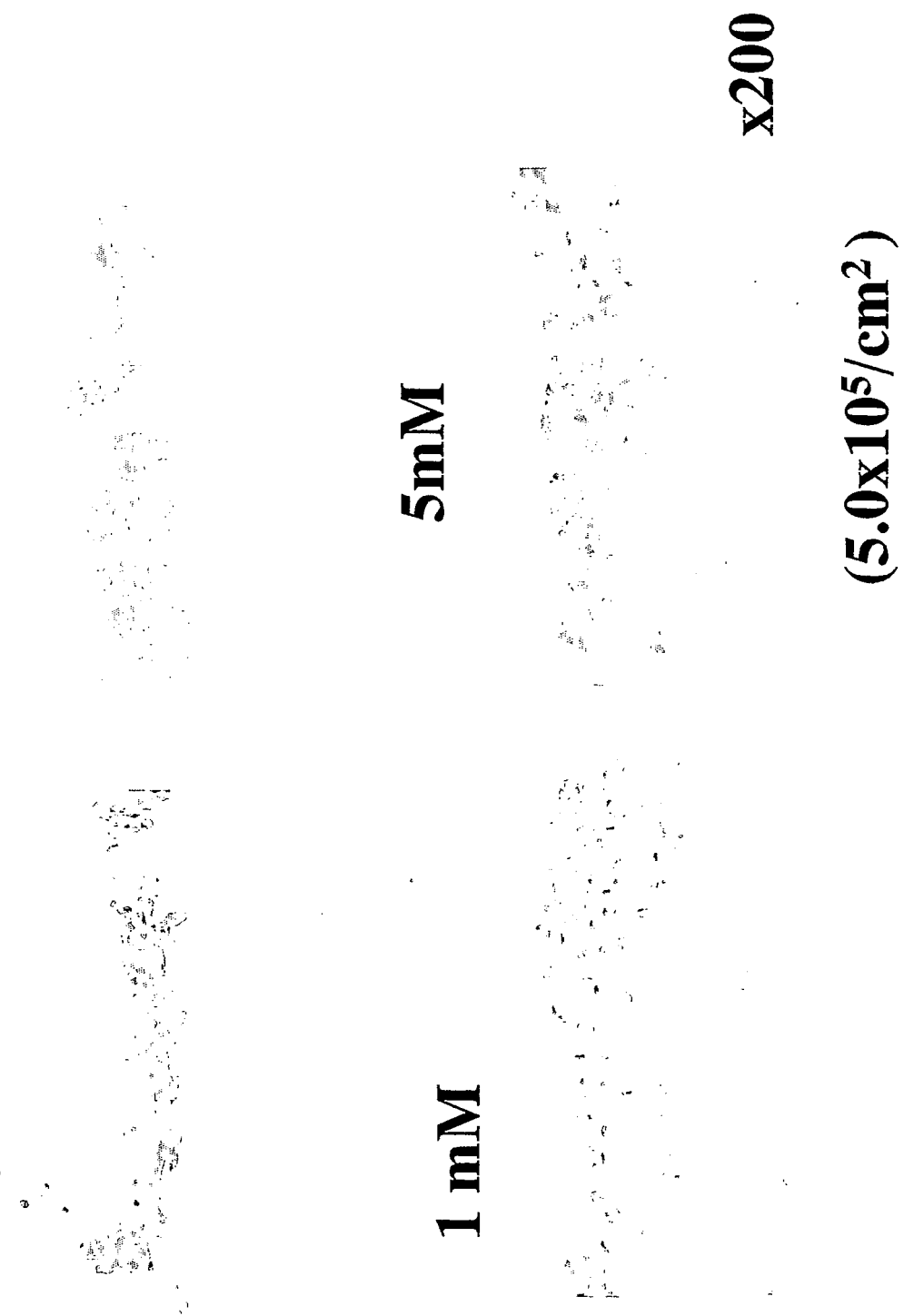
FIG. 2 shows high magnification histology of a synthetic tissue when ascorbic acid 2-phosphate has a concentration of 0 mM, 0.1 mM, 1 mM, and 5 mM. As can be seen, Eosin staining of the synthetic tissue is more intense when ascorbic acid 2-phosphate is added at a concentration of more than 0.1 mM.

An exemplary result is shown in FIG. 1. As shown in the right portion of FIG. 1, when ascorbic acid 2-phosphate was added as an ECM synthesis promoting agent, a contractile three-dimensional tissue of the cells was only slightly observed. On the other hand, by detaching the sheet-like cells from the base of the culture dish and allowing the cells to self organize, the cells were promoted to be layered and were accelerated into a three-dimensional structure, as shown in the left portion of FIG. 1. As shown in a left portion of FIG. 1, large tissue without a hole was also produced when synovial cells were used. This tissue was thick and its extracellular matrix was rich as shown in a right portion of FIG. 1. When ascorbic acid 2-phosphate was added at a concentration of 0.1 mM or more, the formation of an extracellular matrix was promoted (FIG. 2). FIG. 3 shows an enlarged view of a synthetic tissue on Day 3, 7, 14, and 21. As can be seen, after 3 days of culture, the tissue was already so rigid that it can be detached (FIG. 3). As the number of culture days is increased, the density of the extracellular matrix fluctuates and increases.

The tissue was detached from the base of the culture dish and self-contracted. The synthetic tissue was prepared in a sheet form. When the sheet was detached from the dish and was allowed to stand, the sheet self contracted into a three-dimensional structure. It is seen that a number of layers of cells exist in the tissue.

Next, various markers including extracellular matrix markers were stained.

FIG. 4 shows the result of staining extracellular matrix. It can be seen that various extracellular matrix components (collagen I, II, III, fibronectin, vitronectin, etc.) existed. Immunostaining was conducted, so that collagen I and III were strongly stained while collagen II staining was limited to a portion. By being strongly magnified, it can be confirmed that collagen was stained at a site slightly away from the nuclei, i.e., collagen was a part of the extracellular matrix. On the other hand, fibronectin and vitronectin, which are believed to be important cell adhesion molecules. By being strongly magnified, it can be confirmed that fibronectin and vitronectin were stained at a region close to nuclei unlike collagen, i.e., fibronectin and vitronectin existed around the cells.

These results demonstrated that cells of at least 3 to 8 passages are preferable for production of synthetic tissue.

Figure 6:
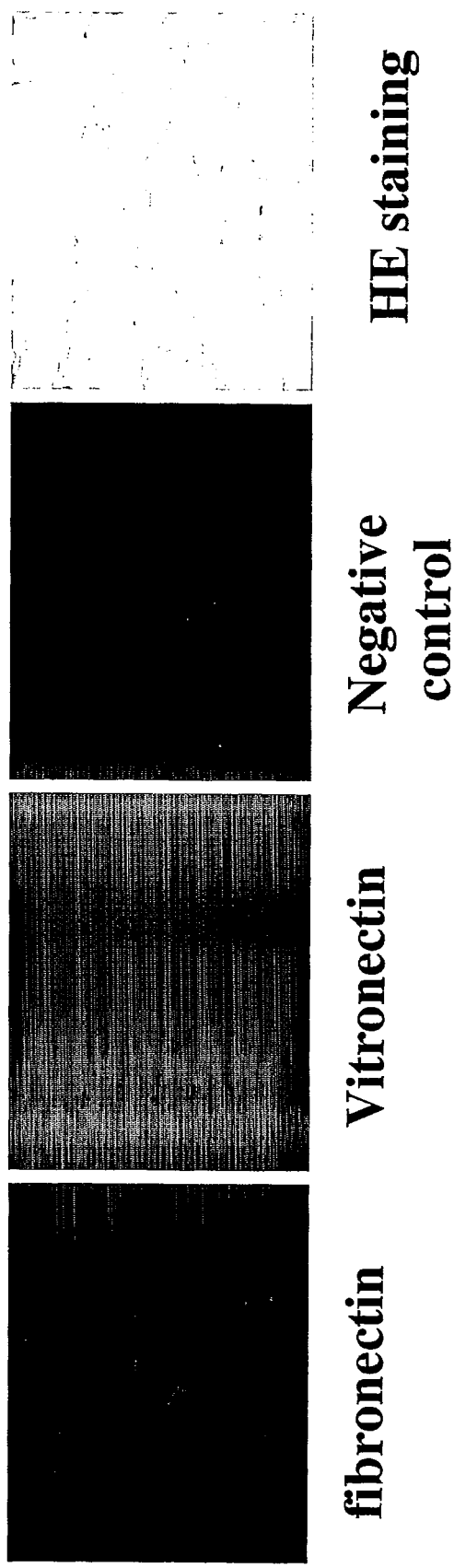
FIG. 6 shows exemplary histology of a commercially available stained collagen sponge as a control. From the left, staining of fibronectin, vitronectin, non-IgG-immune as a negative control and HE staining are shown.

For comparison, a normal tissue and a collagen sponge (CMI, Amgen, USA) were stained. FIG. 5 shows the normal tissue (normal synovial membrane tissue, tendon tissue, cartilage tissue, skin, and meniscus tissue). FIG. 6 shows the stained collagen sponge, which was the comparative example. From the left, fibronectin, vitronectin, negative control, and HE staining are indicated. As can be seen, the conventional synthetic tissue was not stained with fibronectin or vitronectin. Therefore, the synthetic tissue of the present invention is different from conventional synthetic tissues. Existing collagen scaffolds do not contain fibronectin and vitronectin (adhesion agents). In view of this, the originality of the synthetic tissue of the present invention is clearly understood. No stain in found in the extracellular matrix. When the synthetic tissue of this example was compared with normal tissue, the synthetic tissue has a lower extracellular matrix density and had a structure different from normal tissue.

Further, when the synthetic tissue of the present invention was contacted with a filter paper in order to remove moisture from the tissues, the filter is adhered to the synthetic tissue, and it was difficult to manually detach the synthetic tissue of the present invention.

Figure 7:
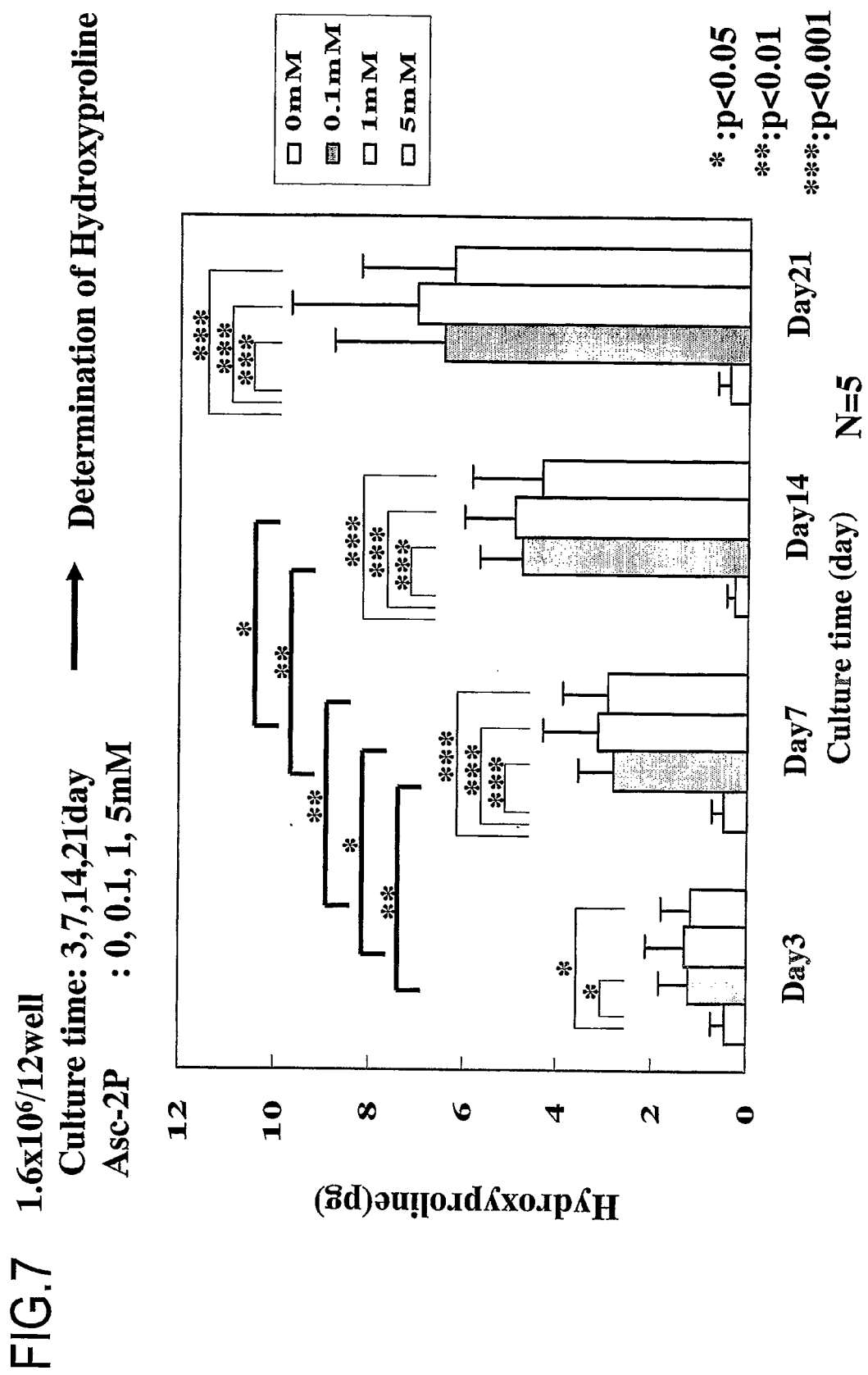
FIG. 7 shows the results of collagen content measurement. When 0.1 mM or more of ascorbic acid diphosphate is added, collagene content in the synthetic tissue of the present invention is significantly increased in any of the culture periods. However, substantially no difference among the concentrations of 0.1 mM, 1 mM and 5 mM were found.
Figure 8:
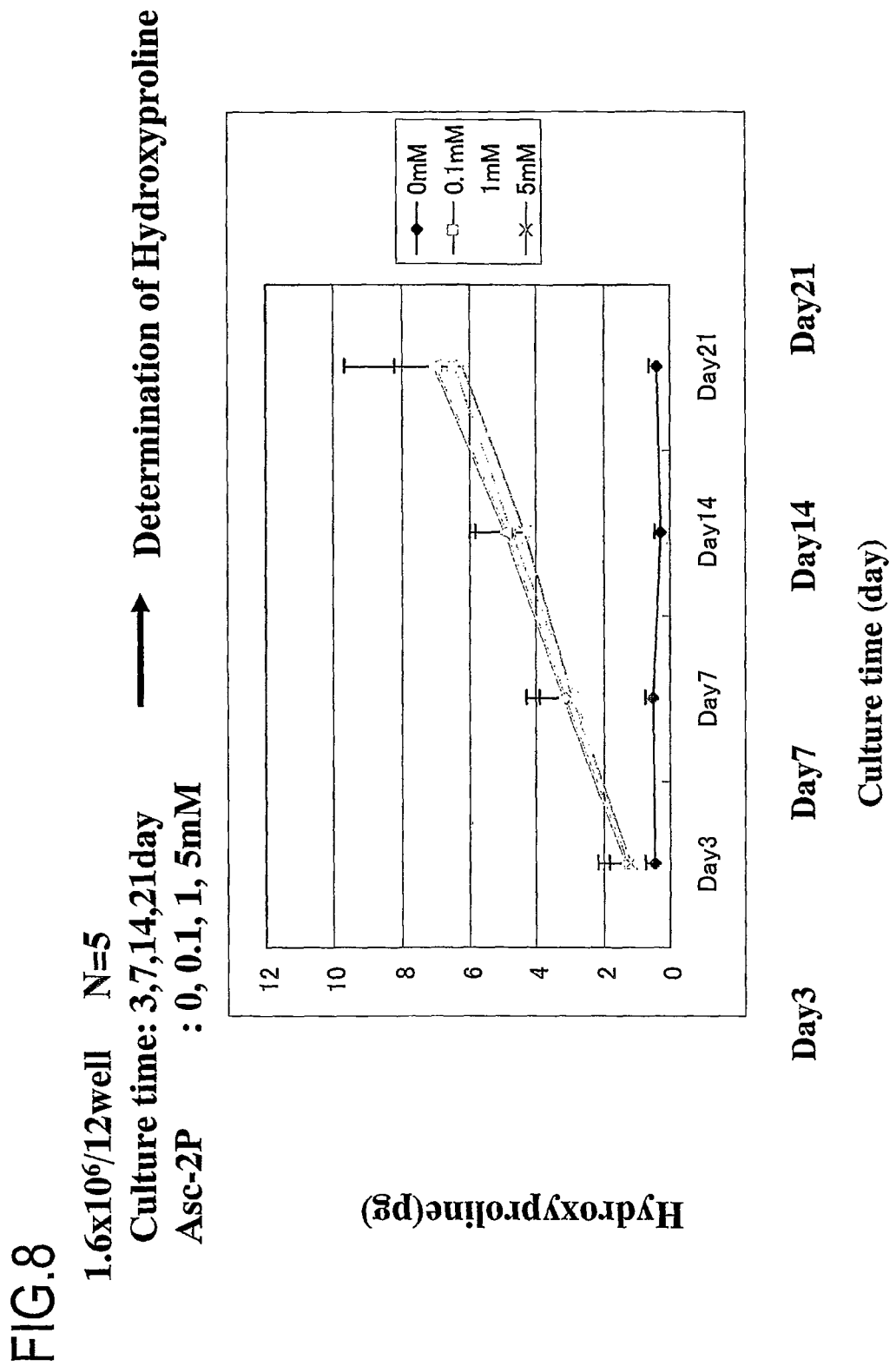
FIG. 8 shows the results of collagen content measurement. When 0.1 mM or more of ascorbic acid diphosphate is added, collagene content in the synthetic tissue of the present invention is significantly increased in any of the culture periods. However, substantially no difference among the concentrations of 0.1 mM, 1 mM and 5 mM were found.

In order to determine the collagen concentration, the collagen content was measured. The result is shown in FIGS. 7 and 8. As can be seen, the amount of hydroxyproline clearly indicates that when 0.1 mM or more ascorbic acid 2-phosphate was added, the production of collagen was significantly promoted. The amount of produced collagen is substantially proportional to the time period of culture (FIG. 8).

Example 2

Measurement of Collagen Production

Next, it was determined whether or not collagen (extracellular matrix) is sufficiently secreted after implantation of a synthetic tissue of the present invention. The following protocol was used.

<Method>
Culture periods: 3 days, 7 days, 14 days, and 21 days,
Concentrations of ascorbic acid 2-phosphate: 0 mM, 0.1 mM, 1 mM, and 5 mM
Under the above-described conditions, a synovial membrane-derived synthetic tissue was produced.

6 N HCl was added to culture medium for the synthetic tissue, followed by hydrolysis at 105° C. for 18 hours. The medium was oxidized with chloramine T. Thereafter, the synthetic tissue was subjected to color development using Ehrlich's Reagent Solution (2 g of p-dimethylamino-benzaldehyde+3 ml of 60% perchloric acid; isopropanol was diluted at 3:13), followed by measurement of absorbance.

<Results>
1) The quantities of collagen produced was dependent on the ascorbic acid concentration in the following manner: 0 mM<<5 mM<1 mM≤0.1 mM (FIGS. 7 and 8).
2) it was demonstrated that the quantity of produced collogen is increased with an increase in the culture time period.

Example 3

Influences of the Size of a Dish, the Number of Cells, and the Number of Passages Next, influences of the size of a dish and the number of passages were investigated.

Figure 9:
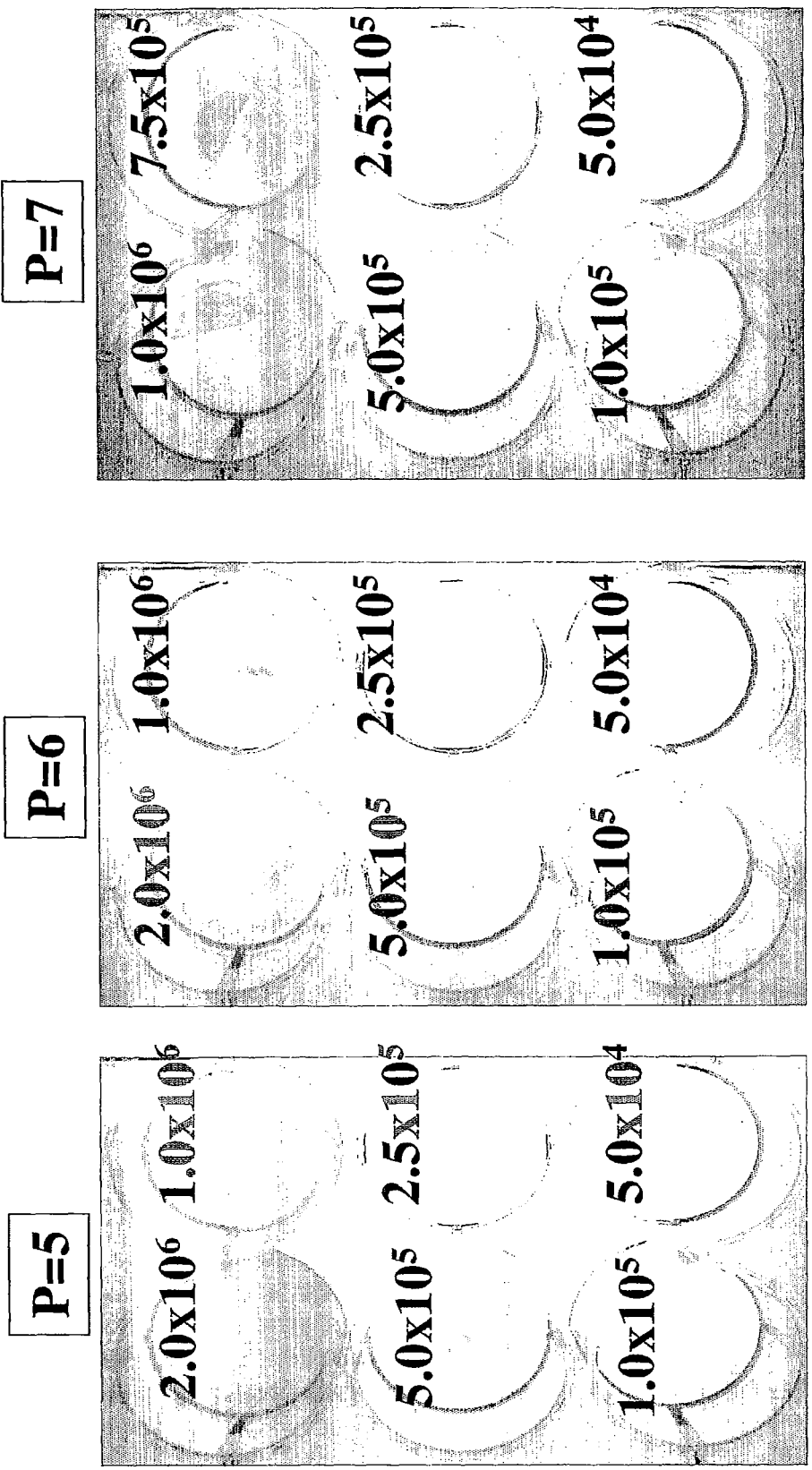
FIG. 9 shows a production of synthetic tissues using a different number of cells. P represents the number of passages. Numeral figures in the photograph indicate the number of cells per cm$^2$.

FIG. 9 shows the formation of synthetic tissues where the number of cells and the number of the passage were changed. A synthetic tissue was formed in all concentrations tested.

Figure 10:
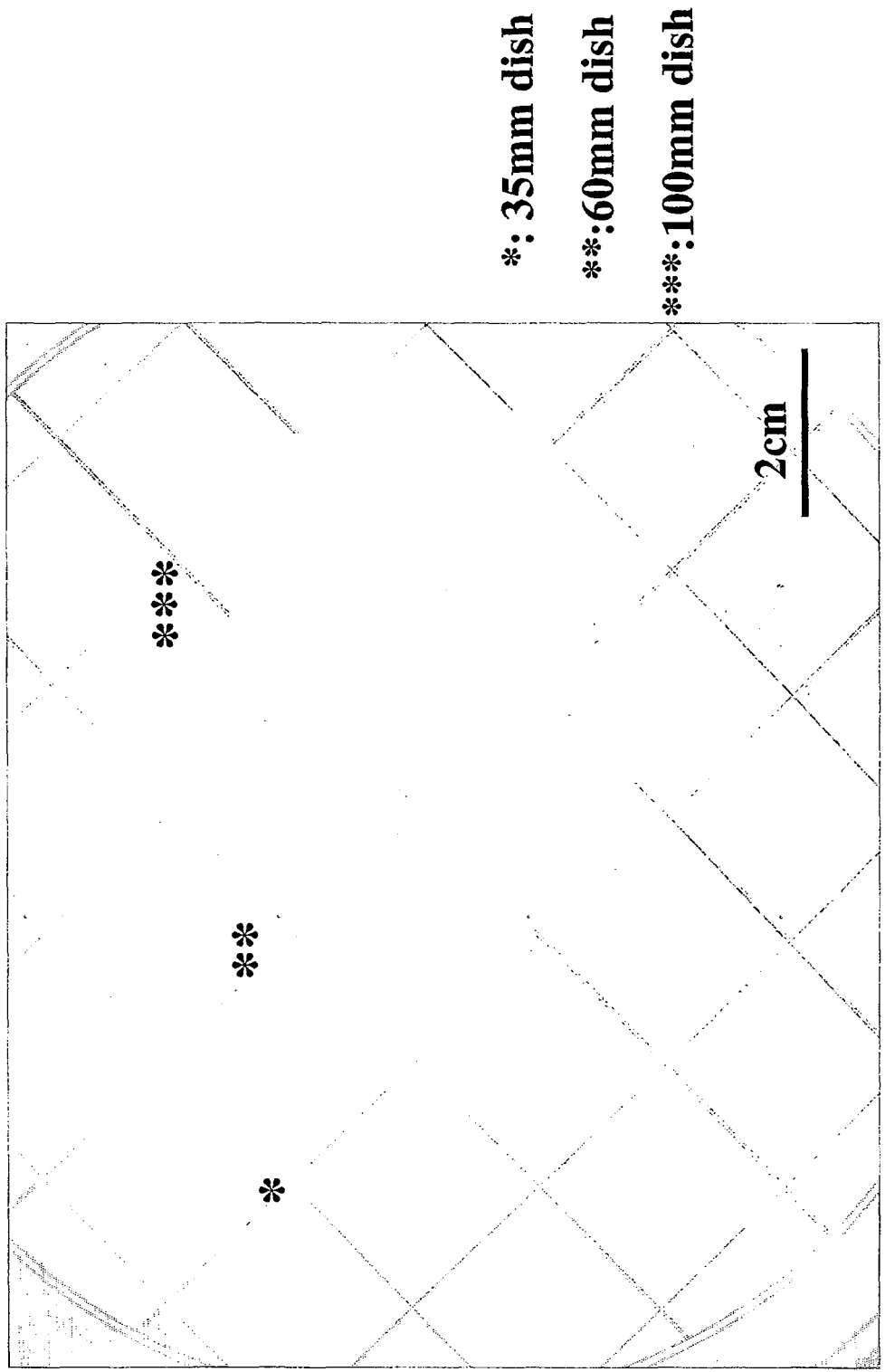
FIG. 10 shows a production of synthetic tissues using dishes with different sizes. * indicates culture in a 35-mm dish.  indicates culture in a 60-mm dish. * indicates culture in a 100-mm dish.

Under the conditions of the above-described Example 1, a similar experiment was conducted where the sizes of dishes were 35 mm, 65 mm, and 100 mm and the number of passages were 5 to 7 (FIG. 10).

The results are shown in FIGS. 9 and 10. FIG. 9 shows the states of synthetic tissues, where the number of passages was changed. FIG. 10 shows the states of synthetic tissues, where the size of a dish was changed. As can be seen from the figures, it was demonstrated that a synthetic tissue can be formed using any size of dish and any number of passages.

As shown in FIG. 9, basically, a greater number of cells may be preferable for the purpose of matrix production. However, when an excessive number of cells were provided, the cells produced an excessive level of contraction force, so that the cell sheet was detached on the day following the start of culture. Therefore, it was demonstrated that when a larger synthetic tissue is desired, it is preferable to dessimate cells at a relatively small concentration. Particularly, in order to control the strength or the like of a synthetic tissue, a relatively small cell concentration seems to be preferable. As can be seen from the figure, when the number of passages was five, the resultant cell sheet was spontaneously detached if the cell concentration was $5.0 \times 10^5/cm^2$, and was not spontaneously detached if the cell concentration was $2.5 \times 10^5/cm^2$. Also, when the number of passages was six or more, the resultant cell sheet was spontaneously detached if the cell concentration was $7.5 \times 10^5/cm^2$, and was not spontaneously detached if the cell concentration was $5.0 \times 10^5/cm^2$. Therefore, the production of a preferable synthetic tissue of the present invention seems to require a sufficient number of cells and a relatively great number of passages. Fourth passage cells were used to produce a trial synthetic tissue. It was spontaneously detached when the cell concentration was $40 \times 10^5/cm^2$. Thus, there seems to be a close relationship between the strength of a synthetic tissue and the number of passages. Various synthetic tissues can be produced, depending on the application. According to these results, cells capable of withstanding implantation seems to be obtained by culturing fifth passage cells at a concentration of $4.0 \times 10^5/cm^2$, however, the present invention seems not to be limited to this.

Similarly, the strength of tissues consisting of other cells is demonstrated to be able to be regulated by changing the cell concentration. Under the conditions described in Example 1, myoblasts can be used to produce a synthetic tissue and the influence of cell density on the strength of the synthetic tissue can be measured. Under the conditions described in Example 28, synovial cells can be used to produce a synthetic tissue and the influence of cell density on the strength of the synthetic tissue can be measured. Under the conditions described in Example 12, fat-derived cells can be used to produce a synthetic tissue and the influence of cell density on the strength of the synthetic tissue can be measured.

Example 4

Measurement of Mechanical Properties

In this example, cells ($4 \times 10^5$ cells/cm$^2$) were cultured in medium containing ascorbic acid 2-phosphate for three weeks. Following detachment at 48 hours, the mechanical properties of the tissue were investigated. The protocol will be described below.

Figure 11:
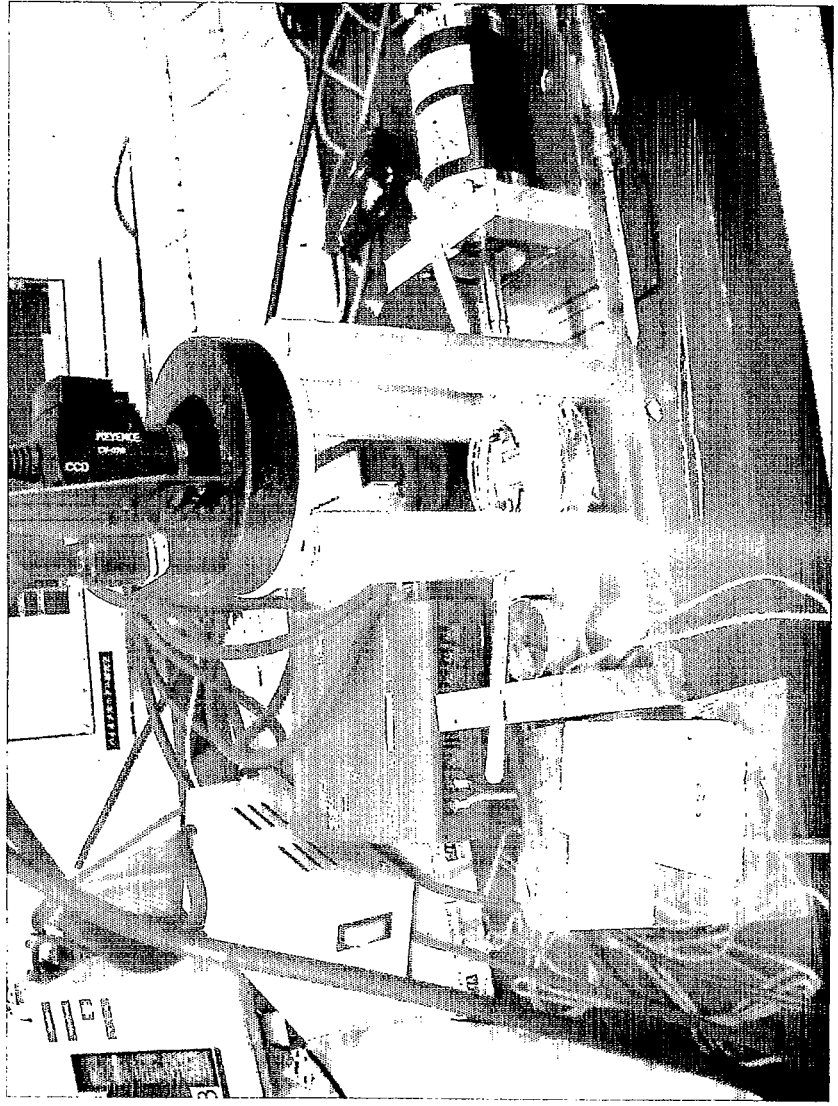
FIG. 11 shows an exemplary mechanical testing system for measuring mechanical properties.
Figure 12:
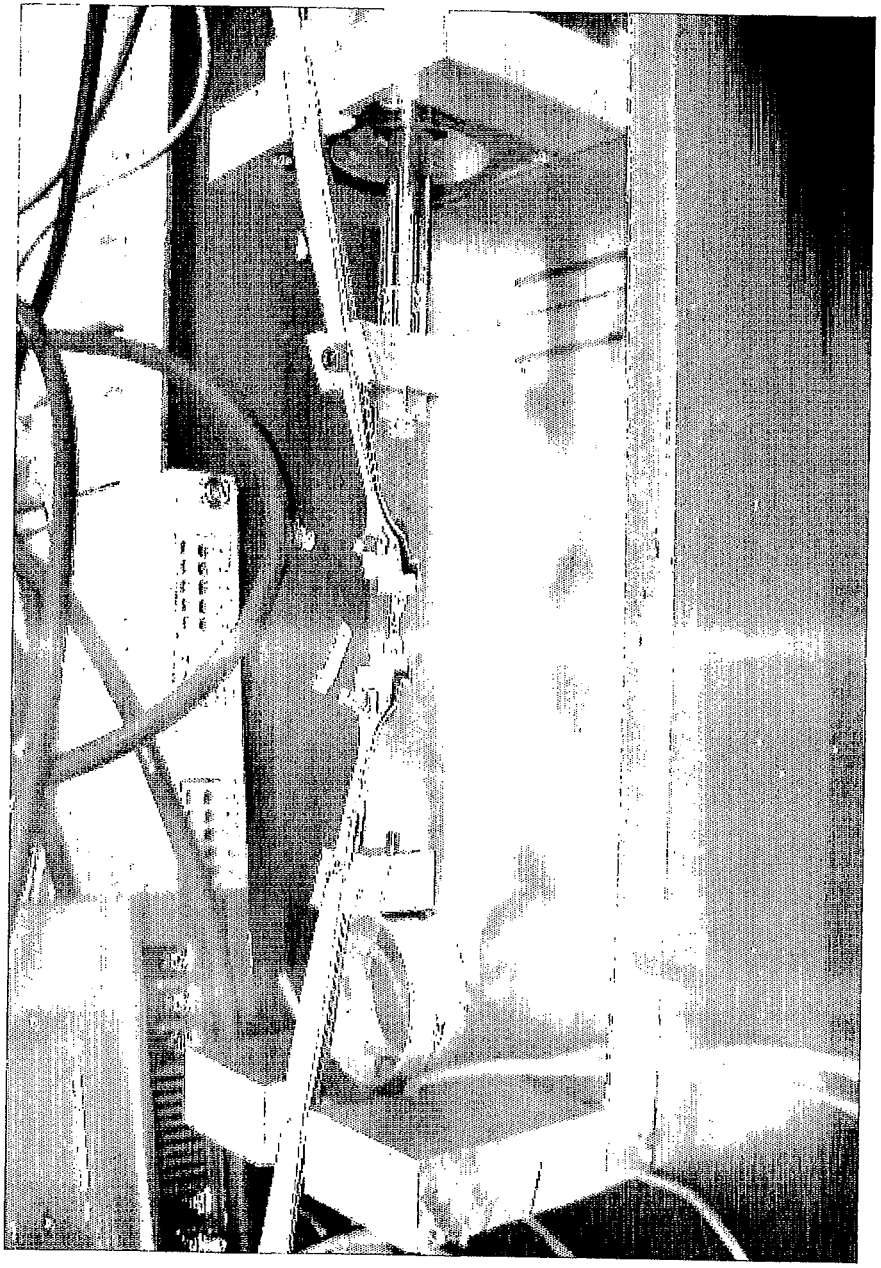
FIG. 12 shows a test piece holding portion of an apparatus for measuring mechanical properties.
Figure 13:
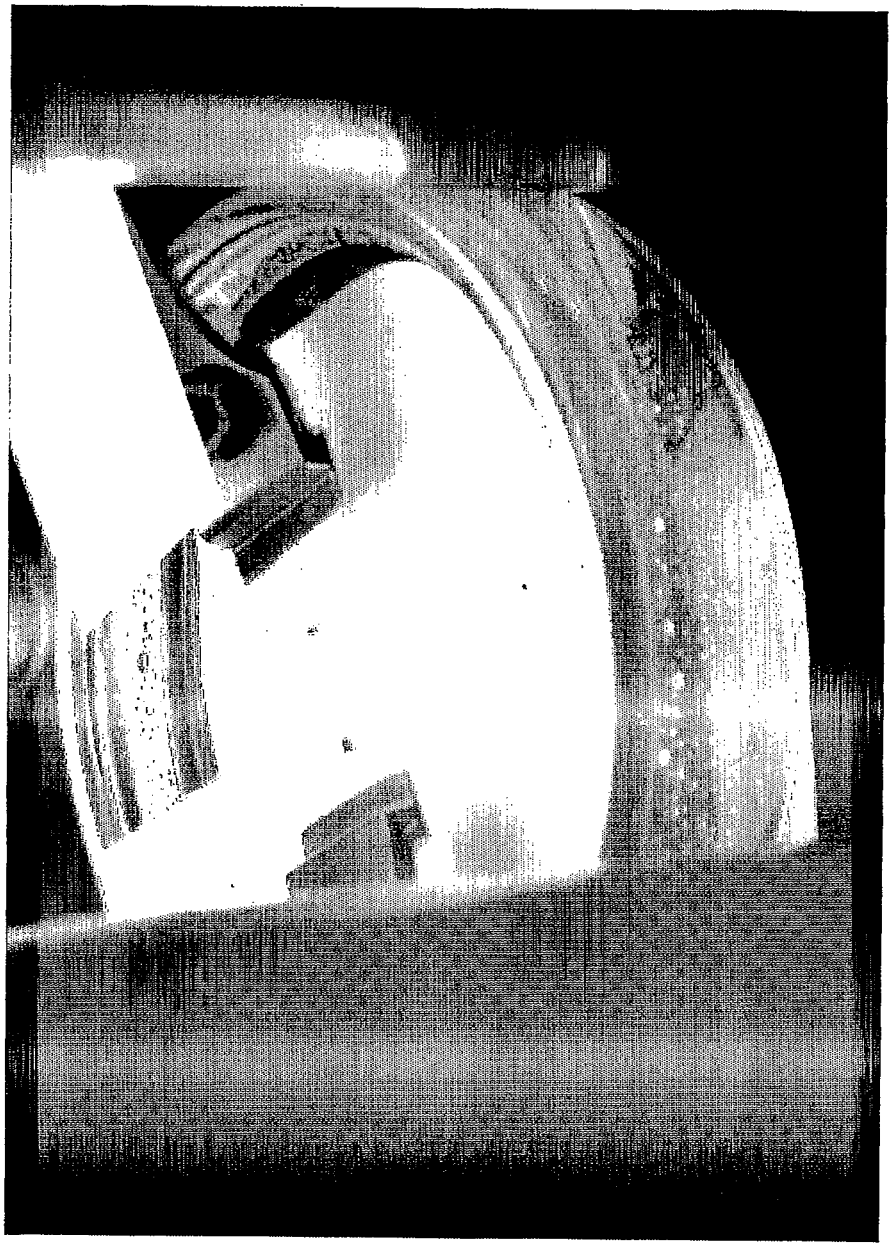
FIG. 13 shows an enlarged view of an apparatus for measuring mechanical properties. A test piece is provided with a marker.
Figure 14:
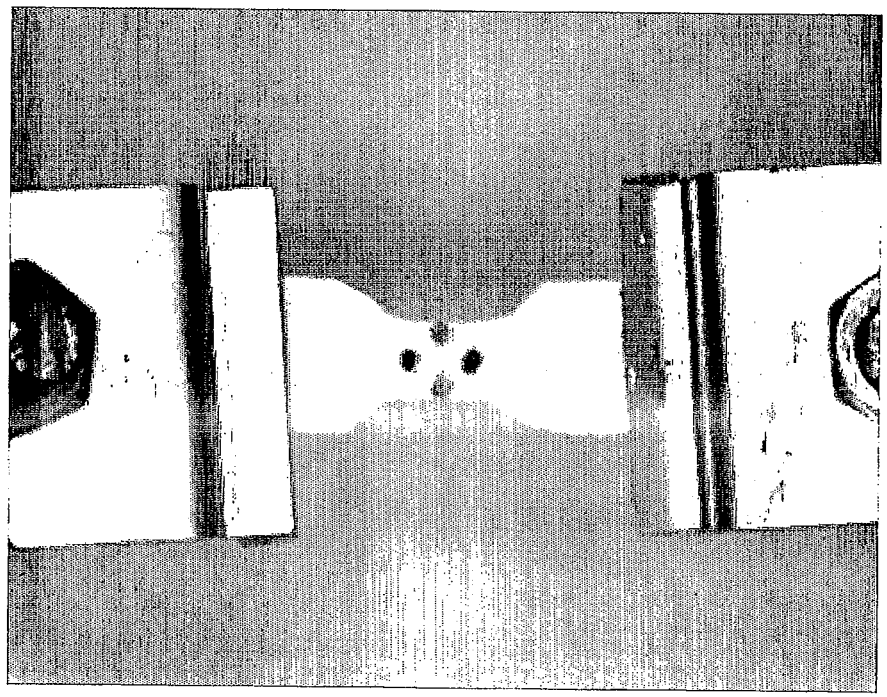
FIG. 14 shows an enlarged view of a test piece holding portion.
Figure 15:
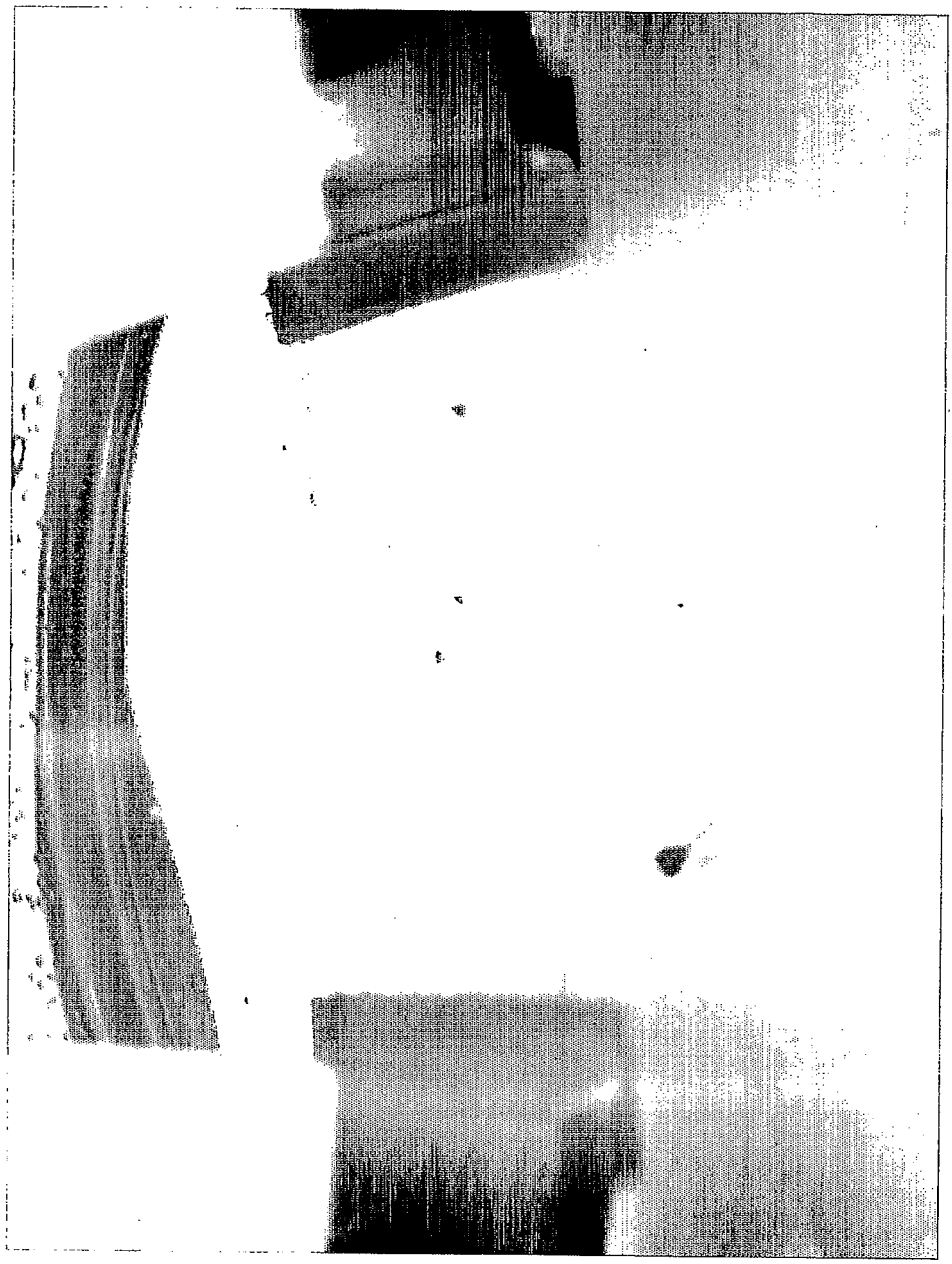
FIG. 15 shows a disrupted synthetic tissue after a tensile test.

The mechanical properties were examined by a tensile test. FIGS. 11 and 12 show the outer appearance of a testing apparatus. FIG. 11 shows a test piece holding portion (an original piece is shown). As shown in FIG. 12, the opposite ends of a synthetic tissue were held by the test piece holding portion. A marker was attached to the synthetic tissue for ease of measurement. FIG. 13 shows the attachment of the marker. FIG. 14 shows an enlarged view of the test piece holding portion. FIG. 15 shows the state of the synthetic tissue after a tensile test.

A synthetic tissue was held as shown in the figures and a marker was attached to the synthetic tissue, followed by a tensile test. The maximum load was 1.89 N, and the Young's modulus was 19.2 Mega pascal. As a reference, the maximum load (tension) of cartilage is typically 0.7 and that of skin is 1.2. The Young's modulus of cartilage is 10 MPa and that of skin is 35 Mpa. Thus, it was demonstrated that the synthetic tissue of the present invention has substantially the same mechanical strength as that of skin, cartilage, or the like, and can resist surgical handling.

Figure 16:
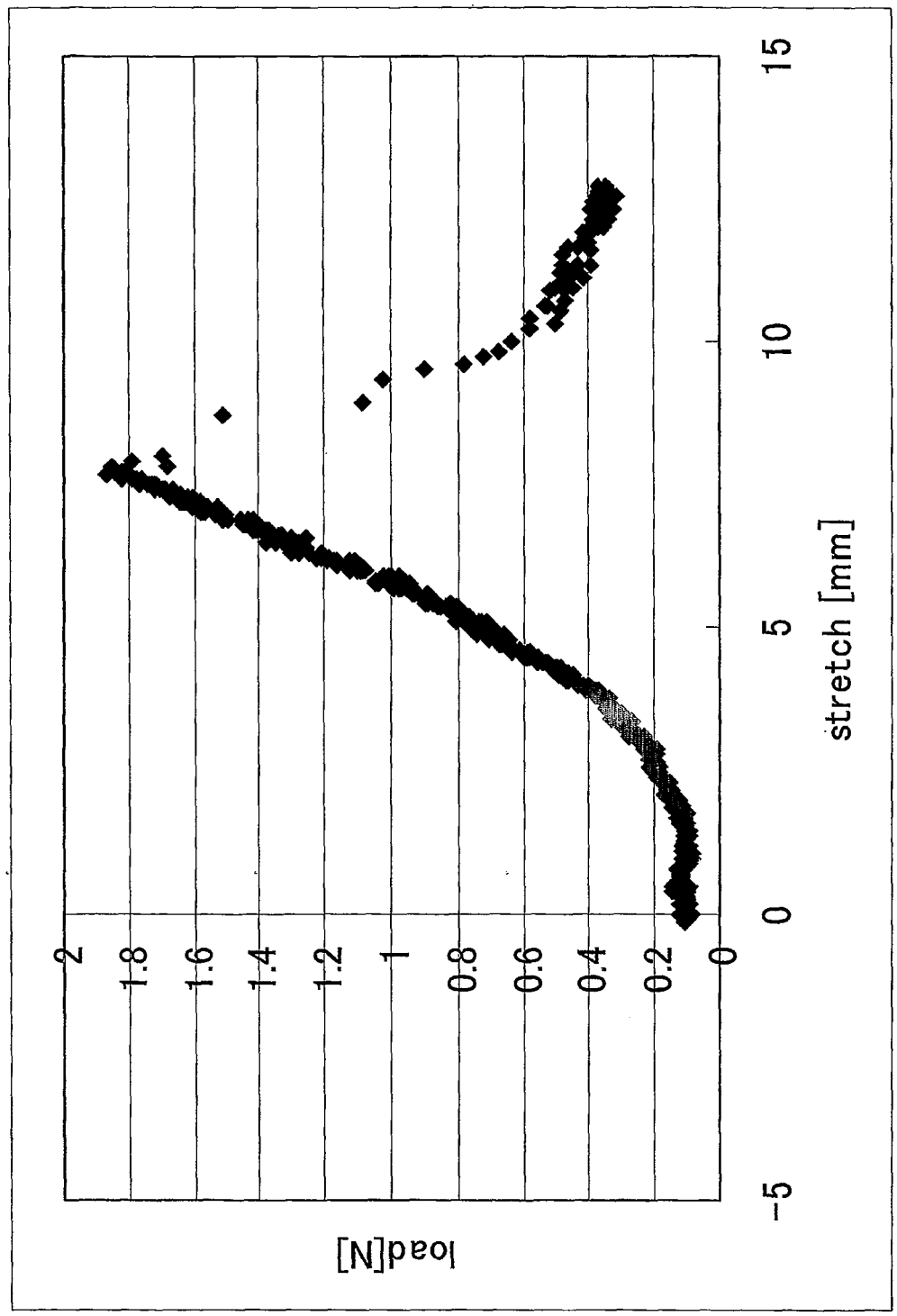
FIG. 16 shows the results (load-deformation curve) of a tensile test of a synthetic tissue (derived from synovium) of the present invention.
Figure 17:
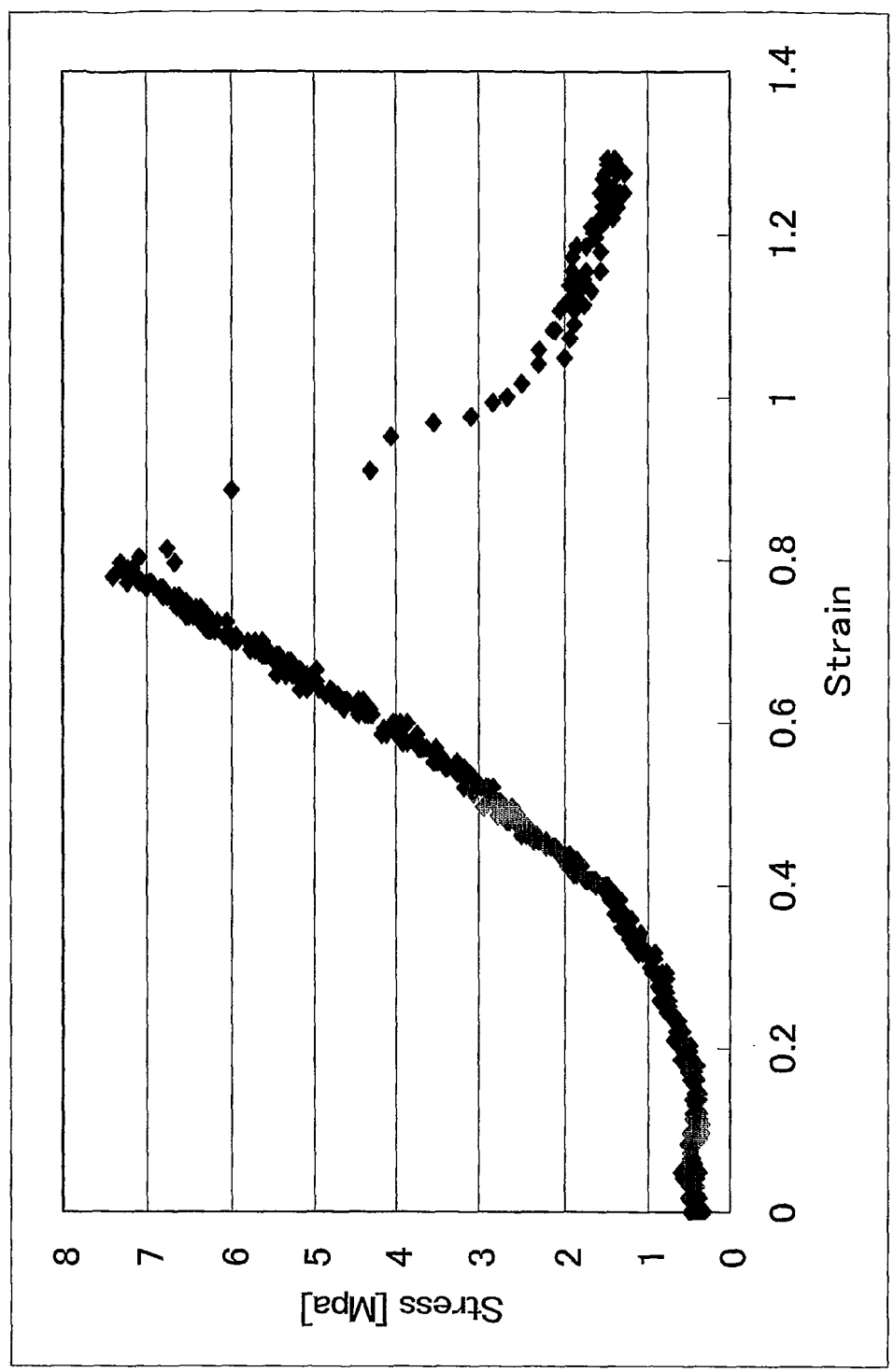
FIG. 17 shows the results (stress-strain curve) of a mechanical properties test of a synthetic tissue (derived from synovial membrane tissue) of the present invention.

The results of the experiment are shown in FIGS. 16 and 17. The results demonstrate that the maximum load was 1.89 N and 1.9 N, respectively. Young's modulus (tangent tensile modulus) was 19.2 MPa.

Example 5

Determination of Self-Supporting Ability

Next, the self-supporting ability of a synthetic tissue of the present invention was tested. The synthetic tissue was held and tested using curved fine forceps A-11 (made of stainless steel; full length: 120 mm; curved: 20 mm, tip: 0.1 mm; manufactured by Natsume Seisakusho). It was determined by visual inspection whether or not the synthetic tissue has self-supporting ability. If the synthetic tissue was divided into a plurality of pieces, it was determined to lacking self-supporting ability. The same result was obtained when another forceps, e.g., curved fine forceps A-12-2 (made of stainless steel, full length: 100 mm; tip: 0.05 mm; manufactured by Natsume Seisakusho) were used by another experimenter performing the same experiment.

The self-supporting ability may be determined immediately after detaching a synthetic tissue off or after preserving a detached synthetic tissue.

None of the synthetic tissues comprising cardiomyocytes, myoblasts, and synovial cells, which are produced in the presence of a three-dimensional promoting agent comprising ascorbic acid as described in the above examples, had self-supporting ability. In contrast, it was already difficult to hold a synthetic tissue produced in the absence of such an agent with forceps upon detachment, so that lack of self-supporting ability was confirmed.

Therefore, 1) if a sheet is easily detached by circumferential pipetting; and 2) if the detached sheet is easily attached to a target site by lightly touching an edge thereof, the sheet spontaneously contracts to have sufficient strength.

Therefore, self-supporting ability is a property which was first obtained by the method of the present invention.

Example 6

Osteogenic Differentiation Induction

In this example, it was determined whether or not the synthetic tissue of the present invention works when osteogenesis was induced in the synthetic tissue.

It was confirmed that synovial cells can be cultured in osteogenesis induction medium (10% FBS-DMEM+0.1 µM dexamethasone, 10 mM beta glycerophosphate, 0.2 mM ascorbic acid 2-phosphate) from the beginning to produce a synthetic tissue.

Figure 18:
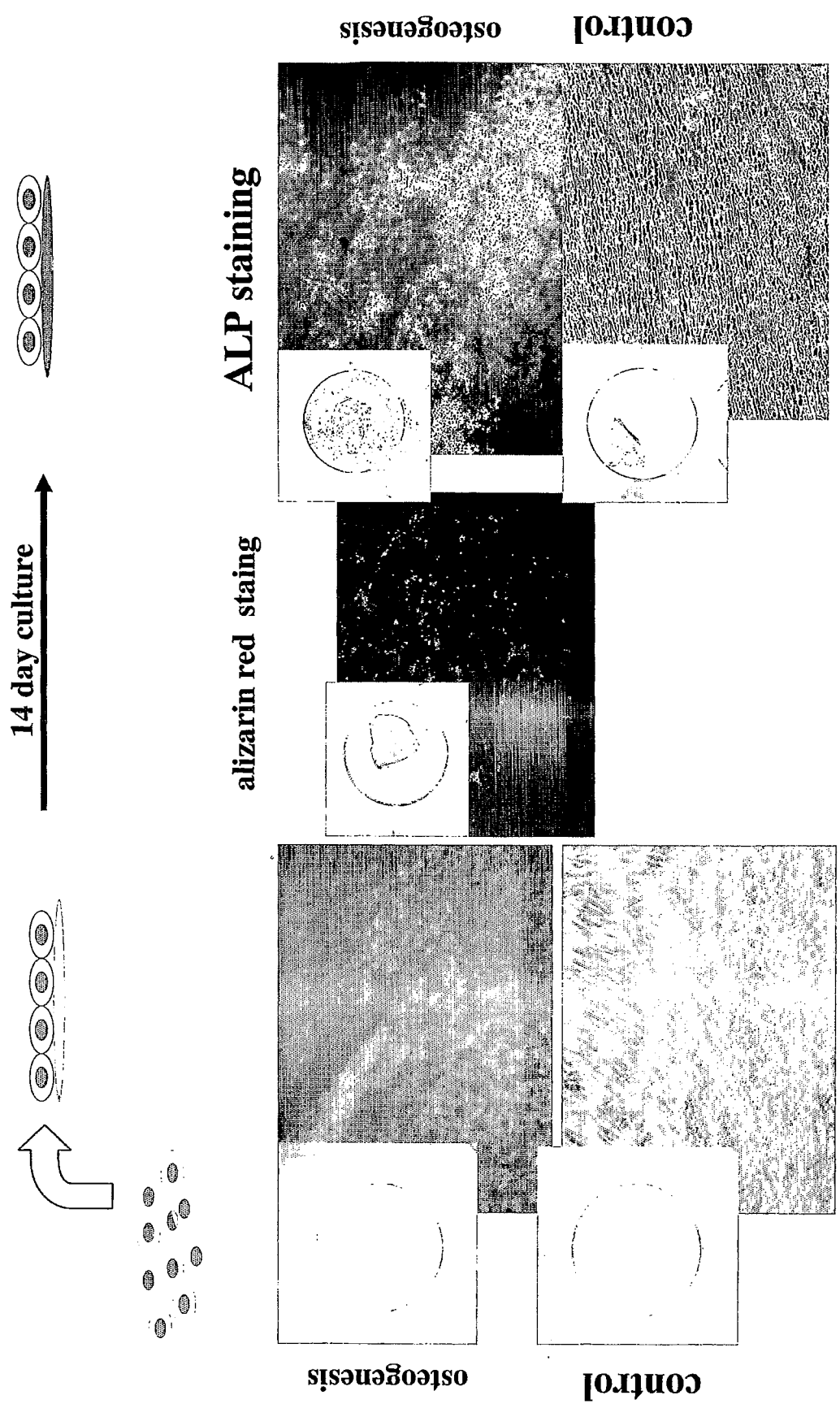
FIG. 18 shows an exemplary osteogenic induction experiment of the synthetic tissue of the present invention and the results. The upper half portion shows a scheme for osteogenesis induction. The induction was conducted in the presence of 0.1 µM dexamethasone, 10 mM β-glycerophosphate, and 50 µg/ml ascorbic acid 2-phosphate. The lower left portion shows a control. The middle left portion shows a synthetic tissue differentiated into a bone by osteogenic induction. The middle lane portion shows Alizarin Red staining. The lower right portion shows an ALP-stained control. The middle right portion shows positive ALP-staining in a synthetic tissue by osteogenic induction.

Also, it was confirmed that a synthetic tissue was produced without osteogenesis induction, and thereafter, the medium was exchanged with osteogenesis induction medium and the tissue was cultured, so that calcificated bone was generated in the synthetic tissue. The result is shown in FIG. 18.

Whereas a synthetic tissue without differentiation induction appears to be transparent, an ossificated synthetic tissue has a white colour. The synthetic tissue was strongly stained with Alizarin Red, and was also strongly stained by alkali phosphatase (ALP) staining as compared to the control. Thus, it was confirmed that the synthetic tissue of synovial cells is capable of osteogenesis.

Example 7

Chondrogenesis Induction

In this example, it was determined whether or not chondrogenesis induction can be used for the production method of the synthetic tissue of the present invention.
(Culture Conditions)
Cell density: $4\times10^4$ cells/cm$^2$
Conditions: $CO_2$ 5%, air 95%, 37° C.
These conditions and a chondrogenesis induction medium described below were used to produce a synthetic tissue.

Cartilage differentiation induction medium: DMEM (GIBCO), FBS (HyClone) 10%, ITS+Premix (insulin, transferrin, selenious acid) (BD Biosciences) 6.25 µg/ml, dexamethasone (Sigma) $10^{-7}$ M, ascorbic acid (WAKO) 50 µg/ml, pyrubic acid (SIGMA) 100 µg/ml.

Figure 19:
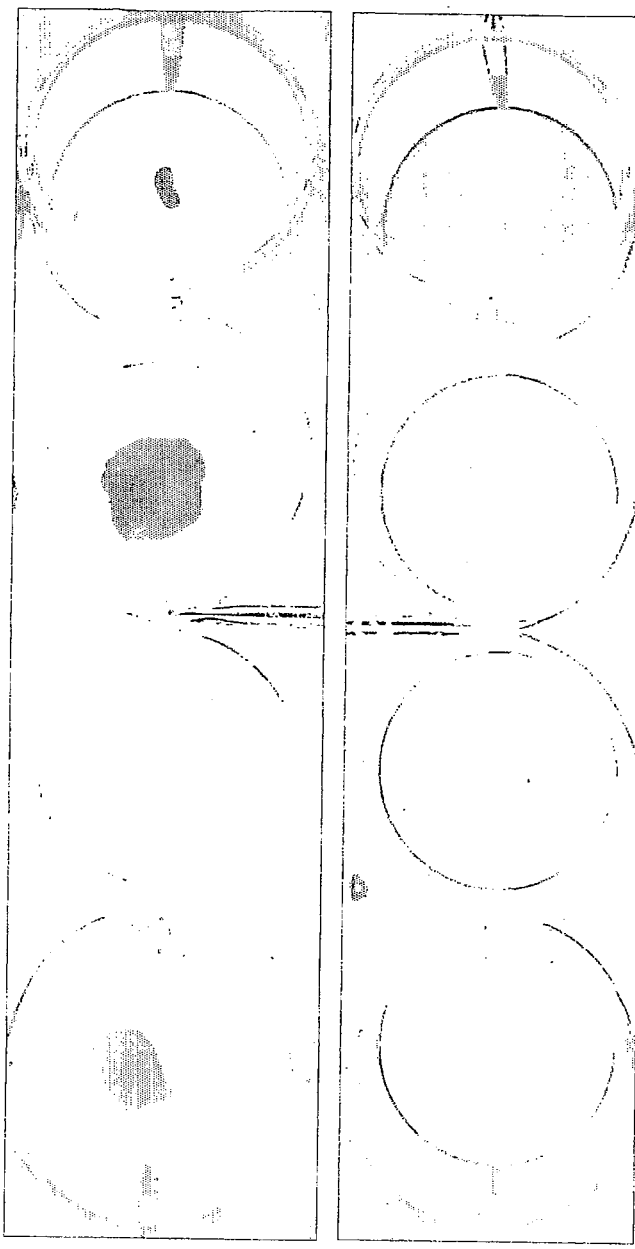
FIG. 19 shows the results of chondrogenic differentiation of a synthetic tissue of the present invention. This figure shows cultured synthetic tissues (A) and monolayer (B) using, from the leftmost, normal culture medium, chondrogenic medium, chondrogenic medium plus BPM-2 and chondrogenic medium plus TGF-β1, respectively. Note that A) synthetic tissues have more intense staining of Alcian blue than B) monolayer culture. Also, note that addition of TGF-β results in detachment of a synthetic tissue from the container without mechanical stimulation. (A) Most right lane.
Figure 20:
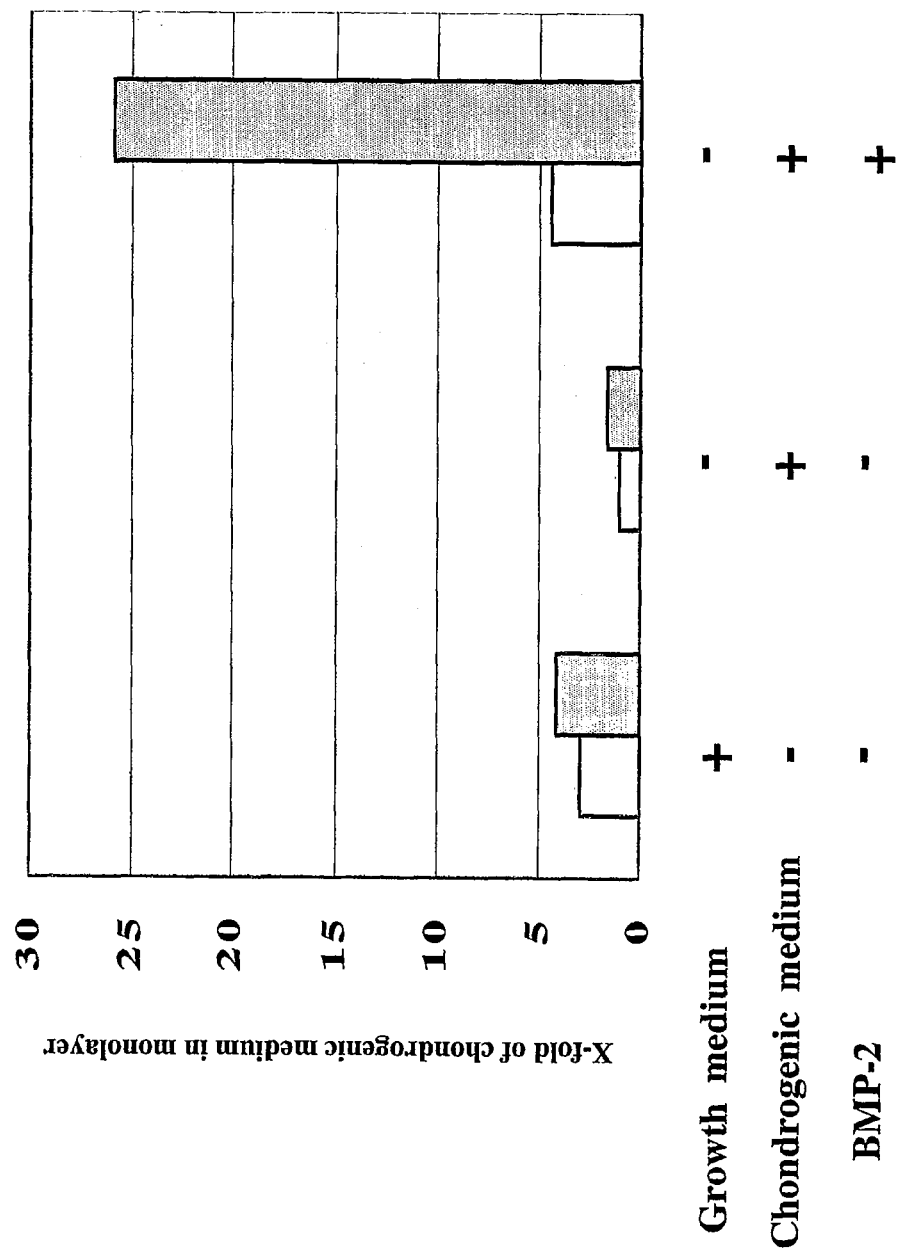
FIG. 20 shows semi-quantification of Alcian blue staining for comparison of a synthetic tissue of the present invention with a single cell sheet under chondrogenic stimulation as in FIGS. 19 and 39. The left (blue) shows a result of monolayer, and the right (red) shows a result of the synthetic tissue.

The results are shown in FIG. 19. The cells were induced into cartilage. From the left, a typical medium, a chondrogenesis induction medium, a chondrogenesis induction medium+BMP-2, and a chondrogenesis induction medium+TGF-b1 were used to culture a synthetic tissue. All of the tissues were stained blue with Alcian blue staining. It was confirmed that a cartilage-like matrix production was accelerated. Such an effect is significant for cells cultured in medium containing BMP-2. The result of quantification of staining ability is shown in FIG. 20.

Figure 21:
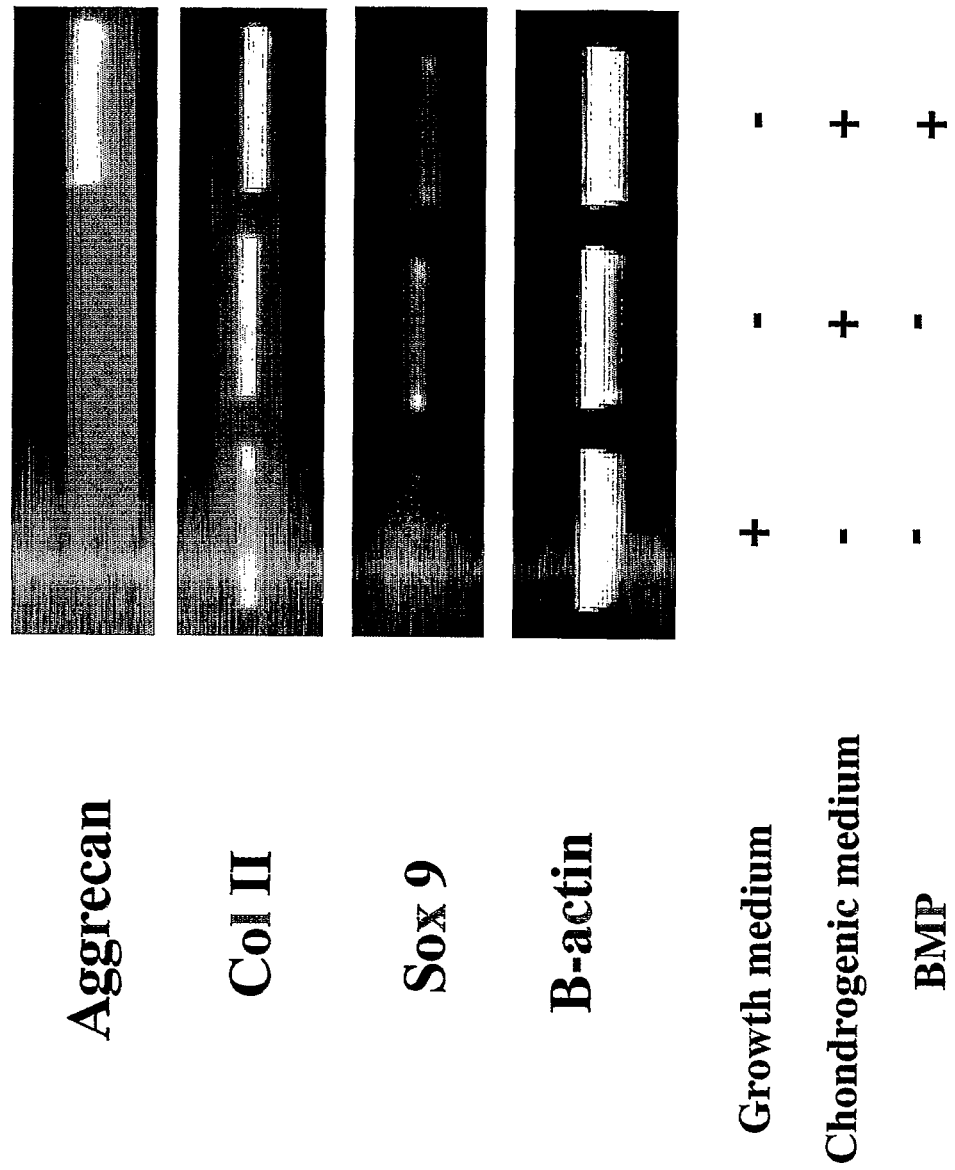
FIG. 21 shows the expression of various chondrogenic marker genes (aggrecan, Col II, Sox9, B-actin) under chondrogenic stimulation.
Figure 22:
FIG. 22 shows the comparison of the expression of chondrogenic marker genes within a synthetic tissue and a monolayer culture of synovial cells under chondrogenic stimulation as in FIGS. 19 and 21.

Expression of cartilage-associated genes (aggrecan, Col II, Sox9) in the synthetic tissue is shown in FIG. 21. When the synthetic tissue was transferred from the typical medium (leftmost column) to the chondrogenesis induction medium (middle column), expression of the Sox9 gene, which is a chondrogenesis marker, was increased. When the synthetic tissue was further cultured in the chondrogenesis induction medium+BMP-2, expression of the collagen II gene was also increased. Thus, stronger chondrogenesis could be confirmed. FIG. 22 shows the results of comparison of a chondrogenesis reaction between a monolayer culture synovial cell and a synovial cell in a three-dimensional synthetic tissue, when the same differentiation inducing stimulus was applied. When counted from the left, odd-numbered columns indicate monolayer culture, while even-numbered columns indicate three-dimensional synthetic tissue, where culture was performed under the same culture conditions. When the chondrogenesis induction medium or the chondrogenesis induction medium+BMP-2 was added as a stimulus, it was confirmed that the chondrogenesis marker gene was significantly expressed in the synthetic tissue. Thus, the three-dimensional synthetic tissue was confirmed to have strong chondrogenesis ability.

Example 8

Repair of a Pig Cartilage

Next, it was determined whether or not cartilage can be repaired. An allogenic synthetic tissue was used.

To determine the presence or absence of the adhesion capability of a synthetic tissue, an allogenic synthetic tissue was implanted onto a pig cartilage piece. The synthetic tissue was prepared under conditions where the number of cells was $4\times10^6$ cells/35-mm dish, the concentration of ascorbic acid was 1 mM, and the culture period was 7 to 14 days. A wound having a diameter of 6 mm was generated on the cartilage piece. An upper layer zone thereof was cut off from the cartilage piece using a scalpel. Chondroitinase ABC (1 U/ml) was added. The cartilage piece was allowed to react for 5 minutes. A synthetic tissue was sized to have a diameter of 6 mm and was implanted, followed by culture for 7 days. The synthetic tissue is closely attached to the attachment surface of the cartilage piece. Fibronectin aggregated on the attachment surface (FIG. 23).

Figure 24:
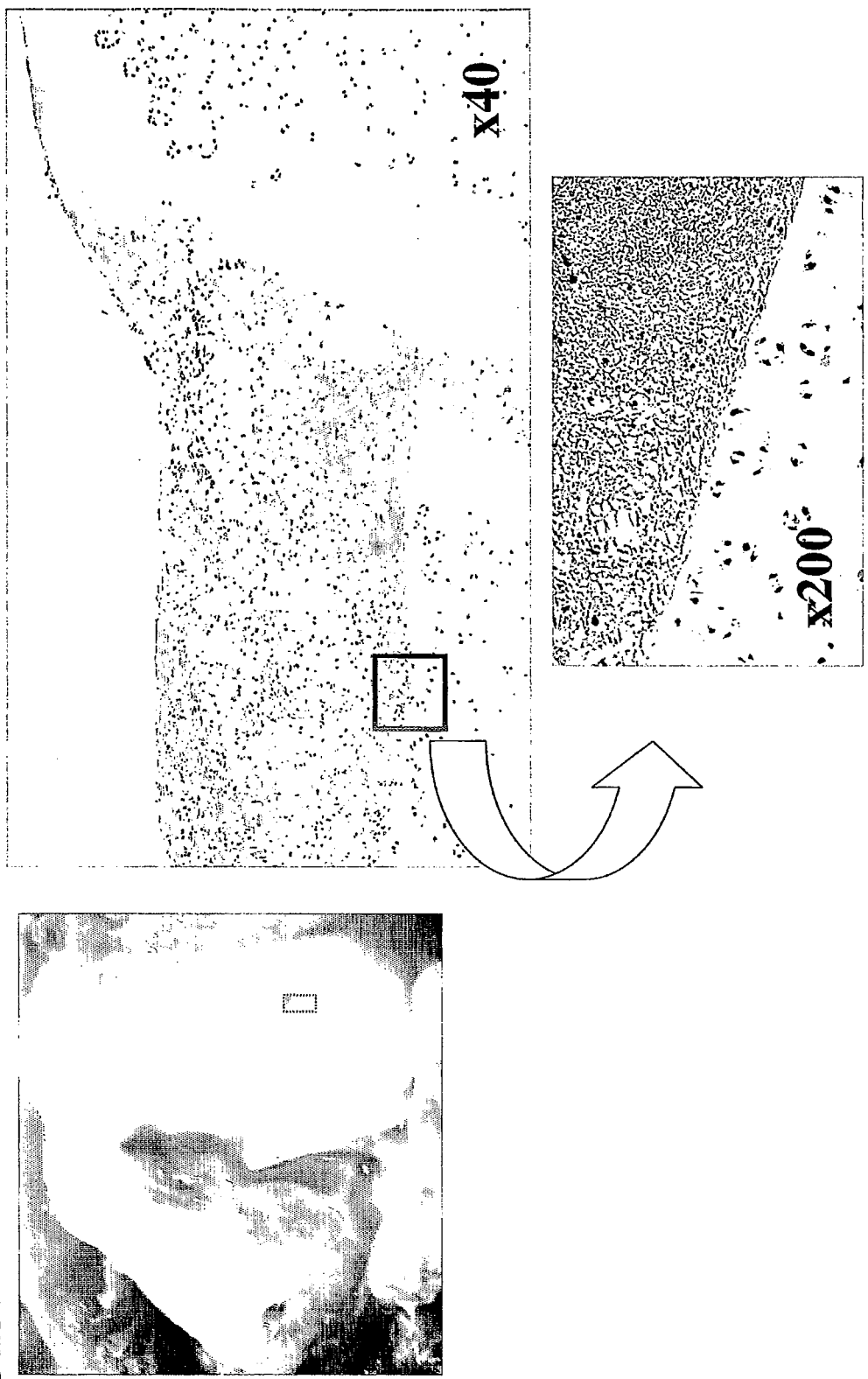
FIG. 24 shows an in vivo cartilage implantation experiment of the present invention and the 10 day results. A synthetic tissue is firmly adhered to a partial cartilage injury. The left shows a macroscopic view of the result. The upper right shows a histology (×40) and the lower right shows a histology at higher magnification (×200).
Figure 25:
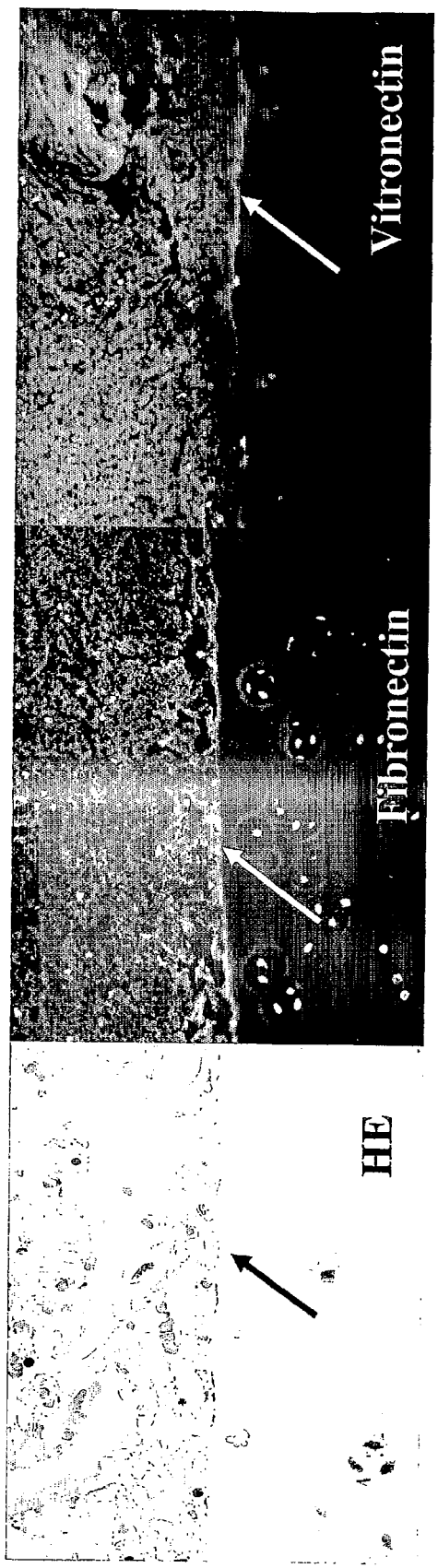
FIG. 25 shows the adhesion of a synthetic tissue of the present invention in a cartilage implantation experiment. The state on day 10 is shown. The left portion shows the result of HE staining, the middle portion shows the result of fibronectin staining, and the right portion shows the result of vitronectin staining.

Next, pig cartilage implantation was performed. As described above, a wound having a diameter of 6 mm was created in a medial femoral condyle. An upper layer zone thereof was cut off from the cartilage piece using a scalpel. Chondroitinase ABC (1 U/ml) was added. The cartilage piece was allowed to react for 5 minutes. A allogenic synthetic tissue was sized to have a diameter of 6 mm and was implanted, followed by culture for 7 days. The results are shown in FIG. 24. FIG. 25 shows a strongly enlarged view of a culture portion of a surface of the cartilage adhered to the synthetic tissue of FIG. 24. The left portion of FIG. 25 is a photograph showing the result of HE staining, the middle portion is a photograph showing the result of staining with anti-fibronectin antibodies, and the right portion is a photograph showing the result of staining with anti-vitronectin antibodies. As indicated by an arrow (the interface between the synthetic tissue and the cartilage tissue), it was demonstrated that the matrix of the synthetic tissue was directly attached to the cartilage matrix, but not via cells. It is shown that fibronectin and vitronectin were accumulated at the adhesion surface. Thus, the results suggest that these adhesion molecules are involved in adhesion between a synthetic tissue and a recipient tissue. Therefore, the present invention is also characterized in that the synthetic tissue is more effectively adhered to in vivo tissue than conventional synthetic tissues, or cells.

Figure 26:
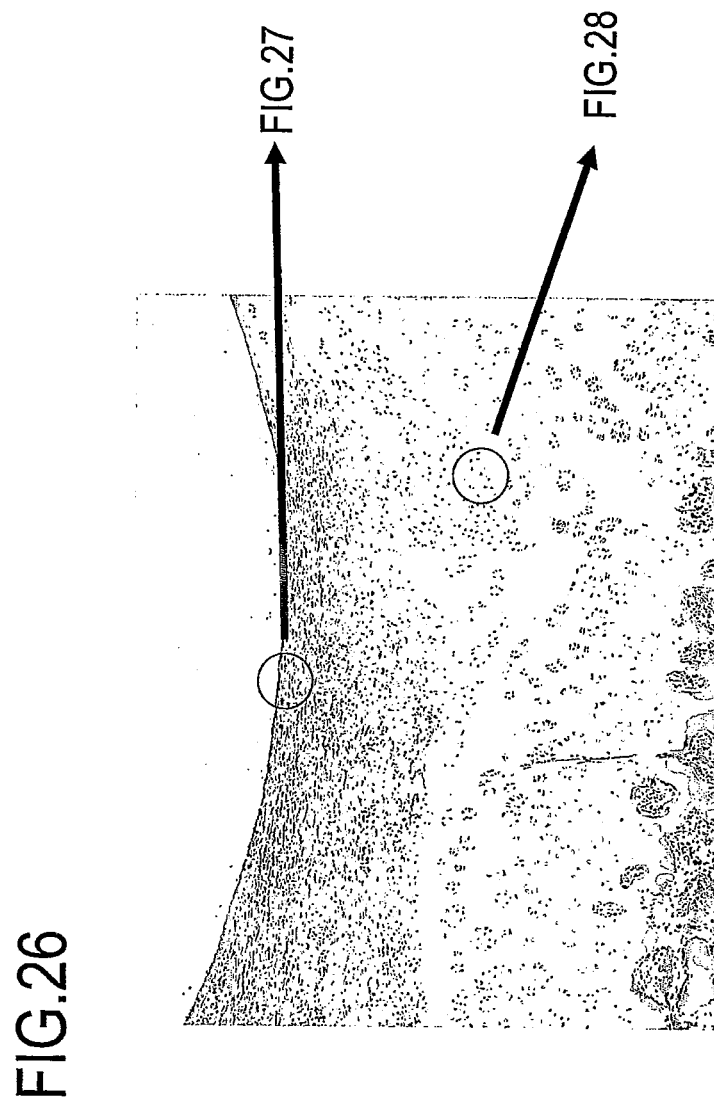
FIG. 26 shows the 1-month result of an in vivo implantation experiment of the present invention. A synthetic tissue is integrated with adjacent cartilage tissue without inflammation. Further, a superficial portion of the synthetic tissue contained a number of fibroblast-like cells (FIG. 27), and a deep portion of the synthetic tissue contained a number of chondrocyte-like cells (FIG. 28), indicating the chondrogenesis of the synthetic tissue after the implantation at particularly deep portions.
Figure 27:
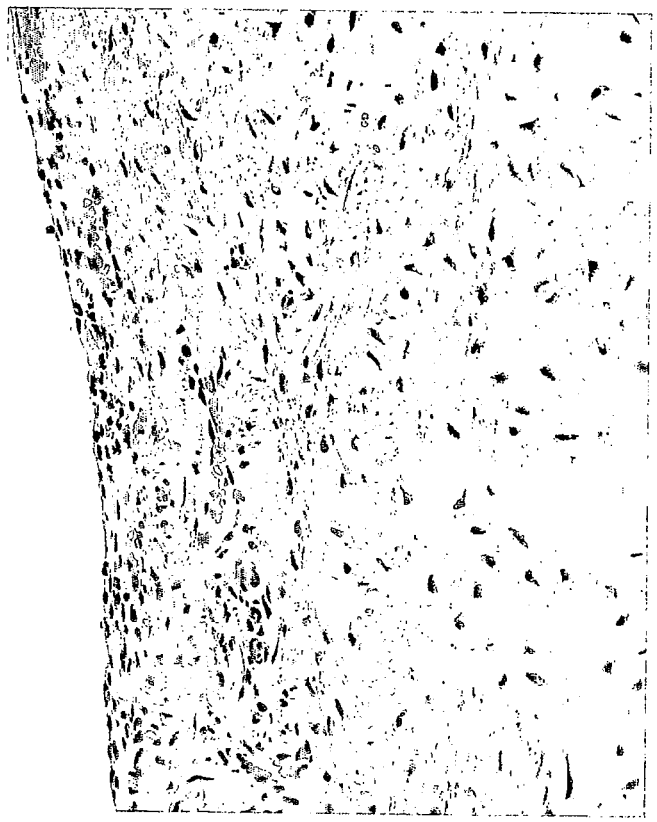
FIG. 27 shows a superficial portion of a synthetic tissue at one month after implantation.
Figure 28:
FIG. 28 shows a deep portion of a synthetic tissue at one month after implantation.

Further, the tissue was examined after one month of implantation. The result is shown in FIG. 26. As can be seen, it is confirmed that the synthetic tissue was biologically integrated with the cartilage injury portion and was accepted without inflammation. The surface layer portion of the synthetic tissue was made mainly of fibroblast-like cells as shown in FIG. 27. On the other hand, a deeper layer portion of the synthetic tissue was made mainly of cartilage-like cells as shown in FIG. 28. Therefore, the implanted synthetic tissue had differentiated into cartilage-like tissue over time. No significant rejection was confirmed in any period of time, and rejection which is expected for allogenic implantation, was not observed.

Therefore, it was found that the allogenic synthetic tissue can be implanted without a side effect.

Example 9

Repair of a Pig Meniscus

Next, it was determined whether or not the synthetic tissue of the present invention is applicable to repair of meniscus.

As in the above-described Example 6, an allogenic synthetic tissue was prepared under conditions where the number of cells was $40\times10^6$ cells/35-mm dish, the concentration of ascorbic acid was 1 mM, and the culture period of time was 7 to 14 days. A portion having a diameter of 6.5 mm was removed from a meniscus (FIG. 29), and the synthetic tissue was implanted thereinto. The portion containing the implant was covered with a collagen sheet (Nipro) for protection until the synthetic tissue was accepted (FIG. 30). The pig was kept for one month. The protocol is described below.

(Anesthesia)

A pig 15 to 17 weeks old (LWD ternary hybrid) was intramuscularly injected via the dorsal portion of its neck with 20 mg/kg Ketaral+10 mg/kg Seractal. Thereafter, an infusion route was provided in the ear vein, and thereafter, the respiratory tract was secured using endotracheal intubation. Diprivan was continuously administered at a rate of 0.5 mg/kg/hr to maintain anesthesia. An antibiotic (Cefamezin, 1 g) was administered to prevent post-operational infection.

(Operation)

The animal was positioned and an operation portion was cleaned with a sterilized drape. A knee joint was accessed by medial para-patellar approach. After detecting the internal articular capsule, the middle portion at the medial collateral ligament (MCL) of the knee was defected. A cylinder-shaped cavity (diameter: 6.5 mm) was created using the mosaic plasty DP (Smith & Nephew) (FIG. 29). The cavity was filled with the synthetic tissue (FIG. 30), followed by the coverage with fascia. After hemostasis was confirmed, the incised internal collateral ligament was repaired, and the articular capsule, the subcutaneous tissue, and the epidermis were sutured. A cast was fixed to the knee joint in its incurvation position. The operation was ended.

(Evaluation Method)

Visual inspection and histological study were performed.

(Results)

Figure 31:
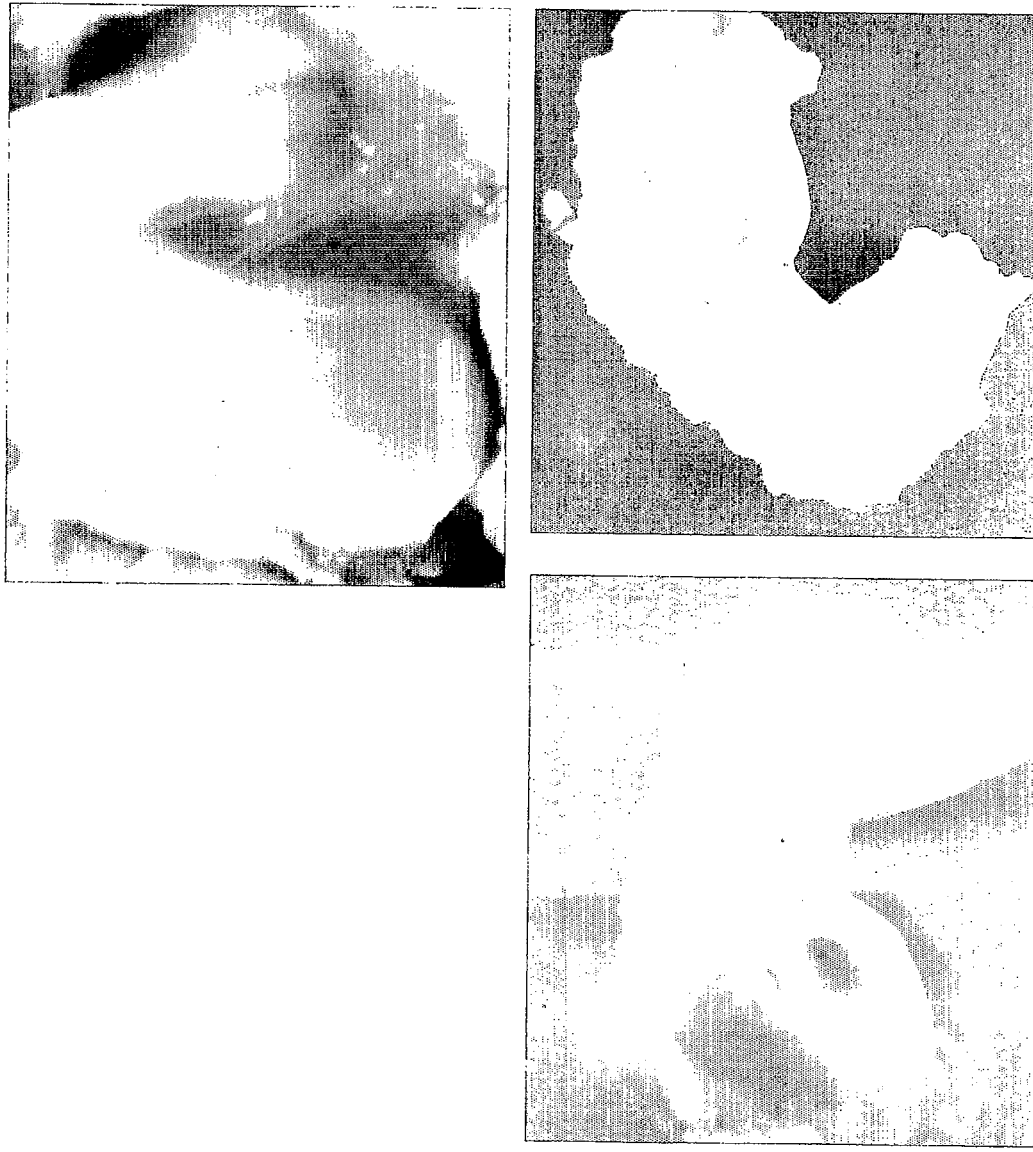
FIG. 31 shows the results of a meniscus repair experiment using a synthetic tissue of the present invention. A visual inspection four weeks after operation is shown. The upper portion shows a state of a cartilage. It is shown that substantially no degeneration or injury due to friction or the like was found on the corresponding chondral surface, i.e., the meniscal defect was recovered. The lower left and right portions show a repaired defect.
Figure 32:
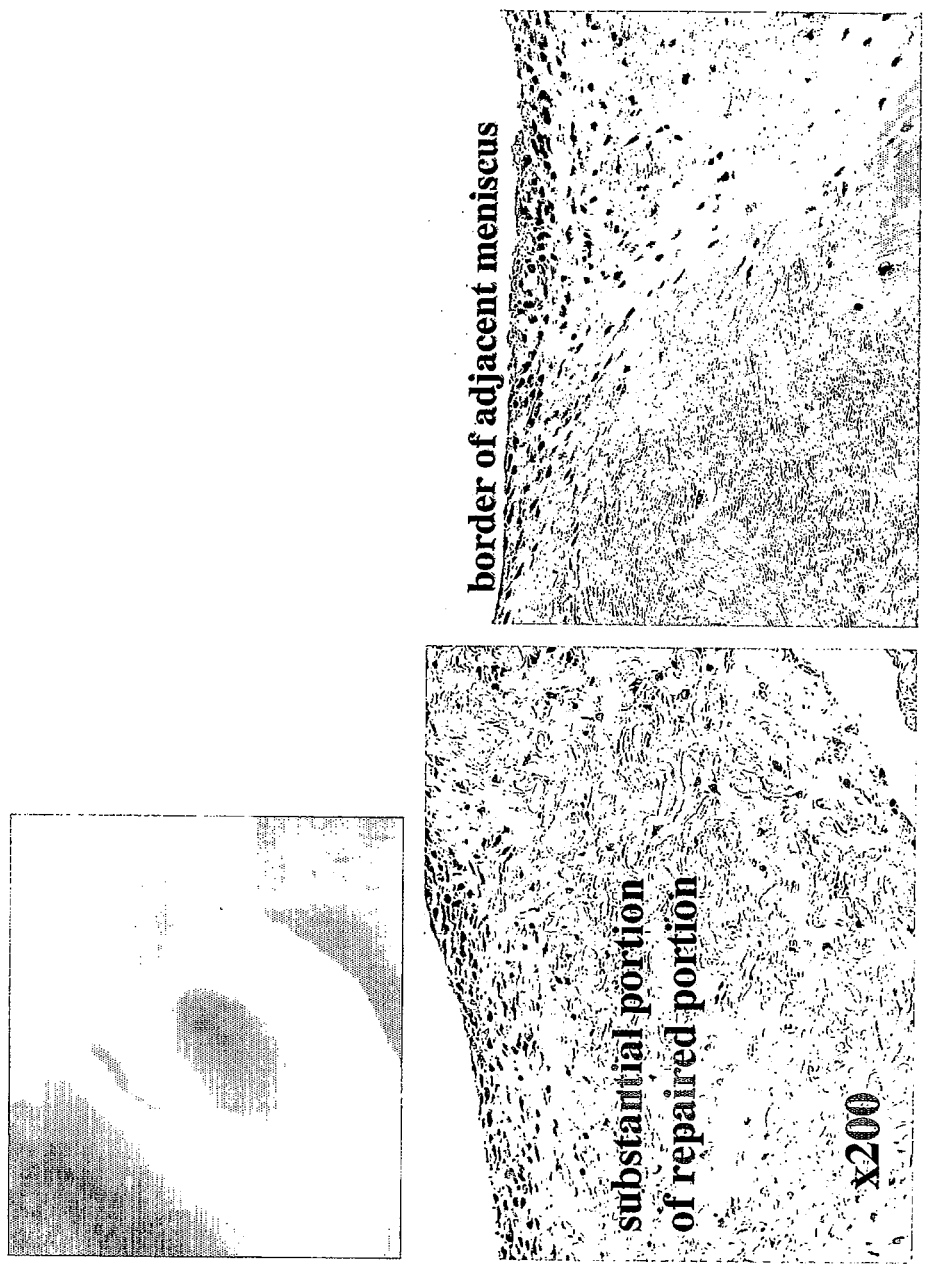
FIG. 32 shows the results of a meniscus repair experiment using a synthetic tissue of the present invention. The upper portion shows a macroscopic view. The lower left portion shows histology of a repaired tissue. The lower right portion shows histology of a border between the repaired tissue and its adjacent meniscus (magnification: ×200).

Four weeks after operation, the animals receiving the synthetic tissue was significantly repaired according to visual finding (FIG. 31) and histological finding (FIG. 32).

Remarkably, an eosin positive result was observed in the synthetic tissue four weeks after implantation. Also, the formation of a meniscus tissue-like matrix was observed and the biological integration of the synthetic tissue and its adjacent meniscus tissue was completed.

Example 10

Repair of Pig Tendon/Ligament Tissues

Tendon/ligament tissues were subjected to a repair operation. The state of the wound of a tendon/ligament tissue is confirmed. In this case, a portion of synovial cells are collected. The synovial cells are cultured. The cells are used to produce a synthetic tissue using a protocol as described in Example 1.

Next, by operation, the vicinity of the wound site of the tendon/ligament tissue is cut off to obtain a fresh portion, on which the above-described synthetic tissue is in turn placed. In this case, since the synthetic tissue has adhesion molecules, the synthetic tissue is adhered to the portion without suture. The protocol is described below.

(Anesthesia)

A pig 15 to 17 weeks old (LWD ternary hybrid) was intramuscularly injected via the dorsal portion of its neck with 20 mg/kg Ketaral+10 mg/kg Seractal. Thereafter, an infusion route was provided in the ear vein, and thereafter, the respiratory tract was secured using endotracheal intubation. Diprivan was continuously administered at a rate of 0.5 mg/kg/hr to maintain anesthesia. An antibiotic (Cefamezin, 1 g) was administered to prevent post-operational infection.

(Operation)

The animal was positioned and an operation portion was cleaned with a sterilized drape. A knee joint was accessed by medial para-patellar approach. After detecting the internal articular capsule, the middle portion of the capsule was dissected. The lower thighs were bent and laterally rotated, and were further pulled forward, so that the anterior horn portion of the internal meniscus was exposed. In this place, a cylinder-shaped cavity (diameter: 6.5 mm) was created using the mosaic plasty DP (Smith & Nephew). The cavity was filled with the synthetic tissue. In order to protect the synthetic tissue until it was accepted, the meniscus was wrapped with a collagen sheet (Nipro) which was fixed by suture. After hemostasis was confirmed, the incised internal collateral ligament was repaired, and the articular capsule, the subcutaneous tissue, and the epidermis were sutured. A cast was fixed to the knee joint in its incurvation position. The operation was ended.

(Evaluation Method)

Histological study was performed based on Frank's method (J. Orthop. Res., 13, 923-9, 1995).

(Results)

According to visual finding and histological finding 6 weeks after operation, the group filled with the synthetic tissue had significantly better healing quality.

Example 11

Repair of a Pig Bone

In this example, repair of bone is experimentally conducted. Using a protocol as described in Example 1, synovial cells are collected and cultured to produce a synthetic tissue.

Next, a sheet of this synthetic tissue is applied to a bone. The synthetic tissue is applied to an affected portion mainly by covering it over a cortical bone as well as a periosteum. As a result, it is demonstrated that the synthetic tissue comprising synovial cells is effective for repair of a bone. The protocol is described below.

(Anesthesia)

A pig 15 to 17 weeks old (LWD ternary hybrid) was intramuscularly injected via the dorsal portion of its neck with 20 mg/kg Ketaral+10 mg/kg seractal. Thereafter, an infusion route was provided in the ear vein, and thereafter, the respiratory tract was secured using endotracheal intubation. Diprivan was continuously administered at a rate of 0.5 mg/kg/hr to maintain anesthesia. An antibiotic (Cefamezin, 1 g) was administered to prevent post-operational infection.

(Operation)

The animal was positioned and an operation portion was cleaned with a sterilized drape. A second metatarsal bone was accessed from a longitudinal incised portion. The periosteum of the second metatarsal bone was ablated as much as possible so that the surface of the second metatarsal bone was exposed. A window of 1.5 cm (horizontal)×3 cm (vertical) was created on the surface of the second metatarsal bone using a chisel. The window was covered with the outstretched synthetic tissue. After confirming the attachment of the synthetic tissue, the subcutaneous tissue and the epidermis were sutured. A cast is fixed to the lower thigh. The operation was ended.

(Evaluation Method)

Radiography, micro CT, and histology.

(Results)

Four weeks after operation, evaluation confirmed that osteogenesis was accelerated in the window portion for the group filled with the synthetic tissue.

Example 12

Pig Fat-Derived Tissue

Next, cells derived from adipose tissue were used to produce a synthetic tissue.

A) Cells were collected as follows.

1) A specimen was removed from the fat-pad of a knee joint.
2) The specimen was washed with PBS.
3) The specimen was cut into as many pieces as possible using scissors.
4) 10 ml of collagenase (0.1%) was added to the specimen, followed by shaking for one hour in a water bath at 37° C.
5) An equal amount of DMEM (supplement with 10% FBS) was added, followed by filtration using a 70 µl filter (available from Millipore or the like).
6) Cells which passed through the filter and residues which remained on the filter were placed in a 25-cm² flask (available from Falcon or the like) containing 5 ml of DMEM supplemented with 10% FBS.
7) Cells attached to the bottom of the flask (including mesenchymal stem cells) were removed and subjected to the production of a synthetic tissue as follows.

B) Production of Synthetic Tissue

Figure 33:
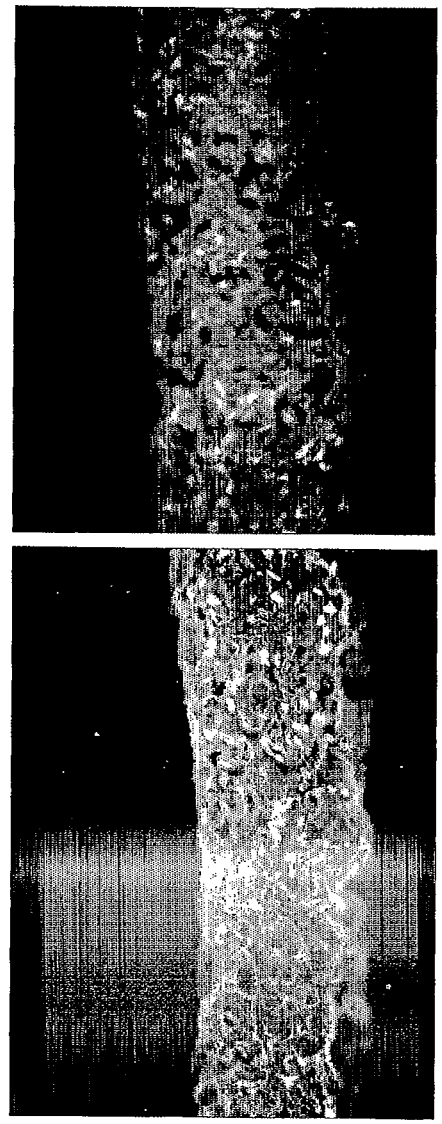
FIG. 33 shows an immunohistochemistry of a synthetic tissue derived from adipose tissue. From the left, H&E staining, fibronectin staining, and vitronectin staining.

Next, the above-described fat-derived cells were used to produce a synthetic tissue. The concentrations of ascorbic acid 2-phosphate were 0 mM (absent), 0.1 mM, 0.5 mM, 1.0 mM, and 5.0 mM. The synthetic tissue was produced in accordance with the above-described method which was used to produce synovial cells (Example 1). Cells were dessimated at an initial concentration of $5 \times 10^4$ cells/cm². The result is shown in FIG. 33. The cells were cultured for 14 days. A synthetic tissue was also formed from an adipose tissue-derived cell and had as rich fibronectin and vitronectin as the synovial cell-derived synthetic tissue. Collagen I and III were similarly expressed richly.

C) Implantation Experiment

Next, the above-described synthetic tissue is subjected to an implantation experiment in Example 8 (cartilage repair) and in Example 9 (meniscus repair). As a result, it is demonstrated that a repairing capability is possessed by the fat-derived synthetic tissue as with a synovial cell-derived synthetic tissue.

Figure 34:
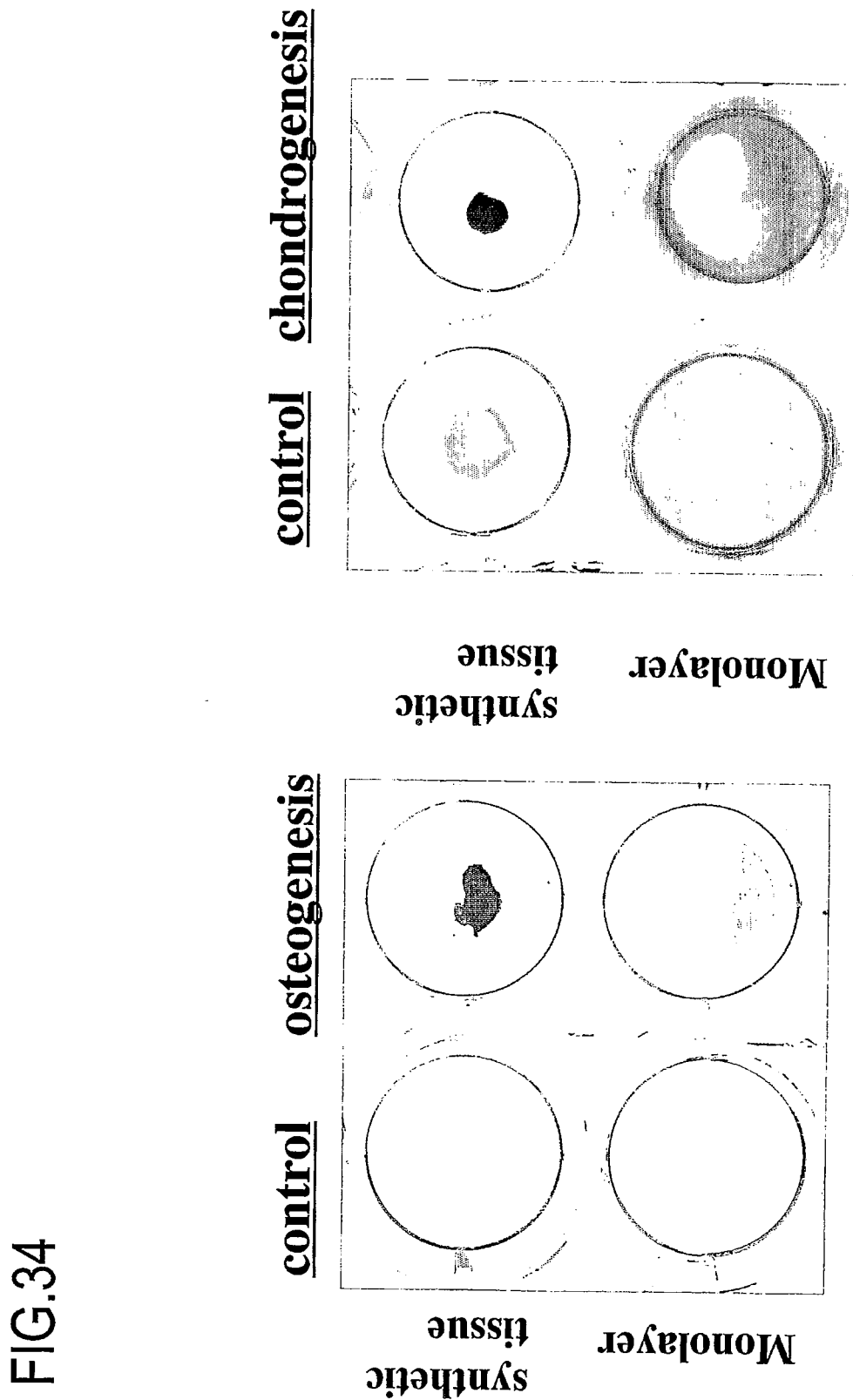
FIG. 34 shows the results of osteogenic or chondrogenic induction of a synthetic tissue derived from adipose tissue.

D) Differentiation Induction of a Fat-Derived Synthetic Tissue into Bone/Cartilage The synthetic tissue of this example was induced to differentiate into a cartilage or a bone. The results are shown in FIG. 34. The left portion of the figure indicates the results of an osteogenesis experiment. The upper portion indicates a synthetic tissue, while the lower portion indicates monolayer culture. The synthetic tissue had a positive reaction to Alizarin Red in an osteogenesis induction medium. Thus, osteogenesis was confirmed. The right portion indicates a chondrogenesis induction experiment. In this experiment, the synthetic tissue was differentiated with a stimulus due to chondrogenesis induction medium+BMP-2 into a cartilage-like tissue which was positive to Alcian blue. Thus, it was demonstrated that the fat-derived synthetic tissue also has the ability to differentiate into a bone and a cartilage as with a synovial cell-derived synthetic tissue.

Example 13

Versatility of Shape of Synthetic Tissue

In this example, a difference in function due to the shape of a synthetic tissue is measured. The synthetic tissue may be crumpled up and implanted into an affected portion instead of using a sheet of the synthetic tissue. Thereby, it is determined whether or not a tailor-made operation can be conducted, depending on the shape or the like of a wound portion.

In this example, it is investigated whether or not a synthetic tissue can be implanted when it is in the shape of a ball, a line, or a tube. The synthetic tissue is confirmed not to require suture, since it has an adhesion molecule.

Example 14

Treatment Using a Synovial Cell

In this example, a synovial cell is collected from a patient having an injured meniscus, and it is determined whether or not the synovial cell can be used to produce a synthetic tissue.

(Collection of a Human Synovial Cell)

A human patient, who has a clinical symptom is diagnosed by an imaging technique as having cartilage injury or meniscus injury, is subjected to arthroscopy under lumber anesthesia or general anesthesia. In this case, several milligrams of synovial membrane is collected. The collected synovial membrane is transferred to a 50-ml centrifuge tube (manufactured by Falcon) and washed with phosphate buffered saline (PBS). Thereafter, the sample is transferred to a 10-cm diameter culture dish (Falcon) and is cut into small pieces using a sterilized blade. Thereafter, 10 ml of 0.1% collagenase (Sigma) is added to the cut pieces in the dish. The dish is shaken in a constant temperature bath at 37° C. for 1 hour 30 minutes. To the solution, 10 ml of medium (DMEM, Gibco) containing self-serum previously collected or bovine serum (FBS) is added to inactivate the collagenase, followed by centrifugation at 1500 rpm for 5 minutes to pellet the cells. Thereafter, 5 ml of the serum-containing medium is added again. The culture medium is passed through a 70-µl filter (Falcon). The collected cells are transferred to a 25 cm² flask (Falcon), followed by culture in a $CO_2$ incubator at 37° C.

(Subculture of a Synovial Cell)

During primary culture, medium is exchanged two times every week. When cells become confluent, the cells are subcultured. For initial subculture, the medium is suctioned and thereafter the cells are washed with PBS. Trypsin-EDTA (Gibco) is added to the cells which are in turn allowed to stand for 5 minutes. Thereafter, the serum-containing medium is added and the resultant mixture was transferred to a 50-ml centrifuge tube (Falcon), followed by centrifugation at 1500 rpm for 5 minutes. Thereafter, 15 ml of the serum-containing medium is added to the pellet. The cells are placed in a 150-cm² culture dish (Falcon). Subsequent subculture is performed so that the cell ratio was 1:3. The same procedure is repeated up to 4 to 5 passages.

(Production of a Synthetic Tissue)

The synovial cell of 4 to 5 passages is treated with trypsin-EDTA. The synovial cells ($4.0 \times 10^6$) are dispersed in 2 ml of medium containing 0.2 mM ascorbic acid 2-phosphate on a 35-ml culture dish (Falcon), followed by culture in a $CO_2$ incubator at 37° C. for 7 days. As a result, a culture cell-extracellular matrix complex is formed. The complex is mechanically detached from the culture dish by pipetting the periphery thereof two or more hours before an implantation operation. After detachment, the culture cell-extracellular matrix complex contracts into a three-dimensional tissue having a diameter of about 15 mm and a thickness of about 0.1 mm.

Example 15

Production of a Synthetic Tissue from a Human Adipocyte

A collection-intended site (e.g., around a knee joint) from a patient under local anesthesia is resected. Several milligrams of adipocytes are collected from the site. The collected adipocytes were treated in a manner similar to that of the synovial cells. As a result, a three-dimensional synthetic tissue can be produced.

Example 16

Implantation of a Synthetic Tissue into a Joint Cartilage Injury Portion

The synthetic tissue produced in Example 14 or 15 is used for actual implantation. A human subject is subjected to lumbar anesthesia or general anesthesia. Thereafter, the inside of a joint is opened at minimum incision for arthroscopy. After detecting a cartilage injury portion, the size of the cartilage injury is measured. A circular portion of the cartilage is dissected from the bone-cartilage interface using the mosaic plasty harvesting system (Smith and Nephew) and a dental explorer, where the circular portion fully contains the injured cartilage. The synthetic tissue was implanted into the cavity in a portion of cartilage. The synthetic tissue is adhered to the base of the cavity several minutes after implantation. When an affected portion receives a high mechanical stress, the fixation of the synthetic tissue may be reinforced using fibrin glue (initial fixation is reinforced). The present invention is not limited to this. After fixation, the articular capsule, the subcutaneous tissue, and the skin are sutured collectively. After closing the incision site, the joint is fixed using a cast or an orthosis for 2 to 3 weeks. Thereafter, rehabilitation is started within a limited range of motion. When an affected portion is present in a weight-bearing joint (e.g., a knee, a ankle joint, etc.). A full load is able to be applied after 6 to 8 weeks.

As a result, symptoms are cured or ameliorated as follows: a reduction in joint pain when a load or an exercise is applied; elimination of joint effusion; recovery of a joint range of motion; recovery of muscle strength around the joint; prevention of osteoarthritis; and the like. Thus, it is observed that the synthetic tissue of the present invention has no significant side effects and improves the function of a repaired portion.

Example 17

Implantation into a Meniscus Injury Portion

In this example, the synthetic tissue produced in Example 14 or 15 is actually implanted into a meniscus injury portion.

A meniscus injury portion is detected in a human subject under lumbar anesthesia or general anesthesia, using an arthroscope. A rupture portion of an injury meniscus is filled with the synthetic tissue. Thereafter, the injured meniscus and the synthetic tissue are sutured together. All surgical procedures are performed under an arthroscope. After surgery, a knee orthosis is used for 2 to 3 weeks. Thereafter, rehabilitation is started within a limited range of motion. A full weight bearing is permitted after 5 to 6 weeks.

As a result, symptoms are cured or ameliorated as follows: a reduction in joint pain when a load or an exercise is applied to the knee joint; elimination of hydrarthrosis; recovery of a joint range of motion; recovery of muscle strength around the joint; recovery of activity; doing sports again; and the like. Thus, it is observed that the synthetic tissue of the present invention has no significant side effects and improves the function of a repaired portion.

Example 18

Implantation into an Achilles Tendon

The synthetic tissue produced in Example 14 or 15 is implanted into an Achilles tendon injury portion.

A human subject under lumbar anesthesia or general anesthesia is subjected to Achilles tendon by para-tendon approach. The portion of degenative tear is detected and then curetted. The synthetic tissue is implanted into the portion of degenerative tear. After implantation, conventional tendon repair is performed. In addition, the surface layer of the repaired portion is covered with the synthetic tissue, which is in turn sutured and fixed thereto. After closing the incision site, a cast is fixed to the lower limb for 4 weeks. A full weight bearing is permitted after 6 to 8 weeks.

As a result, symptoms are cured or ameliorated as follows: recovery of activity level (from walking to a sport level); a reduction in pain; and a decrease in possibility of re-rupture. Thus, it is observed that the synthetic tissue of the present invention has no significant side effects and improves the function of a repaired portion.

Example 19

Treatment of Intractable Pseudarthrosis

In this example, intractable pseudarthrosis is treated using the synthetic tissue produced in Example 14 or 15. A feature of intractable pseudarthrosis is that a periosteum, which is a source of supplying cells in a bone fracture therapy, is severely damaged and lost. Implantation of the synthetic tissue is considered to be appropriate in such a case.

A bone fracture portion is opened in a human subject under anesthesia. Thereafter, the bone fracture portion is curetted. After the remaining portion is fixed with a plate or an intramedullary nail, the injured periosteum is covered with the synthetic tissue. The synthetic tissue is sutured and fixed to adjacent periosteum tissue. After closing the incision site, the joint adjacent to the bone fracture portion is fixed with a cast for 3 to 4 weeks. In the case of a lower limb bone, full weight bearing is permitted after 6 to 8 weeks.

As a result, symptoms are cured or ameliorated as follows: elimination of pain; recovery of muscle strength around the joint; and recovery of an activity level. Thus, it is observed that the synthetic tissue of the present invention has no significant side effects and improves the function of a repaired portion.

Example 20

Implantation into a Rotator Cuff Injury Portion

In this example, a synthetic tissue is implanted into a rotator cuff injury portion. The synthetic tissue is produced as described in Example 1. Under general anesthesia, the rotator cuff injury portion is detected by transdeltoid approach.

After detecting the rotator cuff injury portion, the portion is curetted and is subjected to a typical rotator cuff repair operation. Thereafter, the surface layer of the repaired rotator cuff portion is covered with the synthetic tissue. After closing the incision site, the shoulder joint is fixed with an orthosis for 2 to 3 weeks. Thereafter, rehabilitation is started within a limited range of motion. After 6 weeks, full range of motion is permitted.

As a result, symptoms are cured or ameliorated as follows: remission of shoulder pain (particularly, night pain); recovery of a joint range of motion; recovery of muscle strength around the shoulder; and recovery of activity. Thus, it is observed that the synthetic tissue of the present invention has no significant side effects and improves the function of a repaired portion.

Example 21

Study on the Possibility of Cell Differentiation Induction Before and After Production of a Synthetic Tissue In this example, a synthetic tissue is produced using a human synovial cell.

Figure 35:
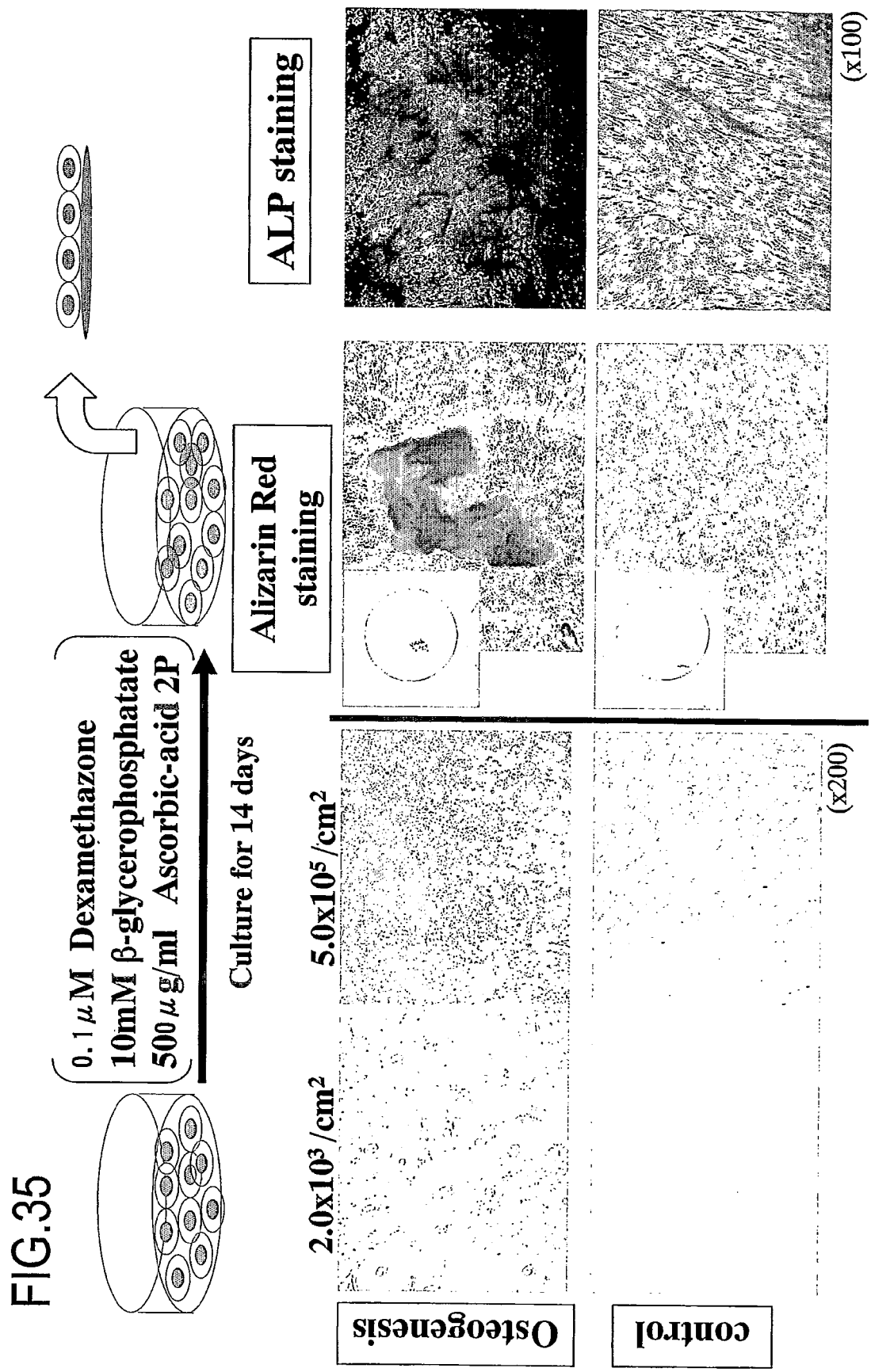
FIG. 35 shows the results of a synthetic tissue with osteogenic induction when dexamethasone and β-glycerophosphate were added in culture medium prior to a detachment procedure.
Figure 36:
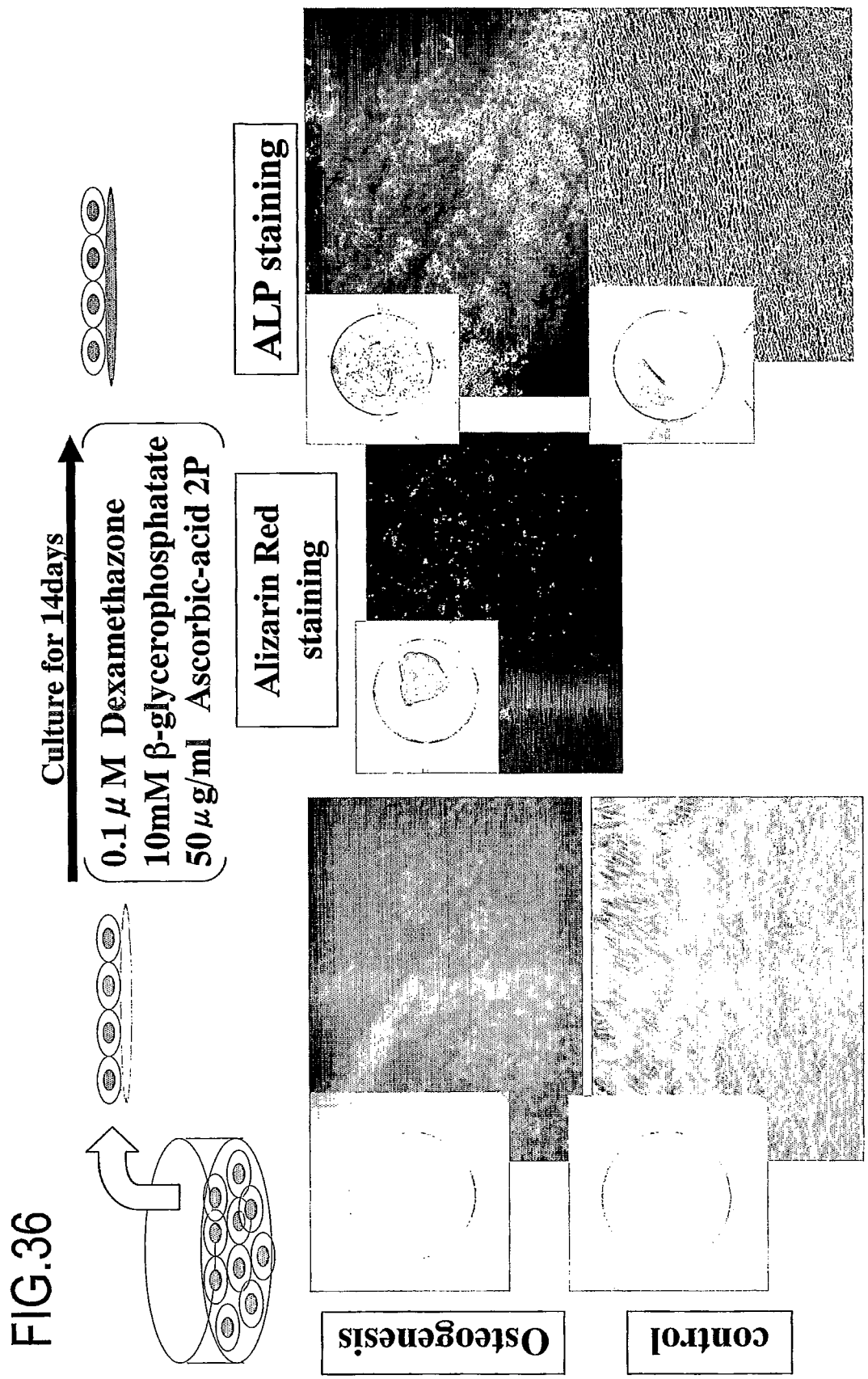
FIG. 36 shows the results of a synthetic tissue with osteogenic induction when dexamethasone and β-glycerophosphate were added in culture medium after a detachment procedure.

The production process of the synthetic tissue using a human synovial cell is shown in the upper portions of FIGS. 35 and 36. FIG. 35 shows production of a synthetic tissue after a human synovial cell is subjected to differentiation induction. FIG. 36 shows that a synthetic tissue is produced before the tissue is subjected to differentiation induction. The differentiation induction is performed by culturing a human synovial cell in DMEM medium containing 0.1 µM dexamethasone, 10 mM β-glycerophosphate, and 50 µg/ml ascorbic acid 2-phosphate for 14 days. The synthetic tissue is stained with Alzarin red and alkali phosphatase (ALP). The results of the staining are shown in the lower portions of FIGS. 35 and 36. As can be seen from FIG. 35, in either case, the synthetic tissue is produced and exhibits an osteogenic reaction positive to the Alzarin red and ALP staining. Therefore, it is demonstrated that the differentiation induction of a tissue can be performed either before or after production of a synthetic tissue.

Example 22

Study on Timing of Differentiation for Production of a Synthetic Tissue in the Case of Human Cells In this example, a synthetic tissue was produced using cells derived from adipose tissue.

A) The cells were collected as follows.

1) A specimen was collected from a fat-pad of a knee joint.
2) The specimen was washed with PBS.
3) The specimen was cut into as many pieces as possible.
4) 10 ml of collagenase (0.1%) was added, followed by shaking in 37° C. water bath for one hour.
5) An equal amount of DMEM (supplemented with 10% FBS) was added. The resultant mixture was passed through a 70-µl filter (available from Millipore, etc.).
6) Cells passing through the filter and cells remaining on the filter were cultured in 25-cm$^2$ flask containing 5 ml of DMEM medium supplemented with 10% FBS.
7) The cells (including a mesenchymal stem cell) attached to the base of the flask were used to produce a synthetic tissue as follows.

B) Production of a Synthetic Tissue

Next, the fat-derived cells were used to produce a synthetic tissue. Ascorbic acid 2-phosphate was used at a concentration of 0 mM (absence), 0.1 mM, 0.5 mM, 1.0 mM, or 5.0 mM. The production was conducted in accordance with the method for producing a synthetic tissue from a synovial cells (Example 1). The cells were disseminated at an initial density of $5 \times 10^4$ cells/cm$^2$.

The cells were used to study the importance of the differentiation timing using the conditions as described in Example 21.

As a result, it was similarly demonstrated that the differentiation timing has no particular influence on the adipocyte-derived synthetic tissue of the present invention.

Example 23

Confirmation of Biological Integration

Figure 37:
FIG. 37 shows histology of biological integration of collagen gel containing synovial cells with cartilage after implantation. There is failure in integration observed (arrow).

It is known that conventional collagen gel does not always achieve biological integration after implantation. In this example, a conventional collagen gel (3% type I collagen, Koken, Tokyo, Japan) was used. Synovial cells ($1 \times 10^5$ cells/ml) were embedded in the gel. The resultant gel was implanted into a cavity in a portion of cartilage. As a result, as can be seen from FIG. 37, the integration between the collagen gel and its adjacent cartilage was insufficient, so that a crack was observed (arrow in FIG. 37).

Figure 38:
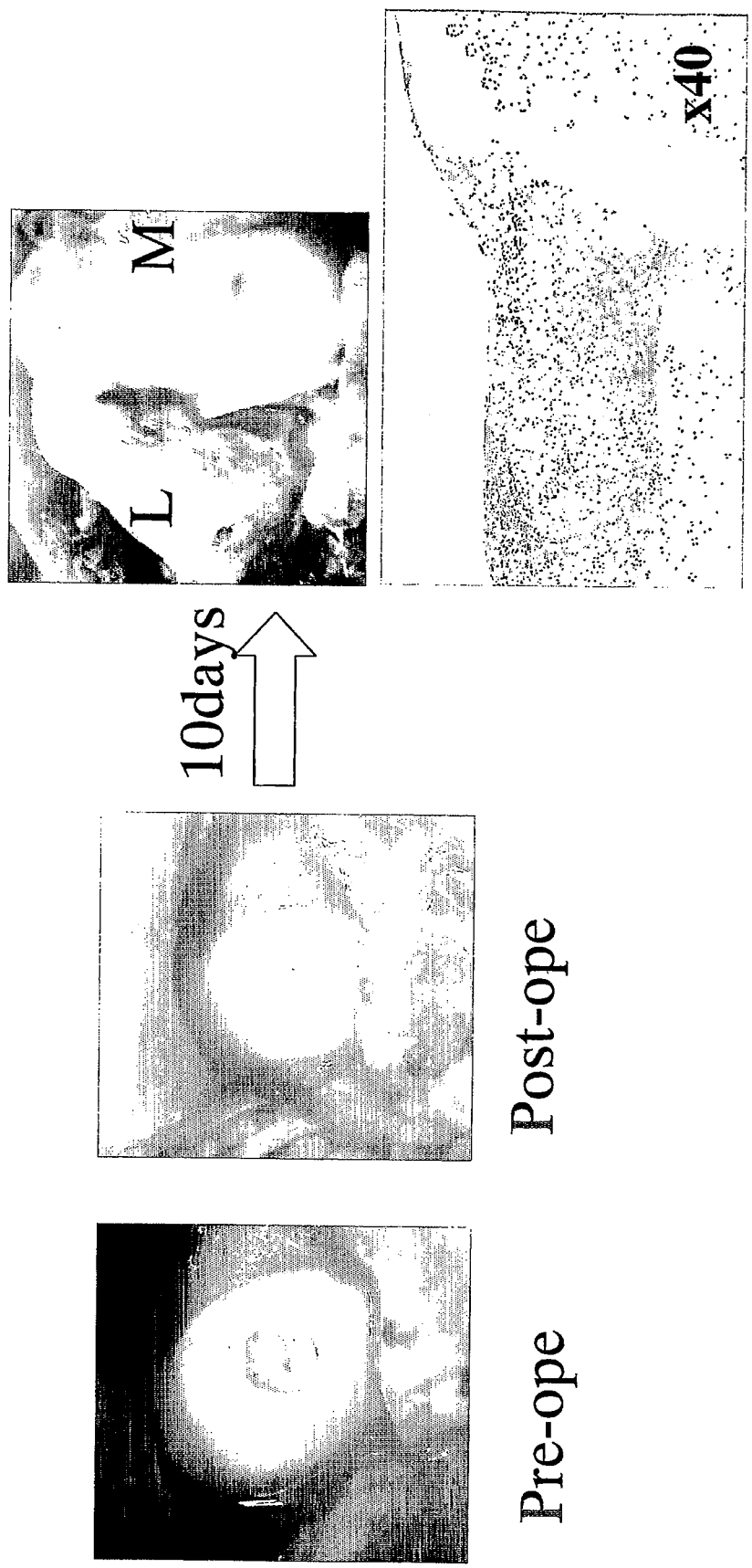
FIG. 38 shows biological integration after implantation to a chondral defect when a synthetic tissue of the present invention was used. The biological integration is completely established.

On the other hand, when a synthetic tissue of the present invention as produced in Example 1 is introduced into a pig, biological integration is histologically established as shown in FIG. 38.

Example 24

Study on Conditions for Detachment During Production of a Synthetic Tissue

In this example, it was determined whether or not chemical detachment can be used instead of physical detachment (mechanical detachment (e.g., pipetting, etc.)) during the production of the synthetic tissue of the present invention.

(Conditions for Culture)
Cell density: $4 \times 10^4$ cells/cm$^2$
Conditions: $CO_2$ 5%, air 95%, 37° C.
Medium: DMEM/F12 (FBS 10%) supplemented with 10 ng/ml TGFβ1.

This medium was used to conduct culture under the conditions described in Examples 14 and 15 to produce a synthetic tissue.

When TGF-β was added, the monolayer culture cells could be more easily detached from the culture dish.

Medium: DMEM (GIBCO), FBS (HyClone) 10%, ITS+ Premix (insulin, transferrin, selenious acid) (BD Biosciences) 6.25 µg/ml, dexamethasone (Sigma) $10^{-7}$ M, ascorbic acid (WAKO) 50 µg/ml, pyrubic acid (SIGMA) 100 µg/ml.

Figure 39:
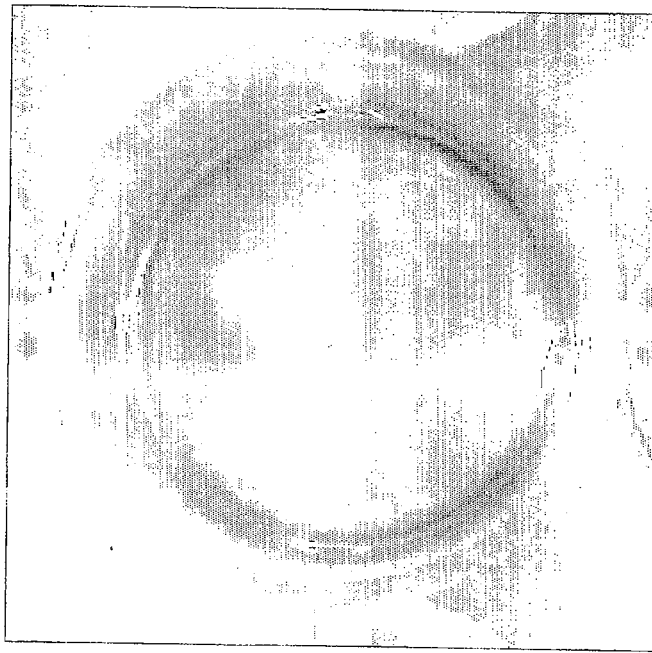
FIG. 39 shows the effect of TGF-β on the detachment of a synthetic tissue. Addition of TGF-β leads to active detachment of the synthetic tissue.

The results are shown in FIGS. 19 and 39. The rightmost column in FIG. 19 shows the case where TGF-β was added. In this case, cells were detached from a culture dish during monolayer culture. Therefore, a synthetic tissue could not be satisfactorily produced. FIG. 39 shows the result of a tissue which was detached without a physical stimulus when TGF-β was added in monolayer culture. These results indicate that TGF-β has the effect of detaching culture cells.

Example 25

Actin Regulatory Agent

Dihydrocytochalasin B and Y27632 (Yamanouchi Pharmaceutical), which are known to have an actin depolymerizing function, were used to study their influence on the contraction of a synthetic tissue.

Figure 40:
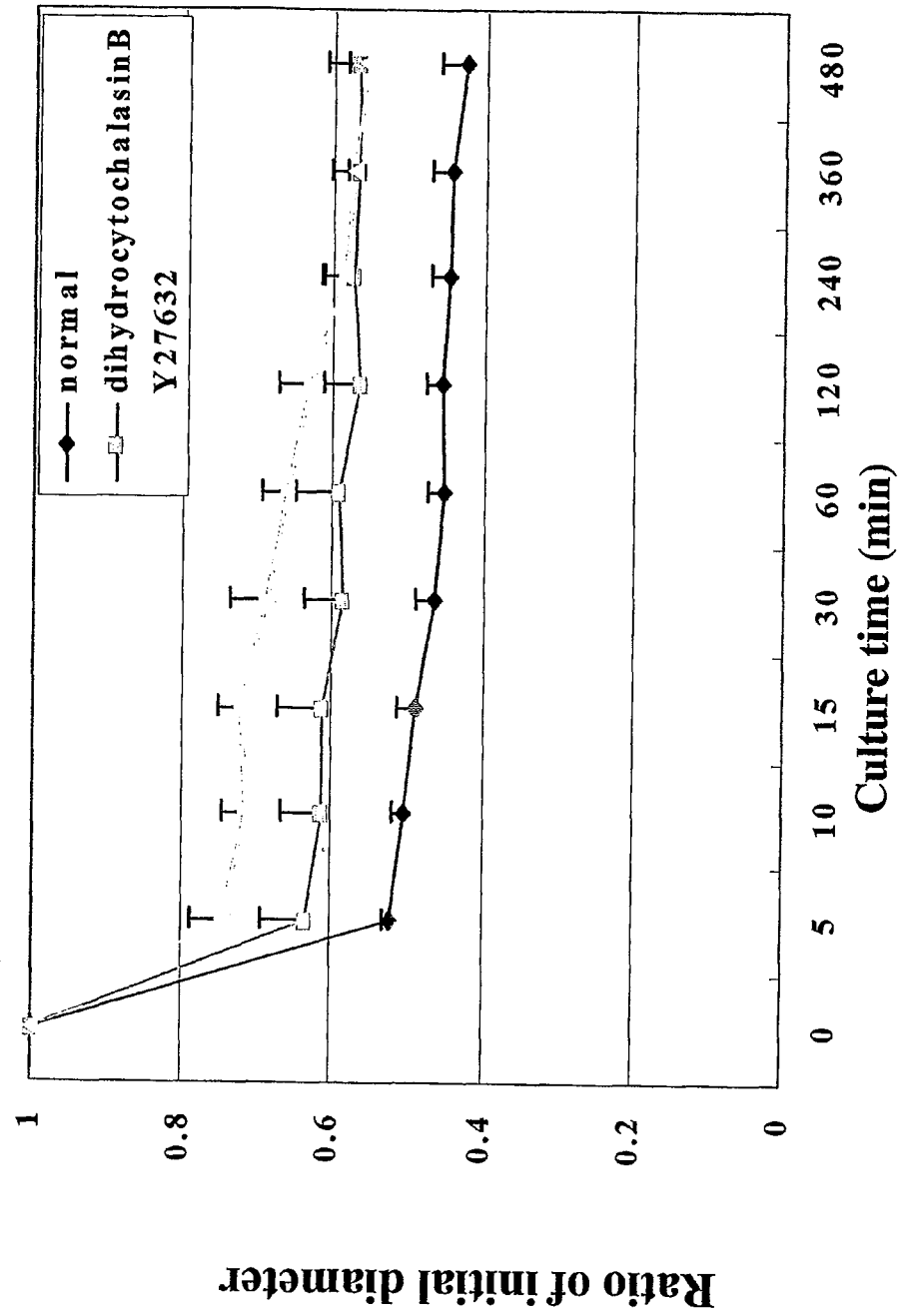
FIG. 40 shows a transition in contraction of a synthetic tissue of the present invention where dihydrochytochalasin or Y27632 was added or not. Data is shown in predetermined culture time intervals.

A synovium-derived synthetic tissue was produced by monolayer culture. The tissue was detached from a culture dish. The tissue was cultured in medium in the presence of dihydrocytochalasin B (3 µM) and Y27632 (10 µM). The transition of the radius of the tissue is shown every unit culture time in FIG. 40. As can be seen from the figure, contraction was inhibited by the addition of these actin depolymerizing agents. Dihydrocytochalasin B and Y27632 are representative exemplary actin polymerization inhibitors. It will be understood by those skilled in the art that other actin polymerization inhibitors, such as cytochalasin D and the like, have a similar function.

Example 26

Production of an Artificial Bone/Cartilage Column as a Complex of a Synthetic Tissue and an Artificial Bone A 12-well culture dish was used to produce a synthetic tissue.

A column-like artificial bone (NEO BONE: MMT) having a diameter of 5 mm×6 mm was placed in a 96-well culture dish. The synthetic tissue was implanted on to the artificial bone. 100 µl of medium (DMEM, 10% FBS) was placed in each well of the dish, followed by culture for 2 hours. As a result, the synthetic tissue was attached to the artificial bone, thereby obtaining a tissue complex.

This complex was cultured in cartilage induction medium (DMEM, 10% FBS, ITS+Premix, sodium pyrubate, ascorbic acid 2-phosphate, 500 ng/ml BMP-2) for 14 days.

Figure 41:
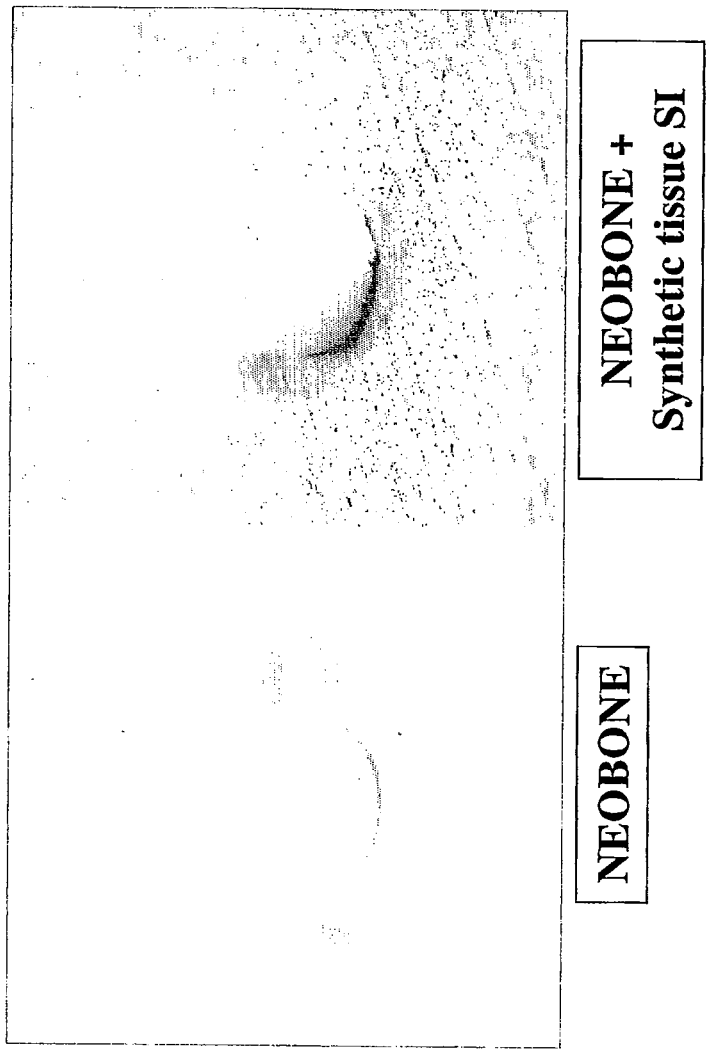
FIG. 41 shows a photograph indicating adhesion of a synthetic tissue of the present invention with an artificial bone after fourteen days of culture in chondrogenic medium.

The result is shown in FIG. 41.

As can be seen from FIG. 41, it is demonstrated that the synthetic tissue of the present invention was satisfactorily adhered to the other synthetic tissue (i.e., the artificial bone). Therefore, it will be understood that the synthetic tissue of the present invention can be combined with other synthetic tissues into a tissue complex.

Example 27

Figure 42:
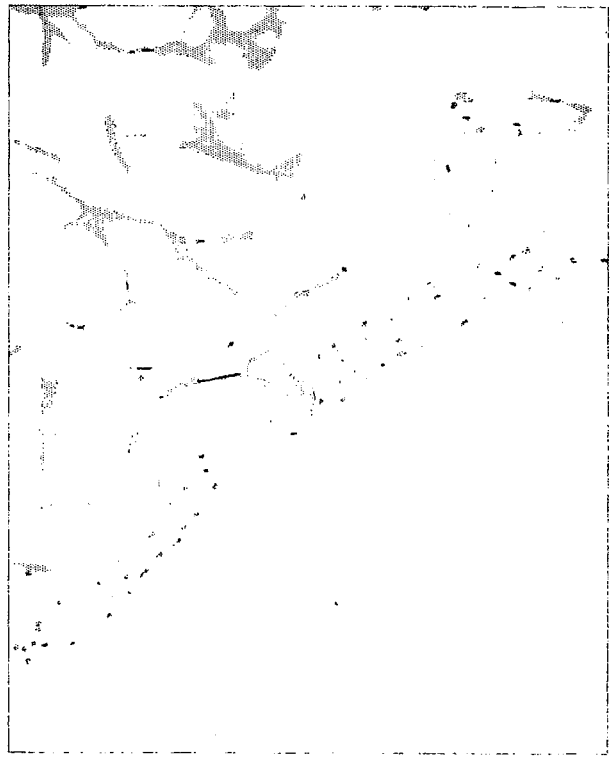
FIG. 42 shows histology of a synthetic tissue cultured on a collagen synthetic tissue (CMI collagen sponge, Amgen, USA), which is a microfibrous collagen medical device, for 7 days.

Composite Tissue Obtained by Attaching a Synthetic Tissue to a Collagen Scaffold In this example, a microfibrous collagen medical device (specifically, a collagen synthetic tissue (CMI (Collagen Meniscal Implant) collagen sponge, Amgen, USA)) was attached to a synthetic tissue instead of NEO BONE in Example 26. The result is shown in FIG. 42 (enlarged photograph). The synthetic tissue of the present invention is observed to be biologically integrated with the surface of the CMI. Thus, it was demonstrated that a microfibrous collagen medical device, which is a conventional synthetic tissue, can be combined with the synthetic tissue of the present invention to obtain a tissue complex.

Example 28

Production of a Synthetic Tissue Using a Myoblast

In this example, an influence of ascorbic acid or a derivative thereof on the production of a synthetic tissue when a myoblast was used, was studied. The synthetic tissue was produced as in Example 1.

After the myoblast was well grown, $5 \times 10^6$ myoblast cells were cultured to form a synthetic tissue. For culture, SkBM Basal Medium (Clonetics (Cambrex)) was used. Next, ascorbic acid 2-phosphate (0.5 mM), a magnesium salt of ascorbic acid 1-phosphate (0.1 mM), and L-ascorbic acid Na (0.1 mM) were added to the medium. After four days of culture, the tissue was detached. As a control, a synthetic tissue was produced in medium without ascorbic acids.

(Results)

Figure 43:
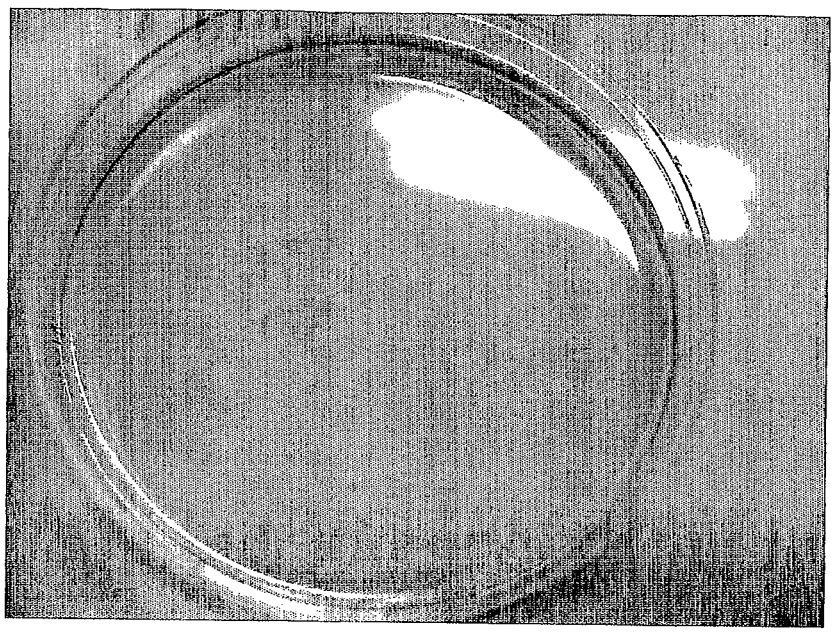
FIG. 43 shows a skeletal muscle-derived sheet developed by a synthetic tissue production method without ascorbic acid.
Figure 44:
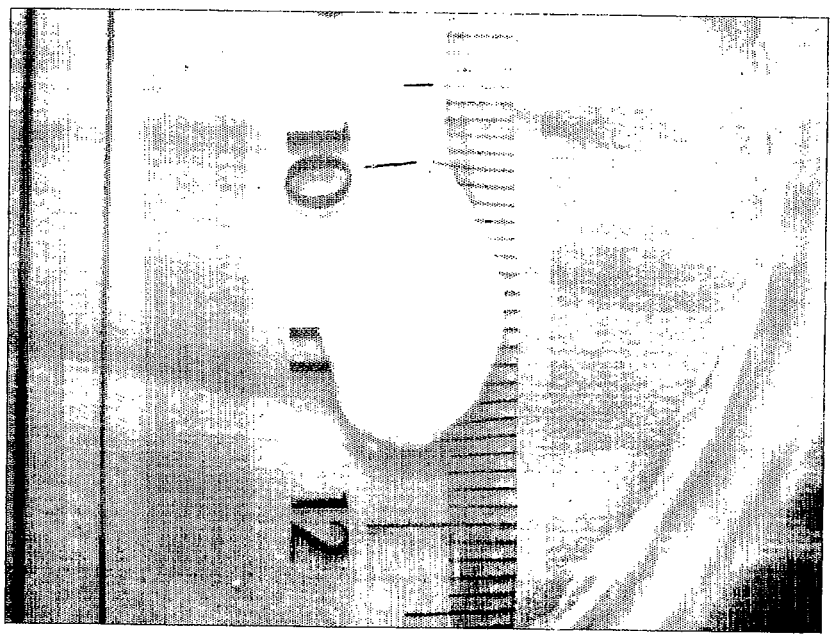
FIG. 44 shows a skeletal muscle-derived synthetic tissue developed by a synthetic tissue production method with ascorbic acid according to the present invention.
Figure 45:
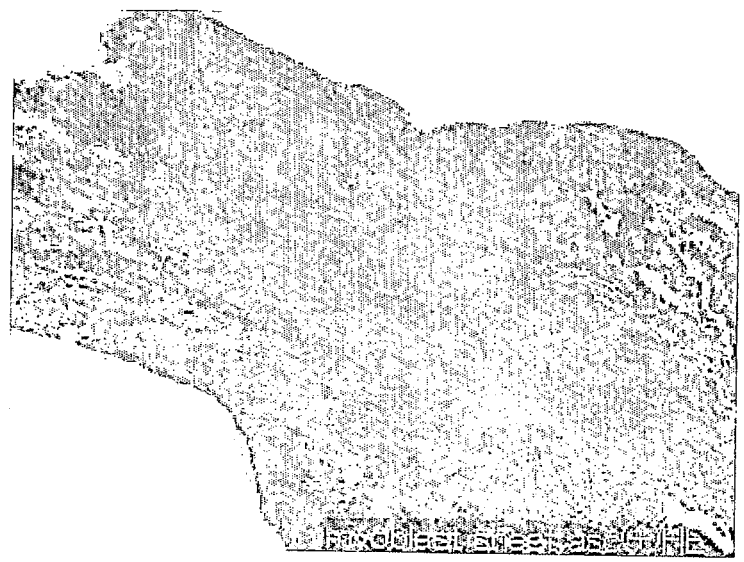
FIG. 45 shows histology of the synthetic tissue as shown in FIG. 44 (HE staining).

When ascorbic acids were used, the synthetic tissue was easily detached as compared to when the ascorbic acid-free culture system was used. Also, in the ascorbic acid-free culture system, the tissue was cultured to about several millimeters. When the tissue exceeded such a level, a crack or the like occurred in the tissue so that the tissue did not grow satisfactorily. In addition, it was substantially difficult to detach the tissue. Thus, no implantable synthetic tissue was produced (FIG. 43). In contrast, the synthetic tissue of the present invention, which was cultured in medium containing ascorbic acids, was grown to a size which allows implantation, and was easily isolated (FIG. 44). Biological integration was investigated, so that extracellular matrices were highly interacted (FIG. 45).

Example 29

Effect of a Synthetic Tissue in the Presence of Ascorbic Acids

The synthetic tissue of Example 28, which was produced in the presence of ascorbic acids, was implanted into a dilated cardiomyopathy rat. In 28 rats, the left anterior descending (LAD) was ligated for two weeks to produce injured hearts. The synthetic tissue of the present invention was implanted into some of the injured hearts, while the synthetic tissue of the present invention was not implanted into the other injured hearts. As controls, rats without injury to their hearts were obtained.

The rats were anesthetized and operated. The heart function of the rats was monitored on Day 14 and 28 after surgery. A ultrasonic instrument (Sonos 5500) having an anular array converter operating at 12 MHz was used to perform endocardiography. Parasternal minor axis imaging and parasternal major axis imaging were performed in a B-imaging mode and an M-imaging mode. In addition to the anterior wall pressure, general parameters (e.g., left ventricular telediastolic diameter, left ventricular telesystolic diameter, internal diameter contraction rate, and ejection fraction) were measured.

Two and four weeks after implantation, the rats were sacrificed with an excessive amount of pentobarbital. The heart was dissected, fixed with 10% formalin, and embedded in paraffin. In a low temperature bath, the heart was cut along the longitudinal axis thereof from the base to the apex to prepare a series of sections having a thickness of 5 mm. Thereafter, the sections were treated for standard histology.

All of the rats with implants were completely cured, and survived for substantially the same period of time as normal rats. Therefore, it was demonstrated that the present invention can completely cure diseases, which are conventionally said to be intractable, in the presence of a specific ECM synthesis promoting agent.

Example 30

Combined Therapy

A combined therapy of the synthetic tissue produced in the examples and a gene therapy was performed. The combined therapy was intended to promote vascularization in a portion which a synthetic tissue was implanted; promotion of acceptance of an implanted synthetic tissue; and suppression of cell necrosis in a synthetic tissue.

(Methods)

A hemagglutinating virus of Japan (HVJ)-liposome complex was prepared in accordance with Kaneda Y., Iwai K., Uchida T., Increased expression of DNA co-introduced with nuclear protein in adult rat liver. Science, 1989; 243:375-378. The procedure will be briefly described below. A DNA solution (200 µl) was added, followed by shaking for 30 seconds. The solution was allowed to stand at 37° C. in a constant temperature bath for 30 seconds. This step was performed 8 times. Thereafter, ultrasonication was performed for 5 seconds, followed by shaking for 30 seconds. BSS (0.3 ml) was added, followed by shaking at 37° C. in a constant temperature bath. Inactivated HVJ was added. The mixture was placed on ice for 10 minutes. The mixture was then shaken at 37° C. in a constant temperature bath for one hour. A 60% sucrose solution (1 ml) and a 30% sucrose solution (6 ml) were layered in a centrifuge tube. A HVJ liposome solution was placed on top of the layered sucrose solution. Additional BSS was added to the tube. Centrifugation was performed at 62,800 g at 4° C. for 1.5 hours. A solution immediately above the 30% sucrose solution layer was recovered. The solution was preserved at 4° C. and was used for gene introduction.

About 0.2 ml of Sendai virus liposome-plasmid complex (including 15 µg of human HGF cDNA) was injected into a cardiac infarction region. For a control group, an empty vector was introduced into a heart muscle having infarction. The human HGF concentration of heart tissue was measured with an enzyme linked immunosolvent assay (ELISA) using an anti-human HGF monoclonal antibody (Institite of Immunology, Tokyo, Japan) (Ueda H., Sawa Y., Matsumoto K. et al., Gene Transfection of Hepatocyte Growth Factor Attenuates reperfusion Injury in the Heart, Ann. Thorac. Surg., 1999, 67:1726-1731). The synthetic tissue produced in Example 30 was used. The cardiac infarction models produced by ligating LAD were subjected to three different therapies: 1) a cell sheet group; 2) a gene therapy group; 3) a combined therapy group; and 4) a control group. Changes in heart function and cardiomuscular tissue were studied.

(Results)

For the synthetic tissue implanted group and the combined therapy group, the contractibility and expansibility of the heart were ameliorated. In addition, for the combined therapy group, it can be confirmed that vasculization was observed in the cardiac infarction portion, and the acceptance of implanted cells was improved.

Conclusion

By combining a synthetic tissue and a gene therapy, the decreased heart function ameliorating effect, the vasculization effect, and the cell protecting effect are obtained, so that a higher level of amelioration of the decreased heart function can be observed.

Although certain preferable embodiments have been described herein, it is not intended that such embodiments be construed as limitations on the scope of the invention except as set forth in the appended claims. Various other modifications and equivalents will be apparent to and can be readily made by those skilled in the art, after reading the description herein, without departing from the scope and spirit of this invention. All patents, published patent applications and publications cited herein are incorporated by reference as if set forth fully herein.

INDUSTRIAL APPLICABILITY

The present invention usefully provides a basic therapeutic method, technique, pharmaceutical agent, and medical device for diseases which are conventionally difficult to treat. Particularly, the present invention provides an epoch-making therapy and prevention because it promotes recovery to a substantially native state. The present invention also provides a pharmaceutical-agent, cell, tissue, composition, system, kit, and the like, which are used for such an epoch-making therapy and prevention.

There is a demand for repair and regeneration of joint tissues, mainly including bones and cartilages which are targeted by the present invention. The number of bone fracture patients, which are targeted by bone regeneration, accounts for several hundreds of thousands per year. It is also said that there are 30 million potential patients having osteoarthritis which is targeted by the cartilage regenerative therapy. Thus, the potential market is huge. The present invention is also highly useful for peripheral industries. Acute competition has been started in the regenerative medical research on joint tissues, mainly including bone and cartilage. The synthetic tissue of the present invention is a safe and original material made of cells collected from an organism, such as a patient or the like, and is highly useful in view of the lack of side effects or the like.

The invention claimed is:

1. An implantable synthetic autograft or allograft tissue for implantation in a recipient, which is substantially made of (i) cells that are autologous or allogeneic relative to the recipient and which thereby constitute the synthetic autograft or allograft tissue, said cells being selected from the group consisting of myoblasts, mesenchymal stem cells, adipocytes, synovial cells and bone marrow cells; and (ii) an extracellular matrix (ECM) derived from the cells constituting the synthetic autograft or allograft tissue, said extracellular matrix comprising fibronectin, collagen I, collagen III, and vitronectin, wherein the synthetic autograft or allograft tissue is free of scaffolds and comprises multiple layers of said cells, and is formed by a method that comprises detaching a cultured monolayer of said cells from a culture container without contacting the cells with a protein degrading enzyme, under conditions and for a time sufficient to obtain a detached, self-contracted synthetic tissue, wherein the fibronectin, collagen I, collagen III, and vitronectin are evenly distributed in the synthetic autograft or allograft tissue, wherein the fibronectin, collagen I, collagen III, and vitronectin three-dimensionally wrap the cells, and wherein the implantable synthetic autograft or allograft tissue has integration ability with its surroundings when implanted and has sufficient strength to provide self-supporting ability.

2. The implantable synthetic autograft or allograft tissue of claim 1, wherein the extracellular matrix is integrated throughout the tissue.

3. The implantable synthetic autograft or allograft tissue of claim 1 which comprises 10 or more layers of said cells.

4. The implantable synthetic autograft or allograft tissue of claim 1 which has a thickness of at least about 50 μm and is dimensioned so as to fit an injured site in a tissue or organ.

* * * * *